United States Patent
Imai et al.

(10) Patent No.: US 12,233,071 B2
(45) Date of Patent: Feb. 25, 2025

(54) MEDICAMENT FOR TREATING COUGH

(71) Applicant: NIPPON CHEMIPHAR CO., LTD, Tokyo (JP)

(72) Inventors: Toshiyasu Imai, Misato (JP); Junzo Kamei, Tokyo (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 0 days.

(21) Appl. No.: 18/135,499

(22) Filed: Apr. 17, 2023

(65) Prior Publication Data

US 2023/0248738 A1    Aug. 10, 2023

Related U.S. Application Data

(63) Continuation of application No. 16/979,383, filed as application No. PCT/JP2019/010652 on Mar. 14, 2019, now Pat. No. 11,666,582.

(30) Foreign Application Priority Data

Mar. 14, 2018 (JP) ................................. 2018-046152
Sep. 3, 2018 (JP) ................................. 2018-164852

(51) Int. Cl.
| | | |
|---|---|---|
| C07D 243/10 | (2006.01) | |
| A61K 31/551 | (2006.01) | |
| A61P 11/14 | (2006.01) | |
| A61P 43/00 | (2006.01) | |
| C07D 401/12 | (2006.01) | |
| C07D 401/14 | (2006.01) | |
| C07D 403/10 | (2006.01) | |
| C07D 413/14 | (2006.01) | |

(52) U.S. Cl.
CPC .................................. A61K 31/551 (2013.01)

(58) Field of Classification Search
CPC .. C07D 243/10; C07D 401/12; C07D 401/14; C07D 403/10; C07D 413/14; A61K 31/551; A61P 11/14; A61P 43/00
See application file for complete search history.

(56) References Cited

U.S. PATENT DOCUMENTS

| | | |
|---|---|---|
| 2008/0287467 A1 | 11/2008 | Tamura et al. |
| 2010/0256123 A1 | 10/2010 | Sakuma et al. |
| 2011/0319610 A1 | 12/2011 | Sakuma et al. |
| 2013/0172550 A1 | 7/2013 | Sakuma et al. |
| 2013/0178625 A1 | 7/2013 | Ushioda et al. |
| 2013/0184459 A1 | 7/2013 | Ushioda et al. |
| 2013/0281441 A1 | 10/2013 | Sakuma et al. |
| 2014/0357858 A1 | 12/2014 | Ushioda et al. |
| 2016/0244434 A1 | 8/2016 | Sakuma et al. |
| 2017/0081294 A1 | 3/2017 | Sakuma et al. |
| 2018/0319752 A1 | 11/2018 | Sakuma et al. |

FOREIGN PATENT DOCUMENTS

| | | |
|---|---|---|
| EP | 2058304 A1 | 5/2009 |
| WO | 2008/023847 A1 | 2/2008 |
| WO | 2005/107804 A1 | 11/2008 |
| WO | 2010/093061 A1 | 8/2010 |
| WO | 2012/008478 A1 | 1/2012 |
| WO | 2012/014910 A1 | 2/2012 |
| WO | 2012/017876 A1 | 2/2012 |
| WO | 2013/105608 A1 | 7/2013 |
| WO | 2015/005467 A1 | 1/2015 |
| WO | 2015/005468 A1 | 1/2015 |
| WO | 2017/188365 A1 | 11/2017 |

OTHER PUBLICATIONS

Kamei et al., "Involvement of P2X receptor subtypes in ATP-induced enhancement of the cough reflex sensitivity", European Journal of Pharmacology 528, Oct. 2005, pp. 158-161.
Kamei et al., Journal of Pharmacological Sciences (Folia Pharmacol. Jpn.), 131, (2008) pp. 429-433. translation.
ISR issued in International Patent Application No. PCT/JP2019/010652, dated May 14, 2019, translation.
Extended Search Report issued in EPO Patent Application No. 19767275.1, Nov. 10, 2021.

*Primary Examiner* — Brenda L Coleman
(74) *Attorney, Agent, or Firm* — GREENBLUM & BERNSTEIN, P.L.C.

(57) ABSTRACT

The present invention pertains to a medicament for preventing or treating cough, including, as an active ingredient, a compound having P2X4 receptor antagonistic action, a tautomer, stereoisomer, or pharmaceutically acceptable salt of the compound, or a hydrate or solvate thereof.

12 Claims, 14 Drawing Sheets

**P<0.01 vs. PW-post value

**P<0.01 vs. PW value

MEDICAMENT FOR TREATING COUGH

This is a continuation of U.S. application Ser. No. 16/979,383, which is a US National Stage entry of PCT/JP2019/010652, filed Mar. 14, 2019, which claims priority to JP App. No. 2018-046152, filed Mar. 14, 2018 and JP App. No. 2018-164852, filed Sep. 3, 2018. The disclosure of each of the above-identified documents is incorporated herein by reference in its entirety.

TECHNICAL FIELD

The present invention relates to a prophylactic or therapeutic agent for cough.

BACKGROUND ART

Cough is an intrinsic biological defense response to a foreign material and/or pathogen entering the airway. However, excessive (pathological) cough causes a patient's pain and exhaustion.

Cough is grouped, depending on the duration, into acute cough lasting less than 3 weeks, persistent cough lasting from 3 weeks to less than 8 weeks, and chronic cough lasting 8 weeks or longer.

The major cause of acute cough is an airway infection including common cold, and the frequency of the infection decreases as the duration becomes longer. Infection itself rarely causes chronic cough. Meanwhile, chronic cough is defined such that "the only symptom is cough lasting 8 weeks or longer, the cause of which cannot be identified by general examination such as an interview, physical examination, routine chest radiograph, and/or spirography.

In addition, pathological cough is grouped into dry cough without phlegm and wet cough with phlegm. The former occurs upon cough hypersensitivity or airway spasm caused by various mechanical/chemical stimuli. By contrast, the latter is mainly caused by phlegm-induced mechanical stimuli (cough to expectorate phlegm).

Antitussive agents can clinically suppress cough by blocking any site in a peripheral or central pathway for cough.

Codeine, which is a central nervous system acting medicament, blocks a common pathway among cough mechanisms and thus exerts considerable effects. Nowadays, such a central nervous system acting medicament is often prescribed.

This may be because the cough mechanisms are largely unclear and even the currently revealed mechanisms are still complicated. For instance, there may be tracheal/alveolar inflammation, foreign material, or phlegm accumulation. In these cases, receptors (cough receptors) at the site detect the event to transmit it, via afferent nerves such as glossopharyngeal nerve and superior laryngeal nerve, to a center, what is called a cough center, where cough reflex in the respiratory center of medulla oblongata in the brain stem is integrated. When the information is transmitted from the cough receptors to the cough center, activity of the central regulatory neural mechanism for respiratory movement is modulated. The resulting signal is transmitted via efferent nerves such as vagus nerve and phrenic nerve to the diaphragm and thorax muscles. Then, a strong expiratory effort occurs, accompanied by a rapid increase in intrapleural pressure, leading to cough reflux. This is a mechanism.

In view of the current findings, representative examples of a cough induction-related receptor seem to involve rapid adapting receptors (RARs), which are Aδ fiber terminal receptors or receptors at the bronchopulmonary C fiber terminal. ATP (adenosine triphosphate) has been known to involve Aδ fiber and C fiber. It has been revealed that ATP diversely involves pain signal transduction through various ATP receptor subtypes that are expressed on dorsal root ganglion (DRG) neurons, dorsal horn neurons, spinal microglia, the higher central nervous system, and others. ATP receptors are largely classified into an ion-channel-type ATP receptor (P2X) and a G protein-coupled ATP receptor (P2Y), which are revealed to have 7 subtypes (P2X1-7) and 8 subtypes (P2Y1, 2, 4, 6, and 11-14), respectively.

Among the ATP receptor subtypes, the P2X receptors are shown to co-exist with, for instance, a capsaicin receptor TRPV1 and be expressed on C and Aδ fibers of the dorsal root ganglion nerve (Non Patent Literature 2)

Meanwhile, Kamei and colleagues in Non Patent Literature 1 have reported that in an experiment in which guinea pigs were stimulated with citric acid to induce cough (hereinafter, citric acid-induced cough), ATP elicited a concentration-dependent and significant increase and this effect was completely inhibited by TNP-ATP inhalation pretreatment but not by PPADS aerosol.

It has been known that TNP-ATP is a P2X1-4 receptor antagonist and PPADS is a P2X1, 2, 3, 5, or 7 receptor antagonist.

Then, stimulation of P2X receptors in the airway, in particular, P2X4 receptor is reportedly suggested to be necessary for augmenting ATP-induced cough reflux.

Kamei and colleagues in Non Patent Literature 2 have reported that when the possibility of involvement of ATP receptors in the modulation of cough reflux was investigated, data was obtained that indicated the involvement in expression of cough reflux by directly modulating excitation of Aδ fiber. In addition, the number of coughs that were induced by citric acid and were increased depending on the concentration of ATP was decreased by use of TNP-ATP, which is a P2X-type receptor antagonist. Thus, ATP may increase cough reflux by enhancing, through ATP receptors on the airway, in particular, P2X-type receptors, the sensitivity of RARs or cough receptors, said the report.

Patent Literature 1 discloses a respiratory disease therapeutic including a P2X receptor antagonistic compound, and claims 7 and 8 further stipulate that "the P2X receptor is P2X4 receptor".

However, the P2X receptor antagonistic compound is not specifically disclosed. Regarding the P2X4 receptor antagonistic compound, neither the name or the structure and the like of the compound nor information required for manufacture or identification of the compound is disclosed. Here, not every P2X-type receptor antagonist exhibits an antitussive effect.

Further, the present applicants have filed P2X4 receptor antagonist-related Japanese Patent Applications, such as Patent Literatures 2 to 8. Any of the applications neither describes nor suggests the prophylaxis or treatment of cough.

CITATION LIST

Patent Literature

Patent Literature 1: WO 2005/107804
Patent Literature 2: WO 2008/023847
Patent Literature 3: WO 2010/093061
Patent Literature 4: WO 2012/008478
Patent Literature 5: WO 2012/014910
Patent Literature 6: WO 2012/017876

Patent Literature 7: WO 2013/105608
Patent Literature 8: WO 2015/005468
Patent Literature 9: WO 2015/005467

Non Patent Literature

Non Patent Literature 1: European Journal of Phaemacology 528, 158-161 (2005)
Non Patent Literature 2: Folia Pharmacol. Jpn., 131, 429-433 (2008)

SUMMARY OF INVENTION

Technical Problem

The present invention addresses the problem of providing a medicament for preventing or treating cough. More specifically, provided is a medicament for preventing or treating acute cough, persistent cough, or chronic cough, in particular, chronic cough.

As described above, a central nervous system acting medicament such as codeine blocks a common pathway among the cough mechanisms and thus exerts a large effect. However, there is a problem of stopping cough that is necessary as biological defense and should not be stopped essentially. In addition, the central nervous system acting medicament is frequently accompanied by side effects such as constipation and drowsiness caused by its effect on central nervous system except for cough. Further, even use of the maximum dose of codeine is often resistant to cough caused by cough variant asthma or gastroesophageal reflux disease. When these matters are taken into consideration, it is unpreferable that the central nervous system acting medicament is used to block cough. Hence, a more selective means should be used for cough suppression.

Solution to Problem

The present inventors have conducted intensive research to solve the above problem and, as a result, have found that compounds having P2X4 receptor antagonistic action and represented by general formulas (AI) to (HII) are useful in prophylaxis or treatment of cough. Then, the present invention has thus been completed.

Specifically, the present invention provides a medicament for preventing or treating cough, the medicament including, as an active ingredient, a compound having P2X4 receptor antagonistic action, a tautomer, stereoisomer, or pharmaceutically acceptable salt of the compound, or a hydrate or solvate thereof.

For instance, each compound represented by general formulas (AI) to (HII) below may be used as the compound having P2X4 receptor antagonistic action.

More preferably, a compound represented by general formula (AI), (EI), (FI), or (GI) below may be used as the compound having P2X4 receptor antagonistic action.

The compound having P2X4 receptor antagonistic action acts selectively on peripheral P2X4 receptors and can inhibit cough peripherally. Thus, the compound having P2X4 receptor antagonistic action can exert effects on peripheral ATP receptors (P2X4 receptors) such as those on airway tissues and primary afferent fiber cell bodies (DRG: dorsal root ganglions) that transmit cough reflux stimuli. Accordingly, the compound may be useful as a peripheral antitussive agent without direct effects on the cough center present in the medulla oblongata.

A medicament of the present invention may be used for preventing or treating, for instance, cough, preferably acute cough, persistent cough, or chronic cough and more preferably chronic cough. Further, it is possible to be used for preventing or treating cough such as a disease responsible for chronic cough including dry cough (e.g., cough caused by cough variant asthma, atopic cough, allergic cough) and wet cough (e.g., chronic obstructive pulmonary disease, asthma).

From other viewpoints, the present invention provides: use of a compound having P2X4 receptor antagonistic action, a tautomer, stereoisomer, or pharmaceutically acceptable salt of the compound, or a hydrate or solvate thereof for the manufacture of the above medicament; and a method for preventing or treating cough, including the step of administering, to a mammal including a human, a prophylactically or therapeutically effective amount of a compound having P2X4 receptor antagonistic action, a tautomer, stereoisomer, or pharmaceutically acceptable salt of the compound, or a hydrate or solvate thereof, wherein the cough is selected from dry cough such as cough caused by cough variant asthma, atopic cough, cough caused by gastroesophageal reflux, chemical-induced cough, or allergic cough or wet cough such as cough caused by sinobronchial syndrome, cough caused by chronic bronchitis, cough caused by chronic obstructive pulmonary disease, or cough caused by asthma.

Advantageous Effects of Invention

A medicament of the present invention is useful as a medicament for preventing or treating cough, preferably acute cough, persistent cough, or chronic cough and more preferably chronic cough, and should be further highly effective in prophylaxis or treatment of cough such as a disease responsible for chronic cough including dry cough (e.g., cough caused by cough variant asthma, atopic cough, cough caused by gastroesophageal reflux, chemical-induced cough, or allergic cough) or wet cough (e.g., cough caused by sinobronchial syndrome, cough caused by chronic bronchitis, cough caused by chronic obstructive pulmonary disease, or cough caused by asthma). The medicament is useful, in particular, for dry cough, and is especially useful for cough caused by cough variant asthma, atopic cough, or allergic cough.

DESCRIPTION OF EMBODIMENTS

Figure 1:
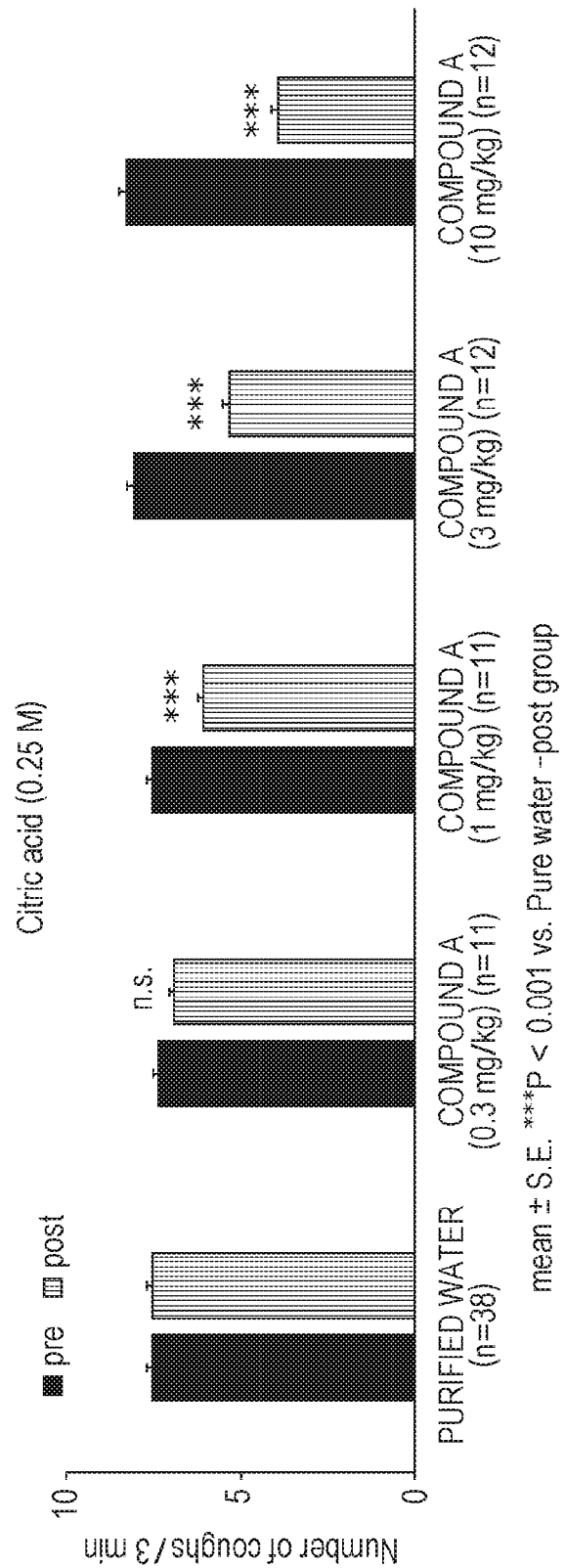
FIG. 1 is a graph showing cough inhibitory action of compound A on citric acid (0.25 M)-induced cough after compound A was orally administered to pretreatment mice.

A medicament of the present invention may be used as a medicament for preventing or treating cough and may be used as a medicament for the following use.

A medicament of the present invention may be used as a medicament for preventing or treating cough, wherein the cough is acute cough, persistent cough, or chronic cough.

A medicament of the present invention may be used as a medicament for preventing or treating cough, wherein the cough is chronic cough.

A medicament of the present invention may be used as a medicament for preventing or treating cough, wherein the cough is dry cough that is, for instance, cough caused by cough variant asthma, atopic cough, cough caused by gastroesophageal reflux, chemical-induced cough, or allergic cough.

A medicament of the present invention may be used as a medicament for preventing or treating cough, wherein the cough is wet cough that is, for instance, cough caused by sinobronchial syndrome, cough caused by chronic bronchitis, cough caused by chronic obstructive pulmonary disease, or cough caused by asthma.

It is possible to use, as an active ingredient in a medicament of the present invention, a compound represented by any one of the following general formulas (AI) to (HII), a tautomer, stereoisomer, or pharmaceutically acceptable salt of the compound, or a hydrate or solvate thereof.

Abbreviations used in, for instance, the following tables are as follows.

Me: methyl group; Et: ethyl group; Pr: n-propyl group; iPr: isopropyl group; tBu: tert-butyl group; Ac: acetyl group; and Ph: phenyl group.

In the tables presented below, substituents may be designated with position numbers of their substitution positions. In addition, to distinguish the apparently identical position numbers in chemical formulas, a prime "'" may be given to one of the position numbers for convenience. Nevertheless, as long as the structure can be specified unequivocally, the position numbers in the compound name may be expressed without using the prime.

(A-1) A compound, a tautomer, stereoisomer, or pharmaceutically acceptable salt of the compound, or a hydrate or solvate thereof, the compound represented by the following general formula (AI):

[Chem. 1]

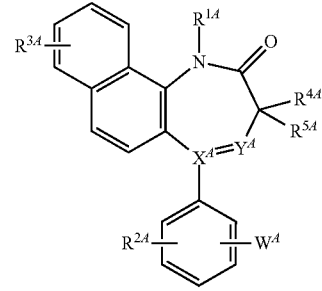

(AI)

wherein $R^{1A}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{2A}$ and $R^{3A}$ are the same or different and represent a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{4A}$ and $R^{5A}$ are the same or different and represent a hydrogen atom, a $C_{1-8}$ alkyl group, a $C_{1-8}$ alkyl group substituted with 1 to 3 halogen atoms, or a phenyl-substituted $C_{1-3}$ alkyl group, $W^A$ represents an optionally substituted, 5- or 6-membered heterocyclic ring comprising 1 to 4 atoms of nitrogen as a ring constituent element, and when $X^A$ is N, $Y^A$ is C=O and a double line composed of a solid line and a dashed line denotes a single bond and when $X^A$ is C, $Y^A$ is N and a double line composed of a solid line and a dashed line denotes a double bond.

(A-2) A compound, a tautomer, stereoisomer, or pharmaceutically acceptable salt of the compound, or a hydrate or solvate thereof, the compound represented by the following general formula (AII):

[Chem. 2]

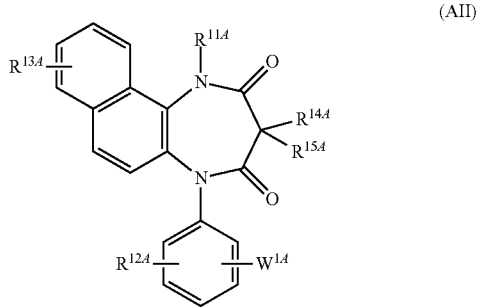

(AII)

wherein $R^{11A}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{12A}$ and $R^{13A}$ are the same or different and represent a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{14A}$ and $R^{15A}$ are the same or different and represent a hydrogen atom, a $C_{1-8}$ alkyl group, a $C_{1-8}$ alkyl group substituted with 1 to 3 halogen atoms, or a phenyl-substituted $C_{1-3}$ alkyl group, and $W^{1A}$ represents an optionally substituted, 5- or 6-membered heterocyclic ring comprising 1 to 4 atoms of nitrogen as a ring constituent element.

Examples of the $C_{1-8}$ alkyl group of $R^{1A}$, $R^{2A}$, $R^{3A}$, $R^{4A}$, and $R^{5A}$ or $R^{11A}$, $R^{12A}$, $R^{13A}$, $R^{14A}$, and $R^{15A}$ in general formula (AI) or (AII) include a methyl, ethyl, propyl, isopropyl, butyl, i-butyl, t-butyl, pentyl or hexyl group.

Examples of the $C_{2-8}$ alkenyl group of $R^{1A}$ or $R^{11A}$ include an allyl group.

Examples of the $C_{1-8}$ alkyl group substituted with 1 to 3 halogen atoms in $R^{1A}$, $R^{2A}$, $R^{3A}$, $R^{4A}$, and $R^{5A}$ or $R^{11A}$, $R^{12A}$, $R^{13A}$, $R^{14A}$, and $R^{15A}$ include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the phenyl-substituted $C_{1-3}$ alkyl group of $R^{1A}$, $R^{4A}$, and $R^{5A}$ or $R^{11A}$, $R^{14A}$, and $R^{15A}$ include a benzyl group.

Examples of the $C_{1-8}$ alkoxy group of $R^{2A}$ and $R^{3A}$ or $R^{12A}$ and $R^{13A}$ include a methoxy, ethoxy, propoxy, isopropoxy, butoxy, i-butoxy, t-butoxy, pentyloxy, or hexyloxy group.

Examples of the $C_{1-8}$ alkoxy group substituted with 1 to 3 halogen atoms in $R^{2A}$ and $R^{3A}$ or $R^{12A}$ and $R^{13A}$ include a methyl, ethyl, propyl, isopropyl, butyl, or t-butyl group substituted with 1 to 3 halogen atoms such as fluorine, chlorine, or bromine atoms, and preferably a trifluoromethoxy, 2-chloroethoxy, 2-bromoethoxy, or 2-fluoroethoxy group.

Examples of the halogen atom of $R^{2A}$ and $R^{3A}$ or $R^{12A}$ and $R^{13A}$ include a fluorine, chlorine, or bromine atom.

Examples of the $C_{1-8}$ alkylamino group of $R^{2A}$ and $R^{3A}$ or $R^{12A}$ and $R^{13A}$ include a methylamino or ethylamino group.

Examples of the $C_{1-8}$ dialkylamino group of $R^{2A}$ and $R^{3A}$ or $R^{12A}$ and $R^{13A}$ include a dimethylamino group or a diethylamino group.

Examples of the $C_{2-8}$ acylamino group of $R^{2A}$ and $R^{3A}$ or $R^{12A}$ and $R^{13A}$ include an acetylamino group.

Examples of the $C_{2-8}$ acylamino group substituted with 1 to 3 halogen atoms in $R^{2A}$ and $R^{3A}$ or $R^{12A}$ and $R^{13A}$ include a trifluoromethylcarbonylamino group.

Examples of the $C_{1-8}$ alkylsulfonylamino group of $R^{2A}$ and $R^{3A}$ or $R^{12A}$ and $R^{13A}$ include a methylsulfonylamino group.

Examples of the $C_{2-8}$ acyl group of $R^{2A}$ and $R^{3A}$ or $R^{12A}$ and $R^{13A}$ include an acetyl group.

Examples of the alkoxycarbonyl group (the number of carbon atoms in an alkoxy moiety is from 1 to 8) of $R^{2A}$ and $R^{3A}$ or $R^{12A}$ and $R^{13A}$ include a methoxycarbonyl group or an ethoxycarbonyl group.

Examples of the $C_{1-8}$ alkylthio group of $R^{2A}$ and $R^{3A}$ or $R^{12A}$ and $R^{13A}$ include a methylthio group.

Examples of the $C_{1-8}$ alkylsulfinyl group of $R^{2A}$ and $R^{3A}$ or $R^{12A}$ and $R^{13A}$ include a methylsulfinyl group.

Examples of the $C_{1-8}$ alkylsulfonyl group of $R^{2A}$ and $R^{3A}$ or $R^{12A}$ and $R^{13A}$ include a methylsulfonyl group.

Examples of the optionally substituted, 5- or 6-membered heterocyclic ring comprising 1 to 4 atoms of nitrogen as a ring constituent element in $W^A$ or $W^{1A}$ include tetrazole, 1,2,4-triazole, 1,2,3-triazole, 1,2,4-oxadiazole, pyrazole, imidazole, oxazole, isoxazole, pyrrole, thiazole, pyridine, or pyrrolidine.

Examples of a substituent of the optionally substituted, 5- or 6-membered heterocyclic ring comprising 1 to 4 atoms of nitrogen as a ring constituent element in $W^A$ or $W^{1A}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, a cyano group, an oxo group, or a thioxo group.

In general formula (AI), 1 to 3 $R^{2A}$ or $R^{3A}$ substituents, which are the same or different, may be present, in a benzene ring having the $R^{2A}$ or $R^{3A}$ substituents. Likewise, in general formula (AII), 1 to 3 $R^{12A}$ and $R^{13A}$ substituents, which are the same or different, may be present, in a benzene ring having the $R^{12A}$ or $R^{13A}$ substituents.

The following compounds are preferable as compounds represented by general formula (AI).

(A-1-1) A compound described in (A-1), wherein $W^A$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(A-1-2) A compound described in (A-1) or (A-1-1), wherein $W^A$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(A-1-3) A compound described in (A-1) or any of (A-1-1) to (A-1-2), wherein $W^A$ is 5-oxo-1,2,4-oxadiazole or 5-thioxo-1,2,4-oxadiazole.

(A-1-4) A compound described in (A-1) or any of (A-1-1) to (A-1-3), wherein $W^A$ is tetrazole.

(A-1-5) A compound described in (A-1) or any of (A-1-1) to (A-1-4), wherein $R^{1A}$ is a hydrogen atom or a $C_{1-8}$ alkyl group.

(A-1-6) A compound described in (A-1) or any of (A-1-1) to (A-1-5), wherein $R^{1A}$ is a hydrogen atom.

(A-1-7) A compound described in (A-1) or any of (A-1-1) to (A-1-6), wherein $R^{4A}$ is a hydrogen atom and $R^{5A}$ is a hydrogen atom or a $C_{1-8}$ alkyl group.

(A-1-8) A compound described in (A-1) or any of (A-1-1) to (A-1-7), wherein both $R^{4A}$ and $R^{5A}$ are a hydrogen atom.

(A-1-9) A compound described in (A-1) or any of (A-1-1) to (A-1-8), wherein $R^{2A}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a carboxyl group, a $C_{2-8}$ acyl group, or an alkoxycarbonyl group (the number of carbon atoms in an alkoxy moiety is from 1 to 8).

(A-1-10) A compound described in (A-1) or any of (A-1-1) to (A-1-9), wherein $R^{2A}$ is a hydrogen atom.

(A-1-11) A compound described in (A-1) or any of (A-1-1) to (A-1-10), wherein $R^{3A}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a carboxyl group, a $C_{2-8}$ acyl group, or an alkoxycarbonyl group (the number of carbon atoms in an alkoxy moiety is from 1 to 8).

(A-1-12) A compound described in (A-1) or any of (A-1-1) to (A-1-11), wherein $R^{3A}$ is a hydrogen atom.

(A-1-13) A compound described in (A-1) or any of (A-1-1) to (A-1-12), wherein $X^A$ is N, $Y^A$ is C=O, and the double line composed of a solid line and a dashed line denotes a single bond.

(A-1-14) A compound described in (A-1) or any of (A-1-1) to (A-1-12), wherein $X^A$ is C, $Y^A$ is N, and the double line composed of a solid line and a dashed line denotes a double bond.

The following compounds are preferable as compounds represented by general formula (AII).

(A-2-1) A compound described in (A-2), wherein $W^A$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(A-2-2) A compound described in (A-2) or (A-2-1), wherein $W^A$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(A-2-3) A compound described in (A-2) or any of (A-2-1) to (A-2-2), wherein $W^A$ is 5-oxo-1,2,4-oxadiazole or 5-thioxo-1,2,4-oxadiazole.

(A-2-4) A compound described in (A-1) or any of (A-2-1) to (A-2-3), wherein $W^A$ is tetrazole.

(A-2-5) A compound described in (A-1) or any of (A-2-1) to (A-2-4), wherein $R^{1A}$ is a hydrogen atom or a $C_{1-8}$ alkyl group.

(A-2-6) A compound described in (A-1) or any of (A-2-1) to (A-2-5), wherein $R^{1A}$ is a hydrogen atom.

(A-2-7) A compound described in (A-1) or any of (A-2-1) to (A-2-6), wherein $R^{4A}$ is a hydrogen atom and $R^{5A}$ is a hydrogen atom or a $C_{1-8}$ alkyl group.

(A-2-8) A compound described in (A-1) or any of (A-2-1) to (A-2-7), wherein both $R^{4A}$ and $R^{5A}$ are a hydrogen atom.

(A-2-9) A compound described in (A-1) or any of (A-2-1) to (A-2-8), wherein $R^{2A}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a carboxyl group, a $C_{2-8}$ acyl group, or an alkoxycarbonyl group (the number of carbon atoms in an alkoxy moiety is from 1 to 8).

(A-2-10) A compound described in (A-1) or any of (A-2-1) to (A-2-9), wherein $R^{2A}$ is a hydrogen atom.

(A-2-11) A compound described in (A-1) or any of (A-2-1) to (A-2-10), wherein $R^{3A}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a carboxyl group, a $C_{2-8}$ acyl group, or an alkoxycarbonyl group (the number of carbon atoms in an alkoxy moiety is from 1 to 8).

(A-2-12) A compound described in (A-1) or any of (A-2-1) to (A-2-11), wherein $R^{3A}$ is a hydrogen atom.

The following shows representative compounds included in general formula (AI).

<Representative Compound A-100>

[Chem. 3]

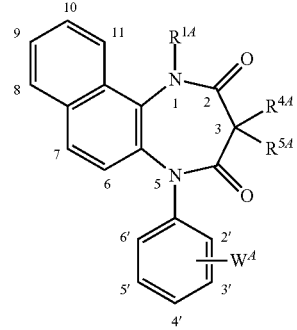

wherein $R^{1A}$, $R^{4A}$, $R^{5A}$, and $W^A$, and $W^A$ substitution positions are as described in Tables 1 to 3.

In Tables 1 to 3, each $W^A$ substitution position indicates a substitution position on a benzene ring. Specifically, positions 2, 3, and 4 in the tables correspond to positions 2', 3', and 4', respectively, in the formula of representative compound A-100.

TABLE 1

| $R^{1A}$ | $W^A$ SUBSTITUTION POSITION | $W^A$ | $R^{4A}/R^{5A}$ |
|---|---|---|---|
| H | 2- | 1H-Tetrazol-5-yl | H/H |
| H | 3- | 1H-Tetrazol-5-yl | H/H |
| H | 3- | (1-Methyl-1H-tetrazol)-5-yl | H/H |
| H | 4- | 1H-Tetrazol-5-yl | H/H |
| Me | 3- | 1H-Tetrazol-5-yl | H/H |
| Me | 3- | 1H-Tetrazol-5-yl | Me/H |
| Bn | 3- | 1H-Tetrazol-5-yl | H/H |
| H | 3- | 1H-Tetrazol-5-yl | H/H |
| H | 3- | 1H-Tetrazol-5-yl | Me/Me |
| H | 3- | (1,2,3-Triazol)-5-yl | H/H |
| H | 3- | (1,2,4-Triazol)-3-yl | H/H |
| H | 4- | (1,2,4-Triazol)-3-yl | H/H |

TABLE 2

| $R^{1A}$ | $W^A$ SUBSTITUTION POSITION | $W^A$ | $R^{4A}/R^{5A}$ |
|---|---|---|---|
| H | 2- | (1,2,4-Triazol)-1-yl | H/H |
| H | 3- | (1,2,4-Triazol)-1-yl | H/H |
| H | 3- | [5-(Trifluoromethyl)-1,2,4-triazol]-3-yl | H/H |
| H | 3- | [5-(Trifluoromethyl)-1,2,4-triazol]-3-yl | Et/H |
| H | 3- | [5-Fluoro-1,2,3-triazol]-4-yl | H/H |
| H | 3- | [5-Fluoro-1,2,3-triazol]-4-yl | Me/Me |
| H | 3- | [5-Cyano-1,2,3-triazol]-4-yl | H/H |
| H | 4- | 1H-Imidazol-1-yl | H/H |
| H | 4- | 1H-Imidazol-1-yl | Pr/H |
| H | 3- | 1H-Imidazol-2-yl | H/H |
| H | 3- | 1H-Imidazol-4-yl | H/H |
| H | 3- | Imidazolin-2-yl | H/H |

TABLE 3

| $R^{1A}$ | $W^A$ SUBSTITUTION POSITION | $W^A$ | $R^{4A}/R^{5A}$ |
|---|---|---|---|
| H | 2- | Pyrazol-3-yl | H/H |
| H | 3- | Pyrazol-4-yl | H/H |
| H | 3- | Pyrazol-5-yl | Me/H |
| H | 3- | (1,2,4-Oxadiazol)-3-yl | H/H |
| H | 3- | (1,3,4-Oxadiazol)-2-yl | H/H |
| H | 3- | (5-Oxo-1,2,4-oxadiazol)-3-yl | H/H |
| H | 3- | Pyrrol-1-yl | H/H |
| H | 4- | Pyrrolidin-2-yl | H/H |
| Me | 4- | Pyrrolidin-2-yl | Me/H |
| H | 4- | (1,3-Oxazol)-5-yl | H/H |
| H | 3- | (1,3-Oxazol)-5-yl | H/H |
| H | 2- | (1,3-Thiazol)-5-yl | H/H |

<Representative Compound A-200>

[Chem. 4]

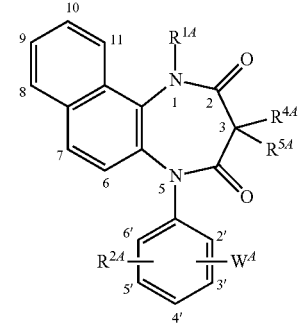

wherein $R^{1A}$, $R^{2A}$, $R^{4A}$, $R^{5A}$, and $W^A$, and $W^A$ substitution positions are as described in Tables 4 and 5.

In tables 4 and 5, each $W^A$ substitution position indicates a substitution position on a benzene ring. Specifically, positions 2, 3, and 4 in the tables correspond to positions 2', 3', and 4', respectively, in the formula of representative compound A-200.

TABLE 4

| $R^{1A}$ | $R^{2A}$ | $W^A$ SUBSTITUTION POSITION | $W^A$ | $R^{4A}/R^{5A}$ |
|---|---|---|---|---|
| H | 4-OH | 3- | 1H-Tetrazol-5-yl | H/H |
| H | 4-OMe | 3- | 1H-Tetrazol-5-yl | H/H |
| Me | 2-Cl | 3- | 1H-Tetrazol-5-yl | H/H |
| H | 2,6-Cl | 3- | 1H-Tetrazol-5-yl | H/H |
| H | 4-F | 3- | 1H-Tetrazol-5-yl | H/H |
| H | 4-Br | 3- | 1H-Tetrazol-5-yl | Et/H |
| H | 3-OMe | 4- | (1-Methyl-1H-tetrazol)-5-yl | H/H |
| H | 4-Me | 3- | 1H-Tetrazol-5-yl | H/H |

TABLE 5

| $R^{1A}$ | $R^{2A}$ | $W^A$ SUBSTITUTION POSITION | $W^A$ | $R^{4A}/R^{5A}$ |
|---|---|---|---|---|
| H | 4-Cl | 3- | (1,2,3-Triazol)-5-yl | Me/H |
| H | 4-CF$_3$ | 3- | (1,2,3-Triazol)-5-yl | H/H |
| H | 3-SMe | 4- | (1,2,4-Triazol)-1-yl | H/H |
| H | 3-SO$_2$Me | 4- | 1H-Imidazol-1-yl | H/H |
| H | 3-NHSO$_2$Me | 4- | 1H-Imidazol-1-yl | H/H |
| H | 4-OMe | 3- | 1H-Imidazol-4-yl | H/H |
| H | 4-F | 2- | Pyrazol-3-yl | H/H |

13

<Representative Compound A-300>

[Chem. 5]

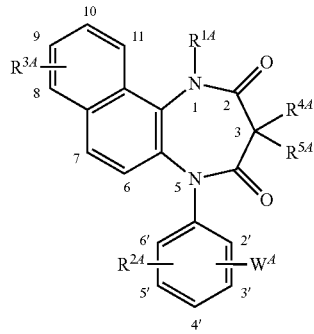

wherein $R^{1A}$, $R^{2A}$, $R^{3A}$, $R^{4A}$, $R^{5A}$, and $W^A$, and $W^A$ substitution positions are as described in Tables 6 and 7.

In Tables 6 and 7, each $W^A$ substitution position indicates a substitution position on a benzene ring. Specifically, positions 3 and 4 in the tables correspond to positions 3' and 4', respectively, in the formula of representative compound A-300.

TABLE 6

| $R^{1A}$ | $R^{2A}$ | $W^A$ SUBSTITUTION POSITION | $W^A$ | $R^{3A}$ | $R^{4A}/R^{5A}$ |
|---|---|---|---|---|---|
| H | H | 3- | 1H-Tetrazol-5-yl | 9-Br | H/H |
| H | 4-OMe | 3- | 1H-Tetrazol-5-yl | 9-Cl | H/H |
| H | 4-OH | 3- | 1H-Tetrazol-5-yl | 10-OMe | H/H |
| H | 2-Cl | 3- | 1H-Tetrazol-5-yl | 9-Br | H/H |
| H | 2,6-Cl | 3- | 1H-Tetrazol-5-yl | 9-Me | H/H |
| H | H | 3- | 1H-Tetrazol-5-yl | 10-Cl | Me/H |
| H | 3-OMe | 4- | (1-Methyl-1H-tetrazole)-5-yl | 9-GF$_3$ | H/H |

TABLE 7

| $R^{1A}$ | $R^{2A}$ | $W^A$ SUBSTITUTION POSITION | $W^A$ | $R^{3A}$ | $R^{4A}/R^{5A}$ |
|---|---|---|---|---|---|
| H | 4-Me | 3- | 1H-Tetrazol-1-yl | 9-CN | Pr/H |
| Me | H | 3- | (1,2,3-Triazole)-5-yl | 9-OH | H/H |
| Et | H | 3- | (1,2,3-Triazole)-5-yl | 10-F | H/H |
| H | 3-Br | 4- | (1,2,4-Triazole)-1-yl | 9-SMe | H/H |
| Allyl | H | 4- | 1H-Imidazol-1-yl | 8-OMe | H/H |
| H | H | 3- | 1H-Imidazol-1-yl | 10-OMe | Me/Me |

14

<Representative Compound A-400>

[Chem. 6]

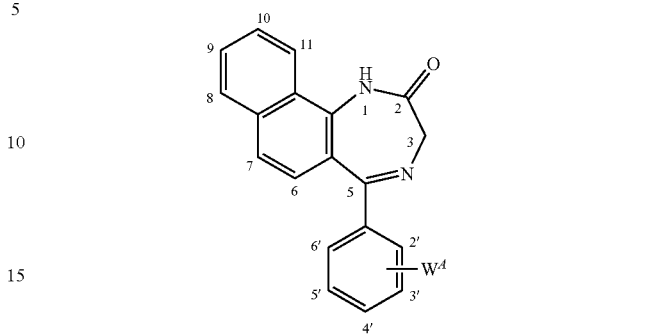

wherein $W^A$ and $W^A$ substitution positions are as described in Table 8.

In Table 8, each $W^A$ substitution position indicates a substitution position on a benzene ring. Specifically, positions 3 and 4 in the table correspond to positions 3' and 4', respectively, in the formula of representative compound A-400.

TABLE 8

| $W^A$ SUBSTITUTION POSITION | $W^A$ |
|---|---|
| 3- | 1H-Tetrazol-5-yl |
| 4- | 1H-Tetrazol-5-yl |
| 3- | 5-Thioxo-1,2,4-oxadiazol-3-yl |

(B-1) A compound, a tautomer, stereoisomer, or pharmaceutically acceptable salt of the compound, or a hydrate or solvate thereof, the compound represented by the following general formula (BI):

[Chem. 7]

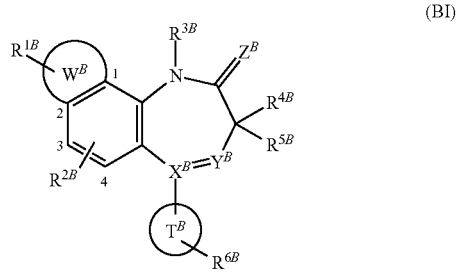

(BI)

wherein $R^{1B}$ and $R^{2B}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{3B}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{4B}$ and $R^{5B}$ are the same or different and represent a hydrogen atom, a $C_{1-8}$ alkyl group, a $C_{1-8}$ alkyl group substituted with 1 to 3 halogen atoms, a halogen atom, a hydroxyl group, a nitro group, a cyano group, an amino group, or a phenyl-substituted $C_{1-3}$ alkyl group, $R^{6B}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group,

[Chem. 8]

optionally contains, as ring constituent elements, 1 to 2 heteroatoms selected from N, S, or O and represents a 5- to 8-membered non-aromatic ring condensed with a benzene ring at positions 1 and 2,

[Chem. 9]

represents an aromatic ring selected from a benzene ring, a naphthalene ring, a thiophene ring, a pyridine ring, a pyrimidine ring, an indole ring, an indazole ring, a benzotriazole ring, a benzisoxazole ring, a benzimidazole ring, or a quinoline ring, $Z^B$ represents O or S, and when $X^B$ is N, $Y^B$ is C=O or C=S and a double line composed of a solid line and a dashed line denotes a single bond and when $X^B$ is C, $Y^B$ is N and a double line composed of a solid line and a dashed line denotes a double bond.

(B-2) A compound, a tautomer, stereoisomer, or pharmaceutically acceptable salt of the compound, or a hydrate or solvate thereof, the compound represented by the following general formula (BII):

[Chem. 10]

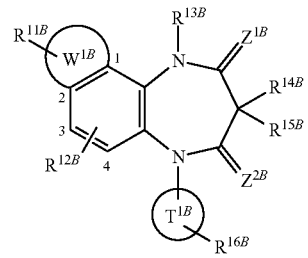

(BII)

wherein $R^{11B}$ and $R^{12B}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{13B}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{14B}$ and $R^{15B}$ are the same or different and represent a hydrogen atom, a $C_{1-8}$ alkyl group, a $C_{1-8}$ alkyl group substituted with 1 to 3 halogen atoms, a halogen atom, a hydroxyl group, a nitro group, a cyano group, an amino group, or a phenyl-substituted $C_{1-3}$ alkyl group, $R^{16B}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group,

[Chem. 11]

optionally contains, as ring constituent elements, 1 to 2 heteroatoms selected from N, S, or O and represents a 5- to 8-membered non-aromatic ring condensed with a benzene ring at positions 1 and 2,

[Chem. 12]

represents an aromatic ring selected from a benzene ring, a naphthalene ring, a thiophene ring, a pyridine ring, a pyrimidine ring, an indole ring, an indazole ring, a benzotriazole ring, a benzisoxazole ring, a benzimidazole ring, or a quinoline ring, and $Z^{1B}$ and $Z^{2B}$ are the same or different and represent O or S.

(B-3) A compound, a tautomer, stereoisomer, or pharmaceutically acceptable salt of the compound, or a hydrate or solvate thereof, the compound represented by the following general formula (BIII):

[Chem. 13]

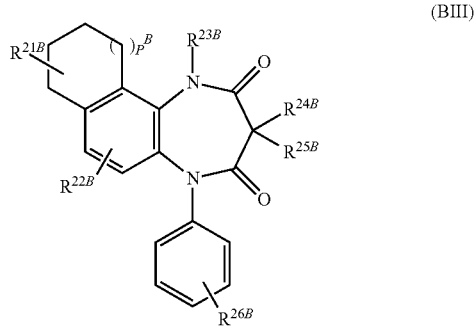

(BIII)

wherein $R^{21B}$ and $R^{22B}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{23B}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{Z-3}$ alkyl group, $R^{24B}$ and $R^{25B}$ are the same or different and represent a hydrogen atom, a $C_{1-8}$ alkyl group, a $C_{1-8}$ alkyl group substituted with 1 to 3 halogen atoms, a halogen atom, a hydroxyl group, a nitro group, a cyano group, an amino group, or a phenyl-substituted $C_{1-3}$ alkyl group, $R^{26B}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group, and $p^B$ is 0 or 1.

Examples of the $C_{1-8}$ alkyl group of $R^{1B}$, $R^{2B}$, $R^{3B}$, $R^{4B}$, $R^{5B}$, or $R^{6B}$ in general formula (BI) include a methyl, ethyl, propyl, isopropyl, butyl, i-butyl, t-butyl, pentyl, or hexyl group.

Examples of the $C_{2-8}$ alkenyl group of $R^{1B}$, $R^{2B}$, $R^{3B}$, or $R^{6B}$ include an allyl group.

Examples of the $C_{1-8}$ alkyl group substituted with 1 to 3 halogen atoms in $R^{1B}$, $R^{2B}$, $R^{3B}$, $R^{4B}$, $R^{5B}$, or $R^{6B}$ include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the phenyl-substituted $C_{1-3}$ alkyl group of $R^{3B}$, $R^{4B}$, or $R^{5B}$ include a benzyl group.

Examples of the $C_{1-8}$ alkoxy group of $R^{1B}$, $R^{2B}$, or $R^{6B}$ include a methoxy, ethoxy, propoxy, isopropoxy, butoxy, i-butoxy, t-butoxy, pentyloxy, or hexyloxy group.

Examples of the $C_{1-8}$ alkoxy group substituted with 1 to 3 halogen atoms in $R^{1B}$, $R^{2B}$, or $R^{6B}$ include a methoxy, ethoxy, propoxy, isopropoxy, butoxy, or t-butoxy group substituted with 1 to 3 halogen atoms such as fluorine, chlorine, or bromine atoms, and preferably a trifluoromethoxy, chloromethoxy, 2-chloroethoxy, 2-bromoethoxy, or 2-fluoroethoxy group.

Examples of the halogen atom of $R^{1B}$, $R^{2B}$, $R^{4B}$, $R^{5B}$, or $R^{6B}$ include a fluorine, chlorine, or bromine atom.

Examples of the $C_{1-8}$ alkylamino group of $R^{1B}$, $R^{2B}$, or $R^{6B}$ include a methylamino or ethylamino group.

Examples of the $C_{2-8}$ dialkylamino group of $R^{1B}$, $R^{2B}$, or $R^{6B}$ include a dimethylamino or diethylamino group.

Examples of the $C_{2-8}$ acylamino group of $R^{1B}$, $R^{2B}$, or $R^{6B}$ include an acetylamino group.

Examples of the $C_{2-8}$ acylamino group substituted with 1 to 3 halogen atoms in $R^{1B}$, $R^{2B}$, or $R^{6B}$ include a trifluoromethylcarbonylamino group.

Examples of the $C_{1-8}$ alkylsulfonylamino group of $R^{1B}$, $R^{2B}$, or $R^{6B}$ include a methylsulfonylamino group.

Examples of the $C_{2-8}$ acyl group of $R^{1B}$, $R^{2B}$, or $R^{6B}$ include an acetyl group.

Examples of the alkoxycarbonyl group (the number of carbon atoms in an alkoxy moiety is from 1 to 8) of $R^{1B}$, $R^{2B}$, or $R^{6B}$ include a methoxycarbonyl group or an ethoxycarbonyl group.

Examples of the $C_{1-8}$ alkylthio group of $R^{1B}$, $R^{2B}$, or $R^{6B}$ include a methylthio group.

Examples of the $C_{1-8}$ alkylsulfinyl group of $R^{1B}$, $R^{2B}$, or $R^{6B}$ include a methylsulfinyl groups.

Examples of the $C_{1-8}$ alkylsulfonyl group of $R^{1B}$, $R^{2B}$, or $R^{6B}$ include a methylsulfonyl group.

Examples of a preferable substituent of the optionally substituted phenyl group of $R^{6B}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, or a cyano group.

Examples of a preferable heterocyclic ring group for the optionally substituted heterocyclic ring group of $R^{6B}$ include a tetrazolyl, triazolyl, pyridyl, imidazolyl, oxazolyl or thiazolyl group and further optionally include an oxadiazole group.

Examples of a preferable substituent of the optionally substituted heterocyclic ring group of $R^{6B}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, a cyano group, or oxo and further optionally include a phenyl group.

Examples of

[Chem. 14]

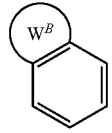

include tetrahydronaphthalene, indane, indoline, tetrahydroquinoline, or tetrahydroisoquinoline.

In general formula (BI), $R^{1B}$, $R^{2B}$, or $R^{6B}$ substituents, which are the same or different, may be present, in a ring having the $R^{1B}$, $R^{2B}$, or $R^{6B}$ substituents.

Regarding the above listed examples, for $R^{1B}$ to $R^{6B}$ in general formula (BI), comprising a $C_{1-8}$ alkyl group, a $C_{2-8}$ alkenyl group, a $C_{1-8}$ alkyl group substituted with 1 to 3 halogen atoms, a phenyl-substituted $C_{2-3}$ alkyl group, a $C_{1-8}$ alkoxy group, a $C_{1-8}$ alkoxy group substituted with 1 to 3 halogen atoms, a halogen atom, a $C_{1-8}$ alkylamino group, a $C_{1-8}$ dialkylamino, a $C_{2-8}$ acylamino group, a $C_{2-8}$ acylamino group substituted with 1 to 3 halogen atoms, a $C_{1-8}$ alkylsulfonylamino group, a $C_{2-8}$ acyl group, an alkoxycarbonyl group (the number of carbon atoms in an alkoxy moiety is from 1 to 8), a $C_{1-8}$ alkylthio group, a $C_{1-8}$ alkylsulfinyl group, a $C_{1-8}$ alkylsulfonyl group, an optionally substituted phenyl group, or an optionally substituted heterocyclic ring group, the same applies to $R^{11B}$ to $R^{16B}$ in general formula (BII) and $R^{21B}$ to $R^{26B}$ in general formula (BIII).

Likewise, regarding the optionally substituted heterocyclic ring group of $R^{16B}$ in general formula (BII) or $R^{26B}$ in general formula (BIII), examples of the substituent include a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a $C_{1-8}$ alkylamino group, and a $C_{2-8}$ dialkylamino group, examples of which are included in those listed for $R^{1B}$ to $R^{6B}$ in general formula (BI).

Examples of

[Chem. 15]

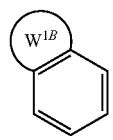

include tetrahydronaphthalene, indane, indoline, tetrahydroquinoline, or tetrahydroisoquinoline.

In general formula (BII), $R^{11B}$, $R^{12B}$, or $R^{16B}$ substituents, which are the same or different, may be present, in a benzene ring having the $R^{11B}$, $R^{12B}$, or $R^{16B}$ substituents.

In general formula (BIII), $R^{21B}$, $R^{22B}$, or $R^{26B}$ substituents, which are the same or different, may be present in a benzene ring having the $R^{21B}$, $R^{22B}$, or $R^{26B}$ substituents.

The following compounds are preferable as compounds included in general formula (BI).

(B-1-1) A compound described in (B-1), wherein $R^{1B}$ is a hydrogen atom, a $C_{1-8}$ alkyl group, a $C_{2-8}$ alkenyl group, a $C_{1-8}$ alkyl group substituted with 1 to 3 halogen atoms, a halogen atom, a hydroxyl group, an amino group, a $C_{1-8}$ alkylamino group, a $C_{2-8}$ dialkylamino group, or a $C_{2-8}$ acylamino group.

(B-1-2) A compound described in (B-1) or (B-1-1), wherein $R^{2B}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, or a $C_{2-8}$ acylamino group substituted with 1 to 3 halogen atoms.

(B-1-3) A compound described in (B-1) or any of (B-1-1) or (B-1-2), wherein $R^{3B}$ is a hydrogen atom, a $C_{1-8}$ alkyl group, or a $C_{1-8}$ alkyl group substituted with 1 to 3 halogen atoms.

(B-1-4) A compound described in (B-1) or any of (B-1-1) to (B-1-3), wherein $R^{4B}$ and $R^{5B}$ are the same or different and are a hydrogen atom, a $C_{1-8}$ alkyl group, or a $C_{1-8}$ alkyl group substituted with 1 to 3 halogen atoms.

(B-1-5) A compound described in (B-1) or any of (B-1-1) to (B-1-4), wherein $R^{6B}$ is a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, or an optionally substituted heterocyclic ring group.

(B-1-6) A compound described in (B-1) or any of (B-1-1) to (B-1-5), wherein $R^{6B}$ is a 5- or 6-membered heterocyclic ring comprising 1 to 4 atoms of nitrogen as a ring constituent element.

(B-1-7) A compound described in (B-1) or any of (B-1-1) to (B-1-6), wherein $R^{6B}$ is a tetrazolyl, triazolyl, pyridyl, pyrazolyl, oxadiazolyl, isoxazolyl, pyrrolyl, pyrrolidinyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(B-1-8) A compound described in (B-1) or any of (B-1-1) to (B-1-7), wherein $R^{6B}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a cyano group, or an amino group.

(B-1-9) A compound described in (B-1) or any of (B-1-1) to (B-1-8), wherein $R^{6B}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(B-1-10) A compound described in (B-1) or any of (B-1-1) to (B-1-9), wherein $R^{6B}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(B-1-11) A compound described in (B-1) or any of (B-1-1) to (B-1-9), wherein $R^{6B}$ is 5-oxo-1,2,4-oxadiazole or 5-thioxo-1,2,4-oxadiazole.

(B-1-12) A compound described in (B-1) or any of (B-1-1) to (B-1-11), wherein $R^{6B}$ is tetrazole.

(B-1-13)
A compound described in (B-1) or any of (B-1-1) to (B-1-12), wherein

[Chem. 16]

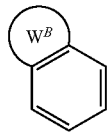

is tetrahydronaphthalene, indane, indoline, tetrahydroquinoline, or tetrahydroisoquinoline.

(B-1-14)
A compound described in (B-1) or any of (B-1-1) to (B-1-13), wherein

[Chem. 17]

is a benzene ring.

(B-1-15) A compound described in (B-1) or any of (B-1-1) to (B-1-14), wherein $X^B$ is N, $Y^B$ is C=O, and the double line composed of a solid line and a dashed line denotes a single bond.

(B-1-16) A compound described in (B-1) or any of (B-1-1) to (B-1-14), wherein $X^B$ is C, $Y^B$ is N, and the double line composed of a solid line and a dashed line denotes a double bond.

(B-1-17) A compound described in (B-1) or any of (B-1-1) to (B-1-16), wherein $Z^B$ is O.

The following compounds are preferable as compounds included in general formula (BII).

(B-2-1) A compound described in (B-2), wherein $R^{11B}$ is a hydrogen atom, a $C_{1-8}$ alkyl group, a $C_{2-8}$ alkenyl group, a $C_{1-8}$ alkyl group substituted with 1 to 3 halogen atoms, a halogen atom, a hydroxyl group, an amino group, a $C_{1-8}$ alkylamino group, a $C_{2-8}$ dialkylamino group, or a $C_{2-8}$ acylamino group.

(B-2-2) A compound described in (B-2) or (B-2-1), wherein $R^{12B}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, or a $C_{2-8}$ acylamino group substituted with 1 to 3 halogen atoms.

(B-2-3) A compound described in (B-2) or any of (B-2-1) or (B-2-2), wherein $R^{13B}$ is a hydrogen atom, a $C_{1-8}$ alkyl group, or a $C_{1-8}$ alkyl group substituted with 1 to 3 halogen atoms.

(B-2-4) A compound described in (B-2) or any of (B-2-1) to (B-2-3), wherein $R^{14B}$ and $R^{15B}$ are the same or different and are a hydrogen atom, a $C_{1-8}$ alkyl group, or a $C_{1-8}$ alkyl group substituted with 1 to 3 halogen atoms.

(B-2-5) A compound described in (B-2) or any of (B-2-1) to (B-2-4), wherein $R^{16B}$ is a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, or an optionally substituted heterocyclic ring group.

(B-2-6) A compound described in (B-2) or any of (B-2-1) to (B-2-5), wherein $R^{16B}$ is a 5- or 6-membered heterocyclic ring comprising 1 to 4 atoms of nitrogen as a ring constituent element.

(B-2-7) A compound described in (B-2) or any of (B-2-1) to (B-2-6), wherein $R^{16B}$ is a tetrazolyl, triazolyl, pyridyl, pyrazolyl, oxadiazolyl, isoxazolyl, pyrrolyl, pyrrolidinyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(B-2-8) A compound described in (B-2) or any of (B-2-1) to (B-2-7), wherein $R^{16B}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a cyano group, or an amino group.

(B-2-9) A compound described in (B-2) or any of (B-2-1) to (B-2-8), wherein $R^{16B}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(B-2-10) A compound described in (B-2) or any of (B-2-1) to (B-2-9), wherein $R^{16B}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(B-2-11) A compound described in (B-2) or any of (B-2-1) to (B-2-9), wherein $R^{16B}$ is 5-oxo-1,2,4-oxadiazole or 5-thioxo-1,2,4-oxadiazole.

(B-2-12) A compound described in (B-2) or any of (B-2-1) to (B-2-11), wherein $R^{16B}$ is tetrazole.

(B-2-13)
A compound described in (B-2) or any of (B-2-1) to (B-2-12), wherein

[Chem. 18]

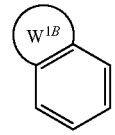

is tetrahydronaphthalene, indane, indoline, tetrahydroquinoline, or tetrahydroisoquinoline.

(B-2-14)
A compound described in (B-2) or any of (B-2-1) to (B-2-13), wherein

[Chem. 19]

is a benzene ring.

(B-2-15) A compound described in (B-2) or any of (B-2-1) to (B-2-14), wherein both $Z^{1B}$ and $Z^{2B}$ are O.

The following compounds are preferable as compounds represented by general formula (BIII).

(B-3-1) A compound described in (B-3), wherein $R^{21B}$ is a hydrogen atom, a $C_{1-8}$ alkyl group, a $C_{2-8}$ alkenyl group, a $C_{1-8}$ alkyl group substituted with 1 to 3 halogen atoms, a halogen atom, a hydroxyl group, an amino group, a $C_{1-8}$ alkylamino group, a $C_{2-8}$ dialkylamino group, or a $C_{2-8}$ acylamino group.

(B-3-2) A compound described in (B-3) or (B-3-1), wherein $R^{22B}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, or a $C_{2-8}$ acylamino group substituted with 1 to 3 halogen atoms.

(B-3-3) A compound described in (B-3) or any of (B-3-1) or (B-3-2), wherein $R^{23B}$ is a hydrogen atom, a $C_{1-8}$ alkyl group, or a $C_{1-8}$ alkyl group substituted with 1 to 3 halogen atoms.

(B-3-4) A compound described in (B-3) or any of (B-3-1) to (B-3-3), wherein $R^{24B}$ and $R^{25B}$ are the same or different and are a hydrogen atom, a $C_{1-8}$ alkyl group, or a $C_{1-8}$ alkyl group substituted with 1 to 3 halogen atoms.

(B-3-5) A compound described in (B-3) or any of (B-3-1) to (B-3-4), wherein $R^{26B}$ is a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, or an optionally substituted heterocyclic ring group.

(B-3-6) A compound described in (B-3) or any of (B-3-1) to (B-3-5), wherein $R^{26B}$ is a 5- or 6-membered heterocyclic ring comprising 1 to 4 atoms of nitrogen as a ring constituent element.

(B-3-7) A compound described in (B-3) or any of (B-3-1) to (B-3-6), wherein $R^{26B}$ is a tetrazolyl, triazolyl, pyridyl, pyrazolyl, oxadiazolyl, isoxazolyl, pyrrolyl, pyrrolidinyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(B-3-8) A compound described in (B-3) or any of (B-3-1) to (B-3-7), wherein $R^{26B}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a cyano group, or an amino group.

(B-3-9) A compound described in (B-3) or any of (B-3-1) to (B-3-8), wherein $R^{26B}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(B-3-10) A compound described in (B-3) or any of (B-3-1) to (B-3-9), wherein $R^{26B}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(B-3-11) A compound described in (B-3) or any of (B-3-1) to (B-3-10), wherein $R^{26B}$ is 5-oxo-1,2,4-oxadiazole or 5-thioxo-1,2,4-oxadiazole.

(B-3-12) A compound described in (B-3) or any of (B-3-1) to (B-3-11), wherein $R^{26B}$ is tetrazole.

Note that $R^{3B}$ in general formula (BI), $R^{13B}$ in general formula (BII), or $R^{23B}$ in general formula (BIII) may be a $C_{2-8}$ acyl group such as acetyl.

In addition, $R^{6B}$ in general formula (BI), $R^{16B}$ in general formula (BII), or $R^{26B}$ in general formula (BIII) may be a $C_{3-8}$ alkoxycarbonylamino group such as a tert-butoxycarbonylamino group.

Further,

[Chem. 20]

in general formula (BI)
or

[Chem. 21]

in general formula (BII)
may be 2,3-dihydrobenzo[1,4]dioxin.

The following shows representative compounds included in general formula (BI).

<Representative Compound B-100>

[Chem. 22]

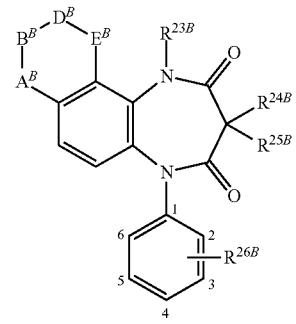

wherein $A^B$-$B^B$-$D^B$-$E^B$, $R^{23B}$, $R^{24B}$, $R^{25B}$, and $R^{26B}$ are as described in Tables 9 to 11.

TABLE 9

| $A^B$-$B^B$-$D^B$-$E^B$ | $R^{23B}$ | $R^{24B}/R^{25B}$ | $R^{26B}$ |
|---|---|---|---|
| CH$_2$CH$_2$CH$_2$CH$_2$ | H | H/H | 3-CN |
| CH$_2$CH$_2$CH$_2$CH$_2$ | H | H/H | 3-OH |
| CH$_2$CH$_2$CH$_2$CH$_2$ | H | H/H | 3-CO$_2$H |
| CH$_2$CH$_2$CH$_2$CH$_2$ | H | H/H | 3-CONH$_2$ |
| C(CH$_3$)$_2$CH$_2$CH$_2$CH$_2$ | H | H/H | 3,4-OMe |
| CH$_2$C(CH$_3$)$_2$CH$_2$CH$_2$ | Me | H/H | 3,4-OMe |
| CH$_2$CH$_2$C(CH$_3$)$_2$CH$_2$ | Et | H/H | 3-OH, 4-F |
| CH$_2$CH$_2$CH$_2$CH$_2$ | H | H/H | 3-NH$_2$ |
| NHCH$_2$CH$_2$CH$_2$ | H | H/H | 3-NHMe |

TABLE 9-continued

| $A^B$-$B^B$-$D^B$-$E^B$ | $R^{23B}$ | $R^{24B}/R^{25B}$ | $R^{26B}$ |
|---|---|---|---|
| NMeCH$_2$CH$_2$CH$_2$ | H | H/H | 3-CF$_3$ |
| OCH$_2$CH$_2$O | H | H/H | 3-NHCH$_2$CF$_3$ |
| OCH$_2$CH$_2$O | Me | H/H | 2-OH, 3-OH |
| C(CH$_3$)$_2$CH$_2$CH$_2$C(CH$_3$)$_2$ | Et | H/H | 3,4,5-Me |

TABLE 10

| $A^B$-$B^B$-$D^B$-$E^B$ | $R^{23B}$ | $R^{24B}/R^{25B}$ | $R^{26B}$ |
|---|---|---|---|
| CH$_2$CH$_2$CH$_2$CH$_2$ | H | Me/H | 4-OH |
| CH$_2$CH$_2$CH$_2$CH$_2$ | H | Me/Me | 4-NH$_2$ |
| CH$_2$CH$_2$CH$_2$CH$_2$ | H | Pr/H | 4-NO$_2$ |
| C(CH$_3$)$_2$CH$_2$CH$_2$CH$_2$ | H | H/H | 4-CN |
| CH$_2$C(CH$_3$)$_2$CH$_2$CH$_2$ | Me | CF$_3$/H | 4-Ph |
| CH$_2$CH$_2$C(CH$_3$)$_2$CH$_2$ | Et | H/H | 4-CH$_2$OH |
| CH$_2$CH$_2$CH$_2$CH$_2$ | H | H/H | 3-CH$_2$OH |
| NHCH$_2$CH$_2$CH$_2$ | H | H/H | 3-Ac |
| NMeCH$_2$CH$_2$CH$_2$ | H | H/H | 3,5-OMe |
| OCH$_2$CH$_2$O | H | H/H | 3-OH, 4-NH$_2$ |
| OCH$_2$CH$_2$O | Me | H/H | 3-CH$_2$NH$_2$ |
| C(CH$_3$)$_2$CH$_2$CH$_2$C(CH$_3$)$_2$ | Et | H/H | 3-SO$_2$CH$_3$ |
| CH$_2$CH$_2$CH$_2$CH$_2$ | H | Me/H | 3-iPr |
| CH$_2$CH$_2$CH$_2$CH$_2$ | H | Me/H | 3-NMe$_2$ |

TABLE 11

| $A^B$-$B^B$-$D^B$-$E^B$ | $R^{23B}$ | $R^{24B}/R^{25B}$ | $R^{26B}$ |
|---|---|---|---|
| CH$_2$CH$_2$CH$_2$CH$_2$ | H | Me/H | 3-Ac |
| C(CH$_3$)$_2$CH$_2$CH$_2$CH$_2$ | H | Pr/H | 3,4-NH$_2$ |
| CH$_2$C(CH$_3$)$_2$CH$_2$CH$_2$ | H | H/H | NHMe |
| CH$_2$CH$_2$C(CH$_3$)$_2$CH$_2$ | Et | H/H | 3-NHCH$_2$CF$_3$ |
| CH$_2$CH$_2$CH$_2$CH$_2$ | H | H/H | 3-NHAc |
| NHCH$_2$CH$_2$CH$_2$ | H | H/H | 3-SO$_2$Me |
| NMeCH$_2$CH$_2$CH$_2$ | H | H/H | 4-Me |
| OCH$_2$CH$_2$O | H | H/H | 4-iPr |
| OCH$_2$CH$_2$O | Me | H/H | 3-Ph |
| C(CH$_3$)$_2$CH$_2$CH$_2$C(CH$_3$)$_2$ | Et | H/H | 3-F, 4-OH |
| CH$_2$CH$_2$CH$_2$CH$_2$ | Ac | H/H | 3-F, 4-OMe |
| CH$_2$CH$_2$CH$_2$CH$_2$ | H | Me/H | 4-NHEt |

<Representative Compound B-200>

[Chem. 23]

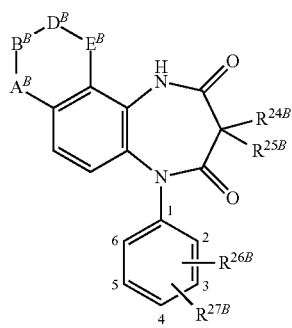

TABLE 12

| $A^B$-$B^B$-$D^B$-$E^B$ | $R^{24B}/R^{25B}$ | Position | $R^{26B}$ | $R^{27B}$ |
|---|---|---|---|---|
| CH$_2$CH$_2$CH$_2$CH$_2$ | H/H | 3 | 1H-Tetrazol-5-yl | H |
| C(CH$_3$)$_2$CH$_2$CH$_2$CH$_2$ | H/H | 3 | 1H-Tetrazol-5-yl | H |
| C(CH$_3$)$_2$CH$_2$CH$_2$CH$_2$ | H/H | 3 | 1H-Tetrazol-1-yl | 4-F |
| C(CH$_3$)$_2$CH$_2$CH$_2$C(CH$_3$)$_2$ | H/H | 3 | 2-Methyl-2H-tetrazol-5-yl | 3-F |
| CH$_2$CH$_2$C(CH$_3$)$_2$CH$_2$ | H/H | 3 | 1,2,3-Triazol-5-yl | 2-F |
| CH$_2$CH$_2$CH$_2$CH$_2$ | H/H | 3 | 1,2,4-Triazol-3-yl | H |
| NHCH$_2$CH$_2$CH$_2$ | H/H | 3 | 5-(Trifluoromethyl)-1,2,4-triazol-3-yl | H |
| NMeCH$_2$CH$_2$CH$_2$ | H/H | 4 | 1H-Imidazol-1-yl | H |
| OCH$_2$CH$_2$O | H/H | 4 | 1H-Imidazol-2-yl | H |
| OCH$_2$CH$_2$O | H/H | 3 | 5-Cyano-1H-1,2,3-triazol-4-yl | H |
| C(CH$_3$)$_2$CH$_2$CH$_2$C(CH$_3$)$_2$ | H/H | 3 | 1-Methyl-1H-tetrazol-5-yl | H |
| CH$_2$CH$_2$CH$_2$CH$_2$ | Me/H | 3 | Pyrazol-3-yl | 4-OH |
| CH$_2$CH$_2$CH$_2$CH$_2$ | Me/Me | 3 | Pyrazol-4-yl | H |

TABLE 13

| $A^B$-$B^B$-$D^B$-$E^B$ | $R^{24B}/R^{25B}$ | Position | $R^{26B}$ | $R^{27B}$ |
|---|---|---|---|---|
| C(CH$_3$)$_2$CH$_2$CH$_2$CH$_2$ | H/H | 3 | 5-Oxo-1,2,4-oxadiazol-3-yl | 4-NH$_2$ |
| CH$_2$C(CH$_3$)$_2$CH$_2$CH$_2$ | CF$_3$/H | 3 | 1,2,4-Oxadiazol-3-yl | H |
| CH$_2$CH$_2$C(CH$_3$)$_2$CH$_2$ | H/H | 3 | 1,3,4-Oxadiazol-2-yl | 4-F |
| CH$_2$CH$_2$CH$_2$CH$_2$ | H/H | 4 | Pyrrol-1-yl | 3-F |
| NHCH$_2$CH$_2$CH$_2$ | H/H | 4 | Pyrrolidin-2-yl | H |
| NMeCH$_2$CH$_2$CH$_2$ | H/H | 2 | 1,3-Oxazol-5-yl | H |
| OCH$_2$CH$_2$O | H/H | 3 | 1,3-Thiazol-5-yl | H |
| OCH$_2$CH$_2$O | H/H | 3 | 5-(Trifluoromethyl)-1H-imidazol-2-yl | H |
| C(CH$_3$)$_2$CH$_2$CH$_2$C(CH$_3$)$_2$ | H/H | 3 | 5-Chloro-1H-imidazol-2-yl | 4-OH |

TABLE 14

| $A^B$-$B^B$-$D^B$-$E^B$ | $R^{24B}/R^{25B}$ | Position | $R^{26B}$ | $R^{27B}$ |
|---|---|---|---|---|
| CH$_2$CH$_2$CH$_2$CH$_2$ | Me/H | 4 | 5-Methyl-1H-imidazol-2-yl | 4-NH$_2$ |
| CH$_2$CH$_2$CH$_2$CH$_2$ | Me/H | 4 | 5-Amino-1H-imidazol-2-yl | 3-F |
| CH$_2$CH$_2$CH$_2$CH$_2$ | Me/H | 3 | 2-Ethyl-2H-tetrazol-5-yl | H |
| C(CH$_3$)$_2$CH$_2$CH$_2$CH$_2$ | Pr/H | 3 | 2-(2,2,2-Trifluoroethyl)-2H-tetrazol-5-yl | 2,6-F |
| CH$_2$C(CH$_3$)$_2$CH$_2$CH$_2$ | H/H | 3 | 1,3-Oxazol-2-yl | H |
| CH$_2$CH$_2$C(CH$_3$)$_2$CH$_2$ | H/H | 3 | 1,3-Thiazol-2-yl | H |
| CH$_2$CH$_2$CH$_2$CH$_2$ | H/H | 4 | 3,5-Dimethylisoxazol-4-yl | H |
| NH$_2$CH$_2$CH$_2$NH | H/H | 3 | 3-Methyl-1,2,4-oxadiazol-5-yl | H |

<Representative Compound B-300>

[Chem. 24]

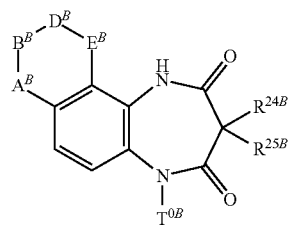

wherein $A^B$-$B^B$-$D^B$-$E^B$, $R^{24B}$, $R^{25B}$, $R^{26B}$, and $R^{27B}$ are as described in Tables 12 to 14; and the "Position" in the tables indicates a $R^{26B}$ substitution position.

wherein $A^B$-$B^B$-$D^B$-$E^B$, $R^{24B}$, $R^{25B}$, and $T^{OB}$ are as described in Tables 15 to 17.

TABLE 15

| $A^B$-$B^B$-$D^B$-$E^B$ | $R^{24B}/R^{25B}$ | $T^{OB}$ |
|---|---|---|
| CH₂CH₂CH₂CH₂ | H/H | Pyrimidin-2-yl |
| C(CH₃)₂CH₂CH₂CH₂ | H/H | Pyrimidin-5-yl |
| CH₂C(CH₃)₂CH₂CH₂ | H/H | Pyridin-2-yl |
| CH₂CH₂C(CH₃)₂CH₂ | H/H | Pyridin-3-yl |
| CH₂CH₂CH₂CH₂ | H/H | Pyridin-4-yl |
| NHCH₂CH₂ | Me/H | Thiophen-2-yl |
| NMeCH₂CH₂ | H/H | Thiophen-3-yl |
| OCH₂CH₂ | H/H | Thiophen-3-yl |
| OCH₂O | H/H | 5-Hydroxypyridin-3-yl |
| C(CH₃)₂CH₂CH₂C(CH₃)₂ | H/H | 5-Methoxypyridin-3-yl |
| CH₂CH₂CH₂CH₂ | F/H | 5-Aminopyridin-3-yl |
| CH₂CH₂CH₂CH₂ | Me/Me | 5-Chloropyridin-3-yl |
| CH₂CH₂CH₂CH₂ | Pr/H | 6-Chloropyridin-3-yl |

TABLE 16

| $A^B$-$B^B$-$D^B$-$E^B$ | $R^{24B}/R^{25B}$ | $T^{OB}$ |
|---|---|---|
| CH₂CH₂CH₂CH₂ | Pr/H | 6-Chloropyridin-3-yl |
| CH₂CH₂CH₂CH₂ | H/H | 1H-Indazol-6-yl |
| C(CH₃)₂CH₂CH₂CH₂ | H/H | 1H-Indazol-5-yl |
| CH₂C(CH₃)₂CH₂CH₂ | H/H | 1H-Indazol-4-yl |
| CH₂C(CH₃)₂CH₂CH₂ | H/H | 1H-Benzotriazol-6-yl |
| C(CH₃)₂CH₂CH₂CH₂ | H/H | 1H-Benzotriazol-4-yl |
| CH₂CH₂CH₂CH₂ | H/H | 1H-Benzimidazol-6-yl |
| CH₂C(CH₃)₂CH₂CH₂ | H/H | 1H-Indazol-4-yl |
| CH₂C(CH₃)₂CH₂CH₂ | H/H | 1H-Indol-6-yl |
| C(CH₃)₂CH₂CH₂CH₂ | H/H | 1H-Indol-5-yl |
| C(CH₃)₂CH₂CH₂CH₂ | H/H | 1H-Indol-4-yl |
| CH₂C(CH₃)₂CH₂CH₂ | H/H | Benzisoxazol-6-yl |
| C(CH₃)₂CH₂CH₂CH₂ | H/H | 1H-Benzimidazol-5-yl |

TABLE 17

| $A^B$-$B^B$-$D^B$-$E^B$ | $R^{24B}/R^{25B}$ | $T^{OB}$ |
|---|---|---|
| C(CH₃)₂CH₂CH₂CH₂ | H/H | 1H-Benzimidazol-6-yl |
| CH₂C(CH₃)₂CH₂CH₂ | H/H | 2-(Trifluoromethyl)-1H-benzimidazol-5-yl |
| CH₂CH₂CH₂CH₂ | H/H | Quinolin-5-yl |
| C(CH₃)₂CH₂CH₂CH₂ | H/H | Quinolin-8-yl |

<Representative Compound B-400>

[Chem. 25]

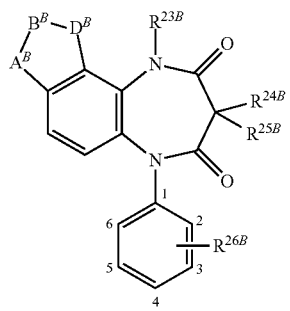

TABLE 18

| $A^B$-$E^B$-$D^B$ | $R^{23B}$ | $R^{24B}/R^{25B}$ | $R^{26B}$ |
|---|---|---|---|
| CH₂CH₂CH₂ | H | H/H | 3-CN |
| CH₂CH₂CH₂ | H | H/H | 3-OH |
| CH₂CH₂CH₂ | H | H/H | 3-CO₂H |
| CH₂CH₂CH₂ | H | H/H | 3-CONH₂ |
| OCH₂O | H | H/H | 3,4-OMe |
| OCH₂O | Me | H/H | 3,4-OMe |
| OCH₂O | Et | H/H | 3-OH, 4-F |
| OCH₂O | H | H/H | 3-NH₂ |
| CH₂CH₂CH₂ | H | H/H | 3-NHMe |
| CH₂CH₂CH₂ | H | H/H | 3-CF₃ |
| CH₂CH₂CH₂ | H | H/H | 3-NHCH₂CF₃ |
| CH₂CH₂CH₂ | Me | H/H | 2-OH, 3-OH |
| OCH₂O | Et | H/H | 3,4,5-Me |

TABLE 19

| $A^B$-$B^B$-$D^B$ | $R^{23B}$ | $R^{24B}/R^{25B}$ | $R^{26B}$ |
|---|---|---|---|
| OCH₂O | H | Me/H | 4-OH |
| OCH₂O | H | Me/Me | 4-NH₂ |
| OCH₂O | H | Pr/H | 4-NO₂ |
| CH₂CH₂CH₂ | H | H/H | 4-CN |
| CH₂CH₂CH₂ | Me | CF₃/H | 4-Ph |
| CH₂CH₂CH₂ | Et | H/H | 4-CH₂OH |
| OCH₂O | H | H/H | 3-CH₂OH |
| CH₂CH₂CH₂ | H | H/H | 3-Ac |
| CH₂CH₂CH₂ | H | H/H | 3,5-OMe |
| CH₂CH₂CH₂ | H | H/H | 3-OH, 4-NH₂ |
| OCH₂O | Me | H/H | 3-CH₂NH₂ |
| CH₂CH₂CH₂ | Et | H/H | 3-SO₂CH₃ |
| CH₂CH₂CH₂ | H | Me/H | 3-iPr |
| CH₂CH₂CH₂ | H | Me/H | 3-NMe₂ |
| OCH₂O | H | Me/H | 3-Ac |
| CH₂CH₂CH₂ | H | Pr/H | 3,4-NH₂ |

TABLE 20

| $A^B$-$B^B$-$D^B$ | $R^{23B}$ | $R^{24B}/R^{25B}$ | $R^{26B}$ |
|---|---|---|---|
| CH₂CH₂CH₂ | H | H/H | NHMe |
| CH₂CH₂CH₂ | Et | H/H | 3-NHCH₂CF₃ |
| OCH₂O | H | H/H | 3-NHAc |
| CH₂CH₂CH₂ | H | H/H | 3-SO₂Me |
| CH₂CH₂CH₂ | H | H/H | 4-Me |
| CH₂CH₂CH₂ | H | H/H | 4-iPr |
| OCH₂O | Me | H/H | 3-Ph |
| CH₂CH₂CH₂ | Et | H/H | 3-F, 4-OH |
| CH₂CH₂CH₂ | Ac | H/H | 3-F, 4-OMe |

<Representative Compound B-500>

[Chem. 26]

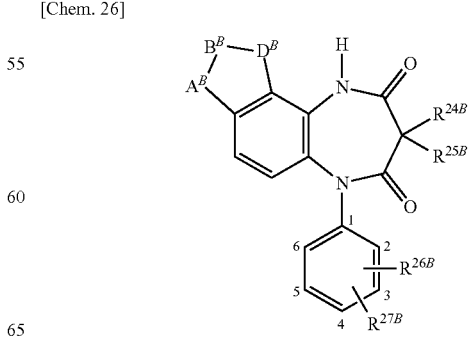

wherein $A^B$-$B^B$-$D^B$, $R^{23B}$, $R^{24B}$, $R^{25B}$, and $R^{26B}$ are as described in Tables 18 to 20.

wherein $A^B$-$B^B$-$D^B$, $R^{24B}$, $R^{25B}$, $R^{26B}$, and $R^{27B}$ are as described in Tables 21 to 23; and the "Position" in the tables indicates a $R^{26B}$ substitution position.

TABLE 21

| $A^B$-$B^B$-$D^B$ | $R^{24B}/R^{25B}$ | Position | $R^{26B}$ | $R^{27B}$ |
|---|---|---|---|---|
| CH₂CH₂CH₂ | H/H | 3 | 1H-Tetrazol-5-yl | H |
| CH₂CH₂CH₂ | H/H | 4 | 1H-Tetrazol-5-yl | H |
| CH₂CH₂CH₂ | H/H | 3 | 1H-Tetrazol-1-yl | 4-F |
| CH₂CH₂CH₂ | H/H | 3 | 2-Methyl-2H-tetrazol-5-yl | H |
| OCH₂O | H/H | 3 | 1,2,3-Triazol-5-yl | 2-F |
| OCH₂O | H/H | 3 | 1,2,4-Triazol-3-yl | H |
| OCH₂O | H/H | 3 | 5-(Trifluoromethyl)-1,2,4-triazol-3-yl | H |
| OCH₂O | H/H | 4 | 1H-Imidazol-1-yl | H |
| CH₂CH₂CH₂ | H/H | 4 | 1H-Imidazol-2-yl | H |
| CH₂CH₂CH₂ | H/H | 3 | 5-Cyano-1H-1,2,3-triazol-4-yl | H |
| CH₂CH₂CH₂ | H/H | 3 | 1-Methyl-1H-tetrazol-5-yl | H |
| CH₂CH₂CH₂ | Me/H | 3 | Pyrazol-3-yl | 4-OH |

TABLE 22

| $A^B$-$B^B$-$D^B$ | $R^{24B}/R^{25B}$ | Position | $R^{26B}$ | $R^{27B}$ |
|---|---|---|---|---|
| OCH₂O | Me/Me | 3 | Pyrazol-4-yl | H |
| OCH₂O | H/H | 3 | 5-Oxo-1,2,4-oxadiazol-3-yl | 4-NH₂ |
| OCH₂O | CF₃/H | 3 | 1,2,4-Oxadiazol-3-yl | H |
| CH₂CH₂CH₂ | H/H | 3 | 1,3,4-Oxadiazol-2-yl | 4-F |
| CH₂CH₂CH₂ | H/H | 4 | Pyrrol-1-yl | 3-F |
| CH₂CH₂CH₂ | H/H | 4 | Pyrrolidin-2-yl | H |
| OCH₂O | H/H | 2 | 1,3-Oxazol-5-yl | H |
| CH₂CH₂CH₂ | H/H | 3 | 1,3-Thiazol-5-yl | H |
| CH₂CH₂CH₂ | H/H | 3 | 5-(Trifluoromethyl)-1H-imidazol-2-yl | H |
| CH₂CH₂CH₂ | H/H | 3 | 5-Chloro-1H-imidazol-2-yl | 4-OH |
| OCH₂O | Me/H | 4 | 5-Methyl-1H-imidazol-2-yl | 4-NH₂ |
| CH₂CH₂CH₂ | Me/H | 4 | 5-Amino-1H-imidazol-2-yl | 3-F |

TABLE 23

| $A^B$-$B^B$-$D^B$ | $R^{24B}/R^{25B}$ | Position | $R^{26B}$ | $R^{27B}$ |
|---|---|---|---|---|
| CH₂CH₂CH₂ | Me/H | 3 | 2-Ethyl-2H-tetrazol-5-yl | H |
| CH₂CH₂CH₂ | Pr/H | 3 | 2-(2,2,2-Trifluoroethyl)-2H-tetrazol-5-yl | 2,6-F |
| OCH₂O | H/H | 3 | 1,3-Oxazol-2-yl | H |
| CH₂CH₂CH₂ | H/H | 3 | 1,3-Thiazol-2-yl | H |
| CH₂CH₂CH₂ | H/H | 4 | 3,5-Dimethylisoxazol-4-yl | H |
| CH₂CH₂CH₂ | H/H | 3 | 3-Methyl-1,2,4-oxadiazol-5-yl | H |

<Representative Compound B-600>

[Chem. 27]

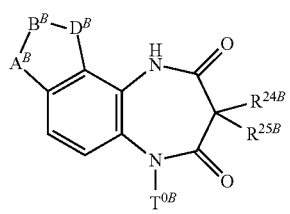

wherein $A^B$-$B^B$-$D^B$, $R^{24B}$, $R^{25B}$, and $T^{OB}$ are as described in Tables 24 to 26.

TABLE 24

| $A^B$-$B^B$-$D^B$ | $R^{24B}/R^{25B}$ | $T^{OB}$ |
|---|---|---|
| CH₂CH₂CH₂ | H/H | Pyrimidin-2-yl |
| CH₂CH₂CH₂ | H/H | Pyrimidin-5-yl |
| CH₂CH₂CH₂ | H/H | Pyridin-2-yl |
| CH₂CH₂CH₂ | H/H | Quinolin-2-yl |
| CH₂CH₂CH₂ | H/H | Quinolin-3-yl |
| CH₂CH₂CH₂ | H/H | Pyridin-3-yl |
| OCH₂O | H/H | Pyridin-4-yl |
| OCH₂O | Me/H | Thiophen-2-yl |
| OCH₂O | H/H | Thiophen-3-yl |
| OCH₂O | H/H | Thiophen-3-yl |
| CH₂CH₂CH₂ | H/H | 5-Hydroxypyridin-3-yl |
| CH₂CH₂CH₂ | H/H | 5-Methoxypyridin-3-yl |
| NHCH₂CH₂ | F/H | 5-Aminopyridin-3-yl |

TABLE 25

| $A^B$-$B^B$-$D^B$ | $R^{24B}/R^{25B}$ | $T^{OB}$ |
|---|---|---|
| CH₂CH₂CH₂ | Me/Me | 5-Chloropyridin-3-yl |
| OCH₂O | Pr/H | 6-Chloropyridin-3-yl |
| OCH₂O | Pr/H | 6-Chloropyridin-3-yl |
| OCH₂O | H/H | 1H-Indazol-6-yl |
| OCH₂O | H/H | 1H-Indazol-5-yl |
| CH₂CH₂CH₂ | H/H | 1H-Indazol-4-yl |
| CH₂CH₂CH₂ | H/H | 1H-Benzotriazol-6-yl |
| CH₂CH₂CH₂ | H/H | 1H-Benzotriazol-4-yl |
| OCH₂O | H/H | 1H-Benzimidazol-6-yl |
| CH₂CH₂CH₂ | H/H | 1H-Indazol-4-yl |
| CH₂CH₂CH₂ | H/H | 1H-Indol-6-yl |

TABLE 26

| $A^B$-$B^B$-$D^B$ | $R^{24B}/R^{25B}$ | $T^{OB}$ |
|---|---|---|
| NHCH₂CH₂ | H/H | 1H-Indol-5-yl |
| OCH₂O | H/H | 1H-Indol-4-yl |
| CH₂CH₂CH₂ | H/H | Benzisoxazol-6-yl |
| CH₂CH₂CH₂ | H/H | 1H-Benzimidazol-5-yl |
| CH₂CH₂CH₂ | H/H | 1H-Benzimidazol-6-yl |
| OCH₂O | H/H | 2-Trifluoromethyl-1H-benzimidazol-5-yl |
| CH₂CH₂CH₂ | H/H | Quinolin-5-yl |
| CH₂CH₂CH₂ | H/H | Quinolin-8-yl |

(C-1) A compound, a tautomer, stereoisomer, or pharmaceutically acceptable salt of the compound, or a hydrate or solvate thereof, the compound represented by the following general formula (CI):

[Chem. 28]

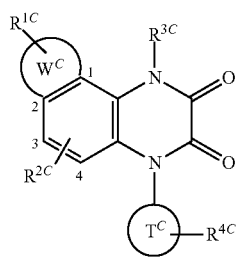

(CI)

wherein $R^{1C}$ and $R^{2C}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{3C}$ represents a hydrogen atom, a $C_{1-8}$ alkyl group, a $C_{2-8}$ alkenyl group, a $C_{1-8}$ alkyl group substituted with 1 to 3 halogen atoms, or an aralkyl group (the number of carbon atoms in an aryl moiety is from 6 to 10 and the number of carbon atoms in an alkylene moiety is from 1 to 3), $R^{4C}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a hydroxyl-substituted $C_{1-8}$ alkyl group, a halogen atom, a hydroxyl group, a nitro group, a cyano group, an amino group, a $C_{1-8}$ alkylamino group, a $C_{1-5}$ alkylamino group substituted with 1 to 5 halogen atoms, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, an optionally substituted benzenesulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group,

[Chem. 29]

is condensed with a benzene ring at positions 1 and 2 and represents a 5- to 8-membered ring optionally comprising, as a ring constituent element, a heteroatom selected from N, S, or O, and

[Chem. 30]

represents an aromatic ring selected from a benzene ring, a naphthalene ring, a pyridine ring, a pyrimidine ring, a quinoline ring, an indole ring, an indoline ring, a benzimidazole ring, an indazole ring, a benzisoxazole ring, or a benztriazole ring.

(C-2) A compound, a tautomer, stereoisomer, or pharmaceutically acceptable salt of the compound, or a hydrate or solvate thereof, the compound represented by the following general formula (CII):

[Chem. 31]

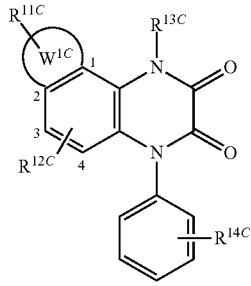

(CII)

wherein $R^{11C}$ and $R^{12C}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{13C}$ represents a hydrogen atom, a $C_{1-8}$ alkyl group, a $C_{2-8}$ alkenyl group, a $C_{1-8}$ alkyl group substituted with 1 to 3 halogen atoms, or an aralkyl group (the number of carbon atoms in an aryl moiety is from 6 to 10 and the number of carbon atoms in an alkylene moiety is from 1 to 3), $R^{14C}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a hydroxyl-substituted $C_{1-8}$ alkyl group, a halogen atom, a hydroxyl group, a nitro group, a cyano group, an amino group, a $C_{1-8}$ alkylamino group, a $C_{1-5}$ alkylamino group substituted with 1 to 5 halogen atoms, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, an optionally substituted benzenesulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group, and

[Chem. 32]

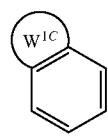

represents a naphthalene ring, a tetrahydronaphthalene ring, or an indane ring.

Examples of the $C_{1-8}$ alkyl group of $R^{1C}$, $R^{2C}$, $R^{3C}$, or $R^{4C}$ in general formula (CI) include a methyl, ethyl, propyl, isopropyl, butyl, i-butyl, t-butyl, pentyl, or hexyl group.

Examples of the $C_{2-8}$ alkenyl group of $R^{1C}$, $R^{2C}$, $R^{3C}$, or $R^{4C}$ include an allyl group.

Examples of the $C_{1-8}$ alkyl group substituted with 1 to 3 halogen atoms in $R^{1C}$, $R^{2C}$, $R^{3C}$, or $R^{4C}$ include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the aralkyl group (the number of carbon atoms in an aryl moiety is from 6 to 10 and the number of carbon atoms in an alkylene moiety is from 1 to 3) of $R^{1C}$, $R^{2C}$, $R^{3C}$, or $R^{4C}$ include a benzyl group.

Examples of the $C_{1-8}$ alkoxy group of $R^{1C}$, $R^{2C}$, or $R^{4C}$ include a methoxy, ethoxy, propoxy, isopropoxy, butoxy, i-butoxy, t-butoxy, pentyloxy, or hexyloxy group.

Examples of the $C_{1-8}$ alkoxy group substituted with 1 to 3 halogen atoms in $R^{1C}$, $R^{2C}$, or $R^{4C}$ include a methoxy, ethoxy, propoxy, isopropoxy, butoxy, or t-butoxy group substituted with 1 to 3 halogen atoms such as fluorine, chlorine, or bromine atoms, and preferably a trifluoromethoxy, chloromethoxy, 2-chloroethoxy, 2-bromoethoxy, or 2-fluoroethoxy group.

Examples of the halogen atom of $R^{1C}$, $R^{2C}$, or $R^{4C}$ include a fluorine, chlorine, or bromine atom.

Examples of the $C_{1-8}$ alkylamino group of $R^{1C}$, $R^{2C}$, or $R^{4C}$ include a methylamino or ethylamino group.

Examples of the $C_{1-5}$ alkylamino group substituted with 1 to 5 halogen atoms in $R^{4C}$ include a 2,2,2-trifluoroethylamino group.

Examples of the $C_{2-8}$ dialkylamino group of $R^{1C}$, $R^{2C}$, or $R^{4C}$ include a dimethylamino or diethylamino group.

Examples of the $C_{2-8}$ acylamino group of $R^{1C}$, $R^{2C}$, or $R^{4C}$ include an acetylamino group. Examples include a benzoylamino group further optionally having a substituent (e.g., a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen).

Examples of the $C_{2-8}$ acylamino group substituted with 1 to 3 halogen atoms in $R^{1C}$, $R^{2C}$, or $R^{4C}$ include a trifluoromethylcarbonylamino group.

Examples of the $C_{1-8}$ alkylsulfonylamino group of $R^{1C}$, $R^{2C}$, or $R^{4C}$ include a methylsulfonylamino group.

Examples of the $C_{2-8}$ acyl group of $R^{1C}$, $R^{2C}$, or $R^{4C}$ include an acetyl group.

Examples of the alkoxycarbonyl group (the number of carbon atoms in an alkoxy moiety is from 1 to 8) of $R^{1C}$, $R^{2C}$, or $R^{4C}$ include a methoxycarbonyl group or an ethoxycarbonyl group.

Examples of the $C_{1-8}$ alkylthio group of $R^{1C}$, $R^{2C}$, or $R^{4C}$ include a methylthio group.

Examples of the $C_{1-8}$ alkylsulfinyl group of $R^{1C}$, $R^{2C}$, or $R^{4C}$ include a methylsulfinyl group.

Examples of the $C_{1-8}$ alkylsulfonyl group of $R^{1C}$, $R^{2C}$, or $R^{4C}$ include a methylsulfonyl group.

Examples of the hydroxyl-substituted $C_{1-8}$ alkyl group of $R^{4C}$ include a hydroxymethyl group.

Examples of the optionally substituted benzenesulfonylamino group of $R^{4C}$ include a benzenesulfonylamino group and preferably an o-nitrobenzenesulfonylamino group optionally having a substituent selected from a C1-8 alkyl group (e.g., a methyl group, an ethyl group), a C1-8 alkoxy group (e.g., a methoxy group, an ethoxy group), a halogen atom (e.g., a fluorine atom, a chlorine atom), or a nitro group.

Examples of a preferable substituent of the optionally substituted phenyl group of $R^{4C}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, or a cyano group.

Examples of a preferable heterocyclic ring group in the optionally substituted heterocyclic ring group of $R^{4C}$ include a tetrazolyl, triazolyl, pyridyl, imidazolyl, oxazolyl or thiazolyl group. Examples further include an oxadiazole group.

Examples of a preferable substituent of the optionally substituted heterocyclic ring of $R^{4C}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, a cyano group, or oxo.

Examples of

[Chem. 33]

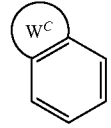

include a naphthalene ring, a tetrahydronaphthalene ring, or an indane ring.

In general formula (CI), $R^{1C}$, $R^{2C}$, or $R^{4C}$ substituents, which are the same or different, may be present, in a ring having the $R^{1C}$, $R^{2C}$, or $R^{4C}$ substituents.

Regarding the above listed examples, for $R^{1C}$, $R^{2C}$, $R^{3C}$, or $R^{4C}$ in general formula (CI), comprising a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a $C_{1-8}$ alkoxy group, a $C_{1-8}$ alkoxy group substituted with 1 to 3 halogen atoms, a halogen atom, an aralkyl group (the number of carbon atoms in an aryl moiety is from 6 to 10 and the number of carbon atoms in an alkylene moiety is from 1 to 3), a hydroxyl-substituted $C_{1-8}$ alkyl group, a halogen atom, a $C_{1-8}$ alkylamino group, a $C_{1-5}$ alkylamino substituted with 1 to 5 halogen atoms, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, an optionally substituted benzenesulfonylamino group, a $C_{2-8}$ acyl group, an alkoxycarbonyl group (the number of carbon atoms in an alkoxy moiety is from 1 to 8), a $C_{1-8}$ alkylthio group, a $C_{1-8}$ alkylsulfinyl group, a $C_{1-8}$ alkylsulfonyl group, an optionally substituted phenyl group, or an optionally substituted heterocyclic ring group, the same applies to $R^{11C}$, $R^{12C}$, $R^{13C}$, or $R^{14C}$ in general formula (CII).

Regarding the optionally substituted heterocyclic ring group of $R^{14C}$ in general formula (CII), examples of the substituent include a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a $C_{1-8}$ alkylamino group, and a $C_{2-8}$ dialkylamino group, examples of which are included in those listed for $R^{1C}$ to $R^{4C}$ in general formula (CI).

Examples of

[Chem. 34]

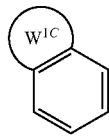

include a naphthalene ring, a tetrahydronaphthalene ring, or an indane ring.

In general formula (CII), $R^{11C}$, $R^{12C}$, or $R^{14C}$ substituents, which are the same or different, may be present, in a benzene ring having the $R^{11C}$, $R^{12C}$, or $R^{14C}$ substituents.

The following compounds are preferable as compounds included in general formula (CI).

(C-1-1) A compound described in (C-1), wherein $R^{1C}$ and $R^{2C}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(C-1-2) A compound described in (C-1) or (C-1-1), wherein $R^{3C}$ is a hydrogen atom or a $C_{1-8}$ alkyl group.

(C-1-3) A compound described in (C-1) or (C-1-1) or (C-1-2), wherein $R^{4C}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl-substituted $C_{1-8}$ alkyl group, a halogen atom, a hydroxyl group, a cyano group, an amino group, a $C_{1-8}$ alkylamino group, a $C_{2-8}$ dialkylamino group, a $C_{1-8}$ alkylsulfonylamino group, an optionally substituted benzenesulfonylamino group, an optionally substituted phenyl group, or an optionally substituted heterocyclic ring group.

(C-1-4) A compound described in (C-1) or any of (C-1-1) to (C-1-3), wherein $R^{4C}$ is a 5- or 6-membered heterocyclic ring comprising 1 to 4 atoms of nitrogen as a ring constituent element.

(C-1-5) A compound described in (C-1) or any of (C-1-1) to (C-1-4), wherein $R^{4C}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(C-1-6) A compound described in (C-1) or any of (C-1-1) to (C-1-5), wherein $R^{4C}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(C-1-7) A compound described in (C-1) or any of (C-1-1) to (C-1-6), wherein $R^{4C}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(C-1-8) A compound described in (C-1) or any of (C-1-1) to (C-1-7), wherein $R^{4C}$ is 5-oxo-1,2,4-oxadiazole or 5-thioxo-1,2,4-oxadiazole.

(C-1-9) A compound described in (C-1) or any of (C-1-1) to (C-1-8), wherein $R^{4C}$ is tetrazole.

(C-1-10) A compound described in (C-1) or any of (C-1-1) to (C-1-9), wherein $R^{4C}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a cyano group, an amino group, a $C_{1-8}$ alkylamino group, a $C_{2-8}$ dialkylamino group, or a benzenesulfonylamino group optionally having a substituent selected from a $C_{1-8}$ alkyl group, a $C_{1-8}$ alkoxy group, a halogen atom, or a nitro group.

(C-1-11)
A compound described in (C-1) or any of (C-1-1) to (C-1-10), wherein

[Chem. 35]

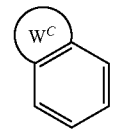

is a naphthalene ring, a tetrahydronaphthalene ring, or an indane ring.

(C-1-12)
A compound described in (C-1) or any of (C-1-1) to (C-1-11), wherein

[Chem. 36]

is a benzene ring or an indole ring.

The following compounds are preferable as compounds included in general formula (CII).

(C-2-1) A compound described in (C-2), wherein $R^{11C}$ and $R^{12C}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(C-2-2) A compound described in (C-2) or (C-2-1), wherein $R^{13C}$ is a hydrogen atom or a $C_{1-8}$ alkyl group.

(C-2-3) A compound described in (C-2) or (C-2-1) or (C-2-2), wherein $R^{14C}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl-substituted $C_{1-8}$ alkyl group, a halogen atom, a hydroxyl group, a cyano group, an amino group, a $C_{1-8}$ alkylamino group, a $C_{2-8}$ dialkylamino group, a $C_{1-8}$ alkylsulfonylamino group, an optionally substituted benzenesulfonylamino group, an optionally substituted phenyl group, or an optionally substituted heterocyclic ring group.

(C-2-4) A compound described in (C-2) or any of (C-2-1) to (C-2-3), wherein $R^{14C}$ is a 5- or 6-membered heterocyclic ring comprising 1 to 4 atoms of nitrogen as a ring constituent element.

(C-2-5) A compound described in (C-2) or any of (C-2-1) to (C-2-4), wherein $R^{14C}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(C-2-6) A compound described in (C-2) or any of (C-2-1) to (C-2-5), wherein $R^{14C}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(C-2-7) A compound described in (C-2) or any of (C-2-1) to (C-2-6), wherein $R^{14C}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(C-2-8) A compound described in (C-2) or any of (C-2-1) to (C-2-7), wherein $R^{14C}$ is 5-oxo-1,2,4-oxadiazole or 5-thioxo-1,2,4-oxadiazole.

(C-2-9) A compound described in (C-2) or any of (C-2-1) to (C-2-8), wherein $R^{14C}$ is tetrazole.

(C-2-10) A compound described in (C-2) or any of (C-2-1) to (C-2-9), wherein $R^{14C}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a cyano group, an amino group, a $C_{1-8}$ alkylamino group, a $C_{2-8}$ dialkylamino group, or a benzenesulfonylamino group optionally having a substituent selected from a $C_{1-8}$ alkyl group, a $C_{1-8}$ alkoxy group, a halogen atom, or a nitro group.

(C-2-11)
A compound described in (C-2) or any of (C-2-1) to (C-2-10), wherein

[Chem. 37]

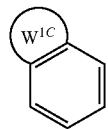

is a naphthalene ring.

Examples further include the following compounds.

(C-2-12) A compound described in (C-2), wherein $R^{11C}$ and $R^{12C}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(C-2-13) A compound described in (C-2) or (C-2-12), wherein $R^{13C}$ is a hydrogen atom or a $C_{1-8}$ alkyl group.

(C-2-14)
A compound described in (C-2) or any of (C-2-12) or (C-2-13), wherein

[Chem. 38]

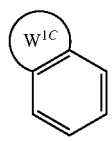

is a naphthalene ring.

(C-2-15) A compound described in (C-2) or any of (C-2-12) to (C-2-14), wherein $R^{14C}$ is $NHSO_2R^C$ (where $R^C$ represents an optionally substituted aryl or heterocyclic ring group).

(C-2-16) A compound described in (C-2-15), wherein $R^C$ is phenyl, naphthyl, quinolyl, pyridyl, or thienyl optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl group, an amino group, a nitro group, nitro, or halogen.

The following shows representative compounds included in general formula (CI).

<Representative Compound C-100>

[Chem. 39]

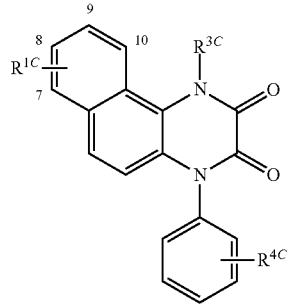

wherein $R^{1C}$, $R^{3C}$, and $R^{4C}$ are as described in Tables 27 to 29.

TABLE 27

| $R^{1C}$ | $R^{3C}$ | $R^{4C}$ |
|---|---|---|
| H | H | 3-OH |
| H | H | 3-OMe |
| H | H | 4-OH |
| H | H | 4-OMe |
| H | H | 2-OH |
| H | H | 2-OMe |
| H | H | 2,3-OH |
| H | H | 3-OH, 4-F |
| H | H | 3,4-OH |
| H | H | 3,4-OMe |
| H | H | 3,4,5-OMe |
| H | H | 3-CN |

TABLE 28

| $R^{1C}$ | $R^{3C}$ | $R^{4C}$ |
|---|---|---|
| H | H | 4-CN |
| H | H | 3-$CO_2H$ |
| H | H | 3-$CO_2Me$ |
| H | H | 3-Br |
| H | H | 3-F |
| H | H | 4-Me |
| H | H | S-$NH_2$ |
| H | H | 3-$NHSO_2Ph$ |
| H | H | 3-$NHSO_2$(2-$NO_2$)Ph |
| H | H | 4-$NHSO_2Ph$ |
| H | Me | 4-$NHSO_2$(2-$NO_2$)Ph |
| H | Et | 3-NHEt |
| H | H | 3-$CH_2OH$ |
| H | H | 4-$CH_2OH$ |

TABLE 29

| $R^{1C}$ | $R^{3C}$ | $R^{4C}$ |
|---|---|---|
| H | H | 3-CF$_3$ |
| H | H | 3-Ph |
| H | H | 3-N(Me)$_2$ |
| H | H | 3,5-OH |
| H | H | 4-OAc |
| H | H | 2-Me |
| 9-Me | H | 3-NH$_2$ |
| 9-Cl | H | 3-NH$_2$ |
| 8-Me | H | 3-NH$_2$ |
| 8-Cl | H | 3-NH$_2$ |

<Representative Compound C-200>

[Chem. 40]

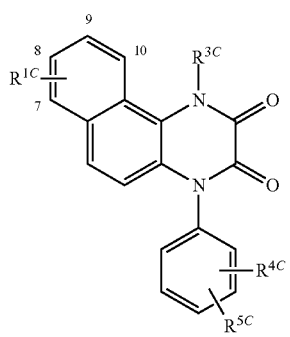

wherein $R^{1C}$, $R^{3C}$, $R^{4C}$, and $R^{5C}$ are as described in Tables 30 to 32; and the "$R^{4C}$ position" in the tables indicates a $R^{4C}$ substitution position.

TABLE 30

| $R^{1C}$ | $R^{3C}$ | $R^{4C}$ Position | $R^{4C}$ | $R^{5C}$ |
|---|---|---|---|---|
| H | H | 3 | 1H-Tetrazol-5-yl | H |
| H | H | 4 | 1H-Tetrazol-5-yl | H |
| 8-Me | H | 3 | 1H-Tetrazol-5-yl | H |
| 8-Cl | H | 3 | 1H-Tetrazol-5-yl | H |
| H | H | 3 | 1H-Tetrazol-5-yl | 4-F |
| H | H | 3 | 1H-Tetrazol-5-yl | 4-Me |
| H | H | 3 | 1H-Tetrazol-5-yl | 5-Br |
| H | H | 3 | 1H-Tetrazol-5-yl | 6-Me |
| H | H | 3 | 1H-Tetrazol-5-yl | 6-Cl |
| H | H | 3 | (5-Thioxo-1,2,4-oxadiazol)-3-yl | H |
| H | H | 3 | (5-Oxo-1,2,4-oxadiazol)-3-yl | H |
| H | H | 3 | (5-Cyano-1H-1,2,3-triazol)-4-yl | H |

TABLE 31

| $R^{1C}$ | $R^{3C}$ | $R^{4C}$ Position | $R^{4C}$ | $R^{5C}$ |
|---|---|---|---|---|
| H | H | 3 | 1H-Tetrazol-5-yl | 6-OH |
| H | H | 3 | (2-Methyl-2H-tetrazol)-5-yl | H |
| H | Me | 3 | (2-Methyl-2H-tetrazol)-5-yl | H |
| H | Et | 3 | (2-Ethyl-2H-tetrazol)-5-yl | H |
| H | H | 3 | (1-Methyl-1H-tetrazol)-5-yl | H |
| H | H | 3 | 4-Methyl-(5-thioxo-1,2,4-oxadiazol)-3-yl | H |
| H | H | 3 | 1-Methyl-1H-imidazol-2-yl | H |
| H | H | 3 | 1-Methyl-1H-imidazol-4-yl | H |
| H | H | 3 | 1,3-Oxazol-2-yl | H |
| H | H | 3 | 1,3-Thiazol-2-yl | H |
| H | H | 3 | Pyrrol-2-yl | H |
| H | H | 3 | Thiophen-2-yl | H |

TABLE 31-continued

| $R^{1C}$ | $R^{3C}$ | $R^{4C}$ Position | $R^{4C}$ | $R^{5C}$ |
|---|---|---|---|---|
| H | H | 3 | 1-H-Imidazol-2-yl | H |
| H | H | 3 | 1-H-Imidazol-4-yl | H |

TABLE 32

| $R^{1C}$ | $R^{3C}$ | $R^{4C}$ Position | $R^{4C}$ | $R^{5C}$ |
|---|---|---|---|---|
| H | H | 3 | Pyrazol-4-yl | H |
| H | H | 3 | 5-(Chloro)-1H-imidazol-2-yl | H |
| H | H | 3 | 5-(Trifluoromethyl)-1H-imidazol-2-yl | H |
| H | H | 3 | (1,2,3-Triazol)-4-yl | H |
| H | H | 3 | (1,2,3-Triazol)-3-yl | H |
| H | H | 3 | 3-Methyl-(1,2,4-oxadiazol)-5-yl | H |
| H | H | 3 | 3,5-Dimethylisoxazol-4-yl | H |
| H | H | 3 | 1-Tetrazol-1-yl | H |
| H | H | 3 | Phenyl | H |
| H | H | 3 | Pyridin-3-yl | H |
| H | H | 3 | Pyrimidin-5-yl | H |
| H | H | 3 | 2-Aminopyridin-5-yl | H |

<Representative Compound C-300>

[Chem. 41]

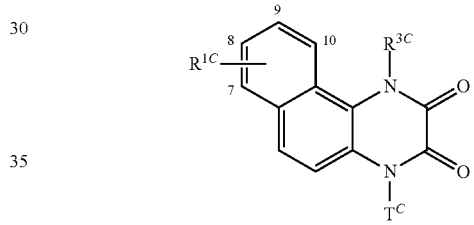

wherein $R^{1C}$, $R^{3C}$, and $T^C$ are as described in Tables 33 and 34.

TABLE 33

| $R^{1C}$ | $R^{3C}$ | $T^C$ |
|---|---|---|
| H | H | 1H-Indol-6-yl |
| H | H | 1H-Indolin-6-yl |
| H | H | 1H-Indol-4-yl |
| H | H | 1H-Indazol-6-yl |
| H | Me | 1H-Indazol-6-yl |
| H | Et | 1H-Indazol-6-yl |
| 8-Me | H | 1H-Indazol-6-yl |
| 8-Cl | H | 1H-Indazol-6-yl |
| H | H | 1H-Indazol-4-yl |
| H | H | 1H-Benzimidazol-6-yl |
| H | H | 2-(Trifluoromethyl)-1H-benzimidazol-6-yl |
| H | H | 1H-Benzotriazol-6-yl |

TABLE 34

| $R^{1C}$ | $R^{3C}$ | $T^C$ |
|---|---|---|
| H | H | 3-Methylbenzisoxazol-6-yl |
| H | H | Pyridin-4-yl |
| H | H | 3-Methoxypyridin-5-yl |
| H | H | 3-Hydroxypyridin-5-yl |
| H | H | Pyridin-3-yl |
| H | H | 7-Hydroxyquinolin-3-yl |
| H | H | Pyrimidin-2-yl |

TABLE 34-continued

| $R^{1C}$ | $R^{3C}$ | $T^C$ |
|---|---|---|
| H | H | Thiophen-2-yl |
| H | H | Pyridin-2-yl |
| H | H | 4-Methylpyridin-2-yl |
| H | H | 2-Bromopyridin-5-yl |

<Representative Compound C-400>

[Chem. 42]

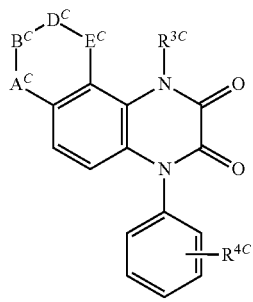

wherein $A^C$-$B^C$-$D^C$-$E^C$, $R^{3C}$, and $R^{4C}$ are as described in Tables 35 to 37.

TABLE 35

| $A^C$-$B^C$-$D^C$-$E^C$ | $R^{3C}$ | $R^{4C}$ |
|---|---|---|
| CH$_2$CH$_2$CH$_2$CH$_2$ | H | 3-OH |
| CH$_2$CH$_2$CH$_2$CH$_2$ | H | 3-OMe |
| CH$_2$CH$_2$CH$_2$CH$_2$ | H | 4-OH |
| CH$_2$CH$_2$CH$_2$CH$_2$ | H | 4-OMe |
| CH$_2$CH$_2$CH$_2$CH$_2$ | H | 2-OH |
| CH$_2$CH$_2$CH$_2$CH$_2$ | H | 2-OMe |
| CH$_2$CH$_2$CH$_2$CH$_2$ | H | 2,3-OH |
| CH$_2$CH$_2$CH$_2$CH$_2$ | H | 3-OH,4-F |
| CH$_2$CH$_2$CH$_2$CH$_2$ | H | 3,4-OH |
| CH$_2$CH$_2$CH$_2$CH$_2$ | H | 3,4-OMe |
| CH$_2$CH$_2$CH$_2$CH$_2$ | H | 3,4,5-OMe |
| CH$_2$CH$_2$CH$_2$CH$_2$ | H | 3-CN |

TABLE 36

| $A^C$-$B^C$-$D^C$-$E^C$ | $R^{3C}$ | $R^{4C}$ |
|---|---|---|
| CH$_2$NHCH$_2$CH$_2$ | H | 4-CN |
| CH$_2$CH$_2$CH$_2$CH$_2$ | H | 3-CO$_2$H |
| CH$_2$NHCH$_2$CH$_2$ | H | 3-CO$_2$Me |
| CH$_2$CH$_2$CH$_2$CH$_2$ | H | 3-Br |
| CH$_2$CH$_2$NHCH$_2$ | H | 3-F |
| CH$_2$CH$_2$OCH$_2$ | H | 4-Me |
| CH$_2$CH$_2$CH$_2$CH$_2$ | H | 3-NH$_2$ |
| CH$_2$CH$_2$CH$_2$CH$_2$ | H | 3-NHSO$_2$Ph |
| CH$_2$CH$_2$CH$_2$CH$_2$ | H | 3-NHSO$_2$(2-NO$_2$)Ph |
| CH$_2$CH$_2$CH$_2$CH$_2$ | H | 4-NHSO$_2$Ph |
| CH$_2$CH$_2$CH$_2$CH$_2$ | Me | 4-NHSO$_2$(2-NO$_2$)Ph |
| CH$_2$CH$_2$CH$_2$CH$_2$ | Et | 3-NHEt |

TABLE 37

| $A^C$-$B^C$-$D^C$-$E^C$ | $R^{3C}$ | $R^{4C}$ |
|---|---|---|
| CH$_2$CH$_2$CH$_2$CH$_2$ | H | 3-CH$_2$OH |
| CH$_2$CH$_2$CH$_2$CH$_2$ | H | 3-NHSO$_2$CH$_3$ |
| CH$_2$CH$_2$CH$_2$CH$_2$ | H | S-CF$_3$ |
| CH$_2$CH$_2$CH$_2$CH$_2$ | H | 3-Ph |

TABLE 37-continued

| $A^C$-$B^C$-$D^C$-$E^C$ | $R^{3C}$ | $R^{4C}$ |
|---|---|---|
| CH$_2$CH$_2$CH$_2$CH$_2$ | H | 3-N(Me)$_2$ |
| CH$_2$CH$_2$CH$_2$CH$_2$ | H | 3,5-OH |
| CH$_2$CH$_2$CH$_2$CH$_2$ | H | 4-OAc |
| CH$_2$CH$_2$CH$_2$CH$_2$ | H | 2-Me |
| CH$_2$CH(Me)CH$_2$CH$_2$ | H | 3-NH$_2$ |

<Representative Compound C-500>

[Chem. 43]

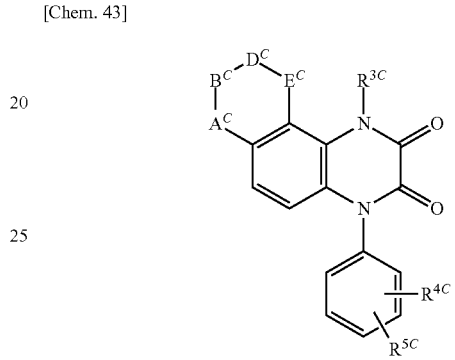

wherein $A^C$-$B^C$-$D^C$-$E^C$, $R^{3C}$, $R^{4C}$, and $R^{5C}$ are as described in Tables 38 to 40; and the "$R^{4C}$ position" in the tables indicates a $R^{4C}$ substitution position.

TABLE 38

| $A^C$-$B^C$-$D^C$-$E^C$ | $R^{3C}$ | $R^{4C}$ Position | $R^{4C}$ | $R^{5C}$ |
|---|---|---|---|---|
| CH$_2$CH$_2$CH$_2$CH$_2$ | H | 3 | 1H-Tetrazol-5-yl | H |
| CH$_2$CH$_2$CH$_2$CH$_2$ | H | 4 | 1H-Tetrazol-5-yl | H |
| CH$_2$NHCH$_2$CH$_2$ | H | 3 | 1H-Tetrazol-5-yl | H |
| CH$_2$CH$_2$OCH$_2$ | H | 3 | 1H-Tetrazol-5-yl | 4-F |
| CH$_2$CH$_2$CH$_2$CH$_2$ | H | 3 | 1H-Tetrazol-5-yl | 4-Me |
| CH$_2$CH$_2$CH$_2$CH$_2$ | H | 3 | 1H-Tetrazol-5-yl | 5-Br |
| CH$_2$CH$_2$CH$_2$CH$_2$ | H | 3 | 1H-Tetrazol-5-yl | 6-Me |
| CH$_2$CH$_2$CH$_2$CH$_2$ | H | 3 | 1H-Tetrazol-5-yl | 6-Cl |
| CH$_2$CH$_2$CH$_2$CH$_2$ | H | 3 | (5-Thioxo-1,2,4-oxadiazol)-3-yl | H |
| CH$_2$CH$_2$CH$_2$CH$_2$ | H | 4 | (5-Oxo-1,2,4-oxadiazol)-3-yl | H |

TABLE 39

| $A^C$-$B^C$-$D^C$-$E^C$ | $R^{3C}$ | $R^{4C}$ Position | $R^{4C}$ | $R^{5C}$ |
|---|---|---|---|---|
| CH$_2$CH$_2$CH$_2$CH$_2$ | H | 3 | (5-Cyano-1H-1,2,3-triazol)-4-yl | H |
| CH$_2$CH$_2$CH$_2$CH$_2$ | H | 3 | 1H-Tetrazol-5-yl | 6-OH |
| CH$_2$CH$_2$CH$_2$CH$_2$ | H | 3 | (2-Methyl-2H-tetrazol)-5-yl | H |
| CH$_2$CH$_2$CH$_2$CH$_2$ | Me | 3 | (2-Methyl-2H-tetrazol)-5-yl | H |
| CH$_2$CH$_2$CH$_2$CH$_2$ | Et | 3 | (2-Ethyl-2H-tetrazol)-5-yl | H |
| CH$_2$NHCH$_2$CH$_2$ | H | 3 | (1-Methyl-1H-tetrazol)-5-yl | H |
| CH$_2$CH$_2$CH$_2$CH$_2$ | H | 3 | 4-Methyl-(5-thioxo-1,2,4-oxadiazol)-3-yl | H |
| CH$_2$CH$_2$CH$_2$CH$_2$ | H | 3 | 1-Methyl-1H-imidazol-2-yl | H |
| CH$_2$CH$_2$CH$_2$CH$_2$ | H | 3 | 1-Methyl-1H-imidazol-4-yl | H |
| CH$_2$CH$_2$CH$_2$CH$_2$ | H | 3 | 1,3-Oxazol-2-yl | H |
| CH$_2$CH$_2$CH$_2$CH$_2$ | H | 3 | 1,3-Thiazol-2-yl | H |
| CH$_2$CH$_2$CH$_2$CH$_2$ | H | 3 | Pyrrol-2-yl | H |
| CH$_2$CH$_2$CH$_2$CH$_2$ | H | 3 | Thiophen-2-yl | H |

TABLE 40

| $A^C$-$B^C$-$D^C$-$E^C$ | $R^{3C}$ | $R^{4C}$ Position | $R^{4C}$ | $R^{5C}$ |
|---|---|---|---|---|
| CH$_2$CH$_2$CH$_2$CH$_2$ | H | 3 | 1-H-Imidazol-2-yl | H |
| CH$_2$CH$_2$CH$_2$CH$_2$ | H | 3 | 1-H-Imidazol-4-yl | H |
| CH$_2$CH$_2$CH$_2$CH$_2$ | H | 4 | Pyrazol-4-yl | H |
| CH$_2$CH$_2$CH$_2$CH$_2$ | H | 3 | 5-(Chloro)-1H-imidazol-2-yl | H |
| CH$_2$CH$_2$CH$_2$CH$_2$ | H | 3 | 5-(Trifluoromethyl)-1H-imidazol-2-yl | H |
| CH$_2$CH$_2$CH$_2$CH$_2$ | H | 3 | (1,2,3-Triazol)-4-yl | H |
| CH$_2$CH$_2$CH$_2$CH$_2$ | H | 3 | (1,2,4-Triazol)-3-yl | H |
| CH$_2$CH$_2$CH$_2$CH$_2$ | H | 3 | 3-Methyl-(1,2,4-oxadiazol)-5-yl | H |
| CH$_2$CH$_2$CH$_2$CH$_2$ | H | 4 | 3,5-Dimethylisoxazol-4-yl | H |
| CH$_2$CH$_2$CH$_2$CH$_2$ | H | 3 | 1-Tetrazol-1-yl | H |
| CH$_2$CH(Me)CH$_2$CH$_2$ | H | 3 | Phenyl | H |
| CH$_2$CH$_2$CH(Me)CH$_2$ | H | 3 | Pyrimidin-5-yl | H |

<Representative Compound C-600>

[Chem. 44]

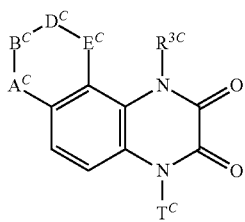

wherein $A^C$-$B^C$-$D^C$-$E^C$, $R^{3C}$, and $T^C$ are as described in Tables 41 and 42.

TABLE 41

| $A^C$-$B^C$-$D^C$-$E^C$ | $R^{3C}$ | $T^C$ |
|---|---|---|
| CH$_2$CH$_2$CH$_2$CH$_2$ | H | 1H-Indol-6-yl |
| CH$_2$CH$_2$CH$_2$CH$_2$ | H | 1H-Indolin-6-yl |
| CH$_2$CH$_2$CH$_2$CH$_2$ | H | 1H-Indol-4-yl |
| CH$_2$CH$_2$CH$_2$CH$_2$ | H | 1H-Indazol-6-yl |
| CH$_2$CH$_2$CH$_2$CH$_2$ | Me | 1H-Indazol-6-yl |
| CH$_2$CH$_2$CH$_2$CH$_2$ | Et | 1H-Indazol-6-yl |
| CH$_2$CH$_2$CH$_2$CH$_2$ | H | 1H-Indazol-4-yl |
| CH$_2$CH$_2$CH$_2$CH$_2$ | H | 1H-Benzimidazol-6-yl |
| CH$_2$CH$_2$CH$_2$CH$_2$ | H | 2-(Trifluoromethyl)-1H-benzimidazol-6-yl |
| CH$_2$CH$_2$CH$_2$CH$_2$ | H | 1H-Benzotriazol-6-yl |
| CH$_2$CH$_2$CH$_2$CH$_2$ | H | 3-Methylbenzisoxazol-6-yl |

TABLE 42

| $A^C$-$B^C$-$D^C$-$E^C$ | $R^{3C}$ | $T^C$ |
|---|---|---|
| CH$_2$CH$_2$CH$_2$CH$_2$ | H | Pyridin-4-yl |
| CH$_2$CH$_2$CH$_2$CH$_2$ | H | 3-Methoxypyridin-5-yl |
| CH$_2$CH$_2$CH$_2$CH$_2$ | H | 3-Hydroxypyridin-5-yl |
| CH$_2$CH$_2$CH$_2$CH$_2$ | H | Pyridin-3-yl |
| CH$_2$CH$_2$CH$_2$CH$_2$ | H | 7-Hydroxyquinolin-3-yl |
| CH$_2$CH$_2$CH$_2$CH$_2$ | H | Pyrimidin-2-yl |
| CH$_2$CH$_2$CH$_2$CH$_2$ | H | Thiophen-2-yl |
| CH$_2$CH$_2$CH$_2$CH$_2$ | H | Pyridin-2-yl |
| CH$_2$CH$_2$CH$_2$CH$_2$ | H | 4-Methylpyridin-2-yl |
| CH$_2$CH$_2$CH$_2$CH$_2$ | H | 2-Bromopyridin-5-yl |
| CH$_2$CH(Me)CH$_2$CH$_2$ | H | 1H-Indol-6-yl |
| CH$_2$CH(Me)CH$_2$CH$_2$ | H | 1H-Indol-5-yl |
| CH$_2$CH(Me)CH$_2$CH$_2$ | H | 1H-Indol-4-yl |

<Representative Compound C-700>

[Chem. 45]

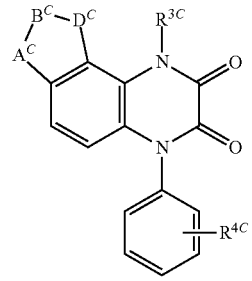

wherein $A^C$-$B^C$-$D^C$, $R^{3C}$, and $R^{4C}$ are as described in Tables 43 to 45.

TABLE 43

| $A^C$-$B^C$-$D^C$ | $R^{3C}$ | $R^{4C}$ |
|---|---|---|
| CH$_2$CH$_2$CH$_2$ | H | 3-OH |
| CH$_2$CH$_2$CH$_2$ | H | 3-OMe |
| CH$_2$CH$_2$CH$_2$ | H | 4-OH |
| CH$_2$CH$_2$CH$_2$ | H | 4-OMe |
| OCH$_2$O | H | 2,3-OH |
| CH$_2$CH$_2$CH$_2$ | H | 3,4-OH |
| NHCH$_2$CH$_2$ | H | 3,4,5-OMe |
| CH$_2$CH$_2$CH$_2$ | H | 3-CN |

TABLE 44

| $A^C$-$B^C$-$D^C$ | $R^{3C}$ | $R^{4C}$ |
|---|---|---|
| CH$_2$CH$_2$CH$_2$ | H | 3-CO$_2$H |
| OCH$_2$O | H | 3-Br |
| CH$_2$CH$_2$CH$_2$ | H | 4-Me |
| CH$_2$NHCH$_2$ | H | 3-NHSO$_2$Ph |
| CH$_2$CH$_2$CH$_2$ | H | 3-NHSO$_2$(2-NO$_2$)Ph |
| CH$_2$CH$_2$CH$_2$ | H | 4NHSO$_2$Ph |
| CH$_2$CH$_2$CH$_2$ | Me | 4-NHSO$_2$(2-NO$_2$)Ph |
| CH$_2$CH$_2$CH$_2$ | Et | 3-NHEt |

TABLE 45

| $A^C$-$B^C$-$D^C$ | $R^{3C}$ | $R^{4C}$ |
|---|---|---|
| CH$_2$CH$_2$CH$_2$ | H | 3-NHSO$_2$CH$_3$ |
| CH$_2$CH$_2$CH$_2$ | H | 3-Ph |
| CH$_2$CH$_2$CH$_2$ | H | S—N(Me)$_2$ |
| CH$_2$CH$_2$NH | H | 2-Me |
| CH$_2$CH(Me)CH$_2$ | H | 3-NH$_2$ |
| CH$_2$CH(Me)CH$_2$ | H | 4-NH$_2$ |

<Representative Compound C-800>

[Chem. 46]

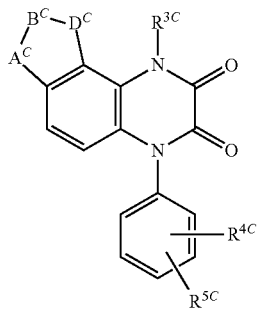

wherein $A^C$-$B^C$-$D^C$, $R^{3C}$, $R^{4C}$, and $R^{5C}$ are as described in Tables 46 to 48; and the "$R^{4C}$ position" in the tables indicates a $R^{4C}$ substitution position.

TABLE 46

| $A^C$-$B^C$-$D^C$ | $R^{3C}$ | $R^{4C}$ Position | $R^{4C}$ | $R^{5C}$ |
|---|---|---|---|---|
| CH₂CH₂CH₂ | H | 3 | 1H-Tetrazol-5-yl | H |
| OCH₂O | H | 4 | 1H-Tetrazol-5-yl | H |
| CH₂CH(Me)CH₂ | H | 3 | 1H-Tetrazol-5-yl | H |
| CH₂CH(Me)CH₂ | H | 4 | 1H-Tetrazol-5-yl | H |
| CH₂CH₂CH₂ | H | 3 | 1H-Tetrazol-5-yl | 4-F |
| CH₂CH₂CH₂ | H | 3 | 1H-Tetrazol-5-yl | 4-Me |
| CH₂CH₂CH₂ | H | 3 | 1H-Tetrazol-5-yl | 5-Br |
| CH₂NHCH₂ | H | 3 | 1H-Tetrazol-5-yl | 6-Me |
| CH₂CH₂CH₂ | H | 3 | (5-Thioxo-1,2,4-oxadiazol)-3-yl | H |

TABLE 47

| $A^C$-$B^C$-$D^C$ | $R^{3C}$ | $R^{4C}$ Position | $R^{4C}$ | $R^{5C}$ |
|---|---|---|---|---|
| CH₂CH₂CH₂ | H | 3 | 1H-Tetrazol-5-yl | 6-OH |
| CH₂CH₂CH₂ | H | 3 | (2-Methyl-2H-tetrazol)-5-yl | H |
| CH₂CH₂CH₂ | Me | 3 | (2-Methyl-2H-tetrazol)-5-yl | H |
| CH₂CH₂CH₂ | Et | 3 | (2-Ethyl-2H-tetrazol)-5-yl | H |
| CH₂CH₂CH₂ | H | 3 | 4-Methyl-(5-thioxo-1,2,4-oxadiazol)-3-yl | H |
| CH₂CH₂CH₂ | H | 3 | 1-Methyl-1H-imidazol-2-yl | H |
| CH₂CH₂CH₂ | H | 3 | 1,3-Oxazol-2-yl | H |
| CH₂CH₂CH₂ | H | 3 | 1,3-Thiazol-2-yl | H |
| CH₂CH₂CH₂ | H | 3 | Thiophen-2-yl | H |

TABLE 48

| $A^C$-$B^C$-$D^C$ | $R^{3C}$ | $R^{4C}$ Position | $R^{4C}$ | $R^{5C}$ |
|---|---|---|---|---|
| CH₂CH₂CH₂ | H | 3 | 1-H-Imidazol-4-yl | H |
| CH₂CH₂CH₂ | H | 3 | Pyrazol-4-yl | H |
| CH₂CH₂CH₂ | H | 3 | 5-(Chloro)-1H-imidazol-2-yl | H |
| CH₂CH₂CH₂ | H | 3 | (1,2,4-Triazol)-3-yl | H |
| CH₂CH₂CH₂ | H | 3 | 1-Tetrazol-1-yl | H |
| OCH₂O | H | 3 | Phenyl | H |
| CH₂CH₂CH₂ | H | 3 | Pyridin-3-yl | H |
| NHCH₂CH₂ | H | 3 | Pyrimidin-5-yl | H |

<Representative Compound C-900>

[Chem. 47]

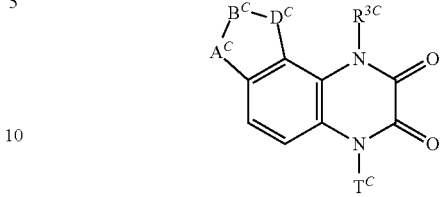

wherein $A^C$-$B^C$-$D^C$, $R^{3C}$, and $T^C$ are as described in Tables 49 and 50.

TABLE 49

| $A^C$-$B^C$-$D^C$ | $R^{3C}$ | $T^C$ |
|---|---|---|
| CH₂CH₂CH₂ | H | 1H-Indol-6-yl |
| OCH₂O | H | 1H-Indolin-6-yl |
| CH₂CH₂CH₂ | Me | 1H-Indazol-6-yl |
| CH₂CH₂CH₂ | Et | 1H-Indazol-6-yl |
| OH₂CH₂CH₂ | H | 1H-Indazol-4-yl |
| CH₂NHCH₂ | H | 1H-Benzotriazol-6-yl |
| CH₂CH₂CH₂ | H | 3-Methylbenzisoxazol-6-yl |

TABLE 50

| $A^C$-$B^C$-$D^C$ | $R^{3C}$ | $T^C$ |
|---|---|---|
| CH₂CH₂CH₂ | H | Pyridin-4-yl |
| CH₂CH₂CH₂ | H | Thiophen-2-yl |
| CH₂NHCH₂ | H | 4-Methylpyridin-2-yl |
| CH₂CH(Me)CH₂ | H | 1H-Indol-6-yl |

(D-1) A compound, a tautomer, stereoisomer, or pharmaceutically acceptable salt of the compound, or a hydrate or solvate thereof, the compound represented by the following general formula (DI):

[Chem. 48]

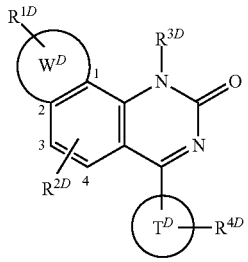

(DI)

wherein $R^{1D}$ and $R^{2D}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{3D}$ represents a hydrogen atom, a $C_{1-8}$ alkyl group, a $C_{2-8}$ alkenyl group, a $C_{1-8}$ alkyl group substituted with 1 to 3 halogen atoms, or an aralkyl group (the number of carbon atoms in an aryl moiety is from 6 to 10 and the number of carbon atoms in an alkylene moiety is from 1 to 3), $R^{4D}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a hydroxyl-substituted $C_{1-8}$ alkyl group, a halogen atom, a hydroxyl group, a nitro group, a cyano group, an amino group, a $C_{1-8}$ alkylamino group, a $C_{1-8}$ alkylamino group substituted with 1 to 5 halogen atoms, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, an optionally substituted benzenesulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group, and

[Chem. 49]

is condensed with a benzene ring at positions 1 and 2 and represents a 5- to 8-membered ring optionally comprising 1 or 2 atoms of nitrogen as a ring constituent element, and

[Chem. 50]

represents an aromatic ring selected from a benzene ring, a naphthalene ring, a pyridine ring, a pyrimidine ring, a quinoline ring, an indole ring, an indoline ring, a benzimidazole ring, a pyrazole ring, an indazole ring, a benzisoxazole ring, or a benzotriazole ring.

(D-2) A compound, a tautomer, stereoisomer, or pharmaceutically acceptable salt of the compound, or a hydrate or solvate thereof, the compound represented by the following general formula (DII):

[Chem. 51]

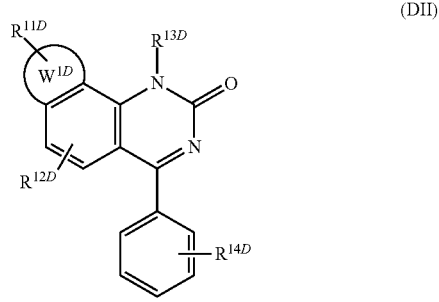

(DII)

wherein $R^{11D}$ and $R^{12D}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{13D}$ represents a hydrogen atom, a $C_{1-8}$ alkyl group, a $C_{2-8}$ alkenyl group, a $C_{1-8}$ alkyl group substituted with 1 to 3 halogen atoms, or an aralkyl group (the number of carbon atoms in an aryl moiety is from 6 to 10 and the number of carbon atoms in an alkylene moiety is from 1 to 3), $R^{14D}$ represents a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, an aralkyl group (the number of carbon atoms in an aryl moiety is from 6 to 10 and the number of carbon atoms in an alkylene moiety is from 1 to 3), a hydroxyl-substituted $C_{1-8}$ alkyl group, a hydroxyl group, a nitro group, a cyano group, an amino group, a $C_{1-8}$ alkylamino group, a $C_{1-5}$ alkylamino group substituted with 1 to 5 halogen atoms, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, an optionally substituted benzenesulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group, and

[Chem. 52]

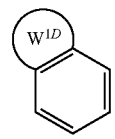

represents a naphthalene ring, a tetrahydronaphthalene ring, or an indane ring.

Examples of the $C_{1-8}$ alkyl group of $R^{1D}$, $R^{2D}$, $R^{3D}$, or $R^{4D}$ in general formula (DI) include a methyl, ethyl, propyl, isopropyl, butyl, i-butyl, t-butyl, pentyl, or hexyl group.

Examples of the $C_{2-8}$ alkenyl group of $R^{1D}$, $R^{2D}$, $R^{3D}$, or $R^{4D}$ include an allyl group.

Examples of the $C_{1-8}$ alkyl group substituted with 1 to 3 halogen atoms in $R^{1D}$, $R^{2D}$, $R^{3D}$, or $R^{4D}$ include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the aralkyl group (the number of carbon atoms in an aryl moiety is from 6 to 10 and the number of carbon atoms in an alkylene moiety is from 1 to 3) of $R^{1D}$, $R^{2D}$, $R^{3D}$, or $R^{4D}$ include a benzyl group.

Examples of the $C_{1-8}$ alkoxy group of $R^{1D}$, $R^{2D}$, or $R^{4D}$ include a methoxy, ethoxy, propoxy, isopropoxy, butoxy, i-butoxy, t-butoxy, pentyloxy, or hexyloxy group.

Examples of the $C_{1-8}$ alkoxy group substituted with 1 to 3 halogen atoms in $R^{1D}$, $R^{2D}$, or $R^{4D}$ include a methoxy, ethoxy, propoxy, isopropoxy, butoxy, or t-butoxy group substituted with 1 to 3 halogen atoms such as fluorine, chlorine, or bromine atoms, and preferably a trifluoromethoxy, chloromethoxy, 2-chloroethoxy, 2-bromoethoxy, or 2-fluoroethoxy group.

Examples of the halogen atom of $R^{1D}$, $R^{2D}$, or $R^{4D}$ include a fluorine, chlorine, or bromine atom.

Examples of the $C_{1-8}$ alkylamino group of $R^{1D}$, $R^{2D}$, or $R^{4D}$ include a methylamino or ethylamino group.

Examples of the $C_{1-5}$ alkylamino group substituted with 1 to 5 halogen atoms in $R^{4D}$ include a 2,2,2-trifluoroethylamino group.

Examples of the $C_{2-8}$ dialkylamino group of $R^{1D}$, $R^{2D}$, or $R^{4D}$ include a dimethylamino or diethylamino group.

Examples of the $C_{2-8}$ acylamino group of $R^{1D}$, $R^{2D}$, or $R^{4D}$ include an acetylamino group.

Examples of the $C_{2-8}$ acylamino group substituted with 1 to 3 halogen atoms in $R^{1D}$, $R^{2D}$, or $R^{4D}$ include a trifluoromethylcarbonylamino group.

Examples of the $C_{1-8}$ alkylsulfonylamino group of $R^{1D}$, $R^{2D}$, or $R^{4D}$ include a methylsulfonylamino group.

Examples of the $C_{2-8}$ acyl group of $R^{1D}$, $R^{2D}$, or $R^{4D}$ include an acetyl group.

Examples of the alkoxycarbonyl group (the number of carbon atoms in an alkoxy moiety is from 1 to 8) of $R^{1D}$, $R^{2D}$, or $R^{4D}$ include a methoxycarbonyl group or an ethoxycarbonyl group.

Examples of the $C_{1-8}$ alkylthio group of $R^{1D}$, $R^{2D}$, or $R^{4D}$ include a methylthio group.

Examples of the $C_{1-8}$ alkylsulfinyl group of $R^{1D}$, $R^{2D}$, or $R^{4D}$ include a methylsulfinyl group.

Examples of the $C_{1-8}$ alkylsulfonyl group of $R^{1D}$, $R^{2D}$, or $R^{4D}$ include a methylsulfonyl group.

Examples of the hydroxyl-substituted $C_{1-8}$ alkyl group of $R^{4D}$ include a hydroxymethyl group.

Examples of the optionally substituted benzenesulfonylamino group of $R^{4D}$ include a benzenesulfonylamino group and preferably an o-nitrobenzenesulfonylamino group optionally having a substituent selected from a $C_{1-8}$ alkyl group (e.g., a methyl group, an ethyl group), a $C_{1-8}$ alkoxy group (e.g., a methoxy group, an ethoxy group), a halogen atom (e.g., a fluorine atom, a chlorine atom), or a nitro group.

Examples of a preferable substituent of the optionally substituted phenyl group of $R^{4D}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, or a cyano group.

Examples of a preferable heterocyclic ring group in the optionally substituted heterocyclic ring group of $R^{4D}$ include a tetrazolyl, triazolyl, pyridyl, imidazolyl, oxazolyl or thiazolyl group.

Examples of a preferable substituent of the optionally substituted heterocyclic ring of $R^{4D}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, a cyano group, or oxo.

Examples of

[Chem. 53]

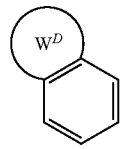

include a naphthalene ring, a tetrahydronaphthalene ring, or an indane ring.

In general formula (DI), $R^{1D}$, $R^{2D}$, or $R^{4D}$ substituents, which are the same or different, may be present, in a ring having the $R^{1D}$, $R^{2D}$, or $R^{4D}$ substituents.

Regarding the above listed examples, for $R^{1D}$, $R^{2D}$, $R^{3D}$, or $R^{4D}$ in general formula (DI), comprising a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a $C_{1-8}$ alkoxy group, a $C_{1-8}$ alkoxy group substituted with 1 to 3 halogen atoms, a halogen atom, an aralkyl group (the number of carbon atoms in an aryl moiety is from 6 to 10 and the number of carbon atoms in an alkylene moiety is from 1 to 3), a hydroxyl-substituted $C_{1-8}$ alkyl group, a halogen atom, a $C_{1-8}$ alkylamino group, a $C_{1-5}$ alkylamino substituted with 1 to 5 halogen atoms, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, an optionally substituted benzenesulfonylamino group, a $C_{2-8}$ acyl group, an alkoxycarbonyl group (the number of carbon atoms in an alkoxy moiety is from 1 to 8), a $C_{1-8}$ alkylthio group, a $C_{1-8}$ alkylsulfinyl group, a $C_{1-8}$ alkylsulfonyl group, an optionally substituted phenyl group, or an optionally substituted heterocyclic ring group, the same applies to $R^{11D}$, $R^{12D}$, $R^{13D}$, or $R^{14D}$ in general formula (DII).

Regarding the optionally substituted heterocyclic ring group of $R^{14D}$ in general formula (DII), examples of the substituent include a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a $C_{1-8}$ alkylamino group, and a $C_{2-8}$ dialkylamino group, examples of which are included in those listed for $R^{1D}$ to $R^{4D}$ in general formula (DI).

Examples of

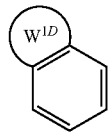

include a naphthalene ring, a tetrahydronaphthalene ring, or an indane ring.

In general formula (DII), $R^{11D}$, $R^{12D}$, or $R^{14D}$ substituents, which are the same or different, may be present, in a benzene ring having the $R^{11D}$, $R^{12D}$, or $R^{14D}$ substituents.

The following compounds are preferable as compounds represented by general formula (DI).

(D-1-1) A compound described in (D-1), wherein $R^{1D}$ and $R^{2D}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(D-1-2) A compound described in (D-1) or (D-1-1), wherein $R^{3D}$ is a hydrogen atom or a $C_{1-8}$ alkyl group.

(D-1-3) A compound described in (D-1) or (D-1-1) or (D-1-2), wherein $R^{4D}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl-substituted $C_{1-8}$ alkyl group, a halogen atom, a hydroxyl group, a cyano group, an amino group, a $C_{1-8}$ alkylamino group, a $C_{2-8}$ dialkylamino group, a $C_{1-8}$ alkylsulfonylamino group, an optionally substituted benzenesulfonylamino group, an optionally substituted phenyl group, or an optionally substituted heterocyclic ring group.

(D-1-4) A compound described in (D-1) or any of (D-1-1) to (D-1-3), wherein $R^{4D}$ is a 5- or 6-membered heterocyclic ring comprising 1 to 4 atoms of nitrogen as a ring constituent element.

(D-1-5) A compound described in (D-1) or any of (D-1-1) to (D-1-4), wherein $R^{4D}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(D-1-6) A compound described in (D-1) or any of (D-1-1) to (D-1-7), wherein $R^{4D}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(D-1-7) A compound described in (D-1) or any of (D-1-1) to (D-1-6), wherein $R^{4D}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(D-1-8) A compound described in (D-1) or any of (D-1-1) to (D-1-7), wherein $R^{4D}$ is 5-oxo-1,2,4-oxadiazole or 5-thioxo-1,2,4-oxadiazole.

(D-1-9) A compound described in (D-1) or any of (D-1-1) to (D-1-8), wherein $R^{4D}$ is tetrazole.

(D-1-10) A compound described in (D-1) or any of (D-1-1) to (D-1-9), wherein $R^{4D}$ is a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl group, a cyano group, an amino group, a $C_{1-8}$ alkylamino group, a $C_{2-8}$ dialkylamino group, or a benzenesulfonylamino group optionally having a substituent selected from a $C_{1-8}$ alkyl group, a $C_{1-8}$ alkoxy group, a halogen atom, or a nitro group.

(D-1-11)
A compound described in (D-1) or any of (D-1-1) to (D-1-10), wherein

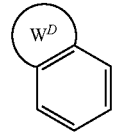

is a naphthalene ring, a tetrahydronaphthalene ring, or an indane ring.

(D-1-12)
A compound described in (D-1) or any of (D-1-1) to (D-1-11), wherein

is a benzene ring or an indole ring.

The following compounds are preferable as compounds represented by general formula (DII).

(D-2-1) A compound described in (D-2), wherein $R^{11D}$ and $R^{12D}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(D-2-2) A compound described in (D-2) or (D-2-1), wherein $R^{13D}$ is a hydrogen atom.

(D-2-3) A compound described in (D-2) or (D-2-1) or (D-2-2), wherein $R^{14D}$ is a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl-substituted $C_{1-8}$ alkyl group, a hydroxyl group, a cyano group, an amino group, a $C_{1-8}$ alkylamino group, a $C_{2-8}$ dialkylamino group, a $C_{1-8}$ alkylsulfonylamino group, an optionally substituted benzenesulfonylamino group, an optionally substituted phenyl group, or an optionally substituted heterocyclic ring group.

(D-2-4) A compound described in (D-2) or any of (D-2-1) to (D-2-3), wherein $R^{14D}$ is a 5- or 6-membered heterocyclic ring comprising 1 to 4 atoms of nitrogen as a ring constituent element.

(D-2-5) A compound described in (D-2) or any of (D-2-1) to (D-2-4), wherein $R^{14D}$ is a tetrazolyl, triazolyl, pyridyl, imidazolyl, oxazolyl, or thiazolyl group optionally having a substituent selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(D-2-6) A compound described in (D-2) or any of (D-2-1) to (D-2-5), wherein $R^{14D}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(D-2-7) A compound described in (D-2) or any of (D-2-1) to (D-2-6), wherein $R^{14D}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(D-2-8) A compound described in (D-2) or any of (D-2-1) to (D-2-7), wherein $R^{14D}$ is 5-oxo-1,2,4-oxadiazole or 5-thioxo-1,2,4-oxadiazole.

(D-2-9) A compound described in (D-2) or any of (D-2-1) to (D-2-8), wherein $R^{14D}$ is tetrazole.

(D-2-10) A compound described in (D-2) or any of (D-2-1) to (D-2-9), wherein $R^{14D}$ is a $C_{1-8}$ alkoxy group, a $C_{1-8}$ alkyl group substituted with 1 to 3 halogen atoms, a $C_{1-8}$ alkoxy group substituted with 1 to 3 halogen atoms, a hydroxyl group, a cyano group, an amino group, a $C_{1-8}$ alkylamino group, a $C_{2-8}$ dialkylamino group, or a benzenesulfonylamino group optionally having a substituent selected from a $C_{1-8}$ alkyl group, a $C_{1-8}$ alkoxy group, a halogen atom, or a nitro group.

(D-2-11)

A compound described in (D-2) or any of (D-2-1) to (D-2-10), wherein

[Chem. 57]

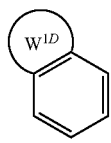

is a naphthalene ring.

The following shows representative compounds included in general formula (DI).

<Representative Compound D-100>

[Chem. 58]

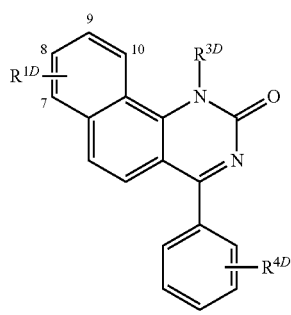

wherein $R^{1D}$, $R^{3D}$, and $R^{4D}$ are as described in Table 51.

TABLE 51

| $R^{1D}$ | $R^{3D}$ | $R^{4D}$ |
|---|---|---|
| H | H | 3-OH |
| 8-Me | H | 3-OMe |
| 8-Cl | H | 4-OH |
| 9-Me | H | 3,4-OH |
| 9-Cl | H | 3-CN |
| H | H | 4-CN |
| H | H | 3-$CO_2$H |
| H | H | 3-$NH_2$ |
| H | H | 3-NHMe |
| H | Me | 3-NHMe |
| H | Et | 3-NHEt |
| H | H | 3-$NHCH_2CF_3$ |
| H | H | 3-$NHSO_2$Ph |
| H | H | 3-$NHSO_2$(2-$NO_2$)Ph |
| H | H | 1H-Tetrazol-5-yl |
| H | H | 1H-Tetrazol-1-yl |
| H | H | (2-Methyl-2H-tetrazol)-5-yl |
| H | H | 1,3-Oxazol-2-yl |
| H | H | 1-H-Imidazol-2-yl |
| H | H | (1,2,4-Triazol)-3-yl |

<Representative Compound D-200>

[Chem. 59]

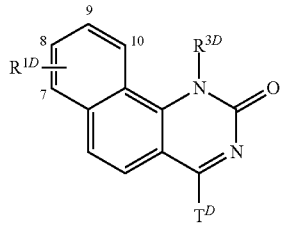

wherein $R^{1D}$, $R^{3D}$, and $T^D$ are as described in Table 52.

TABLE 52

| $R^{1D}$ | $R^{3D}$ | $T^D$ |
|---|---|---|
| H | H | 1H-Indol-6-yl |
| 8-Me | H | 1H-Indol-4-yl |
| 8-Cl | H | 1H-Indazol-6-yl |
| 9-Me | H | 1H-Indazol-4-yl |
| 9-Cl | H | 1H-Indolin-6-yl |
| H | Me | 1H-Benzimidazol-6-yl |
| H | Et | 1H-Benzotriazol-6-yl |
| H | H | 3-Methylbenzisoxazol-6-yl |
| H | H | Pyridin-3-yl |
| H | H | 1H-Pyrazol-4-yl |
| H | H | Pyridin-2-yl |
| H | H | 4-Methylpyridin-2-yl |
| H | H | 2-Bromopyridin-5-yl |

<Representative Compound D-300>

[Chem. 60]

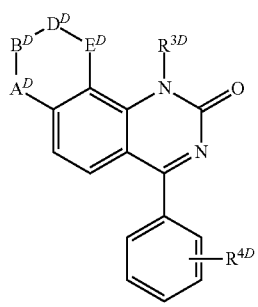

wherein $A^D$-$B^D$-$D^D$-$E^D$, $R^{3D}$, and $R^{4D}$ are as described in Table 53.

TABLE 53

| $A^D$-$B^D$-$D^D$-$E^D$ | $R^{3D}$ | $R^{4D}$ |
|---|---|---|
| CH$_2$CH$_2$CH$_2$CH$_2$ | H | 3-OH |
| CH$_2$CH$_2$CH$_2$ | H | 3-OMe |
| CH$_2$CH$_2$(CH$_2$)$_2$CH$_2$ | H | 4-OH |
| CH$_2$CH$_2$(CH$_2$)$_3$CH$_2$ | H | 3,4-OH |
| CH$_2$CH$_2$CH$_2$CH$_2$ | H | 3-CN |
| CH$_2$CH$_2$NHCH$_2$ | H | 4-CN |
| CH$_2$CH$_2$CH$_2$CH$_2$ | H | 3-CO$_2$H |
| CH$_2$CH$_2$NHCH$_2$ | H | 3-NH$_2$ |
| CH$_2$CH$_2$CH$_2$CH$_2$ | H | 3-NHMe |
| CH$_2$CH$_2$CH$_2$CH$_2$ | Me | 3-NHMe |
| CH$_2$CH$_2$CH$_2$CH$_2$ | Et | 3-NHEt |
| CH$_2$CH$_2$CH$_2$CH$_2$ | H | 3-NHCH$_2$CF$_3$ |
| CH$_2$CH$_2$CH$_2$CH$_2$ | H | 3-NHSO$_2$Ph |
| CH$_2$CH$_2$CH$_2$CH$_2$ | H | 3-NHSO$_2$(2-NO$_2$)Ph |
| CH$_2$CH$_2$CH$_2$CH$_2$ | H | 1H-Tetrazol-5-yl |
| CH$_2$NHCH$_2$CH$_2$ | H | 1H-Tetrazol-1-yl |
| CH$_2$CH(Me)CH$_2$CH$_2$ | H | (2-Methyl-2H-tetrazol)-5-yl |
| CH$_2$CH(Me)CH$_2$CH$_2$ | H | 1,3-Oxazol-2-yl |
| CH$_2$CH$_2$CH(Me)CH$_2$ | H | 1-H-Imidazol-2-yl |
| CH$_2$CH$_2$CH(Me)CH$_2$ | H | (1,2,4-Triazol)-3-yl |

<Representative Compound D-400>

[Chem. 61]

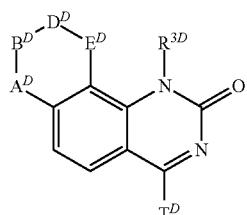

wherein $A^D$-$B^D$-$D^D$-$E^D$, $R^{3D}$, and $T^D$ are as described in Table 54.

TABLE 54

| $A^D$-$B^D$-$D^D$-$E^D$ | $R^{3D}$ | $T^D$ |
|---|---|---|
| CH$_2$CH$_2$CH$_2$CH$_2$ | H | 1H-Indol-6-yl |
| CH$_2$CH$_2$CH$_2$ | H | 1H-Indol-4-yl |
| CH$_2$CH$_2$(CH$_2$)$_2$CH$_2$ | H | 1H-Indazol-6-yl |
| CH$_2$CH$_2$(CH$_2$)$_3$CH$_2$ | H | 1H-Indazol-4-yl |
| CH$_2$CH$_2$CH$_2$CH$_2$ | Me | 1H-Indolin-6-yl |
| CH$_2$NHCH$_2$CH$_2$ | Et | 1H-Benzimidazol-6-yl |

TABLE 54-continued

| $A^D$-$B^D$-$D^D$-$E^D$ | $R^{3D}$ | $T^D$ |
|---|---|---|
| CH$_2$CH$_2$CH$_2$CH$_2$ | H | 1H-Benzotriazol-6-yl |
| CH$_2$CH$_2$CH$_2$CH$_2$ | H | 3-Methylbenzisoxazol-6-yl |
| CH$_2$CH$_2$CH$_2$CH$_2$ | H | Pyridin-3-yl |
| CH$_2$N(Me)CH$_2$CH$_2$ | H | 1H-Pyrazol-4-yl |
| CH$_2$CH(Me)CH$_2$CH$_2$ | H | Pyridin-2-yl |
| CH$_2$CH$_2$CH(Me)CH$_2$ | H | 4-Methylpyridin-2-yl |
| CH$_2$CH$_2$CH(Me)CH$_2$ | H | 2-Bromopyridin-5-yl |

(E-1) A compound, a tautomer, stereoisomer, or pharmaceutically acceptable salt of the compound, or a hydrate or solvate thereof, the compound represented by the following general formula (EI):

[Chem. 62]

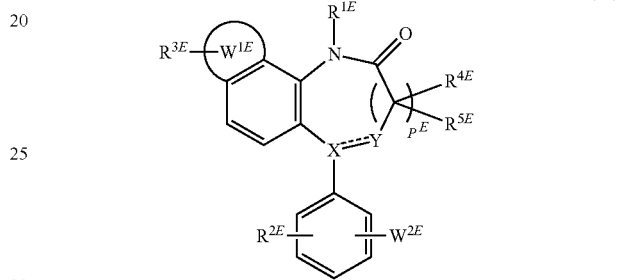

(EI)

wherein $R^{1E}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{2E}$ and $R^{3E}$ are the same or different and represent a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{4E}$ and $R^{5E}$ are the same or different and represent a hydrogen atom, a $C_{1-8}$ alkyl group, a $C_{1-8}$ alkyl group substituted with 1 to 3 halogen atoms, or a phenyl-substituted $C_{1-3}$ alkyl group,

[Chem. 63]

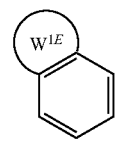

represents naphthalene or tetrahydronaphthalene, $W^{2E}$ represents an optionally substituted heterocyclic ring, when $X^E$ is N, $Y^E$ is C=O and a double line composed of a solid line and a dashed line denotes a single bond and when $X^E$ is C, $Y^E$ is N and a double line composed of a solid line and a dashed line denotes a double bond, and $P^E$ is 0 or 1.

Examples of the $C_{1-8}$ alkyl group of $R^{1E}$, $R^{2E}$, $R^{3E}$, $R^{4E}$, or $R^{5E}$ in general formula (EI) include a methyl, ethyl, propyl, isopropyl, butyl, i-butyl, t-butyl, pentyl, or hexyl group.

Examples of the $C_{2-8}$ alkenyl group of $R^{1E}$ include an allyl group.

Examples of the $C_{1-8}$ alkyl group substituted with 1 to 3 halogen atoms in $R^{1E}$, $R^{2E}$, $R^{3E}$, $R^{4E}$, or $R^{5E}$ include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the phenyl-substituted $C_{1-3}$ alkyl group of $R^{1E}$, $R^{4E}$, or $R^{5E}$ include a benzyl group.

Examples of the $C_{1-8}$ alkoxy group of $R^{2E}$ or $R^{3E}$ include a methoxy, ethoxy, propoxy, isopropoxy, butoxy, i-butoxy, t-butoxy, pentyloxy, or hexyloxy group.

Examples of the $C_{1-8}$ alkoxy group substituted with 1 to 3 halogen atoms in $R^{2E}$ or $R^{3E}$ include a methyl, ethyl, propyl, isopropyl, butyl, or t-butyl group substituted with 1 to 3 halogen atoms such as fluorine, chlorine, or bromine atoms, and preferably a trifluoromethoxy, 2-chloroethoxy, 2-bromoethoxy, or 2-fluoroethoxy group.

Examples of the halogen atom of $R^{2E}$ or $R^{3E}$ include a fluorine, chlorine, or bromine atom.

Examples of the $C_{1-8}$ alkylamino group of $R^{2E}$ or $R^{3E}$ include a methylamino or ethylamino group.

Examples of the $C_{1-8}$ dialkylamino group of $R^{2E}$ or $R^{3E}$ include a dimethylamino or diethylamino group.

Examples of the $C_{2-8}$ acylamino group of $R^{2E}$ or $R^{3E}$ include an acetylamino group.

Examples of the $C_{2-8}$ acylamino group substituted with 1 to 3 halogen atoms in $R^{2E}$ or $R^{3E}$ include a trifluoromethylcarbonylamino group.

Examples of the $C_{1-8}$ alkylsulfonylamino group of $R^{2E}$ or $R^{3E}$ include a methylsulfonylamino group.

Examples of the $C_{2-8}$ acyl group of $R^{2E}$ or $R^{3E}$ include an acetyl group.

Examples of the alkoxycarbonyl group (the number of carbon atoms in an alkoxy moiety is from 1 to 8) of $R^{2E}$ or $R^{3E}$ include a methoxycarbonyl group or an ethoxycarbonyl group.

Examples of the $C_{1-8}$ alkylthio group of $R^{2E}$ or $R^{3E}$ include a methylthio group.

Examples of the $C_{1-8}$ alkylsulfinyl group of $R^{2E}$ or $R^{3E}$ include a methylsulfinyl group.

Examples of the $C_{1-8}$ alkylsulfonyl group of $R^{2E}$ or $R^{3E}$ include a methylsulfonyl group.

Examples of

[Chem. 64]

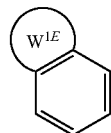

include naphthalene or tetrahydronaphthalene.

The optionally substituted heterocyclic ring of $W^{2E}$ represents a 5- or 6-membered heterocyclic ring comprising 1 to 4 atoms of nitrogen as a ring constituent element.

Examples of the optionally substituted heterocyclic ring of $W^{2E}$ include tetrazole, 1,2,4-triazole, 1,2,3-triazole, 1,2,4-oxadiazole, pyrazole, imidazole, oxazole, isoxazole, pyrrole, thiazole, pyridine, or pyrrolidine.

Examples of an optional substituent of the optionally substituted heterocyclic ring of $W^{2E}$ include a $C_{1-8}$ alkyl group such as a methyl or ethyl group, a $C_{1-8}$ alkyl group substituted with 1 to 3 halogen atoms such as a trifluoromethyl group, a halogen atom such as a fluorine atom, a cyano group, an oxo group, or a thioxo group.

In general formula (EI), 1 to 3 $R^{2E}$ or $R^{3E}$ substituents, which are the same or different, may be present, in a ring having the $R^{2E}$ or $R^{3E}$ substituents.

The following compounds are preferable as compounds represented by general formula (EI).

(E-1-1) A compound described in (E-1), wherein $W^{2E}$ is a 5- or 6-membered heterocyclic ring comprising 1 to 4 atoms of nitrogen as a ring constituent element.

(E-1-2) A compound described in (E-1) or (E-1-1), wherein $W^{2E}$ is tetrazole, 1,2,4-triazole, 1,2,3-triazole, 1,2,4-oxadiazole, pyrazole, or imidazole optionally having a substituent selected from a $C_{1-8}$ alkyl group, a $C_{1-8}$ alkyl group substituted with 1 to 3 halogen atoms, a halogen atom, a cyano group, an oxo group, or a thioxo group.

(E-1-3) A compound described in (E-1) or any of (E-1-1) to (E-1-2), wherein $W^{2E}$ is tetrazole, 1,2,4-triazole, or 1,2,3-triazole optionally having a substituent selected from a $C_{1-8}$ alkyl group, a $C_{1-8}$ alkyl group substituted with 1 to 3 halogen atoms, a halogen atom, or a cyano group.

(E-1-4) A compound described in (E-1) or any of (E-1-1) to (E-1-3), wherein $W^{2E}$ is 5-oxo-1,2,4-oxadiazole or 5-thioxo-1,2,4-oxadiazole.

(E-1-5) A compound described in (E-1) or any of (E-1-1) to (E-1-4), wherein $W^{2E}$ is tetrazole.

(E-1-6)

A compound described in (E-1) or any of (E-1-1) to (E-1-5), wherein

[Chem. 65]

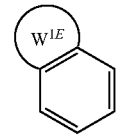

is naphthalene or tetrahydronaphthalene.

(E-1-7)

A compound described in (E-1) or any of (E-1-1) to (E-1-6), wherein

[Chem. 66]

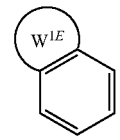

is naphthalene.

(E-1-8) A compound described in (E-1) or any of (E-1-1) to (E-1-7), wherein $R^{1E}$ is a hydrogen atom or a $C_{1-8}$ alkyl group.

(E-1-9) A compound described in (E-1) or any of (E-1-1) to (E-1-8), wherein $R^{1E}$ is a hydrogen atom.

(E-1-10) A compound described in (E-1) or any of (E-1-1) to (E-1-9), wherein $R^{4E}$ is a hydrogen atom and $R^{5E}$ is a hydrogen atom or a $C_{1-8}$ alkyl group.

(E-1-11) A compound described in (E-1) or any of (E-1-1) to (E-1-10), wherein both $R^{4F}$ and $R^{5E}$ are a hydrogen atom.

(E-1-12) A compound described in (E-1) or any of (E-1-1) to (E-1-11), wherein $R^{2E}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a carboxyl group, a $C_{2-8}$ acyl group, or an alkoxycarbonyl group (the number of carbon atoms in an alkoxy moiety is from 1 to 8).

(E-1-13) A compound described in (E-1) or any of (E-1-1) to (E-1-12), wherein $R^{2E}$ is a hydrogen atom.

(E-1-14) A compound described in (E-1) or any of (E-1-1) to (E-1-13), wherein $R^{3E}$ is a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a carboxyl group, a $C_{2-8}$ acyl group, or an alkoxycarbonyl group (the number of carbon atoms in an alkoxy moiety is from 1 to 8).

(E-1-15) A compound described in (E-1) or any of (E-1-1) to (E-1-14), wherein $R^{3E}$ is a hydrogen atom.

(E-1-16) A compound described in (E-1) or any of (E-1-1) to (E-1-15), wherein $X^E$ is N, $Y^E$ is C=O, and the double line composed of a solid line and a dashed line denotes a single bond.

(E-1-17) A compound described in (E-1) or any of (E-1-1) to (E-1-15), wherein $X^E$ is C, $Y^E$ is N, and the double line composed of a solid line and a dashed line denotes a double bond.

(E-1-18) A compound described in (E-1) or any of (E-1-1) to (E-1-17), wherein $P^E$ is 0 r 1.

(E-1-19) A compound described in (E-1) or any of (E-1-1) to (E-1-18), wherein $P^E$ is 1.

<Representative Compound E-100>

The following shows representative compounds included in general formula (EI).

[Chem. 67]

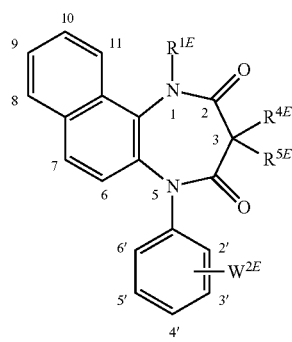

$R^{1E}$, $R^{4E}$, $R^{5E}$, and $W^{2E}$, and $W^{2E}$ substitution positions are as described in Tables 55 to 57.

In Tables 55 to 57, each $W^{2E}$ substitution position indicates a substitution position on a benzene ring. Specifically, positions 2, 3, and 4 in the tables correspond to positions 2', 3', and 4', respectively, in the formula of representative compound E-100.

TABLE 55

| $R^{1E}$ | $W^{2E}$ SUBSTITUTION POSITION | $W^{2E}$ | $R^{4E}/R^{5E}$ |
|---|---|---|---|
| H | 2- | 1H-Tetrazol-5-yl | H/H |
| H | 3- | 1H-Tetrazol-5-yl | H/H |
| H | 3- | (1-Methyl-1H-tetrazol)-5-yl | H/H |
| H | 4- | 1H-Tetrazol-5-yl | H/H |
| Me | 3- | 1H-Tetrazol-5-yl | H/H |
| Me | 3- | 1H-Tetrazol-5-yl | Me/H |
| Bn | 3- | 1H-Tetrazol-5-yl | H/H |
| H | 3- | 1H-Tetrazol-1-yl | H/H |
| H | 3- | 1H-Tetrazol-1-yl | Me/Me |
| H | 3- | (1,2,3-Triazol)-5-yl | H/H |
| H | 3- | (1,2,4-Triazol)-3-yl | H/H |
| H | 4- | (1,2,4-Triazol)-3-yl | H/H |

TABLE 56

| $R^{1E}$ | $W^{2E}$ SUBSTITUTION POSITION | $W^{2E}$ | $R^{4E}/R^{5E}$ |
|---|---|---|---|
| H | 2- | (1,2,4-Triazol)-1-yl | H/H |
| H | 3- | (1,2,4-Triazol)-1-yl | H/H |
| H | 3- | [5-(Trifluoromethyl)-1,2,4-triazol]-3-yl | H/H |
| H | 3- | [5-(Trifluoromethyl)-1,2,4-triazol]-3-yl | Et/H |
| H | 3- | [5-Fluoro-1,2,3-triazol]-4-yl | H/H |
| H | 3- | [5-Fluoro-1,2,3-triazol]-4-yl | Me/Me |
| H | 3- | [5-Cyano-1,2,3-triazol]-4-yl | H/H |
| H | 4- | 1H-Imidazol-1-yl | H/H |
| H | 4- | 1H-Imidazol-1-yl | Pr/H |
| H | 3- | 1H-Imidazol-2-yl | H/H |
| H | 3- | 1H-Imidazol-4-yl | H/H |
| H | 3- | Imidazolin-2-yl | H/H |

TABLE 57

| $R^{1E}$ | $W^{2E}$ SUBSTITUTION POSITION | $W^{2E}$ | $R^{4E}/R^{5E}$ |
|---|---|---|---|
| H | 2- | Pyrazol-3-yl | H/H |
| H | 3- | Pyrazol-4-yl | H/H |
| H | 3- | Pyrazol-5-yl | Me/H |
| H | 3- | (1,2,4-Oxadiazol)-3-yl | H/H |
| H | 3- | (1,3,4-Oxadiazol)-2-yl | H/H |
| H | 3- | (5-Oxo-1,2,4-oxadiazol)-3-yl | H/H |
| H | 3- | Pyrrol-1-yl | H/H |
| H | 4- | Pyrrolidin-2-yl | H/H |
| Me | 4- | Pyrrolidin-2-yl | Me/H |
| H | 4- | (1,3-Oxazol)-5-yl | H/H |
| H | 3- | (1,3-Oxazol)-5-yl | H/H |
| H | 2- | (1,3-Thiazol)-5-yl | H/H |

<Representative Compound E-200>

[Chem. 68]

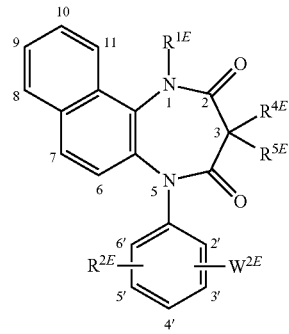

<Representative Compound E-300>

[Chem. 69]

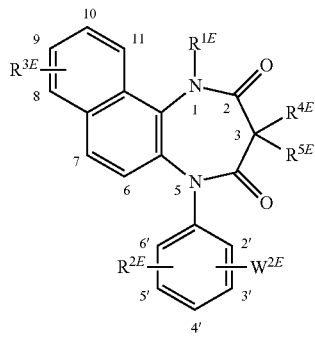

wherein $R^{1E}$, $R^{2E}$, $R^{4E}$, $R^{5E}$, and $W^{2E}$, and $W^{2E}$ substitution positions are as described in Tables 58 and 59.

In Tables 58 and 59, each $W^{2E}$ substitution position indicates a substitution position on a benzene ring. Specifically, positions 2, 3, and 4 in the tables correspond to positions 2', 3', and 4', respectively, in the formula of representative compound E-200.

wherein $R^{1E}$, $R^{2E}$, $R^{3E}$, $R^{4E}$, $R^{5E}$, and $W^{2E}$, and $W^{2E}$ substitution positions are as described in Tables 60 and 61.

In Tables 60 and 61, each $W^{2E}$ substitution position indicates a substitution position on a benzene ring. Specifically, positions 3 and 4 in the tables correspond to positions 3' and 4', respectively, in the formula of representative compound E-300.

TABLE 58

| $R^{1E}$ | $R^{2E}$ | $W^{2E}$ substitution position | $W^{2E}$ | $R^{4E}/R^{5E}$ |
|---|---|---|---|---|
| H | 4-OH | 3- | 1H-Tetrazol-5-yl | H/H |
| H | 4-OMe | 3- | 1H-Tetrazol-5-yl | H/H |
| Me | 2-Cl | 3- | 1H-Tetrazol-5-yl | H/H |
| H | 2,6-Cl | 3- | 1H-Tetrazol-5-yl | H/H |
| H | 4-F | 3- | 1H-Tetrazol-5-yl | H/H |
| H | 4-Br | 3- | 1H-Tetrazol-5-yl | Et/H |
| H | 3-OMe | 4- | (1-Methyl-1H-tetrazol)-5-yl | H/H |
| H | 4-Me | 3- | 1H-Tetrazol-5-yl | H/H |

TABLE 59

| $R^{1E}$ | $R^{2E}$ | $W^{2E}$ substitution position | $W^{2E}$ | $R^{4E}/R^{5E}$ |
|---|---|---|---|---|
| H | 4-Cl | 3- | (1,2,3-Triazol)-5-yl | Me/H |
| H | 4-CF$_3$ | 3- | (1,2,3-Triazol)-5-yl | H/H |
| H | 3-SMe | 4- | (1,2,4-Triazol)-1-yl | H/H |
| H | 3-SO$_2$Me | 4- | 1H-Imidazol-1-yl | H/H |
| H | 3-NHSO$_2$Me | 4- | 1H-Imidazol-1-yl | H/H |
| H | 4-OMe | 3- | 1H-Imidazol-4-yl | H/H |
| H | 4-F | 2- | Pyrazol-3-yl | H/H |

TABLE 60

| $R^{1E}$ | $R^{2E}$ | $W^{2E}$ substitution position | $W^{2E}$ | $R^{3E}$ | $R^{4E}/R^{5E}$ |
|---|---|---|---|---|---|
| H | H | 3- | 1H-Tetrazol-5-yl | 9-Br | H/H |
| H | 4-OMe | 3- | 1H-Tetrazol-5-yl | 9-Cl | H/H |
| H | 4-OH | 3- | 1H-Tetrazol-5-yl | 10-OMe | H/H |
| H | 2-Cl | 3- | 1H-Tetrazol-5-yl | 9-Br | H/H |
| H | 2,6-Cl | 3- | 1H-Tetrazol-5-yl | 9-Me | H/H |
| H | H | 3- | 1H-Tetrazol-5-yl | 10-Cl | Me/H |
| H | 3-OMe | 4- | (1-Methyl-1H-tetrazol)-5-yl | 9-CF$_3$ | H/H |

TABLE 61

| $R^{1E}$ | $R^{2E}$ | $W^{2E}$ substitution position | $W^{2E}$ | $R^{3E}$ | $R^{4E}/R^{5E}$ |
|---|---|---|---|---|---|
| H | 4-Me | 3- | 1H-Tetrazol-1-yl | 9-CN | Pr/H |
| Me | H | 3- | (1,2,3-Triazol)-5-yl | 9-OH | H/H |
| Et | H | 3- | (1,2,3-Triazol)-5-yl | 10-F | H/H |
| H | 3-Br | 4- | (1,2,4-Triazol)-1-yl | 9-SMe | H/H |
| Allyl | H | 4- | 1H-Imidazol-1-yl | 8-OMe | H/H |
| H | H | 3- | 1H-Imidazol-1-yl | 10-OMe | Me/Me |

<Representative Compound E-400>

[Chem. 70]

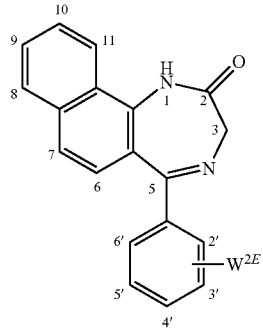

wherein $W^{2E}$ and $W^{2E}$ substitution positions are as described in Table 62.

In Table 62, each $W^{2E}$ substitution position indicates a substitution position on a benzene ring. Specifically, positions 3 and 4 in the table correspond to positions 3' and 4', respectively, in the formula of representative compound E-400.

TABLE 62

| $W^{2E}$ substitution position | $W^{2E}$ |
|---|---|
| 3- | 1H-Tetrazol-5-yl |
| 4- | 1H-Tetrazol-5-yl |
| 3- | 5-Thioxo-1,2,4-oxadiazol-3-yl |

<Representative Compound E-500>

[Chem. 71]

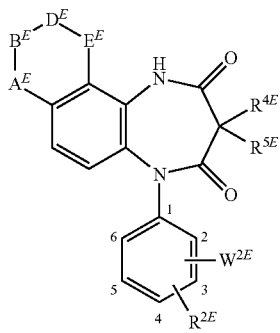

wherein $A^E$-$B^E$-$D^E$-$E^E$, $R^{4E}/R^{5E}$, $W^{2E}$, and $R^{2E}$ are as described in Tables 63 to 65; and the "Position" in the tables indicates a $W^{2E}$ substitution position.

TABLE 63

| $A^E$-$B^E$-$D^E$-$E^E$ | $R^{4E}/R^{5E}$ | Position | $W^{2E}$ | $R^{2E}$ |
|---|---|---|---|---|
| CH$_2$CH$_2$CH$_2$CH$_2$ | H/H | 3 | 1H-Tetrazol-5-yl | H |
| C(CH$_3$)$_2$CH$_2$CH$_2$CH$_2$ | H/H | 3 | 1H-Tetrazol-5-yl | H |
| C(CH$_3$)$_2$CH$_2$CH$_2$CH$_2$ | H/H | 3 | 1H-Tetrazol-1-yl | 4-F |
| C(CH$_3$)$_2$CH$_2$CH$_2$C(CH$_3$)$_2$ | H/H | 3 | 2-Methyl-2H-tetrazol-5-yl | 3-F |
| CH$_2$CH$_2$C(CH$_3$)$_2$CH$_2$ | H/H | 3 | 1,2,3-Triazol-5-yl | 2-F |
| CH$_2$CH$_2$CH$_2$CH$_2$ | H/H | 3 | 1,2,4-Triazol-3-yl | H |

TABLE 63-continued

| $A^E$-$B^E$-$D^E$-$E^E$ | $R^{4E}/R^{5E}$ | Position | $W^{2E}$ | $R^{2E}$ |
|---|---|---|---|---|
| C(CH$_3$)$_2$CH$_2$CH$_2$C(CH$_3$)$_2$ | H/H | 3 | 1-Methyl-1H-tetrazoll-5-yl | H |
| CH$_2$CH$_2$CH$_2$CH$_2$ | Me/H | 3 | Pyrazol-3-yl | 4-OH |
| CH$_2$CH$_2$CH$_2$CH$_2$ | Me/Me | 3 | Pyrazol-4-yl | H |

TABLE 64

| $A^E$-$B^E$-$D^E$-$E^E$ | $R^{4E}/R^{5E}$ | Position | $W^{2E}$ | $R^{2E}$ |
|---|---|---|---|---|
| C(CH$_3$)$_2$CH$_2$CH$_2$CH$_2$ | H/H | 3 | 5-Oxo-1,2,4-oxadiazol-3-yl | 4-NH$_2$ |
| CH$_2$C(CH$_3$)$_2$CH$_2$CH$_2$ | CF$_3$/H | 3 | 1,2,4-Oxadiazol-3-yl | H |
| CH$_2$CH$_2$C(CH$_3$)$_2$CH$_2$ | H/H | 3 | 1,3,4-Oxadiazol-2-yl | 4-F |
| CH$_2$CH$_2$CH$_2$CH$_2$ | H/H | 4 | Pyrrol-1-yl | 3-F |
| C(CH$_3$)$_2$CH$_2$CH$_2$C(CH$_3$)$_2$ | H/H | 3 | 5-Chloro-1H-imidazol-2-yl | 4-OH |

TABLE 65

| $A^E$-$B^E$-$D^E$-$E^E$ | $R^{4E}/R^{5E}$ | Position | $W^{2E}$ | $R^{2E}$ |
|---|---|---|---|---|
| CH$_2$CH$_2$CH$_2$CH$_2$ | Me/H | 4 | 5-Methyl-1H-imidazol-2-yl | 4-NH$_2$ |
| CH$_2$CH$_2$CH$_2$CH$_2$ | Me/H | 4 | 5-Amino-1H-imidazol-2-yl | 3-F |
| CH$_2$CH$_2$CH$_2$CH$_2$ | Me/H | 3 | 2-Ethyl-2H-tetrazol-5-yl | H |
| C(CH$_3$)$_2$CH$_2$CH$_2$CH$_2$ | Pr/H | 3 | 2-(2,2,2-Trifluoroethyl)-2H-tetrazol-5-yl | 2,6-F |
| CH$_2$C(CH$_3$)$_2$CH$_2$CH$_2$ | H/H | 3 | 1,3-Oxazol-2-yl | H |
| CH$_2$CH$_2$C(CH$_3$)$_2$CH$_2$ | H/H | 3 | 1,3-Thiazol-2-yl | H |
| CH$_2$CH$_2$CH$_2$CH$_2$ | H/H | 4 | 3,5-Dimethylisoxazol-4-yl | H |

<Representative Compound E-600>

[Chem. 72]

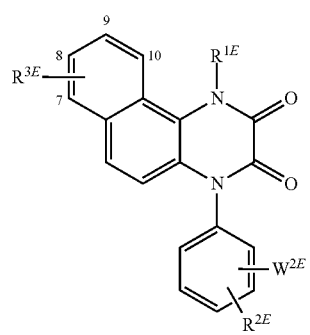

wherein $R^{3E}$, $R^{1E}$, $W^{2E}$, and $R^{2E}$ are as described in Tables 66 to 68; and the "$W^{2E}$ position" in the tables indicates a $W^{2E}$ substitution position on a benzene ring.

TABLE 66

| $R^{3E}$ | $R^{1E}$ | $W^{2E}$ position | $W^{2E}$ | $R^{2E}$ |
|---|---|---|---|---|
| H | H | 3 | 1H-Tetrazol-5-yl | H |
| H | H | 4 | 1H-Tetrazol-5-yl | H |
| 8-Me | H | 3 | 1H-Tetrazol-5-yl | H |
| 8-Cl | H | 3 | 1H-Tetrazol-5-yl | H |

TABLE 66-continued

| R$^{3E}$ | R$^{1E}$ | W$^{2E}$ position | W$^{2E}$ | R$^{2E}$ |
|---|---|---|---|---|
| H | H | 3 | 1H-Tetrazol-5-yl | 4-F |
| H | H | 3 | 1H-Tetrazol-5-yl | 4-Me |
| H | H | 3 | 1H-Tetrazol-5-yl | 5-Br |
| H | H | 3 | 1H-Tetrazol-5-yl | 6-Me |
| H | H | 3 | 1H-Tetrazol-5-yl | 6-Cl |
| H | H | 3 | (5-Thioxo-1,2,4-oxadiazol)-3-yl | H |
| H | H | 3 | (5-Oxo-1,2,4-oxadiazol)-3-yl | H |
| H | H | 3 | (5-Cyano-1H-1,2,3-triazol)-4-yl | H |

TABLE 67

| R$^{3E}$ | R$^{1E}$ | W$^{2E}$ position | W$^{2E}$ | R$^{2E}$ |
|---|---|---|---|---|
| H | H | 3 | 1H-Tetrazol-5-yl | 6-OH |
| H | H | 3 | (2-Methyl-2H-tetrazol)-5-yl | H |
| H | Me | 3 | (2-Methyl-2H-tetrazol)-5-yl | H |
| H | Et | 3 | (2-Ethyl-2H-tetrazol)-5-yl | H |
| H | H | 3 | (1-Methyl-1H-tetrazol)-5-yl | H |
| H | H | 3 | 4-Methyl-(5-thioxo-1,2,4-oxadiazol)-3-yl | H |
| H | H | 3 | 1-Methyl-1H-imidazol-2-yl | H |
| H | H | 3 | 1-Methyl-1H-imidazol-4-yl | H |
| H | H | 3 | 1,3-Oxazol-2-yl | H |
| H | H | 3 | 1,3-Thiazol-2-yl | H |
| H | H | 3 | Pyrrol-2-yl | H |
| H | H | 3 | Thiophen-2-yl | H |
| H | H | 3 | 1-H-Imidazol-2-yl | H |
| H | H | 3 | 1-H-Imidazol-4-yl | H |

TABLE 68

| R$^{3E}$ | R$^{1E}$ | W$^{2E}$ position | W$^{2E}$ | R$^{2E}$ |
|---|---|---|---|---|
| H | H | 3 | Pyrazol-4-yl | H |
| H | H | 3 | 5-(Chloro)-1H-imidazol-2-yl | H |
| H | H | 3 | 5-(Trifluoromethyl)-1H-imidazol-2-yl | H |
| H | H | 3 | (1,2,3-Triazol)-4-yl | H |
| H | H | 3 | (1,2,4-Triazol)-3-yl | H |
| H | H | 3 | 3-Methyl-(1,2,4-oxadiazol)-5-yl | H |
| H | H | 3 | 3,5-Dimethylisoxazol-4-yl | H |
| H | H | 3 | 1-Tetrazol-1-yl | H |
| H | H | 3 | Pyridin-3-yl | H |
| H | H | 3 | Pyrimidin-5-yl | H |
| H | H | 3 | 2-Aminopyridin-5-yl | H |

<Representative Compound E-700>

[Chem. 73]

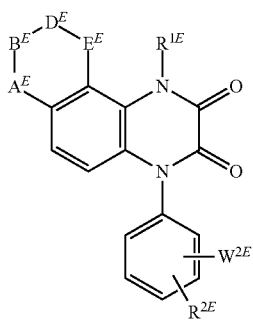

wherein A$^E$-B$^E$-D$^E$-E$^E$, R$^{1E}$, W$^{2E}$, and R$^{2E}$ are as described in Tables 69 to 71; and the "W$^{2E}$ position" in the tables indicates a W$^{2E}$ substitution position on a benzene ring.

TABLE 69

| A$^E$-B$^E$-D$^E$-E$^E$ | R$^{1E}$ | W$^{2E}$ position | W$^{2E}$ | R$^{2E}$ |
|---|---|---|---|---|
| CH$_2$CH$_2$CH$_2$CH$_2$ | H | 3 | 1H-Tetrazol-5-yl | H |
| CH$_2$CH$_2$CH$_2$CH$_2$ | H | 4 | 1H-Tetrazol-5-yl | H |
| CH$_2$NHCH$_2$CH$_2$ | H | 3 | 1H-Tetrazol-5-yl | H |
| CH$_2$CH$_2$OCH$_2$ | H | 3 | 1H-Tetrazol-5-yl | 4-F |
| CH$_2$CH$_2$CH$_2$CH$_2$ | H | 3 | 1H-Tetrazol-5-yl | 4-Me |
| CH$_2$CH$_2$CH$_2$CH$_2$ | H | 3 | 1H-Tetrazol-5-yl | 5-Br |
| CH$_2$CH$_2$CH$_2$CH$_2$ | H | 3 | 1H-Tetrazol-5-yl | 6-Me |
| CH$_2$CH$_2$CH$_2$CH$_2$ | H | 3 | 1H-Tetrazol-5-yl | 6-Cl |
| CH$_2$CH$_2$CH$_2$CH$_2$ | H | 3 | (5-Thioxo-1,2,4-oxadiazol)-3-yl | H |
| CH$_2$CH$_2$CH$_2$CH$_2$ | H | 4 | (5-Oxo-1,2,4-oxadiazol)-3-yl | H |

TABLE 70

| A$^E$-B$^E$-D$^E$-E$^E$ | R$^{1E}$ | W$^{2E}$ position | W$^{2E}$ | R$^{2E}$ |
|---|---|---|---|---|
| CH$_2$CH$_2$CH$_2$CH$_2$ | H | 3 | (5-Cyano-1H-1,2,3-triazol)-4-yl | H |
| CH$_2$CH$_2$CH$_2$CH$_2$ | H | 3 | 1H-Tetrazol-5-yl | 6-OH |
| CH$_2$CH$_2$CH$_2$CH$_2$ | H | 3 | (2-Methyl-2H-tetrazol)-5-yl | H |
| CH$_2$CH$_2$CH$_2$CH$_2$ | Me | 3 | (2-Methyl-2H-tetrazol)-5-yl | H |
| CH$_2$CH$_2$CH$_2$CH$_2$ | Et | 3 | (2-Ethyl-2H-tetrazol)-5-yl | H |
| CH$_2$NHCH$_2$CH$_2$ | H | 3 | (1-Methyl-1H-tetrazol)-5-yl | H |
| CH$_2$CH$_2$CH$_2$CH$_2$ | H | 3 | 4-Methyl-(5-thioxo-1,2,4-oxadiazol)-3-yl | H |
| CH$_2$CH$_2$CH$_2$CH$_2$ | H | 3 | 1-Methyl-1H-imidazol-2-yl | H |
| CH$_2$CH$_2$CH$_2$CH$_2$ | H | 3 | 1-Methyl-1H-imidazol-4-yl | H |
| CH$_2$CH$_2$CH$_2$CH$_2$ | H | 3 | 1,3-Oxazol-2-yl | H |
| CH$_2$CH$_2$CH$_2$CH$_2$ | H | 3 | 1,3-Thiazol-2-yl | H |
| CH$_2$CH$_2$CH$_2$CH$_2$ | H | 3 | Pyrrol-2-yl | H |
| CH$_2$CH$_2$CH$_2$CH$_2$ | H | 3 | Thiophen-2-yl | H |

TABLE 71

| A$^E$-B$^E$-D$^E$-E$^E$ | R$^{1E}$ | W$^{2E}$ position | W$^{2E}$ | R$^{2E}$ |
|---|---|---|---|---|
| CH$_2$CH$_2$CH$_2$CH$_2$ | H | 3 | 1-H-Imidazol-2-yl | H |
| CH$_2$CH$_2$CH$_2$CH$_2$ | H | 3 | 1-H-Imidazol-4-yl | H |
| CH$_2$CH$_2$CH$_2$CH$_2$ | H | 4 | Pyrazol-4-yl | H |
| CH$_2$CH$_2$CH$_2$CH$_2$ | H | 3 | 5-(Chloro)-1H-imidazol-2-yl | H |
| CH$_2$CH$_2$CH$_2$CH$_2$ | H | 3 | 5-(Trifluoromethyl)-1H-imidazol-2-yl | H |
| CH$_2$CH$_2$CH$_2$CH$_2$ | H | 3 | (1,2,3-Triazol)-4-yl | H |
| CH$_2$CH$_2$CH$_2$CH$_2$ | H | 3 | (1,2,4-Triazol)-3-yl | H |
| CH$_2$CH$_2$CH$_2$CH$_2$ | H | 3 | 3-Methyl-(1,2,4-oxadiazol)-5-yl | H |
| CH$_2$CH$_2$CH$_2$CH$_2$ | H | 4 | 3,5-Dimethylisoxazol-4-yl | H |
| CH$_2$CH$_2$CH$_2$CH$_2$ | H | 3 | 1-Tetrazol-1-yl | H |
| CH$_2$CH$_2$CH(Me)CH$_2$ | H | 3 | Pyrimidin-5-yl | H |

<Representative Compound E-800>

[Chem. 74]

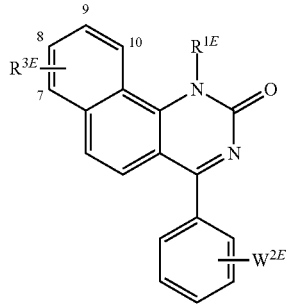

wherein $R^{3E}$, $R^{1E}$, and $W^{2E}$ are as described in Table 72.

TABLE 72

| $R^{3E}$ | $R^{1E}$ | $W^{2E}$ |
|---|---|---|
| H | H | 1H-Tetrazol-5-yl |
| H | H | 1H-Tetrazol-1-yl |
| H | H | (2-Methyl-2H-tetrazol)-5-yl |
| H | H | 1,3-Oxazol-2-yl |
| H | H | 1-H-Imidazol-2-yl |
| H | H | (1,2,4-Triazol)-3-yl |

<Representative Compound E-900>

[Chem. 75]

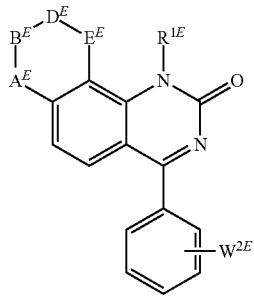

wherein $A^E$-$B^E$-$D^E$-$E^E$, $R^{1E}$, and $W^{2E}$ are as described in Table 73.

TABLE 73

| $A^E$-$B^E$-$D^E$-$E^E$ | $R^{1E}$ | $W^{2E}$ |
|---|---|---|
| CH$_2$CH$_2$CH$_2$CH$_2$ | H | 1H-Tetrazol-5-yl |
| CH$_2$CH(Me)CH$_2$CH$_2$ | H | (2-Methyl-2H-tetrazol)-5-yl |
| CH$_2$CH(Me)CH$_2$CH$_2$ | H | 1,3-Oxazol-2-yl |
| CH$_2$CH$_2$CH(Me)CH$_2$ | H | 1-H-Imidazol-2-yl |
| CH$_2$CH$_2$CH(Me)CH$_2$ | H | (1,2,4-Triazol)-3-yl |

(F-1) A compound, a tautomer, stereoisomer, or pharmaceutically acceptable salt of the compound, or a hydrate or solvate thereof, the compound represented by the following general formula (FI):

[Chem. 76]

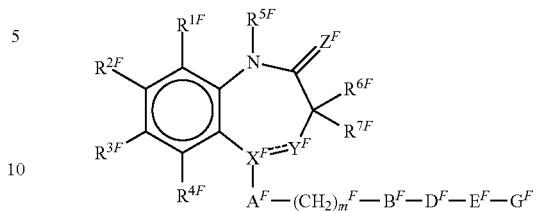

(FI)

wherein $R^{1F}$ and $R^{2F}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), an optionally substituted phenyl group, an optionally substituted pyridyl group, or an aralkyl group (the number of carbon atoms in an aryl moiety is from 6 to 10 and the number of carbon atoms in an alkylene moiety is from 1 to 8), or $R^{1F}$ and $R^{2F}$ are optionally fused with a benzene ring bonded thereto to form a condensed ring selected from a naphthalene ring, a quinoline ring, an isoquinoline ring, a tetrahydronaphthalene ring, an indane ring, a tetrahydroquinoline ring, or tetrahydroisoquinoline ring and a ring fused with $R^{1F}$ and $R^{2F}$ and comprising carbon atoms bonded to respective $R^{1F}$ and $R^{2F}$ is optionally substituted with 1 to 4 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{3F}$ and $R^{4F}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{5F}$ represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $R^{6F}$ and $R^{7F}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, or an amino group, $X^F$ represents C, CH, or N, $Y^F$ represents N, NH, or C(=O), provided that when $X^F$ is N, $Y^F$ is neither N nor NH, and when $X^F$ is C or CH, $Y^F$ is not C(=O), a double line composed of a solid line and a dashed line denotes a single bond or a double bond, $Z^F$ represents an oxygen atom or a sulfur atom, $A^F$ represents a bond or represents a benzene ring, a pyridine ring, a thiophene ring, a pyrimidine ring, a naphthalene ring, a quinoline ring, or an indole ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, an aralkyl group (the number of carbon atoms in an aryl moiety is from 6 to 10 and the number of carbon atoms in an alkylene moiety is from 1 to 8), a phenyl group, or a pyridyl group, $B^F$ represents $N(R^{8F})C(=O)$, NHCONH, $CON(R^{9F})$, NHC(=S)NH, $N(R^{10F})SO_2$, $SO_2N(R^{11F})$, or $OSO_2$, $R^{8F}$, $R^{9F}$, $R^{10F}$, and $R^{11F}$ here represent a hydrogen atom, a $C_{1-8}$ alkyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $D^F$ represents a bond or a $C_{1-6}$ alkylene chain optionally having, as substituents, 1 to 4 substituents, which are the same or different, selected from a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8) and further optionally having a double bond, $E^F$ represents O, S, $NR^{12F}$, or a bond, $R^{12F}$ here represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $G^F$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine or pyrimidine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, a $C_{1-6}$ alkylsulfonyl group, an aralkyl group (the number of carbon atoms in an aryl moiety is from 6 to 10 and the number of carbon atoms in an alkylene moiety is from 1 to 8), an optionally substituted phenyl, an optionally substituted pyridyl group, an optionally substituted imidazolyl group, an optionally substituted oxazolyl group, or an optionally substituted thiazolyl group, and $m^F$ represents an integer of 0 to 5, provided that a case is excluded where $R^{1F}$ and $R^{2F}$ are not fused to form a ring and where $X^F$ is C, $Y^F$ is N, the double line composed of a solid line and a dashed line denotes a double bond, $Z^F$ is an oxygen atom, $A^F$ is a benzene ring, $m^F$ is 0, $B^F$ is C(=O)NH, $E^F$ is a bond, and $G^F$ is a phenyl group.

(F-2) A compound, a tautomer, stereoisomer, or pharmaceutically acceptable salt of the compound, or a hydrate or solvate thereof, the compound represented by the following general formula (FII):

[Chem. 77]

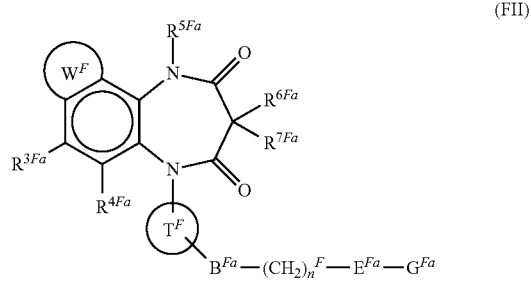

(FII)

wherein

[Chem. 78]

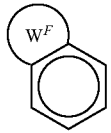

represents a naphthalene ring, a quinoline ring, an isoquinoline ring, a tetrahydronaphthalene ring, an indane ring, a tetrahydroquinoline ring, or a tetrahydroisoquinoline ring, the rings are optionally substituted with 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{3Fa}$ and $R^{4Fa}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{5Fa}$ represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $R^{6Fa}$ and $R^{7Fa}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, or an amino group,

[Chem. 79]

represents a benzene ring, a pyridine ring, a thiophene ring, a pyrimidine ring, a naphthalene ring, a quinoline ring, or an indole ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, an aralkyl group (the number of carbon atoms in an aryl moiety is from 6 to 10 and the number of carbon atoms in an alkylene moiety is from 1 to 8), a phenyl group, or a pyridyl group, $B^{Fa}$ represents $N(R^{8Fa})C(=O)$, $NHCONH$, $CON(R^{9Fa})$, $NHC(=S)NH$, $N(R^{10Fa})SO_2$, $SO_2N(R^{11Fa})$, or $OSO_2$, $R^{8Fa}$, $R^{9Fa}$, $R^{10Fa}$, and $R^{11Fa}$ here represent a hydrogen atom, a $C_{1-8}$ alkyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $E^{Fa}$ represents O, S, $NR^{12Fa}$, or a bond, $R^{12Fa}$ here represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $G^{Fa}$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine or pyrimidine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, a $C_{1-6}$ alkylsulfonyl group, an aralkyl group (the number of carbon atoms in an aryl moiety is from 6 to 10 and the number of carbon atoms in an alkylene moiety is from 1 to 8), an optionally substituted phenyl, an optionally substituted pyridyl group, an optionally substituted imidazolyl group, an optionally substituted oxazolyl group, or an optionally substituted thiazolyl group, and $n^F$ represents an integer of 0 to 5.

Next, the present invention will be described in detail.

As used herein, examples of the $C_{1-8}$ alkyl group include a methyl, ethyl, propyl, isopropyl, butyl, i-butyl, t-butyl, pentyl, or hexyl group.

Examples of the $C_{3-8}$ cycloalkyl group include a cyclopropyl group or a cyclohexyl group.

Examples of the $C_{2-8}$ alkenyl group include an allyl group.

Examples of the $C_{1-8}$ alkoxy group include a methoxy, ethoxy, propoxy, isopropoxy, butoxy, i-butoxy, t-butoxy, pentyloxy, or hexyloxy group.

Examples of the $C_{1-8}$ alkyl group substituted with 1 to 3 halogen atoms include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the $C_{1-8}$ alkoxy group substituted with 1 to 3 halogen atoms include a methoxy, ethoxy, propoxy, isopropoxy, butoxy, or t-butoxy group substituted with 1 to 3 halogen atoms such as fluorine, chlorine, or bromine atoms, and preferably a trifluoromethoxy, chloromethoxy, 2-chloroethoxy, 2-bromoethoxy, or 2-fluoroethoxy group.

Examples of the halogen atom include a fluorine, chlorine, or bromine atom.

Examples of the $C_{1-8}$ alkylamino group include a methylamino or ethylamino group.

Examples of the $C_{2-8}$ dialkylamino group include a dimethylamino or diethylamino group.

Examples of the $C_{2-8}$ acylamino group include an acetylamino group.

Examples of the $C_{2-8}$ acyl group include an acetyl group.

Examples of the alkoxycarbonyl group (the number of carbon atoms in an alkoxy moiety is from 1 to 8) include a methoxycarbonyl group.

Examples of the aralkyl group (the number of carbon atoms in an aryl moiety is from 6 to 10 and the number of carbon atoms in an alkylene moiety is from 1 to 8) include a benzyl group.

Examples of the hydroxyl-substituted $C_{1-8}$ alkyl group include 2-hydroxyethyl group.

Examples of the $C_{1-6}$ alkylsulfinyl group include a methanesulfinyl group.

Examples of the $C_{1-6}$ alkylthio group include a methylthio group.

Examples of the $C_{1-6}$ alkylsulfonyl group include a methanesulfonyl group.

Examples of an optional substituent of the optionally substituted phenyl group, optionally substituted pyridyl group, optionally substituted imidazolyl group, optionally substituted oxazolyl group, or optionally substituted thiazolyl group include a halogen atom, a $C_{1-8}$ alkyl group, a $C_{1-8}$ alkoxy group, a $C_{1-8}$ alkyl group substituted with 1 to 3 halogen atoms, or a $C_{1-8}$ alkoxy group substituted with 1 to 3 halogen atoms.

The following compounds are preferable as compounds represented by general formula (FI).

(F-1-1)

A compound, a tautomer, stereoisomer, or pharmaceutically acceptable salt of the compound, or a hydrate or solvate thereof, the compound represented by (F-1), wherein $R^{1F}$ and $R^{2F}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, an optionally substituted phenyl group, an optionally substituted pyridyl group, or an aralkyl group (the number of carbon atoms in an aryl moiety is from 6 to 10 and the number of carbon atoms in an alkylene moiety is from 1 to 8).

(F-1-2)

A compound, a tautomer, stereoisomer, or pharmaceutically acceptable salt of the compound, or a hydrate or solvate thereof, the compound represented by (F-1) or (F-1-1), wherein $R^{1F}$ and $R^{2F}$ are fused with a benzene ring bonded thereto to form a naphthalene ring or a tetrahydronaphthalene ring, and a cyclohexene ring or the benzene ring fused with $R^{1F}$ and $R^{2F}$ and comprising carbon atoms bonded to respective $R^{1F}$ and $R^{2F}$ is optionally substituted with 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8).

(F-1-3)

A compound, a tautomer, stereoisomer, or pharmaceutically acceptable salt of the compound, or a hydrate or solvate thereof, the compound represented by (F-1) or (F-1-1), wherein $R^{1F}$ and $R^{2F}$ are fused with a benzene ring bonded thereto to form a naphthalene ring, and the benzene ring fused with $R^{1F}$ and $R^{2F}$ and having carbon atoms bonded to respective $R^{1F}$ and $R^{2F}$ is optionally substituted with 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, or an amino group.

(F-1-4)

A compound, a tautomer, stereoisomer, or pharmaceutically acceptable salt of the compound, or a hydrate or solvate thereof, the compound represented by (F-1) or (F-1-1), wherein $R^{1F}$ and $R^{2F}$ are fused with a benzene ring bonded thereto to form a naphthalene ring or a tetrahydronaphthalene ring.

(F-1-5)

A compound, a tautomer, stereoisomer, or pharmaceutically acceptable salt of the compound, or a hydrate or solvate thereof, the compound represented by (F-1) or any of (F-1-1) to (F-1-4), wherein $R^{3F}$ and $R^{4F}$ are the same or different and are a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, or an aralkyl group (the number of carbon atoms in an aryl moiety is from 6 to 10 and the number of carbon atoms in an alkylene moiety is from 1 to 8).

(F-1-6)

A compound, a tautomer, stereoisomer, or pharmaceutically acceptable salt of the compound, or a hydrate or solvate thereof, the compound represented by (F-1) or any of (F-1-1) to (F-1-5), wherein $R^{5F}$ is a hydrogen atom, a $C_{1-8}$ alkyl group, or an aralkyl group (the number of carbon atoms in an aryl moiety is from 6 to 10 and the number of carbon atoms in an alkylene moiety is from 1 to 8).

(F-1-7)

A compound, a tautomer, stereoisomer, or pharmaceutically acceptable salt of the compound, or a hydrate or solvate thereof, the compound represented by (F-1) or any of (F-1-1) to (F-1-6), wherein $R^{5F}$ is a hydrogen atom.

(F-1-8)

A compound, a tautomer, stereoisomer, or pharmaceutically acceptable salt of the compound, or a hydrate or solvate thereof, the compound represented by (F-1) or any of (F-1-1) to (F-1-7), wherein $R^{6F}$ and $R^{7F}$ are the same or different and are a hydrogen atom, a $C_{1-8}$ alkyl group, a $C_{1-8}$ alkoxy group, a $C_{1-8}$ alkyl group substituted with 1 to 3 halogen atoms, or a $C_{1-8}$ alkoxy group substituted with 1 to 3 halogen atoms.

(F-1-9)

A compound, a tautomer, stereoisomer, or pharmaceutically acceptable salt of the compound, or a hydrate or solvate thereof, the compound represented by (F-1) or any of (F-1-1) to (F-1-8), wherein both $R^{6F}$ and $R^{7F}$ are a hydrogen atom.

(F-1-10)

A compound, a tautomer, stereoisomer, or pharmaceutically acceptable salt of the compound, or a hydrate or solvate thereof, the compound represented by (F-1) or any of (F-1-1) to (F-1-9), wherein $R^{3F}$, $R^{4F}$, $R^{5F}$, $R^{6F}$, and $R^{7F}$ are a hydrogen atom.

(F-1-11)

A compound, a tautomer, stereoisomer, or pharmaceutically acceptable salt of the compound, or a hydrate or solvate thereof, the compound represented by (F-1) or any of (F-1-1) to (F-1-10), wherein $X^F$ is N, $Y^F$ is C(=O), and the double line composed of a solid line and a dashed line denotes a single bond.

(F-1-12)

A compound, a tautomer, stereoisomer, or pharmaceutically acceptable salt of the compound, or a hydrate or solvate thereof, the compound represented by (F-1) or any of (F-1-1) to (F-1-11), wherein $X^F$ is C, $Y^F$ is N, the double line composed of a solid line and a dashed line is a double bond.

(F-1-13)

A compound, a tautomer, stereoisomer, or pharmaceutically acceptable salt of the compound, or a hydrate or solvate thereof, the compound represented by (F-1) or any of (F-1-1) to (F-1-12), wherein $Z^F$ is an oxygen atom.

(F-1-14)

A compound, a tautomer, stereoisomer, or pharmaceutically acceptable salt of the compound, or a hydrate or solvate thereof, the compound represented by (F-1) or any of (F-1-1) to (F-1-13), wherein $A^F$ is a phenyl group or a pyridyl group optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, an aralkyl group (the number of carbon atoms in an aryl moiety is from 6 to 10 and the number of carbon atoms in an alkylene moiety is from 1 to 8), a phenyl group, or a pyridyl group.

(F-1-15)

A compound, a tautomer, stereoisomer, or pharmaceutically acceptable salt of the compound, or a hydrate or solvate thereof, the compound represented by (F-1) or any of (F-1-1) to (F-1-14), wherein $A^F$ represents a phenyl group optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(F-1-16)

A compound, a tautomer, stereoisomer, or pharmaceutically acceptable salt of the compound, or a hydrate or solvate thereof, the compound represented by (F-1) or any of (F-1-1) to (F-1-15), wherein $A^F$ is a phenyl group or a pyridyl group.

(F-1-17)

A compound, a tautomer, stereoisomer, or pharmaceutically acceptable salt of the compound, or a hydrate or solvate thereof, the compound represented by (F-1) or any of (F-1-1) to (F-1-16), wherein $A^F$ is a bond.

(F-1-18)

A compound, a tautomer, stereoisomer, or pharmaceutically acceptable salt of the compound, or a hydrate or solvate thereof, the compound represented by (F-1) or any of (F-1-1) to (F-1-17), wherein $B^F$ is NHC(=O), NHCONH, CONH, NHC(=S)NH, NHSO$_2$, SO$_2$NH, or OSO$_2$.

(F-1-19)

A compound, a tautomer, stereoisomer, or pharmaceutically acceptable salt of the compound, or a hydrate or solvate thereof, the compound represented by (F-1) or any of (F-1-1) to (F-1-18), wherein $B^F$ is NHC(=O), NHCONH, or NHSO$_2$.

(F-1-20)

A compound, a tautomer, stereoisomer, or pharmaceutically acceptable salt of the compound, or a hydrate or solvate thereof, the compound represented by (F-1) or any of (F-1-1) to (F-1-19), wherein $B^F$ is NHC(=O) or NHSO$_2$.

(F-1-21)

A compound, a tautomer, stereoisomer, or pharmaceutically acceptable salt of the compound, or a hydrate or solvate thereof, the compound represented by (F-1) or any of (F-1-1) to (F-1-20), wherein $B^F$ is NHC(=O).

(F-1-22)

A compound, a tautomer, stereoisomer, or pharmaceutically acceptable salt of the compound, or a hydrate or solvate thereof, the compound represented by (F-1) or any of (F-1-1) to (F-1-21), wherein $D^F$ is a $C_{1-6}$ alkylene chain optionally having, as substituents, 1 to 4 substituents, which are the same or different, selected from a $C_{1-8}$ alkyl group or a $C_{1-8}$ alkyl group substituted with 1 to 3 halogen atoms and further optionally having a double bond.

(F-1-23)

A compound, a tautomer, stereoisomer, or pharmaceutically acceptable salt of the compound, or a hydrate or solvate thereof, the compound represented by (F-1) or any of (F-1-1) to (F-1-22), wherein $D^F$ is a bond.

(F-1-24)

A compound, a tautomer, stereoisomer, or pharmaceutically acceptable salt of the compound, or a hydrate or solvate thereof, the compound represented by (F-1) or any of (F-1-1) to (F-1-23), wherein $D^F$ has, as substituents, 1 to 4 substituents, which are the same or different, selected from a $C_{1-8}$ alkyl group or a $C_{2-8}$ alkenyl group.

(F-1-25)

A compound, a tautomer, stereoisomer, or pharmaceutically acceptable salt of the compound, or a hydrate or solvate thereof, the compound represented by (F-1) or any of (F-1-1) to (F-1-24), wherein $D^F$ has, as substituents, 1 to 4 substituents, which are the same or different, selected from a $C_{1-3}$ alkyl group or a $C_{2-3}$ alkenyl group.

(F-1-26)

A compound, a tautomer, stereoisomer, or pharmaceutically acceptable salt of the compound, or a hydrate or solvate thereof, the compound represented by (F-1) or any of (F-1-1) to (F-1-25), wherein $E^F$ is a bond.

(F-1-27)

A compound, a tautomer, stereoisomer, or pharmaceutically acceptable salt of the compound, or a hydrate or solvate thereof, the compound represented by (F-1) or any of (F-1-1) to (F-1-26), wherein $G^F$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, or a $C_{1-6}$ alkylsulfonyl group.

(F-1-28)

A compound, a tautomer, stereoisomer, or pharmaceutically acceptable salt of the compound, or a hydrate or solvate thereof, the compound represented by (F-1) or any of (F-1-1) to (F-1-27), wherein $G^F$ is benzene optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, or a $C_{1-6}$ alkylsulfonyl group.

(F-1-29)

A compound, a tautomer, stereoisomer, or pharmaceutically acceptable salt of the compound, or a hydrate or solvate thereof, the compound represented by (F-1) or any of (F-1-1) to (F-1-28), wherein $G^F$ is benzene or pyridine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a halogen atom, a hydroxyl group, a nitro group, an amino group, a $C_{2-8}$ dialkylamino group, a carboxyl group, a $C_{1-6}$ alkylsulfinyl group, a $C_{1-6}$ alkylthio group, or a $C_{1-6}$ alkylsulfonyl group.

(F-1-30)

A compound, a tautomer, stereoisomer, or pharmaceutically acceptable salt of the compound, or a hydrate or solvate thereof, the compound represented by (F-1) or any of (F-1-1) to (F-1-29), wherein $G^F$ is benzene optionally having, as substituents, 1 to 4 substituents, which are the same or different, selected from a $C_{1-8}$ alkyl group substituted with 1 to 3 halogen atoms, a halogen atom, or a hydroxyl group.

(F-1-31)

A compound, a tautomer, stereoisomer, or pharmaceutically acceptable salt of the compound, or a hydrate or solvate thereof, the compound represented by (F-1) or any of (F-1-1) to (F-1-30), wherein $m^F$ is 0.

(F-1-32)

A compound, a tautomer, stereoisomer, or pharmaceutically acceptable salt of the compound, or a hydrate or solvate thereof, the compound represented by (F-1) or any of (F-1-1) to (F-1-31), wherein $A^F$ is a benzene ring, $m^F$ is 0, $B^F$ is NHC(=O) or NHSO$_2$, $D^F$ is a $C_{1-3}$ alkyl group or a bond, $E^F$ is a bond, and $G^F$ represents benzene optionally having, as substituents, 1 to 4 substituents, which are the same or different, selected from a $C_{1-8}$ alkyl group, a $C_{1-8}$ alkyl group substituted with 1 to 3 halogen atoms, a halogen atom, or a hydroxyl group.

(F-1-33)

A compound, a tautomer, stereoisomer, or pharmaceutically acceptable salt of the compound, or a hydrate or solvate thereof, the compound represented by (F-1) or any of (F-1-1) to (F-1-32), wherein $A^F$ is a benzene ring, $m^F$ is 0, $B^F$ is NHC(=O), $D^F$ is a bond, $E^F$ is a bond, and $G^F$ represents benzene optionally having, as substituents, 1 to 4 substituents, which are the same or different, selected from a $C_{1-8}$ alkyl group substituted with 1 to 3 halogen atoms, a halogen atom, or a hydroxyl group.

(F-1-34)

A compound, a tautomer, stereoisomer, or pharmaceutically acceptable salt of the compound, or a hydrate or solvate thereof, the compound represented by (F-1) or any one of (F-1-1) to (F-1-33), wherein $R^{1F}$ and $R^{2F}$ are fused with a benzene ring bonded thereto to form a naphthalene ring, $R^{3F}$, $R^{4F}$, $R^{5F}$, $R^{6F}$, and $R^{7F}$ represent a hydrogen atom, $X^F$ is N, $Y^F$ is C(=O), the double line composed of a solid line and a dashed line denotes a single bond, $Z^F$ represents an oxygen atom, $A^F$ represents a benzene ring, $m^F$ represents 0, $B^F$ represents NHC(=O) or NHSO$_2$, $D^F$ represents a $C_{1-3}$ alkyl group or a bond, $E^F$ represents a bond, and $G^F$ represents benzene optionally having, as substituents, 1 to 4 substituents, which are the same or different, selected from a $C_{1-8}$ alkyl group, a $C_{1-8}$ alkyl group substituted with 1 to 3 halogen atoms, a halogen atom, or a hydroxyl group.

(F-1-35)

In the above general formula (FI), a compound, a tautomer, stereoisomer, or pharmaceutically acceptable salt of the compound, or a hydrate or solvate thereof, the compound represented by (F-1) or any one of (F-1-1) to (F-1-34), wherein $R^{1F}$ and $R^{2F}$ are fused with a benzene ring bonded thereto to form a naphthalene ring, $R^{3F}$, $R^{4F}$, $R^{5F}$, $R^{6F}$, and $R^{7F}$ represent a hydrogen atom, $X^F$ is N, $Y^F$ is C(=O), the double line composed of a solid line and a dashed line denotes a single bond, $Z^F$ represents an oxygen atom, $A^F$ represents a benzene ring, $m^F$ represents 0, $B^F$ represents NHC(=O), $D^F$ represents a bond, $E^F$ represents a bond, and $G^F$ represents benzene optionally having, as substituents, 1 to 4 substituents, which are the same or different, selected from a $C_{1-8}$ alkyl group substituted with 1 to 3 halogen atoms, a halogen atom, or a hydroxyl group.

The following compounds are preferable as compounds represented by general formula (FII).

(F-2-1)

A compound, a tautomer, stereoisomer, or pharmaceutically acceptable salt of the compound, or a hydrate or solvate thereof, the compound represented by (F-2), wherein

[Chem. 80]

is a naphthalene ring or a tetrahydronaphthalene ring optionally substituted with, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8).

(F-2-2)

A compound, a tautomer, stereoisomer, or pharmaceutically acceptable salt of the compound, or a hydrate or solvate thereof, the compound represented by (F-2) or (F-2-1), wherein

[Chem. 81]

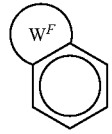

is a naphthalene ring optionally substituted with, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, or an amino group.

(F-2-3)

A compound, a tautomer, stereoisomer, or pharmaceutically acceptable salt of the compound, or a hydrate or solvate thereof, the compound represented by (F-2) or any of (F-2-1) to (F-2-2), wherein $R^{3Fa}$ and $R^{4Fa}$ are the same or different and are a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, or an aralkyl group (the number of carbon atoms in an aryl moiety is from 6 to 10 and the number of carbon atoms in an alkylene moiety is from 1 to 8).

(F-2-4)

A compound, a tautomer, stereoisomer, or pharmaceutically acceptable salt of the compound, or a hydrate or solvate thereof, the compound represented by (F-2) or any of (F-2-1) to (F-2-3), wherein $R^{5Fa}$ is a hydrogen atom, a $C_{1-8}$ alkyl group, or an aralkyl group (the number of carbon atoms in an aryl moiety is from 6 to 10 and the number of carbon atoms in an alkylene moiety is from 1 to 8).

(F-2-5)

A compound, a tautomer, stereoisomer, or pharmaceutically acceptable salt of the compound, or a hydrate or solvate thereof, the compound represented by (F-2) or any of (F-2-1) to (F-2-4), wherein $R^{5Fa}$ is a hydrogen atom.

(F-2-6)

A compound, a tautomer, stereoisomer, or pharmaceutically acceptable salt of the compound, or a hydrate or solvate thereof, the compound represented by (F-2) or any of (F-2-1) to (F-2-5), wherein $R^{6Fa}$ and $R^{7Fa}$ are the same or different and are a hydrogen atom, a $C_{1-8}$ alkyl group, a $C_{1-8}$ alkoxy group, a $C_{1-8}$ alkyl group substituted with 1 to 3 halogen atoms, or a $C_{1-8}$ alkoxy group substituted with 1 to 3 halogen atoms.

(F-2-7)

A compound, a tautomer, stereoisomer, or pharmaceutically acceptable salt of the compound, or a hydrate or solvate thereof, the compound represented by (F-2) or any of (F-2-1) to (F-2-6), wherein both $R^{6Fa}$ and $R^{7Fa}$ are a hydrogen atom.

(F-2-8)

A compound, a tautomer, stereoisomer, or pharmaceutically acceptable salt of the compound, or a hydrate or solvate thereof, the compound represented by (F-2) or any of (F-2-1) to (F-2-7), wherein

[Chem. 82]

is a phenyl group or a pyridyl group optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, an aralkyl group (the number of carbon atoms in an aryl moiety is from 6 to 10 and the number of carbon atoms in an alkylene moiety is from 1 to 8), a phenyl group, or a pyridyl group.

(F-2-9)

A compound, a tautomer, stereoisomer, or pharmaceutically acceptable salt of the compound, or a hydrate or solvate thereof, the compound represented by (F-2) or any of (F-2-1) to (F-2-8), wherein

[Chem. 83]

is a phenyl group optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(F-2-10)

A compound, a tautomer, stereoisomer, or pharmaceutically acceptable salt of the compound, or a hydrate or solvate thereof, the compound represented by (F-2) or any of (F-2-1) to (F-2-9), wherein

[Chem. 84]

is a bond.

(F-2-11)

A compound, a tautomer, stereoisomer, or pharmaceutically acceptable salt of the compound, or a hydrate or solvate thereof, the compound represented by (F-2) or any of (F-2-1) to (F-2-10), wherein $B^{Fa}$ is NHC(=O), NHCONH, CONH, NHC(=S)NH, NHSO$_2$, SO$_2$NH, or OSO$_2$.

(F-2-12)

A compound, a tautomer, stereoisomer, or pharmaceutically acceptable salt of the compound, or a hydrate or solvate thereof, the compound represented by (F-2) or any of (F-2-1) to (F-2-11), wherein $B^{Fa}$ is NHC(=O), NHCONH, or NHSO$_2$.

(F-2-13)

A compound, a tautomer, stereoisomer, or pharmaceutically acceptable salt of the compound, or a hydrate or solvate thereof, the compound represented by (F-2) or any of (F-2-1) to (F-2-12), wherein $E^{Fa}$ is a bond.

(F-2-14)

A compound, a tautomer, stereoisomer, or pharmaceutically acceptable salt of the compound, or a hydrate or solvate thereof, the compound represented by (F-2) or any of (F-2-1) to (F-2-13), wherein $G^{Fa}$ is piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, or a $C_{1-6}$ alkylsulfonyl group.

(F-2-15)

A compound, a tautomer, stereoisomer, or pharmaceutically acceptable salt of the compound, or a hydrate or solvate thereof, the compound represented by (F-2) or any of (F-2-1) to (F-2-14), wherein $G^{Fa}$ is benzene optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, or a $C_{1-6}$ alkylsulfonyl group.

(F-2-16)

A compound, a tautomer, stereoisomer, or pharmaceutically acceptable salt of the compound, or a hydrate or solvate thereof, the compound represented by (F-2) or any of (F-2-1) to (F-2-15), wherein $n^F$ is 0.

In the above general formula (FI), it is preferable that $R^{F1}$ and $R^{F2}$ are fused with a benzene ring bonded thereto to form a condensed ring selected from a naphthalene ring or a tetrahydronaphthalene ring. It is particularly preferable to form a naphthalene ring.

In the above general formula (FI), it is preferable that $R^{F3}$, $R^{F4}$, $R^{F5}$, $R^{F6}$, and $R^{F7}$ represent a hydrogen atom.

In the above general formula (FI), it is preferable that $X^F$ is N, $Y^F$ is C(=O), and the double line composed of a solid line and a dashed line is a single bond.

In the above general formula (FI), it is preferable that $Z^F$ is an oxygen atom.

In the above general formula (FI), it is preferable that $A^F$ represents a benzene ring or a pyridine ring. It is particularly preferable that $A^F$ represents a benzene ring.

In the above general formula (FI), it is preferable that $m^F$ represents from 0 to 4. It is particularly preferable that $m^F$ represents 0.

In the above general formula (FI), it is preferable that $B^F$ represents $N(R^{8F})C(=O)$ or $N(R^{10F})SO_2$. At this time, it is more preferable that $R^{8F}$ and $R^{11F}$ represent a hydrogen atom. In the above general formula (FI), it is particularly preferable that $B^F$ represents $NHC(=O)$.

In the above general formula (FI), it is preferable that $D^F$ represents a bond or has, as substituents, 1 to 4 substituents, which are the same or different, selected from a $C_{1-8}$ alkyl group or a $C_{2-8}$ alkenyl group. It is particularly preferable that $D^F$ represents a bond or has, as substituents, 1 to 4 substituents, which are the same or different, selected from a $C_{1-3}$ alkyl group or a $C_{2-3}$ alkenyl group.

In the above general formula (FI), it is preferable that $E^F$ represents O or a bond. It is particularly preferable that $E^F$ represents a bond.

In the above general formula (FI), it is preferable that $G^F$ represents benzene or pyridine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a halogen atom, a hydroxyl group, a nitro group, an amino group, a $C_{2-8}$ dialkylamino group, a carboxyl group, a $C_{1-6}$ alkylsulfinyl group, a $C_{1-6}$ alkylthio group, or a $C_{1-6}$ alkylsulfonyl group. It is particularly preferable that $G^F$ represents benzene optionally having, as substituents, 1 to 4 substituents, which are the same or different, selected from a $C_{1-8}$ alkyl group substituted with 1 to 3 halogen atoms, a halogen atom, or a hydroxyl group.

In the above general formula (FI), it is preferable that $A^F$ represents a benzene ring, $m^F$ represents 0, $B^F$ represents $NHC(=O)$ or $NHSO_2$, $D^F$ represents a $C_{1-3}$ alkyl group or a bond, $E^F$ represents a bond, and $G^F$ represents benzene optionally having, as substituents, 1 to 4 substituents, which are the same or different, selected from a $C_{1-8}$ alkyl group, a $C_{1-8}$ alkyl group substituted with 1 to 3 halogen atoms, a halogen atom, or a hydroxyl group.

In the above general formula (FI), it is preferable that $A^F$ represents a benzene ring, $m^F$ represents 0, $B^F$ represents $NHC(=O)$, $D^F$ represents a bond, $E^F$ represents a bond, and $G^F$ represents benzene optionally having, as substituents, 1 to 4 substituents, which are the same or different, selected from a $C_{1-8}$ alkyl group substituted with 1 to 3 halogen atoms, a halogen atom, or a hydroxyl group.

In the above general formula (FI), it is more preferable that $R^{F1}$ and $R^{F2}$ are fused with a benzene ring bonded thereto to form a naphthalene ring, $R^{F3}$, $R^{F4}$, $R^{F5}$, $R^{F6}$, and $R^{F7}$ represent a hydrogen atom, $X^F$ is N, $Y^F$ is $C(=O)$, the double line composed of a solid line and a dashed line denotes a single bond, $Z^F$ represents an oxygen atom, $A^F$ represents a benzene ring, $m^F$ represents 0, $B^F$ represents $NHC(=O)$ or $NHSO_2$, $D^F$ represents a $C_{1-3}$ alkyl group or a bond, $E^F$ represents a bond, and GF represents benzene optionally having, as substituents, 1 to 4 substituents, which are the same or different, selected from a $C_{1-8}$ alkyl group, a $C_{1-8}$ alkyl group substituted with 1 to 3 halogen atoms, a halogen atom, or a hydroxyl group.

In the above general formula (FI), it is particularly preferable that $R^{F1}$ and $R^{F2}$ are fused with a benzene ring bonded thereto to form a naphthalene ring, $R^{F3}$, $R^{F4}$, $R^{F5}$, $R^{F6}$, and $R^{F7}$ represent a hydrogen atom, $X^F$ is N, $Y^F$ is $C(=O)$, the double line composed of a solid line and a dashed line denotes a single bond, $Z^F$ represents an oxygen atom, $A^F$ represents a benzene ring, $m^F$ represents 0, $B^F$ represents $NHC(=O)$, $D^F$ represents a bond, $E^F$ represents a bond, and $G^F$ represents benzene optionally having, as substituents, 1 to 4 substituents, which are the same or different, selected from a $C_{1-8}$ alkyl group substituted with 1 to 3 halogen atoms, a halogen atom, or a hydroxyl group.

The following shows representative compounds included in general formula (FI) and/or (FII).

<Representative Compound F-100>

[Chem. 85]

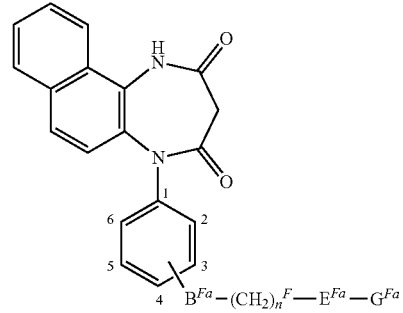

wherein $B^{Fa}$ (substitution position), $n^F$, $E^{Fa}$, and $G^{Fa}$ are as described in Tables 74 to 83.

TABLE 74

| $B^{Fa}$ (Substitution position) | $n^F$ | $E^{Fa}$ | $G^{Fa}$ |
|---|---|---|---|
| NHCO(4) | 0 | Bond | Phenyl |
| NHCO(4) | 0 | Bond | (2-CF$_3$)Phenyl |
| NHCO(4) | 0 | Bond | (3-Br)Phenyl |
| NHCO(4) | 0 | Bond | (4-CF$_3$)Phenyl |
| NHCO(4) | 0 | Bond | (2-Me)Phenyl |
| NHCO(4) | 0 | Bond | (2,6-Me)Phenyl |
| NHCO(4) | 0 | Bond | (2,6-Cl)Phenyl |
| NHCO(4) | 0 | Bond | (3-Cl)Phenyl |
| NHCO(4) | 1 | Bond | Phenyl |
| NHC(=S)NH(4) | 0 | Bond | Phenyl |
| NHCO(4) | 0 | Bond | (2,3-OMe)Phenyl |
| NHCO(4) | 0 | Bond | (2-OMe)Phenyl |
| NHCO(4) | 1 | Bond | (2-Cl)Phenyl |
| NHCO(4) | 0 | Bond | (2,3-Me)Phenyl |
| NHCO(4) | 0 | Bond | (2,5-Me)Phenyl |
| NHCO(4) | 0 | Bond | (2-Cl,5-Br)Phenyl |

TABLE 75

| $B^{Fa}$ (Substitution position) | $n^F$ | $E^{Fa}$ | $G^{Fa}$ |
|---|---|---|---|
| NHCO(4) | 0 | Bond | (2,4-Cl)Phenyl |
| NHCO(4) | 0 | Bond | (2-OH)Phenyl |
| NHCO(4) | 0 | Bond | (2,3-OH)Phenyl |
| NHC(=O)NH(4) | 0 | Bond | Phenyl |
| NHCO(4) | 1 | Bond | (2,6-Cl)Phenyl |
| NHCO(4) | 1 | Bond | (2-OMe)Phenyl |
| NHCO(4) | 1 | Bond | (2-OH)Phenyl |
| NHC(=S)NH(4) | 0 | Bond | (2-Cl)Phenyl |
| NHCO(4) | 0 | Bond | (3-CF$_3$)Phenyl |
| NHCO(4) | 1 | Bond | (2-CF$_3$)Phenyl |
| NHC(=O)NH(4) | 0 | Bond | (2-Cl)Phenyl |
| NHCO(4) | 0 | Bond | (2-Cl,3-OMe)Phenyl |
| NHCO(4) | 2 | Bond | Phenyl |
| NHCO(4) | 0 | Bond | 3-indolyl |
| NHCO(4) | 0 | Bond | (2-Cl,3-OH)Phenyl |
| NHCO(4) | 1 | O | Phenyl |

TABLE 76

| $B^{Fa}$ (Substitution position) | $n^F$ | $E^{Fa}$ | $G^{Fa}$ |
| --- | --- | --- | --- |
| NHCO(4) | 1 | Bond | (2-Cl,4-OMe)Phenyl |
| NHCO(4) | 0 | Bond | (1-Me)imidazol 2-yl |
| NHCO(4) | 1 | Bond | (2,4-Cl)Phenyl |
| NHCO(4) | 1 | Bond | (2-Cl,4-OH)Phenyl |
| NHCO(4) | 1 | Bond | pyridin 3-yl |
| NHCO(4) | 0 | Bond | Benzimidazol 2-yl |
| NHCO(4) | 0 | Bond | (2-Cl)Phenyl |
| NHCO(4) | 0 | Bond | (2-Br)Phenyl |
| NHCO(4) | 0 | Bond | (2-I)Phenyl |
| NHCO(4) | 1 | Bond | (2-Me)Phenyl |
| NHCO(4) | 0 | Bond | Quinoxalin 2-yl |
| NHCO(4) | 0 | Bond | (5-Me)thiophen 2-yl |
| NHCO(3) | 1 | Bond | (2-Cl)Phenyl |
| NHCO(4) | 0 | Bond | (2,4,6-Me)Phenyl |
| NHCO(4) | 0 | Bond | (2-Et)Phenyl |
| NHC(=S)NH(4) | 0 | Bond | (2-Me)Phenyl |

TABLE 77

| $B^{Fa}$ (Substitution position) | $n^F$ | $E^{Fa}$ | $G^{Fa}$ |
| --- | --- | --- | --- |
| NHCO(4) | 0 | Bond | (4-NMe$_2$)Phenyl |
| NHCO(4) | 1 | ◯ | (2,4-Cl)Phenyl |
| NHCO(4) | 1 | ◯ | (2-Me)Phenyl |
| NHCO(4) | 0 | Bond | (2-Ac)Phenyl |
| NHCO(4) | 0 | Bond | (2-tBu)Phenyl |
| NHCO(3) | 0 | Bond | (2-I)Phenyl |
| NHCO(4) | 0 | Bond | (1-Me)piperdin 4-yl |
| NHCO(4) | 0 | Bond | benzofuran 2-yl |
| NHCO(4) | 0 | Bond | (1-Me)indol 3-yl |
| NHCO(4) | 0 | Bond | (2-allyl)Phenyl |
| NHCO(4) | 0 | Bond | (2-nPr)Phenyl |
| NHCO(4) | 0 | Bond | (2-iPrO)Phenyl |
| NHCO(4) | 0 | Bond | 3-Me thiophen 2-yl |
| NHCO(4) | 1 | ◯ | (2-Me,3-Cl)Phenyl |
| NHCO(4) | 0 | Bond | (2-CF$_3$,4-F)Phenyl |
| NHCO(4) | 0 | Bond | (2-OMe,4-F)Phenyl |

TABLE 78

| $B^{Fa}$ (Substitution position) | $n^F$ | $E^{Fa}$ | $G^{Fa}$ |
| --- | --- | --- | --- |
| NHCO(4) | 0 | Bond | (2-OH,4-F)Phenyl |
| NHCO(3) | 1 | Bond | (2-I)Phenyl |
| NHCO(4) | 0 | Bond | (3-NMe$_2$)Phenyl |
| NHCO(4) | 0 | Bond | (2-OMe,4-I)Phenyl |
| NHCO(4) | 0 | Bond | (2-OMe,6-F)Phenyl |
| NHCO(4) | 0 | Bond | (2-OH,4-I)Phenyl |
| NHCO(4) | 0 | Bond | (2-OH,6-F)Phenyl |
| NHCO(4) | 0 | Bond | (2-F)Phenyl |
| NHCO(4) | 0 | Bond | (2-NMe$_2$)Phenyl |
| NHCO(4) | 0 | Bond | (2-OMe,6-Me)Phenyl |
| NHCO(4) | 0 | Bond | (2-OH,6-Me)Phenyl |
| NHCO(4) | 2 | Bond | (2-Me)Phenyl |
| CONH(4) | 0 | Bond | Phenyl |
| CONH(4) | 1 | Bond | Phenyl |
| NHCO(4) | 2 | Bond | (2-Cl)Phenyl |
| CONH(4) | 1 | Bond | (2-Cl)Phenyl |

TABLE 79

| $B^{Fa}$ (Substitution position) | $n^F$ | $E^{Fa}$ | $G^{Fa}$ |
| --- | --- | --- | --- |
| CONH(4) | 0 | Bond | (2-Cl)Phenyl |
| NHCO(4) | 0 | Bond | (5-Br,2,3-methylenedioxy)Phenyl |
| NHCO(4) | 0 | Bond | (2-OMe,6-Br)Phenyl |
| NHCO(4) | 0 | Bond | (2-OH,6-Br)Phenyl |
| NHCO(4) | 0 | Bond | (2-OMe,6-Cl)Phenyl |
| NHCO(4) | 0 | Bond | (2-OH,6-Cl)Phenyl |
| NHCO(4) | 0 | Bond | (2-OH,6-OMe)Phenyl |
| NHCO(4) | 0 | Bond | (2-OMe,6-CF$_3$)Phenyl |
| NHCO(4) | 0 | Bond | (2-OH,6-CF$_3$)Phenyl |
| NHCO(4) | 0 | Bond | (2-Cl,5-SMe)Phenyl |
| NHCO(4) | 0 | Bond | (2-SMe)Phenyl |
| NHCO(4) | 0 | Bond | (3-SMe)Phenyl |
| NHCO(4) | 0 | Bond | (2-OMe,6-Et)Phenyl |
| NHCO(4) | 0 | Bond | (3-SO$_2$Me)Phenyl |
| NHCO(4) | 0 | Bond | (2-OH,6-Et)Phenyl |
| NHCO(4) | 0 | Bond | (3-S(=O)Me)Phenyl |

TABLE 80

| $B^{Fa}$ (Substitution position) | $n^F$ | $E^{Fa}$ | $E^{Fa}$ |
| --- | --- | --- | --- |
| NHCO(4) | 0 | Bond | (2-Cl,5-S(=O)Me)Phenyl |
| NHCO(4) | 0 | Bond | (2-S(=O)Me)Phenyl |
| NHCO(4) | 0 | Bond | (3-Cl)pyridin 2-yl |
| NHCO(4) | 0 | Bond | (2-OMe,3-Cl)Phenyl |
| NHCO(4) | 0 | Bond | (3-Me)pyridin 2-yl |
| NHCO(4) | 0 | Bond | (2-OH,3-Cl)Phenyl |
| NHCO(4) | 0 | Bond | (3-OH)pyridin 2-yl |
| NHCO(4) | 0 | Bond | (3-Vinyl)pyridin 2-yl |
| NHCO(4) | 0 | Bond | (2-Et)pyridin 2-yl |
| NHSO$_2$(4) | 0 | Bond | (2-NO$_2$)Phenyl |
| NHSO$_2$(4) | 0 | Bond | Phenyl |
| NHSO$_2$(4) | 0 | Bond | (3-Br)Phenyl |
| NHSO$_2$(4) | 0 | Bond | (3-OMe)Phenyl |
| NHSO$_2$(3) | 0 | Bond | (2-NO$_2$)Phenyl |
| NMeSO$_2$(3) | 0 | Bond | (2-NO$_2$)Phenyl |
| NHSO$_2$(3) | 0 | Bond | naphthalen 2-yl |

TABLE 81

| $B^{Fa}$ (Substitution position) | $n^F$ | $E^{Fa}$ | $G^{Fa}$ |
| --- | --- | --- | --- |
| NHSO$_2$(3) | 0 | Bond | naphthalen 1-yl |
| NHSO$_2$(4) | 0 | Bond | Cyclohexyl |
| NHSO$_2$(4) | 0 | Bond | pyridin 3-yl |
| NHSO$_2$(4) | 0 | Bond | (4-iPr)Phenyl |
| NHSO$_2$(4) | 1 | Bond | Phenyl |
| NHSO$_2$(4) | 0 | Bond | thiophen 2-yl |
| NHSO$_2$(4) | 0 | Bond | naphthalen 2-yl |
| NBnSO$_2$(4) | 0 | Bond | (2-NO$_2$)Phenyl |
| NMeSO$_2$(4) | 0 | Bond | (3-Br)Phenyl |
| NMeSO$_2$(4) | 0 | Bond | (2-NO$_2$)Phenyl |
| N(CH$_2$CH$_2$OH)SO$_2$(4) | 0 | Bond | (2-NO$_2$)Phenyl |
| NHSO$_2$(4) | 1 | Bond | (2-Cl)Phenyl |
| NHSO$_2$(4) | 1 | Bond | (3-Br)Phenyl |
| NHSO$_2$(4) | 0 | Bond | (2-CF$_3$)Phenyl |
| NHSO$_2$(4) | 1 | Bond | (2-Br)Phenyl |
| NHSO$_2$(4) | 1 | Bond | (2-Me)Phenyl |

TABLE 82

| $B^{Fa}$ (Substitution position) | $n^F$ | $E^{Fa}$ | $G^{Fa}$ |
|---|---|---|---|
| $NHSO_2(4)$ | 1 | Bond | $(2-NO_2)$Phenyl |
| $NHSO_2(4)$ | 2 | Bond | Phenyl |
| $NHSO_2(4)$ | 1 | Bond | (4-Cl)Phenyl |
| $NMeSO_2(4)$ | 1 | Bond | $(2-CF_3)$Phenyl |
| $NMeSO_2(4)$ | 1 | Bond | (2-Et)Phenyl |
| $NMeSO_2(4)$ | 1 | Bond | (2,3-Me)Phenyl |
| $NMeSO_2(4)$ | 2 | Bond | (2-Cl)Phenyl |
| $NMeSO_2(4)$ | 1 | Bond | $(2-NO_2)$Phenyl |
| $NMeSO_2(4)$ | 1 | Bond | $(2-NH_2)$Phenyl |
| $NMeSO_2(4)$ | 1 | Bond | $(2-NMe_2)$Phenyl |

TABLE 83

| $B^{Fa}$ (Substitution position) | $n^F$ | $E^{Fa}$ | $G^{Fa}$ |
|---|---|---|---|
| NHCO(4) | 0 | Bond | pyridin 4-yl |
| NHCO(4) | 1 | O | pyridin 3-yl |
| NHCO(4) | 0 | Bond | pyridin 3-yl |
| NHCO(4) | 0 | Bond | (2-Me)pyridin 3-yl |
| NHCO(4) | 0 | Bond | (2-Cl)pyridin 3-yl |
| NHCO(4) | 1 | O | pyridin 2-yl |
| NHCO(4) | 0 | Bond | $(4-CF_3)$pyridin 3-yl |
| NHCO(4) | 0 | Bond | (2-iPr)Phenyl |

<Representative Compound F-200>

[Chem. 86]

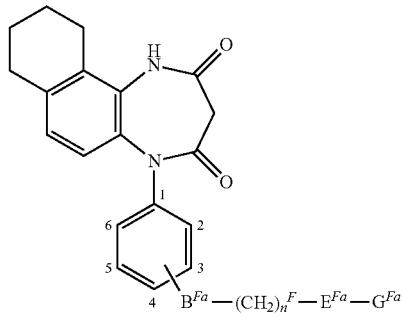

wherein $B^{Fa}$ (substitution position), $n^F$, $E^{Fa}$, and $G^{Fa}$ are as described in Tables 84 and 85.

TABLE 84

| $B^{Fa}$ (Substitution position) | $n^F$ | $E^{Fa}$ | $G^{Fa}$ |
|---|---|---|---|
| NHCO(4) | 0 | Bond | Cyclohexyl |
| NHCO(4) | 0 | Bond | (6-Me)pyridin-2-yl |
| NHCO(4) | 0 | Bond | (2-Me)pyridin-3-yl |
| NHCO(4) | 0 | Bond | (2-OMe,3-Me)Phenyl |
| NHCO(4) | 0 | Bond | (2,3-Cl)Phenyl |
| NHCO(4) | 0 | Bond | (2-OH,3-Me)Phenyl |
| NHCO(4) | 0 | Bond | (2-I)Phenyl |
| NHCO(4) | 1 | Bond | (1-Me)pyrrol 2-yl |
| NHCO(4) | 1 | Bond | (2-tBu)Phenyl |
| NHCO(4) | 0 | Bond | (2-Isopropenyl)phenyl |
| NHCO(4) | 0 | Bond | (2-iPr)Phenyl |
| NHCO(4) | 1 | Bond | morpholin 2-yl |
| NHCO(4) | 0 | Bond | (2-Cl)pyridin 2-yl |

TABLE 85

| $B^{Fa}$ (Substitution position) | $n^F$ | $E^{Fa}$ | $G^{Fa}$ |
|---|---|---|---|
| $NHSO_2(4)$ | 0 | Bond | $(2-NO_2)$Phenyl |
| $NMeSO_2(4)$ | 0 | Bond | $(2-NO_2)$Phenyl |
| $SO_2NH(4)$ | 0 | Bond | Phenyl |
| $OSO_2(4)$ | 0 | Bond | (3-Br)Phenyl |
| $NHSO_2(4)$ | 1 | Bond | (2-Cl)Phenyl |
| $NHSO_2(4)$ | 0 | Bond | (3-Br)Phenyl |
| $NHSO_2(4)$ | 0 | Bond | (3-OMe)Phenyl |
| $NHSO_2(4)$ | 1 | Bond | (2,3-Cl)Phenyl |
| $NHSO_2(4)$ | 1 | Bond | (2,6-Cl)Phenyl |
| $NHSO_2(4)$ | 1 | Bond | (2-I)Phenyl |
| $NMeSO_2(4)$ | 1 | Bond | (2-Cl)Phenyl |

<Representative Compound F-300>

[Chem. 87]

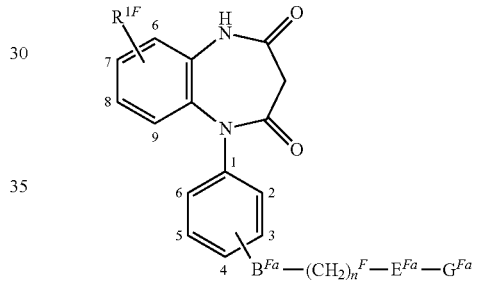

wherein $R^{1F}$, $B^{Fa}$ (substitution position), $n^F$, $E^{Fa}$, and $G^{Fa}$ are as described in Table 86.

TABLE 86

| $R^1$ | $B^{Fa}$ (Substitution position) | $n^F$ | $E^{Fa}$ | $G^{Fa}$ |
|---|---|---|---|---|
| 7-OMe | NHCO(4) | 0 | Bond | (2,3-Me)Phenyl |
| 7-OH | NHCO(4) | 0 | Bond | (2,3-Me)Phenyl |
| 6-Me | NHCO(4) | 0 | Bond | (2,3-Me)Phenyl |
| 6,7-Me | KHCO(4) | 0 | Bond | (2-I)Phenyl |
| 6-Et | NHCO(4) | 0 | Bond | (2-I)Phenyl |
| 7-Ph | NHCO(4) | 0 | Bond | (2-Isopropyl))Phenyl |
| 7-(Pyridin-3yl) | NHCO(4) | 0 | Bond | (2-Isopropyl))Phenyl |
| 7-(Pyridin-2yl) | NHCO(4) | 0 | Bond | (2-Isopropyl)Phenyl |
| 7-Cl | $NHSO_2(4)$ | 0 | Bond | (2-Isopropyl)Phenyl |
| 7-Br | $NHSO_2(4)$ | 0 | Bond | (2-Isopropyl)Phenyl |
| $7-CF_3$ | $MHSO_2(4)$ | 0 | Bond | (2-Isopropyl)Phenyl |
| H | $NHSO_2(4)$ | 0 | Bond | (2-Isopropyl)Phenyl |
| 6-Me,7-Br | $NHSO_2(4)$ | 0 | Bond | (2-Isopropyl)Phenyl |
| 7-OMe | $NHSO_2(4)$ | 1 | Bond | (2-Cl)Phenyl |
| 7-OH | $NHSO_2(4)$ | 1 | Bond | (2-Cl)Phenyl |
| 6-Me | $NHSO_2(4)$ | 1 | Bond | (2-Cl)Phenyl |

<Representative Compound F-400>

[Chem. 88]

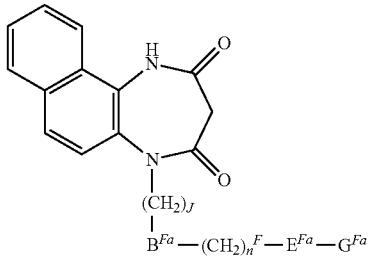

wherein B$^{Fa}$ (substitution position), n$^F$, E$^{Fa}$, and G$^{Fa}$ are as described in Table 87.

TABLE 87

| B$^{Fa}$ (Substitution position) | n$^F$ | E$^{Fa}$ | G$^{Fa}$ |
|---|---|---|---|
| NHCO | 0 | Bond | (2-Cl,3-OMe)Phenyl |
| NHCO | 0 | Bond | (2-I)Phenyl |
| NHSO$_2$ | 1 | Bond | (2-Cl)Phenyl |
| NHSO$_2$ | 1 | Bond | (2-Cl)Phenyl |

<Representative Compound F-500>

[Chem. 89]

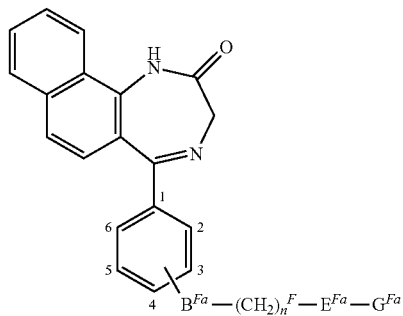

wherein B$^{Fa}$ (substitution position), n$^F$, E$^{Fa}$, and G$^{Fa}$ are as described in Table 88.

TABLE 88

| B$^{Fa}$ (Substitution position) | n$^F$ | E$^{Fa}$ | G$^{Fa}$ |
|---|---|---|---|
| NHCO(4) | 0 | Bond | (2-Cl,3-OMe)Phenyl |
| NHCO(4) | 0 | Bond | (2-Cl,3-OH)Phenyl |
| NHCO(4) | 0 | Bond | (2-tBu)Phenyl |
| NHCO(4) | 0 | Bond | (2-Cl,6-OMe)Phenyl |
| NHCO(4) | 0 | Bond | (2-Cl,6-OH)Phenyl |
| NHSO$_2$(3) | 0 | Bond | Phenyl |
| NHSO$_2$(4) | 1 | Bond | (2-Cl)Phenyl |

<Representative Compound F-600>

[Chem. 90]

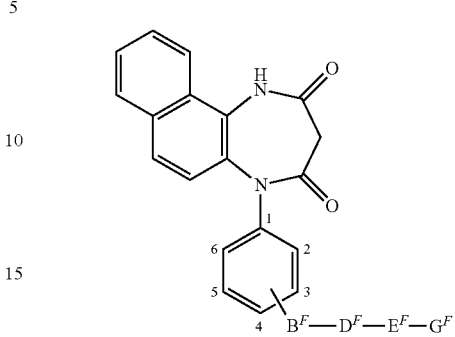

wherein B$^F$ (substitution position), D$^F$, E$^F$, and G$^F$ are as described in Table 89.

TABLE 89

| B$^F$ (Substitution Position) | D$^F$ | E$^F$ | G$^F$ |
|---|---|---|---|
| NHCO(4) | C(Me)H | Bond | Phenyl |
| NHCO(4) | C(Me)$_2$ | Bond | Phenyl |
| NHCO(4) | CH=CH | Bond | Phenyl |
| NHCO(4) | C(Me)H | ◯ | Phenyl |
| NHCO(4) | C(Me)$_2$ | ◯ | Phenyl |
| NHCO(4) | CH=CH | Bond | (2-Me)Phenyl |
| NHCO(4) | CH=CH | Bond | (2-Cl)Phenyl |

<Representative Compound F-700>

[Chem. 91]

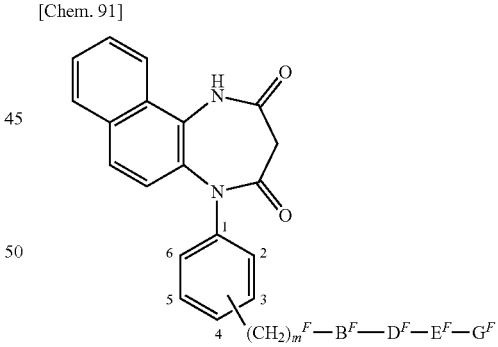

wherein m$^F$ (substitution position), B$^F$, D$^F$, E$^F$, and G$^F$ are as described in Table 90.

TABLE 90

| m$^F$ (Position) | B$^F$ | D$^F$ | E$^F$ | G$^F$ |
|---|---|---|---|---|
| 1(4) | NHCO | Bond | Bond | Phenyl |
| 1(4) | NHCO | Bond | Bond | (2-Cl)Phenyl |
| 1(4) | NHSO$_2$ | CH$_2$ | Bond | (2-Cl)Phenyl |

<Representative Compound F-800>

[Chem. 92]

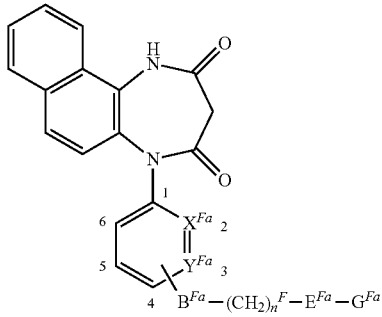

wherein $X^{Fa}$, $Y^{Fa}$, $B^{Fa}$ (substitution position), $n^F$, $E^{Fa}$, and $G^{Fa}$ are as described in Table 91.

TABLE 91

| $X^{Fa}$ | $Y^{Fa}$ | $B^{Fa}$ (Substitution position) | $n^F$ | $E^{Fa}$ | $G^{Fa}$ |
|---|---|---|---|---|---|
| CH | C—F | NHCO(4) | 0 | Bond | (2,3-Me)Phenyl |
| CH | C—OH | NHCO(4) | 0 | Bond | (2,3-Me)Phenyl |
| CH | C—F | NHCO(4) | 0 | Bond | (2-I)Phenyl |
| CH | N | NHCO(4) | 0 | Bond | (2-I)Phenyl |
| CH | N | NHCO(4) | 0 | Bond | Phenyl |
| N | CH | NHCO(4) | 0 | Bond | (2-I)Phenyl |
| CH | N | NHCO(4) | 0 | Bond | (2-Cl)Phenyl |
| CH | N | NHCO(4) | 0 | Bond | (2-OH)Phenyl |
| CH | N | NHC(=O)NH(4) | 0 | Bond | (2-OH)Phenyl |
| CH | N | NHCO(4) | 0 | Bond | (2-OH,6-Me)Phenyl |
| CH | N | NHCO(4) | 0 | Bond | (2-OH,6-Cl)Phenyl |
| CH | N | NHCO(3) | 0 | Bond | (2-OH,6-Cl)Phenyl |
| CH | N | NHCO(4) | 0 | Bond | (2-Cl)pyridin 2-yl |
| CH | N | NHCO(4) | 1 | Bond | (2-Cl)pyridin 2-yl |
| CH | N | NHCO(4) | 0 | Bond | (2-Me)pyridin 2-yl |
| CH | C—OMe | NHSO$_2$(4) | 1 | Bond | (2-Cl)Phenyl |
| CH | C—OH | NHSO$_2$(4) | 1 | Bond | (2-Cl)Phenyl |

<Representative Compound F-900>

[Chem. 93]

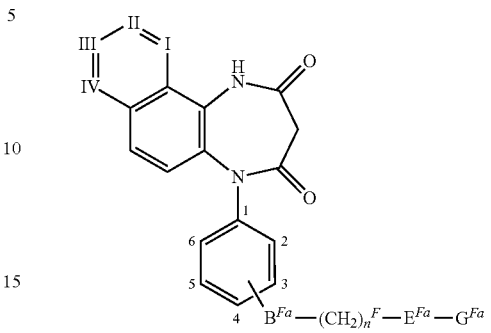

wherein I=II-III=IV, $B^{Fa}$ (substitution position), $n^F$, $E^{Fa}$, and $G^{Fa}$ are as described in Table 92.

TABLE 92

| I=II—III=IV | $B^{Fa}$ (Substitution position) | $n^F$ | $E^{Fa}$ | $G^{Fa}$ |
|---|---|---|---|---|
| N=CH—CH=CH | NHCO(4) | 0 | Bond | (2-I)Phenyl |
| CH=N—CH=CH | NHCO(4) | 0 | Bond | (2-I)Phenyl |
| CH=CH—N=CH | NHCO(4) | 0 | Bond | (2-I)Phenyl |
| CH=CH—CH=N | NHCO(4) | 0 | Bond | (2-I)Phenyl |
| N=CH—CH=CH | NHCO(4) | 1 | O | Phenyl |
| N=CH—CH=CH | NHCO(3) | 0 | Bond | (2-I)Phenyl |
| N=CH—CH=CH | NHCO(4) | 0 | Bond | (2-Cl)Phenyl |
| N=CH—CH=CH | NHCO(4) | 0 | Bond | (2-OH)Phenyl |
| N=CH—CH=CH | NHC(=O)NH(4) | 0 | Bond | (2-OH)Phenyl |
| N=CH—CH=CH | NHCO(4) | 1 | O | (2-OH, 6-Me)Phenyl |
| N=CH—CH=CH | NHCO(4) | 0 | Bond | (2-OH, 6-Cl)Phenyl |
| N=CH—CH=CH | NHCO(3) | 0 | Bond | (2-OH, 6-Cl)Phenyl |
| N=CH—CH=CH | NHCO(4) | 0 | Bond | (2-Cl)pyridin 2-yl |
| N=CH—CH=CH | NHCO(4) | 1 | Bond | (2-Cl)pyridin 2-yl |
| N=CH—CH=CH | NHCO(4) | 0 | Bond | (2-Me)pyridin 2-yl |
| CH=CH—N=CH | NHCO(4) | 0 | Bond | (2-Cl)pyridin 3-yl |

<Representative Compound F-1000>

[Chem. 94]

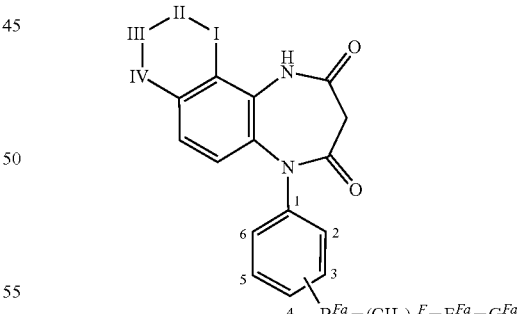

wherein I-II-III-IV, $B^{Fa}$ (substitution position), $n^F$, $E^{Fa}$, and $G^{Fa}$ are as described in Table 93.

TABLE 93

| I—II—III—IV | $B^{Fa}$ (Substitution position) | $n^F$ | $E^{Fa}$ | $G^{Fa}$ |
|---|---|---|---|---|
| NH—CH2—CH2—CH2 | NHCO(4) | 0 | Bond | (2-I)Phenyl |
| CH2—NH—CH2—CH2 | NHCO(4) | 0 | Bond | (2-I)Phenyl |
| CH2—CH2—NH—CH2 | NHCO(4) | 0 | Bond | (2-I)Phenyl |

TABLE 93-continued

| I—II—III—IV | $B^{Fa}$ (Substitution position) | $n^F$ | $E^{Fa}$ | $G^{Fa}$ |
|---|---|---|---|---|
| CH2—CH2—CH2—NH | NHCO(4) | 0 | Bond | (2-I)Phenyl |
| CH2—CH2—NH—CH2 | NHCO(4) | 1 | O | Phenyl |
| CH2—CH2—NH—CH2 | NHCO(3) | 0 | Bond | (2-I)Phenyl |
| CH2—CH2—NH—CH2 | NHCO(4) | 0 | Bond | (2-Cl)Phenyl |
| CH2—CH2—NH—CH2 | NHCO(4) | 0 | Bond | (2-Cl)pyridin 3-yl |
| CH2—CH2—NH—CH2 | NHCO(4) | 0 | Bond | (2-OH)Phenyl |
| CH2—CH2—NH—CH2 | NHC(=O)NH(4) | 0 | Bond | (2-OH)Phenyl |
| CH2—CH2—NH—CH2 | NHCO(4) | 1 | O | (2-OH, 6-Me)Phenyl |
| CH2—CH2—NH—CH2 | NHCO(4) | 0 | Bond | (2-OH, 6-Cl)Phenyl |
| CH2—CH2—NH—CH2 | NHCO(3) | 0 | Bond | (2-OH, 6-Cl)Phenyl |
| CH2—CH2—NH—CH2 | NHCO(4) | 0 | Bond | (2-Cl)pyridin 2-yl |
| CH2—CH2—NH—CH2 | NHCO(4) | 1 | Bond | (2-Cl)pyridin 2-yl |
| CH2—CH2—NH—CH2 | NHCO(4) | 0 | Bond | (2-Me)pyridin 2-yl |
| CH2—CH2—NH—CH2 | NHCO(4) | 0 | Bond | (2-Cl)pyridln 3-y |

<Representative Compound F-1100>

[Chem. 95]

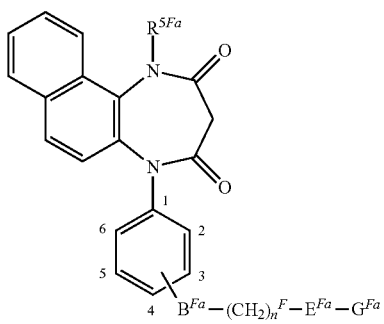

wherein $R^{5Fa}$, $B^{Fa}$ (substitution position), $n^F$, $E^{Fa}$, and $G^{Fa}$ are as described in Table 94.

TABLE 94

| $R^{5Fa}$ | $B^{Fa}$ (Substitution position) | $n^F$ | $E^{Fa}$ | $G^{Fa}$ |
|---|---|---|---|---|
| Bn | NBnSO$_2$(4) | 0 | Bond | (2-NO$_2$)Phenyl |
| Me | NBnSO$_2$(4) | 0 | Bond | (2-NO$_2$)Phenyl |
| Et | NBnSO$_2$(4) | 0 | Bond | (2-NO$_2$)Phenyl |

(G-1) A compound, a tautomer, stereoisomer, or pharmaceutically acceptable salt of the compound, or a hydrate or solvate thereof, the compound represented by the following general formula (GI):

[Chem. 96]

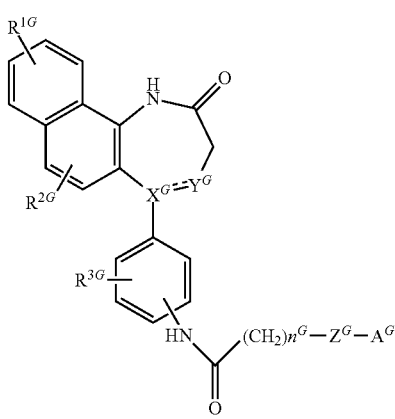

(GI)

wherein $R^{1G}$, $R^{2G}$, and $R^{3G}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $X^G$ represents C or N, $Y^G$ represents N or C(=O), provided that when $X^G$ is C, $Y^G$ represents N, and when $X^G$ is N, $Y^G$ represents C(=O)

a double line composed of a solid line and a dashed line denotes a single bond or a double bond, $n^G$ represents an integer of 0 to 6, $Z^G$ represents O, S, or a bond, and $A^G$ represents a benzene ring, a pyridine ring, a piperazine ring, a piperidine ring, or a morpholine ring optionally having, as substituents, 1 to 5 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or N($R^{4G}$)($R^{5G}$) where $R^{4G}$ and $R^{5G}$ are the same or different and represent a $C_{1-8}$ alkyl group or $R^{4G}$ and $R^{5G}$ and a nitrogen atom bonded to $R^{4G}$ and $R^{5G}$ are fused to represent a 5- to 7-membered ring further optionally comprising, as a ring forming atom, an oxygen atom or a sulfur atom as a heteroatom.

Examples of the $C_{1-8}$ alkyl group in general formula (GI) include a methyl, ethyl, propyl, isopropyl, butyl, i-butyl, t-butyl, pentyl, or hexyl group.

Examples of the $C_{3-8}$ cycloalkyl group include a cyclopropyl group or a cyclohexyl group.

Examples of the $C_{2-8}$ alkenyl group include an allyl group.

Examples of the $C_{1-8}$ alkoxy group include a methoxy, ethoxy, propoxy, isopropoxy, butoxy, i-butoxy, t-butoxy, pentyloxy, or hexyloxy group.

Examples of the $C_{1-8}$ alkyl group substituted with 1 to 3 halogen atoms include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the $C_{1-8}$ alkoxy group substituted with 1 to 3 halogen atoms include a methoxy, ethoxy, propoxy, isopropoxy, butoxy, or t-butoxy group substituted with 1 to 3 halogen atoms such as fluorine, chlorine, or bromine atoms, and preferably a trifluoromethoxy, chloromethoxy, 2-chloroethoxy, 2-bromoethoxy, or 2-fluoroethoxy group.

Examples of the halogen atom include a fluorine, chlorine, or bromine atom.

Examples of the $C_{1-8}$ alkylamino group include a methylamino or ethylamino group.

Examples of the $C_{2-8}$ dialkylamino group include a dimethylamino or diethylamino group.

Examples of the 5- to 7-membered ring together formed by fusing $R^{4G}$ and $R^{5G}$ and a nitrogen atom bonded to $R^{4G}$ and $R^{5G}$ and optionally further comprising, as a ring forming atom, an oxygen atom or a sulfur atom as a heteroatom include morpholin-4-yl, 1H-pyrrol-1-yl, or pyrrolidin-1-yl.

In the above $R^{1G}$, 1 to 4 substituents, which are the same or different, may be present.

In the above $R^{2G}$, 1 to 2 substituents, which are the same or different, may be present.

In the above $R^{3G}$, 1 to 4 substituents, which are the same or different, may be present.

The following compounds are preferable as compounds represented by general formula (GI).

(G-1-1)

A compound, a tautomer, stereoisomer, or pharmaceutically acceptable salt of the compound, or a hydrate or solvate thereof, the compound represented by (G-1), wherein $A^G$ is a benzene ring, a pyridine ring, a piperazine ring, a piperidine ring, or a morpholine ring optionally having, as substituents, 1 to 5 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(G-1-2)

A compound, a tautomer, stereoisomer, or pharmaceutically acceptable salt of the compound, or a hydrate or solvate thereof, the compound represented by (G-1), wherein $A^G$ is a benzene ring or a pyridine ring optionally having, as substituents, 1 to 5 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, an amino group, a $C_{1-8}$ alkylamino group, or a $C_{2-8}$ dialkylamino group.

(G-1-3)

A compound, a tautomer, stereoisomer, or pharmaceutically acceptable salt of the compound, or a hydrate or solvate thereof, the compound represented by (G-1), wherein $A^G$ is a benzene ring optionally having, as substituents, 1 to 5 substituents, which are the same or different, selected from a $C_{1-8}$ alkyl group, a $C_{1-8}$ alkoxy group, a halogen atom, a hydroxyl group, an amino group, a $C_{1-8}$ alkylamino group, or a $C_{2-8}$ dialkylamino group.

(G-1-4)

A compound, a tautomer, stereoisomer, or pharmaceutically acceptable salt of the compound, or a hydrate or solvate thereof, the compound represented by (G-1), wherein where $A^G$ is a pyridine ring having $N(R^{4G})(R^{5G})$ (where regarding $R^{4G}$ and $R^{5G}$, $R^{4G}$ and $R^{5G}$ and a nitrogen atom bonded to $R^{4G}$ and $R^{5G}$ are fused to represent a 5- to 7-membered ring further optionally comprising, as a ring forming atom, an oxygen atom or a sulfur atom as a heteroatom).

(G-1-5)

A compound, a tautomer, stereoisomer, or pharmaceutically acceptable salt of the compound, or a hydrate or solvate thereof, the compound represented by (G-1), wherein where $A^G$ is a pyridine ring optionally having, as a substituent, a substituent selected from morpholin-4-yl, 1H-pyrrol-1-yl, or pyrrolidin-1-yl.

(G-1-6)

A compound, a tautomer, stereoisomer, or pharmaceutically acceptable salt of the compound, or a hydrate or solvate thereof, the compound represented by (G-1) or the compound represented by any of (G-1-1) to (G-1-5), wherein $R^{1G}$, $R^{2G}$, and $R^{3G}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, or a halogen atom.

(G-1-7)

A compound, a tautomer, stereoisomer, or pharmaceutically acceptable salt of the compound, or a hydrate or solvate thereof, the compound represented by (G-1) or the compound represented by any of (G-1-1) to (G-1-5), wherein $R^{1G}$, $R^{2G}$, and $R^{3G}$ are the same or different and are a hydrogen atom or a halogen atom.

(G-1-8)

A compound, a tautomer, stereoisomer, or pharmaceutically acceptable salt of the compound, or a hydrate or solvate thereof, the compound represented by (G-1) or the compound represented by any of (G-1-1) to (G-1-7), wherein $n^G$ is 0.

(G-1-9)

A compound, a tautomer, stereoisomer, or pharmaceutically acceptable salt of the compound, or a hydrate or solvate thereof, the compound represented by (G-1) or the compound represented by any of (G-1-1) to (G-1-7), wherein $n^G$ is 1 or 2.

(G-1-10)

A compound, a tautomer, stereoisomer, or pharmaceutically acceptable salt of the compound, or a hydrate or solvate thereof, the compound represented by (G-1) or the compound represented by any of (G-1-1) to (G-1-9), wherein $Z^G$ is a bond.

(G-1-11)

A compound, a tautomer, stereoisomer, or pharmaceutically acceptable salt of the compound, or a hydrate or solvate thereof, the compound represented by (G-1), wherein $R^{1G}$, $R^{2G}$, and $R^{3G}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, or a hydroxyl group, $X^G$ is N, $Y^G$ is C(=O), the double line composed of a solid line and a dashed line denotes a single bond, $n^G$ is 0, $Z^G$ is a bond, and $A^G$ is a benzene ring or a pyridine ring optionally having, as substituents, 1 to 3 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, an amino group, a $C_{1-8}$ alkylamino group, or $N(R^{4G})(R^{5G})$ where $R^{4G}$ and $R^{5G}$ are the same or different and represent a $C_{1-8}$ alkyl group or $R^{4G}$ and $R^{5G}$ and a nitrogen atom bonded to $R^{4G}$ and $R^{5G}$ are fused to represent a morpholine ring, a pyrrole ring, or a pyrrolidine ring.

(G-1-12)

A compound, a tautomer, stereoisomer, or pharmaceutically acceptable salt of the compound, or a hydrate or solvate thereof, the compound represented by (G-1), wherein $R^{1G}$, $R^{2G}$, and $R^{3G}$ are the same or different and represent a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, or a hydroxyl group, $X^G$ is C, $Y^G$ is N, the double line composed of a solid line and a dashed line denotes a double bond, $n^G$ is an integer of 0 to 3, $Z^G$ is a bond, and $A^G$ represents a benzene ring or a pyridine ring optionally having, as substituents, 1 to 3 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, an amino group, a $C_{1-8}$ alkylamino group, or $N(R^{4G})(R^{5G})$ where $R^{4G}$ and $R^{5G}$ are the same or different and represent a $C_{1-8}$ alkyl group or $R^{4G}$ and $R^{5G}$ and a nitrogen atom bonded to $R^{4G}$ and $R^{5G}$ are fused to represent morpholine, a pyrrole ring, or a pyrrolidine ring.

(G-1-13)

A compound, a tautomer, stereoisomer, or pharmaceutically acceptable salt of the compound, or a hydrate or solvate thereof, the compound represented by (G-1) or the compound represented by any of (G-1-1) to (G-1-12), wherein $X^G$ and NHC(=O) are at para positions of a phenyl group.

In the above general formula (GI), it is preferable that $R^{1G}$, $R^{2G}$, and $R^{3G}$ are a hydrogen atom.

In the above general formula (GI), it is preferable that $X^G$ is C, $Y^G$ is N, and the double line composed of a solid line and a dashed line is a double bond.

In the above general formula (GI), it is preferable that $n^G$ is 0.

In the above general formula (GI), it is preferable that $Z^G$ is a bond.

In the above general formula (GI), it is preferable that $A^G$ represents a pyridine ring optionally having, as substituents, 1 to 3 substituents, which are the same or different, selected from $N(R^{4G})(R^{5G})$ where $R^{4G}$ and $R^{5G}$ are the same or different and represent a $C_{1-8}$ alkyl group. It is more preferable that $A^G$ is a pyridine ring having, as a substituent, a $C_{1-8}$ dialkylamino group. It is suitable that $A^G$ is a pyridine ring having, as a substituent, a dimethylamino group.

In the above general formula (GI), it is preferable that $R^{1G}$, $R^{2G}$, and $R^{3G}$ are a hydrogen atom, $X^G$ is C, $Y^G$ is N, the double line composed of a solid line and a dashed line is a double bond, $n^G$ is 0, $Z^G$ is a bond, and $A^G$ is a pyridine ring having, as a substituent, a $C_{1-8}$ dialkylamino group. It is suitable that $A^G$ is a pyridine ring having, as a substituent, a dimethylamino group.

In the above general formula (GI), it is preferable that $R^{1G}$, $R^{2G}$, and $R^{3G}$ are a hydrogen atom, $X^G$ is N, $Y^G$ is C(=O), the double line composed of a solid line and a dashed line is a single bond, $n^G$ is 0, $Z^G$ is a bond, $A^G$ is a pyridine ring having, as a substituent, a $C_{1-8}$ dialkylamino group. It is suitable that $A^G$ is a pyridine ring having, as a substituent, a dimethylamino group.

The following shows representative compounds included in general formula (GI).

<Representative Compound G-100>

[Chem. 97]

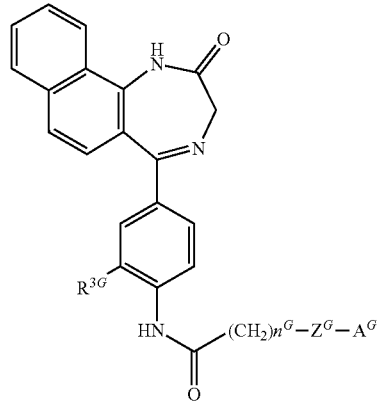

wherein $R^{3G}$, $A^G$, $Z^G$, and $n^G$ are as described in Tables 95 and 96.

TABLE 95

| $R^{3G}$ | $n^G$ | $Z^G$ | $A^G$ |
|---|---|---|---|
| H | 2 | Bond | Pyridin 2-yl |
| H | 0 | Bond | (2-Et, 3-OH)Phenyl |
| H | 0 | Bond | (2-Et)Pyridin 3-yl |
| H | 0 | Bond | (2-Et, 6-OH)Phenyl |
| H | 0 | Bond | (3-Et)Pyridin 2-yl |
| H | 1 | O | Pyridin 2-yl |
| H | 1 | Bond | (2-OMe)Phenyl |
| H | 2 | Bond | Pyridin 3-yl |
| H | 2 | Bond | Phenyl |
| H | 2 | Bond | Cyclohexyl |
| H | 1 | Bond | Pyridin 2-yl |

TABLE 96

| $R^{3G}$ | $n^G$ | $Z^G$ | $A^G$ |
|---|---|---|---|
| H | 1 | Bond | Pyridin 3-yl |
| H | 1 | Bond | Pyridin 4-yl |
| H | 3 | Bond | Pyridin 2-yl |
| H | 1 | Bond | (2-NMe$_2$)Phenyl |
| OH | 1 | O | Pyridin 2-yl |
| OMe | 2 | O | Pyridin 2-yl |
| CN | 2 | Bond | Pyridin 2-yl |
| Me | 2 | Bond | Pyridin 2-yl |
| CF$_3$ | 1 | Bond | Pyridin 2-yl |
| F | 2 | Bond | Pyridin 2-yl |
| H | 0 | Bond | (2-NMe$_2$) pyridin 3-yl |
| F | 2 | Bond | Phenyl |

<Representative Compound G-200>

[Chem. 98]

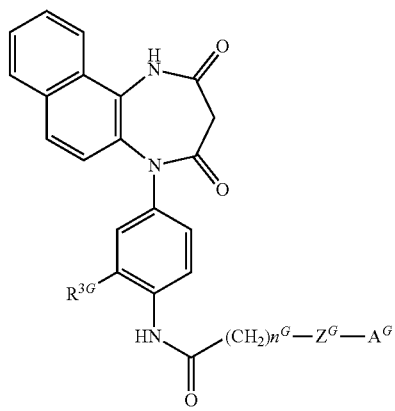

wherein $R^{3G}$, $A^{G}$, $Z^{G}$, and $n^{G}$ are as described in Tables 97 and 98.

TABLE 97

| $R^{3G}$ | $n^{G}$ | $Z^{G}$ | $A^{G}$ |
|---|---|---|---|
| H | 2 | Bond | Pyridin 3-yl |
| H | 2 | Bond | Pyridin 4-yl |
| F | 0 | Bond | (2-t Bu)phenyl |
| H | 2 | Bond | Pyridin 2-yl |
| H | 0 | Bond | (2-NMe$_2$)pyridin 3-yl |
| H | 2 | Bond | Cyclohexyl |
| H | 1 | Bond | Pyridin 2-yl |
| H | 1 | Bond | Pyridin 3-yl |

TABLE 98

| $R^{3G}$ | $n^{G}$ | $Z^{G}$ | $A^{G}$ |
|---|---|---|---|
| H | 1 | Bond | Pyridin 4-yl |
| H | 3 | Bond | Pyridin 2-yl |
| H | 1 | Bond | (2-NMe2)Phenyl |
| OH | 1 | O | Pyridin 2-yl |
| OMe | 2 | O | Pyridin 2-yl |
| CN | 2 | Bond | Pyridin 2-yl |
| Me | 2 | Bond | Pyridin 2-yl |
| CF3 | 1 | Bond | Pyridin 2-yl |
| F | 2 | Bond | Pyridin 2-yl |
| F | 2 | Bond | Phenyl |

<Representative Compound G-300>

[Chem. 99]

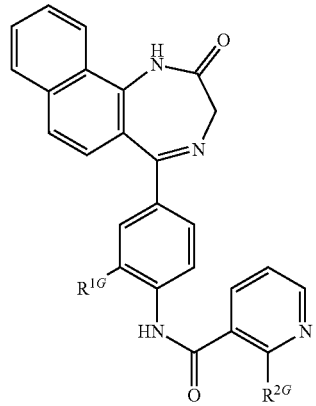

wherein $R^{1G}$, $R^{2G}$, and the salt are as described in Tables 99 and 100.

TABLE 99

| $R^{1G}$ | $R^{2G}$ | Salt |
|---|---|---|
| H | NMe$_2$ | 2HCl |
| H | NMe$_2$ | 2MsOH |
| H | 1H-pyrrol-1-yl | 2HCl |
| H | morpholin-4-yl | 2HCl |
| H | pyrrolidin-1-yl | 2HCl |
| H | iPr | 2HCl |
| H | iPrNH | 2HCl |
| F | NMe$_2$ | |
| OH | HMe$_2$ | |
| F | 1H-pyrrol-1-yl | |
| OH | morpholin-4-yl | |

TABLE 100

| $R^{1G}$ | $R^{2G}$ | Salt |
|---|---|---|
| F | pyrrolidin-1-yl | |
| OH | iPr | |
| F | iPrNH | |
| H | NEt$_2$ | |
| H | NHEt | |
| F | NHMe | |
| Me | 1H-pyrrol-1-yl | |
| Me | morpholin-4-yl | |
| Me | pyrrolidin-1-yl | |

<Representative Compound G-400>

[Chem. 100]

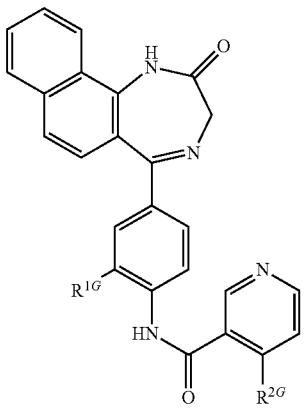

wherein $R^{1G}$, $R^{2G}$, and the salt are as described in Table 101.

TABLE 101

| $R^{1G}$ | $R^{2G}$ | Salt |
|---|---|---|
| H | MMe₂ | 2HCl |
| H | 1H-pyrrol-1-yl | |
| H | morpholin-4-yl | |
| H | pyrroidin-1-yl | |
| H | iPr | |
| H | iPrNH | |
| F | NMe₂ | |

<Representative Compound G-500>

[Chem. 101]

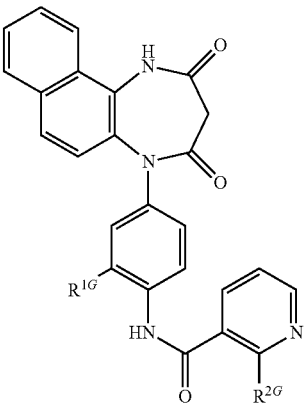

wherein $R^{1G}$, $R^{2G}$, and the salt are as described in Table 102.

TABLE 102

| $R^{1G}$ | $R^{2G}$ | Salt |
|---|---|---|
| H | NMe₂ | HCl |
| H | morpholin-4-yl | HCl |
| H | pyrrolidin-1-yl | |
| H | iPr | |

TABLE 102-continued

| $R^{1G}$ | $R^{2G}$ | Salt |
|---|---|---|
| H | iPrNH | |
| F | NMe₂ | |
| OH | NMe₂ | |
| F | 1H-pyrrol-1-yl | |
| OH | morpholin-4-yl | |
| F | pyrrolidin-1-yl | |
| OH | iPr | |
| F | iPrNH | |
| H | NEt₂ | |
| H | NHEt | |
| F | NHMe | |
| Me | 1H-pyrrol-1-yl | |
| Me | morpholin-4-yl | |

(H-1) A compound, a tautomer, stereoisomer, or pharmaceutically acceptable salt of the compound, or a hydrate or solvate thereof, the compound represented by the following general formula (HI):

[Chem. 102]

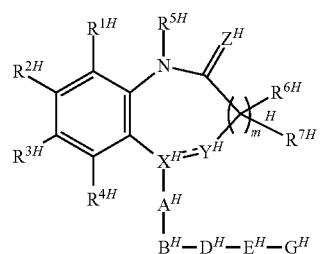

wherein $R^{1H}$ and $R^{2H}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), an optionally substituted phenyl group, an optionally substituted pyridyl group, or an aralkyl group (the number of carbon atoms in an aryl moiety is from 6 to 10 and the number of carbon atoms in an alkylene moiety is from 1 to 8), or $R^{1H}$ and $R^{2H}$ are optionally fused with a benzene ring bonded thereto to form a condensed ring selected from a naphthalene ring, a quinoline ring, an isoquinoline ring, a tetrahydronaphthalene ring, an indane ring, a tetrahydroquinoline ring, or a tetrahydroisoquinoline ring and a ring fused with RH and $R^{2H}$ and comprising carbon atoms bonded to respective $R^{1H}$ and $R^{2H}$ is optionally substituted with 1 to 4 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{3H}$ and $R^{4H}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{5H}$ represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $R^{6H}$ and $R^{7H}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, or an amino group, $X^H$ represents C or N, $Y^H$ represents N or C(=O), provided that when $X^H$ is C, $Y^H$ represents N, and when $X^H$ is N, $Y^H$ represents C(=O), a double line composed of a solid line and a dashed line denotes a single bond or a double bond, $Z^H$ represents O, S, or NH, $A^H$ represents a benzene ring, a pyridine ring, a pyrimidine ring, a pyridazine ring, a thiophene ring, a furan ring, a pyrazole ring, an imidazole ring, a quinoline ring, a benzimidazole ring, or an indane ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $B^H$ represents O, S, $NR^{8H}$, or a bond, $R^{8H}$ here represents a hydrogen atom or a $C_{1-8}$ alkyl group, $D^H$ represents a benzene ring, a pyridine ring, a pyrimidine ring, a pyridazine ring, a thiophene ring, a furan ring, a tetrazole ring, an imidazole ring, an imidazoline ring, a triazole ring, a thiazole ring, an oxazole ring, an isoxazole ring, a pyrazole ring, a pyrrole ring, a pyrrolidine ring, a piperazine ring, a piperidine ring, or a 5- to 8-membered cycloalkyl ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $E^H$ represents $-(C^{R9}H^{R10}H)_n{}^H-T^H-$, $R^{9H}$ and $R^{10H}$ here are the same or different and represent a hydrogen atom, a hydroxyl group, or a $C_{1-8}$ alkyl group, or $R^{9H}$ and $R^{10H}$ are optionally fused to form an ethylene chain, $n^H$ represents an integer of 0 to 8, $T^H$ represents O, S, $NR^{11H}$, or a bond, $R^{11H}$ here represents a hydrogen atom or a $C_{1-8}$ alkyl group, $G^H$ represents a benzene ring, a pyridine ring, an imidazole ring, a pyrrole ring, a pyrazole ring, a thiophene ring, a furan ring, a thiazole ring, an oxazole ring, a pyrimidine ring, a pyridazine ring, a pyrazine ring, a naphthalene ring, a quinoline ring, a quinazoline ring, an indole ring, an indoline ring, a piperazine ring, a piperidine ring, a morpholine ring, or a 5- to 8-membered cycloalkyl ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group, and $m^H$ represents an integer of 0 to 2.

(H-2) A compound, a tautomer, stereoisomer, or pharmaceutically acceptable salt of the compound, or a hydrate or solvate thereof, the compound represented by the following general formula (HIII):

[Chem. 103]

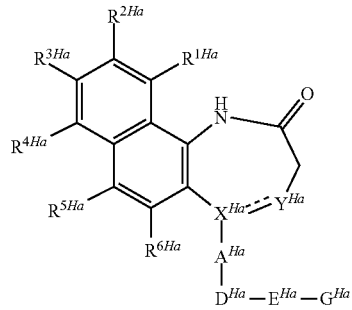

(HIII)

wherein $R^{1Ha}$, $R^{2Ha}$, $R^{3Ha}$, $R^{4Ha}$, $R^{5Ha}$, and $R^6Ha$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), an optionally substituted phenyl group, an optionally substituted pyridyl group, or an aralkyl group (the number of carbon atoms in an aryl moiety is from 6 to 10 and the number of carbon atoms in an alkylene moiety is from 1 to 8), $X^{Ha}$ represents C or N, $Y^{Ha}$ represents N or C(=O), provided that when $X^{Ha}$ is C, $Y^{Ha}$ represents N, and when $X^{Ha}$ is N, $Y^{Ha}$ represents C(=O), a double line composed of a solid line and a dashed line denotes a single bond or a double bond, $A^{Ha}$ represents a benzene ring, a pyridine ring, a pyrimidine ring, a pyridazine ring, a thiophene ring, a furan ring, a pyrazole ring, an imidazole ring, a quinoline ring, a benzimidazole ring, or an indane ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $D^{Ha}$ represents a benzene ring, a pyridine ring, a pyrimidine ring, a pyridazine ring, a thiophene ring, a furan ring, a tetrazole ring, an imidazole ring, an imidazoline ring, a triazole ring, a thiazole ring, an oxazole ring, an isoxazole ring, a pyrazole ring, a pyrrole ring, a pyrrolidine ring, a piperazine ring, a piperidine ring, or a 5- to 8-membered cycloalkyl ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $E^{Ha}$ represents —$(CR^{9Ha}R^{10Ha})_p$-$T^{Ha}$-, $R^{9Ha}$ and $R^{10Ha}$ here are the same or different and represent a hydrogen atom, a hydroxyl group, or a $C_{1-8}$ alkyl group, or $R^{9Ha}$ and $R^{10Ha}$ are optionally fused to form an ethylene chain, p represents an integer of 0 to 8, $T^{Ha}$ represents O, S, $NR^{11Ha}$, or a bond, $R^{11Ha}$ here represents a hydrogen atom or a $C_{1-8}$ alkyl group, and $G^{Ha}$ represents a benzene ring, a pyridine ring, an imidazole ring, a pyrrole ring, a pyrazole ring, a thiophene ring, a furan ring, a thiazole ring, an oxazole ring, a pyrimidine ring, a pyridazine ring, a pyrazine ring, a naphthalene ring, a quinoline ring, a quinazoline ring, an indole ring, an indoline ring, a piperazine ring, a piperidine ring, a morpholine ring, or a 5-to 8-membered cycloalkyl ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group.

Next, the present invention will be described in detail.

As used herein, examples of the $C_{1-8}$ alkyl group include a methyl, ethyl, propyl, isopropyl, butyl, i-butyl, t-butyl, pentyl, or hexyl group.

Examples of the 5- to 8-membered cycloalkyl ring include a cyclopentyl ring or a cyclohexyl ring.

Examples of the $C_{3-8}$ cycloalkyl group include a cyclopropyl group or a cyclohexyl group.

Examples of the $C_{2-8}$ alkenyl group include an allyl group.

Examples of the $C_{1-8}$ alkoxy group include a methoxy, ethoxy, propoxy, isopropoxy, butoxy, i-butoxy, t-butoxy, pentyloxy, or hexyloxy group.

Examples of the $C_{1-8}$ alkyl group substituted with 1 to 3 halogen atoms include a methyl, ethyl, propyl, isopropyl, butyl, or t-butyl group substituted with 1 to 3 halogen atoms such as fluorine, chlorine, or bromine atoms, and preferably a trifluoromethyl, chloromethyl, 2-chloroethyl, 2-bromoethyl, or 2-fluoroethyl group.

Examples of the $C_{1-8}$ alkoxy group substituted with 1 to 3 halogen atoms include a methoxy, ethoxy, propoxy, isopropoxy, butoxy, or t-butoxy group substituted with 1 to 3 halogen atoms such as fluorine, chlorine, or bromine atoms, and preferably a trifluoromethoxy, chloromethoxy, 2-chloroethoxy, 2-bromoethoxy, or 2-fluoroethoxy group.

Examples of the halogen atom include a fluorine, chlorine, or bromine atom.

Examples of the $C_{1-8}$ alkylamino group include a methylamino or ethylamino group.

Examples of the $C_{2-8}$ dialkylamino group include a dimethylamino or diethylamino group.

Examples of the $C_{2-8}$ acylamino group include an acetylamino group.

Examples of the $C_{2-8}$ acyl group include an acetyl group.

Examples of the alkoxycarbonyl group (the number of carbon atoms in an alkoxy moiety is from 1 to 8) include a methoxycarbonyl group.

Examples of the aralkyl group (the number of carbon atoms in an aryl moiety is from 6 to 10 and the number of carbon atoms in an alkylene moiety is from 1 to 8) include a benzyl group.

Examples of the hydroxyl-substituted $C_{1-8}$ alkyl group include 2-hydroxyethyl group.

Examples of an optional substituent of the optionally substituted phenyl group or the optionally substituted pyridyl group include a halogen atom, a $C_{1-8}$ alkyl group, a $C_{1-8}$ alkoxy group, a $C_{1-8}$ alkyl group substituted with 1 to 3 halogen atoms, or a $C_{1-8}$ alkoxy group substituted with 1 to 3 halogen atoms.

In $E^H$ or $E^{Ha}$ of general formula (HI) or (HIII), the wording "$R^{9Ha}$ and $R^{10Ha}$ are optionally fused to form an ethylene chain" means that $E^H$ or $E^{Ha}$ optionally has a double bond.

The following compounds are preferable as present compounds represented by general formula (HI).

(H-1-1)

A compound, a tautomer, stereoisomer, or pharmaceutically acceptable salt of the compound, or a hydrate or solvate thereof, the compound represented by (H-1), wherein $m^H$ is 1.

(H-1-2)

A compound, a tautomer, stereoisomer, or pharmaceutically acceptable salt of the compound, or a hydrate or solvate thereof, the compound represented by (H-1) or (H-1-1), wherein $R^{1H}$ and $R^{2H}$ are fused with a benzene ring bonded thereto to form a naphthalene ring and the naphthalene ring optionally substituted with 1 to 4 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(H-1-3)

A compound, a tautomer, stereoisomer, or pharmaceutically acceptable salt of the compound, or a hydrate or solvate thereof, the compound represented by (H-1) or any of (H-1-1) to (H-1-2), wherein $R^{3H}$ and $R^{4H}$ are the same or different and are a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(H-1-4)

A compound, a tautomer, stereoisomer, or pharmaceutically acceptable salt of the compound, or a hydrate or solvate thereof, the compound represented by (H-1) or any of (H-1-1) to (H-1-3), wherein $R^{5H}$ is a hydrogen atom.

(H-1-5)

A compound, a tautomer, stereoisomer, or pharmaceutically acceptable salt of the compound, or a hydrate or solvate thereof, the compound represented by (H-1) or any of (H-1-1) to (H-1-4), wherein $R^{6H}$ and $R^{7H}$ are a hydrogen atom.

(H-1-6)

A compound, a tautomer, stereoisomer, or pharmaceutically acceptable salt of the compound, or a hydrate or solvate thereof, the compound represented by (H-1) or any of (H-1-1) to (H-1-5), wherein $X^H$ is N and $Y^H$ is C(=O).

(H-1-7)

A compound, a tautomer, stereoisomer, or pharmaceutically acceptable salt of the compound, or a hydrate or solvate thereof, the compound represented by (H-1) or any of (H-1-1) to (H-1-6), wherein $Z^H$ is O.

(H-1-8)

A compound, a tautomer, stereoisomer, or pharmaceutically acceptable salt of the compound, or a hydrate or solvate thereof, the compound represented by (H-1) or any of (H-1-1) to (H-1-7), wherein $A^H$ is a benzene ring or a pyridine ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(H-1-9)

A compound, a tautomer, stereoisomer, or pharmaceutically acceptable salt of the compound, or a hydrate or solvate thereof, the compound represented by (H-1) or any of (H-1-1) to (H-1-8), wherein $D^H$ is a tetrazole ring, an imidazole ring, an imidazoline ring, a triazole ring, a pyrrole ring, a pyrrolidine ring, a piperazine ring, or a piperidine ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(H-1-10)

A compound, a tautomer, stereoisomer, or pharmaceutically acceptable salt of the compound, or a hydrate or solvate thereof, the compound represented by (H-1) or any of (H-1-1) to (H-1-9), wherein $B^H$ is a bond.

(H-1-11)

A compound, a tautomer, stereoisomer, or pharmaceutically acceptable salt of the compound, or a hydrate or solvate thereof, the compound represented by (H-1-10), wherein $D^H$ is bonded via a nitrogen atom to A.

(H-1-12)

A compound, a tautomer, stereoisomer, or pharmaceutically acceptable salt of the compound, or a hydrate or solvate thereof, the compound represented by (H-1) or any of (H-1-1) to (H-1-11), wherein $E^H$ is a $C_{Z}$-5 alkylene chain.

(H-1-13)

A compound, a tautomer, stereoisomer, or pharmaceutically acceptable salt of the compound, or a hydrate or solvate thereof, the compound represented by (H-1) or any of (H-1-1) to (H-1-12), wherein $G^H$ is a benzene ring, a pyridine ring, an imidazole ring, a pyrrole ring, a pyrazole ring, a pyrimidine ring, a pyridazine ring, a pyrazine ring, or a 5- to 7-membered cycloalkyl ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group.

(H-1-14)

A compound, a tautomer, stereoisomer, or pharmaceutically acceptable salt of the compound, or a hydrate or solvate thereof, the compound represented by (H-1), wherein $R^{1H}$ and $R^{2H}$ are fused with a benzene ring bonded thereto to form a naphthalene ring or an indane ring and the naphthalene ring or indane ring is optionally substituted with 1 to 4 substituents, which are the same or different, selected from a $C_{1-8}$ s alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{3H}$ and $R^{4H}$ are the same or different and are a hydrogen atom, a $C_{Z-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{5H}$ is a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{Z-s}$ alkyl group, or an aralkyl group (the number of carbon atoms in an aryl moiety is from 6 to 10 and the number of carbon atoms in an alkylene moiety is from 1 to 8), $R^{6H}$ and $R^{7H}$ are the same or different and are a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, or an amino group, $X^H$ is N, $Y^H$ is C(=O), the double line composed of a solid line and a dashed line is a single bond, $Z^H$ is O, $A^H$ is a benzene ring or a pyridine ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, B is a bond, $D^H$ is a tetrazole ring or an imidazole ring optionally having, as substituents, 1 to 2 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $D^H$ is bonded via a nitrogen atom of $D^H$ to $A^H$ and via a carbon atom of $D^H$ to $E^H$, $E^H$ is $-(CR^{9H}R^{10H})_n-$, $R^{9H}$ and $R^{10H}$ here are the same or different and are a hydrogen atom, a hydroxyl group, or a $C_{1-8}$ alkyl group, n is an integer of 1 to 8, $G^H$ is a benzene ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group, and m is 1.

(H-1-15)

A compound, a tautomer, stereoisomer, or pharmaceutically acceptable salt of the compound, or a hydrate or solvate thereof, the compound represented by (H-1), wherein $R^{1H}$ and $R^{2H}$ are fused with a benzene ring bonded thereto to form a naphthalene ring or an indane ring, $R^{3H}$ and $R^{4H}$ are a hydrogen atom, $R^5$H is a hydrogen atom, $R^6$H and $R^{7H}$ are a hydrogen atom, $X^H$ is N, $Y^H$ is C(=O), the double line composed of a solid line and a dashed line is a single bond, $Z^H$ is O, $A^H$ is a benzene ring optionally having, as substituents, 1 to 4 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $B^H$ is a bond, $D^H$ is a tetrazole ring or an imidazole ring optionally having 1 to 2 substituents selected from a $C_{1-8}$ alkyl group or a $C_{1-8}$ alkyl group substituted with 1 to 3 halogen atoms, $D^H$ is bonded via a nitrogen atom of $D^H$ to $A^H$ and via a carbon atom of $D^H$ to $E^H$, $E^H$ is $-(CR^{9H}R^{10H})_n-$, $R^{9H}$ and $R^{10H}$ here are the same or different and are a hydrogen atom or a $C_{1-8}$ alkyl group, n is an integer of 1 to 4, $G^H$ is a benzene ring optionally having, as substituents, 1 to 5 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, or a carbamoyl group, and $m^H$ is 1.

(H-1-16)

A compound, a tautomer, stereoisomer, or pharmaceutically acceptable salt of the compound, or a hydrate or solvate thereof, the compound represented by (H-1), wherein $R^{1H}$ and $R^{2H}$ are fused with a benzene ring bonded thereto to form a naphthalene ring or an indane ring, $R^{3H}$ and $R^{4H}$ are a hydrogen atom, $R^{5H}$ is a hydrogen atom, $R^{6H}$ and $R^{7H}$ are a hydrogen atom, $X^H$ is N, $Y^H$ is C(=O), the double line composed of a solid line and a dashed line is a single bond, $Z^H$ is O, $A^H$ is a benzene ring optionally having, as substituents, 1 to 4 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $B^H$ is a bond, $D^H$ is an imidazole ring optionally having 1 to 2 substituents selected from a $C_{1-8}$ alkyl group or a $C_{1-8}$ alkyl group substituted with 1 to 3 halogen atoms, $D^H$ is bonded at position 2 of the imidazole ring to $A^H$ and via a nitrogen atom of the imidazole to $E^H$, $E^H$ is $-(CR^{9H}R^{10H})_n-$, $R^{9H}$ and $R^{10H}$ here are the same or different and are a hydrogen atom or a $C_{1-8}$ alkyl group, n is an integer of 1 to 4, $G^H$ is a benzene ring optionally having, as substituents, 1 to 5 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, or a carbamoyl group, and $m^H$ is 1.

(H-2-1)

A compound, a tautomer, stereoisomer, or pharmaceutically acceptable salt of the compound, or a hydrate or solvate thereof, the compound represented by (H-2), wherein $R^{1Ha}$, $R^{2Ha}$, $R^{3Ha}$, $R^{4Ha}$, $R^{5Ha}$, and $R^{6Ha}$ are the same or different and are a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, or a hydroxyl group.

(H-2-2)

A compound, a tautomer, stereoisomer, or pharmaceutically acceptable salt of the compound, or a hydrate or solvate thereof, the compound represented by (H-2) or (H-2-1), wherein $X^{Ha}$ is N and $Y^{Ha}$ is C(=O).

(H-2-3)

A compound, a tautomer, stereoisomer, or pharmaceutically acceptable salt of the compound, or a hydrate or solvate thereof, the compound represented by (H-2) or any of (H-2-1) to (H-2-2), wherein $A^{Ha}$ is a benzene ring or a pyridine ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(H-2-4)

A compound, a tautomer, stereoisomer, or pharmaceutically acceptable salt of the compound, or a hydrate or solvate thereof, the compound represented by (H-2) or any of (H-2-1) to (H-2-3), wherein $A^{Ha}$ is a benzene ring optionally having, as substituents, 1 to 4 substituents, which are the same or different, selected from a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, or an amino group.

(H-2-4)

A compound, a tautomer, stereoisomer, or pharmaceutically acceptable salt of the compound, or a hydrate or solvate thereof, the compound represented by (H-2) or any of (H-2-1) to (H-2-3), wherein $D^{Ha}$ is a tetrazole ring, an imidazole ring, an imidazoline ring, a triazole ring, a pyrrole ring, a pyrrolidine ring, a piperazine ring, or a piperidine ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group.

(H-2-5)

A compound, a tautomer, stereoisomer, or pharmaceutically acceptable salt of the compound, or a hydrate or solvate thereof, the compound represented by (H-2) or any of (H-2-1) to (H-2-4), wherein $D^{Ha}$ is a tetrazole ring.

(H-2-6)

A compound, a tautomer, stereoisomer, or pharmaceutically acceptable salt of the compound, or a hydrate or solvate thereof, the compound represented by (H-2) or any of (H-2-1) to (H-2-5), wherein $D^{Ha}$ is bonded via a nitrogen atom to $A^{Ha}$.

(H-2-7)

A compound, a tautomer, stereoisomer, or pharmaceutically acceptable salt of the compound, or a hydrate or solvate thereof, the compound represented by (H-2) or any of (H-2-1) to (H-2-6), wherein $E^{Ha}$ is a $C_{1-5}$ alkylene chain.

(H-2-8)

A compound, a tautomer, stereoisomer, or pharmaceutically acceptable salt of the compound, or a hydrate or solvate thereof, the compound represented by (H-2) or any of (H-2-1) to (H-2-7), wherein $G^{Ha}$ is a benzene ring, a pyridine ring, an imidazole ring, a pyrrole ring, a pyrazole ring, a pyrimidine ring, a pyridazine ring, a pyrazine ring, or a 5- to 7-membered cycloalkyl ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group.

In the above general formula (HI), it is preferable that when $A^H$ is an optionally substituted benzene ring and $B^H$ is a bond, $X^H$ and $D^H$ are at para positions of the benzene ring.

Also, in the above general formula (HI), it is preferable that when $A^H$ is an optionally substituted pyridine ring and $B^H$ is a bond, $A^H$ is bonded at position 3 of the pyridine ring to $X^H$ and at position 6 of the pyridine ring to $D^H$.

Further, in the above general formula (HII), it is preferable that when $A^{Ha}$ is an optionally substituted benzene ring, $X^{Ha}$ and $D^{Ha}$ are at para positions of the benzene ring.

Furthermore, in the above general formula (HII), it is preferable that when $A^{Ha}$ is an optionally substituted pyridine ring, $A^{Ha}$ is bonded at position 3 of the pyridine ring to $X^{Ha}$ and at position 6 of the pyridine ring to $D^{Ha}$.

In the above general formula (HI), it is preferable that $R^{H1}$ and $R^{H2}$ are fused with a benzene ring bonded thereto to form a condensed ring selected from a naphthalene ring, a tetrahydronaphthalene ring, or an indane ring. It is particularly preferable to form a naphthalene ring.

In the above general formula (HI), it is preferable that $R^{H3}$, $R^{H4}$, $R^{H5}$, $R^{H6}$, and $R^{H7}$ represent a hydrogen atom.

In the above general formula (HI), it is preferable that $X^H$ represents N, $Y^H$ represents C(=O), the double line composed of a solid line and a dashed line denotes a single bond, and $Z^H$ represents O.

In the above general formula (HI), it is preferable that $A^H$ represents a benzene ring or a pyridine ring. It is particularly preferable that $A^H$ represents a benzene ring.

In the above general formula (HI), it is preferable that $B^H$ represents a bond.

In the above general formula (HI), it is preferable that $D^H$ represents a tetrazole ring or an imidazole ring.

In the above general formula (HI), it is preferable that $E^H$ represents $-(CR^{9H}R^{10H})_n{}^H\text{-T-}$ where $R^{9H}$ and $R^{10H}$ represent a hydrogen atom, $n^H$ represents an integer of 0 to 4, and $T^H$ represents a bond. Among them, it is more preferable that $n^H$ represents an integer of 1 or 2.

In the above general formula (HI), it is preferable that $G^H$ represents a benzene ring or a thiophene ring optionally having, as substituents, 1 to 5 substituents, which are the same or different, selected from a $C_{1-8}$ alkyl group, a $C_{1-8}$ alkoxy group, a halogen atom, a hydroxyl group, or a $C_{2-8}$ dialkylamino group. It is more preferable that $G^H$ represents a benzene ring or a thiophene ring optionally having, as substituents, 1 to 5 substituents, which are the same or different, selected from a $C_{1-4}$ alkyl group, a $C_{1-4}$ alkoxy group, a halogen atom, a hydroxyl group, or a $C_{2-4}$ dialkylamino group. It is particularly preferable that $G^H$ represents a benzene ring optionally having, as substituents, 1 to 5 substituents, which are the same or different, selected from a methyl group, a methoxy group, a halogen atom, a hydroxyl group, or a dimethylamino group.

In the above general formula (HI), it is preferable that $R^{H1}$ and $R^{H2}$ are fused with a benzene ring bonded thereto to form a condensed ring selected from a naphthalene ring or an indane ring, $R^{H3}$, $R^{H4}$, $R^{H5}$, $R^{H6}$, and $R^{H7}$ represent a hydrogen atom, $X^H$ represents N, $Y^H$ represents C(=O), the double line composed of a solid line and a dashed line represents a single bond, $Z^H$ represents O, $A^H$ represents a benzene ring or a pyridine ring, $B^H$ represents a bond, $D^H$ represents a tetrazole ring or an imidazole ring, $E^H$ represents $-(CR^{9H}R^{10H})_n{}^H\text{-T-}$, $R^{9H}$ and $R^{10H}$ represent a hydrogen atom, $n^H$ represents an integer of 0 to 4, $T^H$ represents a bond, and $G^H$ is a benzene ring or a thiophene ring optionally having, as substituents, 1 to 5 substituents, which are the same or different, selected from a $C_{1-8}$ alkyl group, a $C_{1-8}$ alkoxy group, a halogen atom, a hydroxyl group, or a $C_{2-8}$ dialkylamino group.

In the above general formula (HI), it is particularly preferable that $R^{H1}$ and $R^{H2}$ are fused with a benzene ring bonded thereto to form a naphthalene ring, $R^{H3}$, $R^{H4}$, $R^{H5}$, $R^{H6}$, and $R^{H7}$ represent a hydrogen atom, $X^H$ represents N, $Y^H$ represents C(=O), the double line composed of a solid line and a dashed line represents a single bond, $Z^H$ represents O, $A^H$ represents a benzene ring, $B^H$ represents a bond, $D^H$ represents a tetrazole ring or an imidazole ring, $E^H$ represents —$(CR^{9H}R^{10H})_n$-T-, $R^{9H}$ and $R^{10H}$ represent a hydrogen atom, $n^H$ represents an integer of 1 or 2, $T^H$ represents a bond, and $G^H$ is a benzene ring optionally having, as substituents, 1 to 5 substituents, which are the same or different, selected from a methyl group, a methoxy group, a halogen atom, a hydroxyl group, or a dimethylamino group.

<Representative Compound H-100>

[Chem. 104]

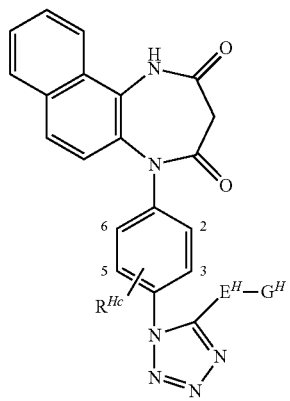

wherein $R^{Hc}$, $E^H$, and $G^H$ are as described in Tables 103 to 105.

TABLE 103

| $R^{Hc}$ | $E^H$ | $G^H$ |
|---|---|---|
| H | $CH_2$ | (2-OMe)Phenyl |
| H | $CH_2$ | (2-OH)Phenyl |
| H | $CH_2$—$CH_2$ | Pyridin 3-yl |
| H | $CH_2$—$CH_2$ | Phenyl |
| H | $CH_2$ | Pyridin 4-yl |
| H | $CH_2$ | Phenyl |
| H | $CH_2$ | Pyridin 3-yl |
| H | $CH_2$—$CH_2$ | Cyclohexyl |
| H | $CH_2$—$CH_2$ | Pyridin 4-yl |
| H | $CH_2$ | Pyridin 2-yl |
| H | $CH_2$—$CH_2$ | Pyridin 2-yl |
| H | $CH_2$ | Imidazol 1-yl |

TABLE 104

| $R^{Hc}$ | $E^H$ | $G^H$ |
|---|---|---|
| H | $CH_2$—$CH_2$ | Imidazol 1-yl |
| H | $CH_2$—$CH_2$ | (2-OMe)Phenyl |
| H | $CH_2$—$CH_2$—$CH_2$ | Phenyl |
| H | NH—$CH_2$ | Pyridin 2-yl |
| H | $CH_2$—NH | Phenyl |
| H | $CH_2$—O | Phenyl |
| H | $CH_2$ | (6-F) Pyridin 2-yl |
| H | $CH_2$—$CH_2$ | (6-F) Pyridin 2-yl |
| H | $C(Me)_2$ | (2-OMe)Phenyl |
| H | $C(Me)$—$CH_2$ | Pyridin 2-yl |
| H | $CH_2$—$C(Me)_2$ | Pyridin 2-yl |
| H | $CH_2$—$CH_2$ | Pyrimidin 2-yl |

TABLE 105

| $R^{Hc}$ | $E^H$ | $G^H$ |
|---|---|---|
| H | $CH_2$—$CH_2$ | Pyrazine 2-yl |
| H | $CH_2$—$CH_2$ | Pyridazin 3-yl |
| H | $CH_2$—$C(Me)_2$ | Pyridin 3-yl |
| 3-F | CH(Me) | (2-OMe)Phenyl |
| 3-Me | $CH_2$—$CH_2$ | Pyridin 3-yl |
| 3-OMe | $CH_2$—$CH_2$ | Phenyl |
| 3,5-F | $CH_2$ | Pyridin 4-yl |
| 3-$NH_2$ | $CH_2$ | Phenyl |
| 3,6-F | $CH_2$ | Pyridin 3-yl |
| 3-OMe | $CH_2$—$CH_2$ | Pyridin 2-yl |
| 3-CN | $CH_2$—$CH_2$ | Pyridin 2-yl |
| 3-$CF_3$ | $CH_2$—$CH_2$ | Pyridin 2-yl |

<Representative Compound H-200>

[Chem. 105]

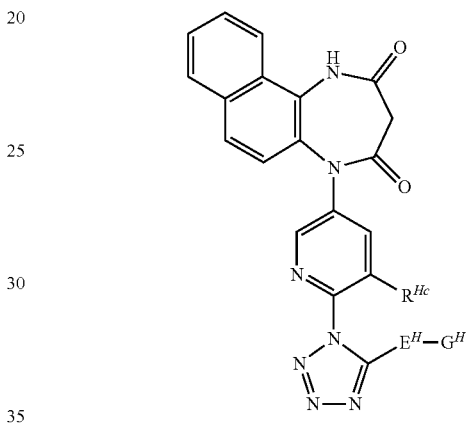

wherein $R^{Hc}$, $E^H$, and $G^H$ are as described in Tables 106 to 108.

TABLE 106

| $R^{Hc}$ | $E^H$ | $G^H$ |
|---|---|---|
| H | $CH_2$ | (2-OMe)Phenyl |
| H | $CH_2$ | (2-OH)Phenyl |
| H | $CH_2$—$CH_2$ | Pyridin 3-yl |
| H | $CH_2$—$CH_2$ | Phenyl |
| H | $CH_2$ | Pyridin 4-yl |
| H | $CH_2$ | Phenyl |
| H | $CH_2$ | Pyridin 3-yl |
| H | $CH_2$—$CH_2$ | Cyclohexyl |
| H | $CH_2$—$CH_2$ | Pyridin 4-yl |
| H | $CH_2$ | Pyridin 2-yl |
| H | $CH_2$ | Pyridin 2-yl |

TABLE 107

| $R^{Hc}$ | $E^H$ | $G^H$ |
|---|---|---|
| H | $CH_2$ | Imidazole 1-yl |
| H | $CH_2$—$CH_2$ | Imidazole 1-yl |
| H | $CH_2$—$CH_2$ | (2-OMe)Phenyl |
| H | $CH_2$ | (2-OMe)Phenyl |
| H | $CH_2$—$CH_2$—$CH_2$ | Phenyl |
| H | $CH_2$ | (6-F) Pyridin 2-yl |
| H | $CH_2$—$CH_2$ | (6-F) Pyridin 2-yl |
| H | $C(Me)_2$ | (2-OMe)Phenyl |
| H | $C(Me)$—$CH_2$ | Pyridin 2-yl |
| H | $CH_2$—$C(Me)_2$ | Pyridin 2-yl |
| H | $CH_2$—$CH_2$ | Pyrimidin 2-yl |

TABLE 108

| $R^{Hc}$ | $E^H$ | $G^H$ |
|---|---|---|
| H | CH₂—CH₂ | Pyrazine 2-yl |
| H | CH₂—CH₂ | Pyridazin 3-yl |
| H | CH₂—C(Me)₂ | Pyridin 3-yl |
| F | CH(Me) | (2-OMe)Phenyl |
| Me | CH₂—CH₂ | Pyridin 3-yl |
| OMe | CH₂—CH₂ | Phenyl |
| F | CH₂ | Pyridin 4-yl |
| Me | CH₂ | Phenyl |
| OMe | CH₂ | Pyridin 3-yl |
| F | CH₂—CH₂ | Pyridin 2-yl |
| CN | CH₂—CH₂ | Pyridin 2-yl |
| F | CH₂—CH₂ | Pyridin 2-yl |

<Representative Compound H-300>

[Chem. 106]

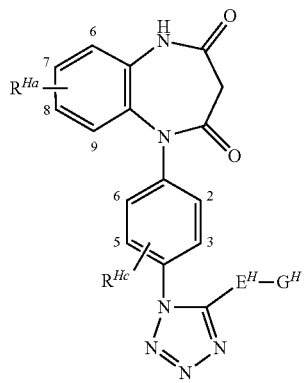

wherein $R^{Ha}$, $R^{Hc}$, $E^H$, and $G^H$ are as described in Tables 109 to 111.

TABLE 109

| $R^{Ha}$ | $R^{Hc}$ | $E^H$ | $G^H$ |
|---|---|---|---|
| 7-OMe | H | CH₂ | (2-OMe)Phenyl |
| 6-OMe | H | CH₂ | (2-OH)Phenyl |
| 6,7-OMe | H | CH₂—CH₂ | Pyridin 3-yl |
| 7-Me | H | CH₂—CH₂ | Phenyl |
| 7-Et | H | CH₂ | Pyridin 4-yl |
| 7-Pr | H | CH₂ | Phenyl |
| 7-iPr | H | CH₂ | Pyridin 3-yl |
| 7-tBu | H | CH₂—CH₂ | Cyclohexyl |
| 7-CN | H | CH₂—CH₂ | Pyridin 4-yl |
| 7-CF₃ | H | CH₂ | Pyridin 2-yl |
| 7-OCF₃ | H | CH₂—CH₂ | Pyridin 2-yl |

TABLE 110

| $R^{Ha}$ | $R^{Hc}$ | $E^H$ | $G^H$ |
|---|---|---|---|
| 7,8-OMe | H | CH₂ | Imidazole 1-yl |
| 6,7-Me | H | CH₂—CH₂ | Imidazole 1-yl |
| 6,7-Cl | H | CH₂—CH₂ | (2-OMe)Phenyl |
| 7,8-Me | H | CH₂ | (2-OMe)Phenyl |
| 7,8-Et | H | CH₂—CH₂—CH₂ | Phenyl |
| 7-Cl | H | CH₂ | (6-F) Pyridin 2-yl |
| 6-OMe | H | CH₂—CH₂ | (6-F) Pyridin 2-yl |
| 6,7-OMe | H | C(Me)₂ | (2-OMe)Phenyl |
| 7-Me | H | C(Me)—CH₂ | Pyridin 2-yl |
| 7-Et | H | CH₂—C(Me)₂ | Pyridin 2-yl |
| 7-Pr | H | CH₂—C(Me)₂ | Pyridin 3-yl |

TABLE 111

| $R^{Ha}$ | $R^{Hc}$ | $E^H$ | $G^H$ |
|---|---|---|---|
| 7-iPr | 3-F | CH(Me) | (2-OMe)Phenyl |
| 7-tBu | 3-Me | CH₂—CH₂ | Pyridin 3-yl |
| 7-CN | 3-OMe | CH₂—CH₂ | Phenyl |
| 7-CF₃ | 3,5-F | CH₂ | Pyridin 4-yl |
| 7-OCF₃ | 3-NH₂ | CH₂ | Phenyl |
| 7,8-OMe | 3,6-F | CH₂ | Pyridin 3-yl |
| 6,7-Me | 3-OMe | CH₂—CH₂ | Pyridin 2-yl |
| 6,7-Et | 3-CN | CH₂—CH₂ | Pyridin 2-yl |
| 7,8-Me | 3-CF₃ | CH₂—CH₂ | Pyridin 2-yl |

<Representative Compound H-400>

[Chem. 107]

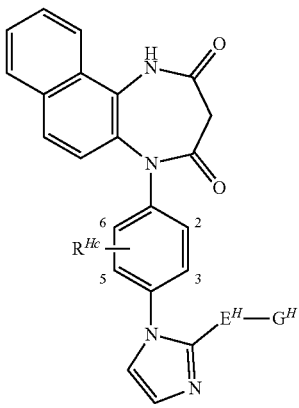

wherein $R^{Hc}$, $E^H$, and $G^H$ are as described in Tables 112 to 114.

TABLE 112

| $R^{Hc}$ | $E^H$ | $G^H$ |
|---|---|---|
| H | CH₂—CH₂ | Phenyl |
| H | CH₂ | (2-OMe)Phenyl |
| H | CH₂ | (2-OH)Phenyl |
| H | CH₂—CH₂ | Pyridin 2-yl |
| H | CH₂—CH₂ | Pyridin 3-yl |
| H | CH₂—CH₂ | (2-CF3)Phenyl |
| H | CH₂—CH₂ | (2-F)Phenyl |
| H | CH₂—CH₂ | (2-OMe)Phenyl |
| H | CH₂ | Pyridin 4-yl |
| H | CH₂ | Phenyl |
| H | CH₂ | Pyridin 3-yl |
| H | CH₂ | Cyclohexyl |
| H | CH₂ | Pyridin 4-yl |

TABLE 113

| $R^{Hc}$ | $E^H$ | $G^H$ |
|---|---|---|
| H | CH₂ | Pyridin 2-yl |
| H | CH₂—CH₂ | Pyridin 2-yl |
| H | CH₂—CH₂ | (4-SO₂Me)Phenyl |
| H | CH₂—CH₂ | (4-F)Phenyl |
| H | CH₂—CH₂ | (4-CF₃)Phenyl |
| H | CH₂—CH₂ | (4-CONH₂)Phenyl |
| H | CH₂—CH₂—CH₂ | Phenyl |
| H | CH₂ | (6-F) Pyridin 2-yl |
| H | CH₂—CH₂ | (6-F) Pyridin 2-yl |
| H | C(Me)₂ | (2-OMe)Phenyl |
| H | C(Me)—CH₂ | Pyridin 2-yl |
| H | CH₂—C(Me)₂ | Pyridin 2-yl |
| H | CH₂—CH₂ | Pyrimidin 2-yl |

TABLE 114

| $R^{Hc}$ | $E^H$ | $G^H$ |
|---|---|---|
| H | $CH_2$—$CH_2$ | Pyrazin 2-yl |
| H | $CH_2$—$CH_2$ | Pyridazin 3-yl |
| H | $CH_2$—$C(Me)_2$ | Pyridin 3-yl |
| 3-F | CH(Me) | (2-OMe)Phenyl |
| 3-Me | $CH_2$—$CH_2$ | Pyridin 3-yl |
| 3-OMe | $CH_2$—$CH_2$ | Phenyl |
| 3,5-F | $CH_2$ | Pyridin 4-yl |
| 3-$NH_2$ | $CH_2$ | Phenyl |
| 3,6-F | $CH_2$ | Pyridin 3-yl |
| 3-OMe | $CH_2$—$CH_2$ | Pyridin 2-yl |
| 3-CN | $CH_2$—$CH_2$ | Pyridin 2-yl |
| 3-$CF_3$ | $CH_2$—$CH_2$ | Pyridin 2-yl |

<Representative Compound H-500>

[Chem. 108]

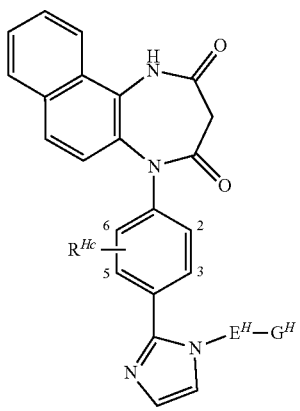

wherein $R^{Hc}$, $E^H$, and $G^H$ are as described in Tables 115 to 117.

TABLE 115

| $R^{Hc}$ | $E^H$ | $G^H$ |
|---|---|---|
| H | $CH_2$—$CH_2$ | Phenyl |
| H | $CH_2$ | (2-OMe)Phenyl |
| H | $CH_2$ | (2-OH)Phenyl |
| H | $CH_2$—$CH_2$ | Pyridin 3-yl |
| H | $CH_2$—$CH_2$ | Phenyl |
| H | $CH_2$ | Pyridin 4-yl |
| H | $CH_2$ | Phenyl |
| H | $CH_2$ | Pyridin 3-yl |
| H | $CH_2$—$CH_2$ | Cyclohexyl |
| H | $CH_2$—$CH_2$ | Pyridin 4-yl |
| H | $CH_2$ | Pyridin 2-yl |
| H | $CH_2$—$CH_2$ | Pyridin 2-yl |

TABLE 116

| $R^{Hc}$ | $E^H$ | $G^H$ |
|---|---|---|
| H | $CH_2$ | Imidazole 1-yl |
| H | $CH_2$—$CH_2$ | Imidazole 1-yl |
| H | $CH_2$—$CH_2$ | (2-OMe)Phenyl |
| H | $CH_2$ | (2-OMe)Phenyl |
| H | $CH_2$—$CH_2$—$CH_2$ | Phenyl |
| H | $CH_2$ | (6-F) Pyridin 2-yl |
| H | $CH_2$—$CH_2$ | (6-F) Pyridin 2-yl |
| H | $C(Me)_2$ | (2-OMe)Phenyl |
| H | $C(Me)$—$CH_2$ | Pyridin 2-yl |
| H | $CH_2$—$C(Me)_2$ | Pyridin 2-yl |

TABLE 116-continued

| $R^{Hc}$ | $E^H$ | $G^H$ |
|---|---|---|
| H | $CH_2$—$CH_2$ | Pyrimidin 2-yl |
| H | $CH_2$—$CH_2$ | Pyrazin 2-yl |

TABLE 117

| $R^{Hc}$ | $E^H$ | $G^H$ |
|---|---|---|
| H | $CH_2$—$CH_2$ | Pyridazin 3-yl |
| H | $CH_2$—$C(Me)_2$ | Pyridin 3-yl |
| 3-F | CH(Me) | (2-OMe)Phenyl |
| 3-Me | $CH_2$—$CH_2$ | Pyridin 3-yl |
| 3-OMe | $CH_2$—$CH_2$ | Phenyl |
| 3,5-F | $CH_2$ | Pyridin 4-yl |
| 3-$NH_2$ | $CH_2$ | Phenyl |
| 3,6-F | $CH_2$ | Pyridin 3-yl |
| 3-OMe | $CH_2$—$CH_2$ | Pyridin 2-yl |
| 3-CN | $CH_2$—$CH_2$ | Pyridin 2-yl |
| 3-$CF_3$ | $CH_2$—$CH_2$ | Pyridin 2-yl |

<Representative Compound H-600>

[Chem. 109]

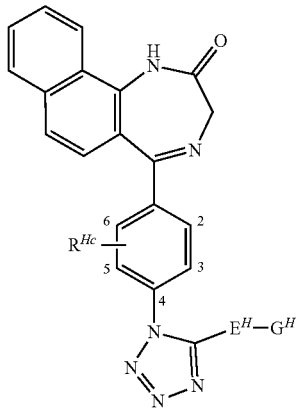

wherein $R^{Hc}$, $E^H$, and $G^H$ are as described in Tables 118 to 120.

TABLE 118

| $R^{Hc}$ | $E^H$ | $G^H$ |
|---|---|---|
| H | $CH_2$—$CH_2$ | Pyridin 2-yl |
| H | $CH_2$ | (2-OMe)Phenyl |
| H | $CH_2$ | (2-OH)Phenyl |
| H | $CH_2$—$CH_2$ | Pyridin 3-yl |
| H | $CH_2$—$CH_2$ | Phenyl |
| H | $CH_2$ | Pyridin 4-yl |
| H | $CH_2$ | Phenyl |
| H | $CH_2$ | Pyridin 3-yl |
| H | $CH_2$—$CH_2$ | Cyclohexyl |
| H | $CH_2$—$CH_2$ | Pyridin 4-yl |
| H | $CH_2$ | Pyridin 2-yl |
| H | $CH_2$ | Imidazol 1-yl |

TABLE 119

| $R^{Hc}$ | $E^H$ | $G^H$ |
|---|---|---|
| H | $CH_2$—$CH_2$ | Imidazol 1-yl |
| H | $CH_2$—$CH_2$ | (2-OMe)Phenyl |
| H | $CH_2$ | (2-OMe)Phenyl |

TABLE 119-continued

| $R^{Hc}$ | $E^H$ | $G^H$ |
|---|---|---|
| H | CH$_2$—CH$_2$—CH$_2$ | Phenyl |
| H | CH$_2$ | (6-F) Pyridin 2-yl |
| H | CH$_2$—CH$_2$ | (6-F) Pyridin 2-yl |
| H | C(Me)$_2$ | (2-OMe)Phenyl |
| H | C(Me)—CH$_2$ | Pyridin 2-yl |
| H | CH$_2$—C(Me)$_2$ | Pyridin 2-yl |
| H | CH$_2$—C(Me)$_2$ | Pyridin 3-yl |
| 3-F | CH(Me) | (2-OMe)Phenyl |
| 3-Me | CH$_2$—CH$_2$ | Pyridin 3-yl |

TABLE 120

| $R^{Hc}$ | $E^H$ | $G^H$ |
|---|---|---|
| 3-OMe | CH$_2$—CH$_2$ | Phenyl |
| 3,5-F | CH$_2$ | Pyridin 4-yl |
| 3-NH$_2$ | CH$_2$ | Phenyl |
| 3,6-F | CH$_2$ | Pyridin 3-yl |
| 3-OMe | CH$_2$—CH$_2$ | Pyridin 2-yl |
| 3-CN | CH$_2$—CH$_2$ | Pyridin 2-yl |
| 3-CF$_3$ | CH$_2$—CH$_2$ | Pyridin 2-yl |

<Representative Compound H-700>

[Chem. 110]

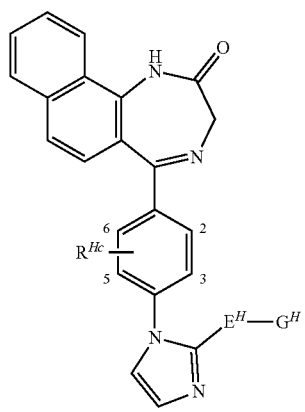

wherein $R^{Hc}$, $E^H$, and $G^H$ are as described in Tables 121 to 123.

TABLE 121

| $R^{Hc}$ | $E^H$ | $G^H$ |
|---|---|---|
| H | CH$_2$—CH$_2$ | Phenyl |
| H | CH$_2$ | (2-OMe)Phenyl |
| H | CH$_2$ | (2-OH)Phenyl |
| H | CH$_2$—CH$_2$ | Pyridin 3-yl |
| H | CH$_2$—CH$_2$ | Phenyl |
| H | CH$_2$ | Pyridin 4-yl |
| H | CH$_2$ | Phenyl |
| H | CH$_2$ | Pyridin 3-yl |
| H | CH$_2$ | Cyclohexyl |
| H | CH$_2$—CH$_2$ | Pyridin 4-yl |
| H | CH$_2$ | Pyridin 2-yl |
| H | CH$_2$—CH$_2$ | Pyridin 2-yl |

TABLE 122

| $R^{Hc}$ | $E^H$ | $G^H$ |
|---|---|---|
| H | CH$_2$ | Imidazole 1-yl |
| H | CH$_2$—CH$_2$ | Imidazole 1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F) Pyridin 2-yl |
| H | CH$_2$—CH$_2$ | (6-F) Pyridin 2-yl |
| H | C(Me)$_2$ | (2-OMe)Phenyl |
| H | C(Me)—CH$_2$ | Pyridin 2-yl |
| H | CH$_2$—C(Me)$_2$ | Pyridin 2-yl |
| H | CH$_2$—CH$_2$ | Pyrimidin 2-yl |
| H | CH$_2$—CH$_2$ | Pyrazin 2-yl |

TABLE 123

| $R^{Hc}$ | $E^H$ | $G^H$ |
|---|---|---|
| H | CH$_2$—CH$_2$ | Pyridazin 3-yl |
| H | CH$_2$—C(Me)$_2$ | Pyridin 3-yl |
| 3-F | CH(Me) | (2-OMe)Phenyl |
| 3-Me | CH$_2$—CH$_2$ | Pyridin 3-yl |
| 3-OMe | CH$_2$—CH$_2$ | Phenyl |
| 3,5-F | CH2 | Pyridin 4-yl |
| 3-NH$_2$ | CH2 | Phenyl |
| 3,6-F | CH2 | Pyridin 3-yl |
| 3-OMe | CH$_2$—CH$_2$ | Pyridin 2-yl |
| 3-CN | CH$_2$—CH$_2$ | Pyridin 2-yl |
| 3-CF$_3$ | CH$_2$—CH$_2$ | Pyridin 2-yl |

<Representative Compound H-800>

[Chem. 111]

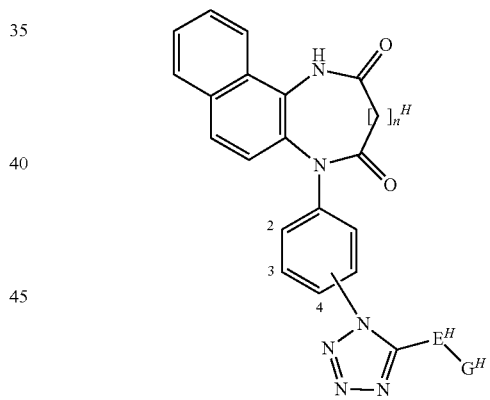

wherein the tetrazole ring substitution position, $E^H$-$G^H$, $n^H$, and the salt are as described in Table 124.

TABLE 124

| Tetrazole ring substitution position | $E^H$-$G^H$ | $n^H$ | Salt |
|---|---|---|---|
| 3 | CH$_2$CH$_2$(2-Py) | 0 | |
| 4 | CH$_2$CH$_2$(6-methylpyridin-2-yl) | 1 | |
| 4 | CH$_2$CH$_2$(3-CN)Ph | 1 | |
| 4 | CH$_2$CH$_2$(3-CONH$_2$)Ph | 1 | |
| 4 | CH$_2$CH$_2$(2-methoxypyridin-3-yl) | 1 | |
| 4 | CH2(2-NMe$_2$)Ph | 1 | MsOH |
| 4 | CH$_2$C(Me)$_2$(2-Py) | 1 | HCl |
| 4 | CH$_2$CH$_2$(3-methoxypyridin-2-yl) | 1 | HCl |
| 3 | CH$_2$CH$_2$CH$_2$(6-methylpyridin-2-yl) | 1 | |
| 3 | CH$_2$CH$_2$CH$_2$(3-CN)Ph | 1 | |

TABLE 124-continued

| Tetrazole ring substitution position | $E^H$-$G^H$ | $n^H$ | Salt |
|---|---|---|---|
| 3 | $CH_2CH_2CH_2$(3-$CONH_2$)Ph | 1 | |
| 3 | $CH_2CH_2CH_2$(2-methoxypyridin-3-yl) | 1 | |
| 3 | $CH_2CH_2$(2-$NMe_2$)Ph | 1 | |
| 3 | $CH_2CH_2C(Me)_2$(2-Py) | 0 | |
| 3 | $CH_2CH_2CH_2$(3-methoxypyridin-2-yl) | 0 | |

<Representative Compound H-900>
Naphthalene Form

[Chem. 112]

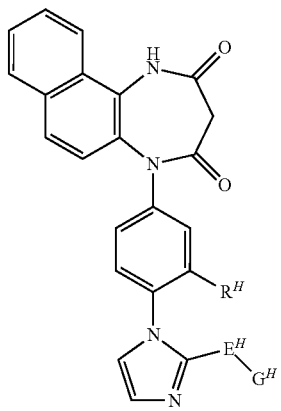

Indane Form

[Chem. 113]

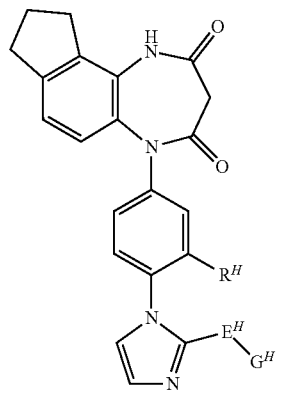

wherein $E^H$-$G^H$, $R^H$, and the salt are as described in Tables 125 and 126.

TABLE 125

| Naphthalene form or Indane form | $E^H$-$G^H$ | $R^H$ | Salt |
|---|---|---|---|
| Naphthalene form | $CH_2CH_2$(3-F)Ph | H | HCl |
| Naphthalene form | $CH_2CH_2$(2-OMe)Ph | H | HCl |
| Naphthalene form | $CH_2CH_2$(4-F)Ph | H | HCl |
| Naphthalene form | $CH_2CH_2$(2-F)Ph | H | HCl |
| Naphthalene form | $CH_2CH_2$(4-CF3)Ph | H | HCl |
| Naphthalene form | $CH_2CH_2$(2,6-Me)Ph | H | HCl |
| Naphthalene form | $CH_2CH_2$(3-CF3)Ph | H | HCl |

TABLE 125-continued

| Naphthalene form or Indane form | $E^H$-$G^H$ | $R^H$ | Salt |
|---|---|---|---|
| Naphthalene form | $CH_2CH_2$(3-OMe)Ph | H | HCl |
| Naphthalene form | $CH_2CH_2$(3-OH)Ph | H | HCl |
| Naphthalene form | $CH_2CH_2$(4-CN)Ph | H | |
| Naphthalene form | $CH_2CH_2$(4-$CONH_2$)Ph | H | |
| Naphthalene form | $CH_2CH_2$(2-CN)Ph | H | |
| Naphthalene form | $CH_2CH_2$(2-$CONH_2$)Ph | H | |
| Naphthalene form | $CH_2CH_2$(3-CN)Ph | H | |
| Naphthalene form | $CH_2CH_2$(3-$CONH_2$)Ph | H | |
| Naphthalene form | $CH_2CH_2$(3-$CONH_2$)Ph | H | HCl |
| Naphthalene form | $CH_2CH_2$(4-$SO_2$Me)Ph | H | HCl |
| Naphthalene form | $CH_2CH_2$(3-OMe, 2-F)Ph | H | HCl |

TABLE 126

| Naphthalene form or Indane form | $E^H$-$G^H$ | $R^H$ | Salt |
|---|---|---|---|
| Indane form | $CH_2CH_2$(3-OMe, 2-F)Ph | H | HCl |
| Naphthalene form | $CH_2CH_2$(3-thienyl) | H | HCl |
| Naphthalene form | $CH_2CH_2$(2-furanyl) | H | HCl |
| Indane form | $CH_2CH_2$(2-F)Ph | H | |
| Naphthalene form | $CH_2CH_2$(2-Pyridyl) | H | 2HCl |
| Indane form | $CH_2CH_2$(3-F)Ph | H | HCl |
| Naphthalene form | $CH_2CH_2$(2-OMe, 3-F)Ph | H | HCl |
| Naphthalene form | $CH_2CH_2$(3-F)Ph | F | |
| Naphthalene form | $CH_2CH_2$(2-OMe)Ph | OH | |
| Naphthalene form | $CH_2CH_2$(4-F)Ph | H | |
| Naphthalene form | $CH_2CH_2$(2-F)Ph | F | |
| Naphthalene form | $CH_2CH_2$(4-$CF_3$)Ph | OH | |
| Naphthalene form | $CH_2CH_2$(2,6-Me)Ph | H | |
| Naphthalene form | $CH_2CH_2$(3-$CF_3$)Ph | F | |
| Naphthalene form | $CH_2CH_2$(3-OMe)Ph | OH | |
| Naphthalene form | $CH_2CH_2$(3-OH)Ph | H | |
| Naphthalene form | $CH_2CH_2$(4-CN)Ph | F | |
| Indane form | $CH_2CH_2$(2,6-Me)Ph | H | |
| Indane form | $CH_2CH_2$(3-CF3)Ph | F | |
| Indane form | $CH_2CH_2$(3-OMe)Ph | OH | |
| Indane form | $CH_2CH_2$(3-OH)Ph | H | |
| Indane form | $CH_2CH_2$(4-CN)Ph | F | |

<Representative Compound H-1000>

[Chem. 114]

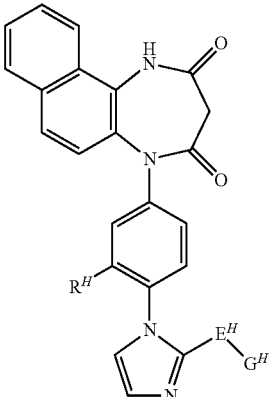

wherein $E^H$-$G^H$, $R^H$, and the salt are as described in Table 127.

TABLE 127

| $E^H$-$G^H$ | $R^H$ |
|---|---|
| bond-Ph | H |
| bond-(2-OMe)Ph | H |
| CH$_2$OPh | H |
| NH-(2-OMe)Ph | H |
| NH—Ph | H |
| CH$_2$SPh | F |
| CH$_2$NHPh | OH |
| bond-(2-F)Ph | F |
| bond-(2CF$_3$)Ph | OH |
| bond-(2Cl)Ph | F |
| bond-(2-Me)Ph | OH |
| bond-(2,6-Me)Ph | F |
| bond-(2,6-F)Ph | OH |
| bond-(2-OH)Ph | F |
| CH$_2$O(2-F)Ph | OH |
| NH-(2,6-Me)Ph | F |
| NH-(2CF$_3$)Ph | OH |
| bond-(3-F)Ph | F |

<Representative Compound H-1100>

[Chem. 115]

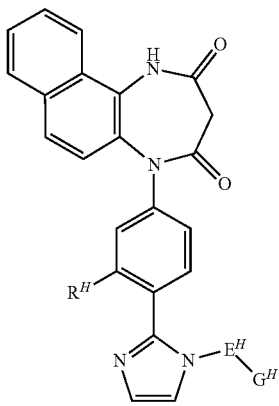

wherein $E^H$-$G^H$, $R^H$, and the salt are as described in Table 128.

TABLE 128

| $E^H$-$G^H$ | $R^H$ | Salt |
|---|---|---|
| CH$_2$CH$_2$Ph | H | HCl |
| CH$_2$(4-Cl)Ph | H | HCl |
| CH$_2$(2-OMe)Ph | H | |
| CH$_2$CH$_2$(3-OMe)Ph | H | |
| CH$_2$CH$_2$(3-OMe)Ph | H | HCl |
| CH$_2$CH$_2$(3-OH)Ph | H | |
| CH$_2$(2,4,6-Me)Ph | H | HCl |
| CH$_2$(2-CF$_3$)Ph | H | HCl |
| CH$_2$(2-CN)Ph | H | |
| CH$_2$(2-CONH$_2$)Ph | H | |
| CH$_2$(2-NH$_2$)Ph | H | |
| CH$_2$CH$_2$Ph | OMe | |
| CH$_2$CH$_2$Ph | OH | |
| CH$_2$(3-CN)Ph | H | |
| CH$_2$(3-CONH$_2$)Ph | H | |
| CH$_2$CH$_2$(3-OMe)Ph | F | |
| CH$_2$CH$_2$(3-OH)Ph | F | |
| CH$_2$CH$_2$(3-F)Ph | H | |
| CH$_2$CH$_2$(2-F)Ph | F | |
| CH$_2$CH$_2$(2-F)Ph | H | |

<Representative Compound H-1200>

[Chem. 116]

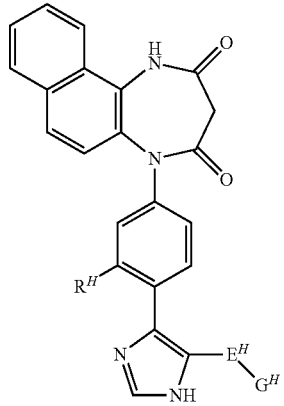

wherein $E^H$-$G^H$, $R^H$, and the salt are as described in Table 129.

TABLE 129

| $E^H$-$G^H$ | $R^H$ | Salt |
|---|---|---|
| bond-Ph | H | HCl |
| CH$_2$CH$_2$Ph | H | HCl |
| CH$_2$CH$_2$(2-F)Ph | H | |
| CH$_2$CH$_2$(3-F)Ph | F | |
| CH$_2$CH$_2$(2-OMe)Ph | F | |
| CH$_2$CH$_2$(3-OMe)Ph | F | |
| CH$_2$CH$_2$(2-OH)Ph | F | |
| CH$_2$CH$_2$(3-OH)Ph | F | |

<Representative Compound H-1300>

[Chem. 117]

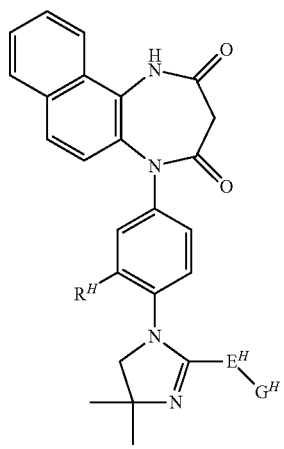

wherein $E^H$-$G^H$, $R^H$, and the salt are as described in Table 130.

TABLE 130

| $E^H$-$G^H$ | $R^H$ | Salt |
|---|---|---|
| CH$_2$CH$_2$Ph | H | HCl |
| CH$_2$CH$_2$(2-F)Ph | H | |

TABLE 130-continued

| $E^H$-$G^H$ | $R^H$ | Salt |
| --- | --- | --- |
| CH$_2$CH$_2$(3-F)Ph | F | |
| CH$_2$CH$_2$(2-OMe)Ph | F | |
| CH$_2$CH$_2$(3-OMe)Ph | F | |
| CH$_2$CH$_2$(2-OH)Ph | F | |
| CH$_2$CH$_2$(3-OH)Ph | F | |

WO 2010/093061 discloses the compounds represented by general formulas (AI) and (AII), WO 2012/008478 discloses the compounds represented by general formulas (BI) to (BIII), WO 2012/014910 discloses the compounds represented by general formulas (CI) and (CII), and WO 2012/017876 discloses the compounds represented by general formulas (DI) and (DII). Thus, these compounds are readily available by consulting these WO pamphlets. All the disclosures in their WO pamphlets are herein incorporated by reference in the entirety.

Although part of general formula (AI) (e.g., compounds A20 and A21 of Examples) is not disclosed in WO 2010/093061, the corresponding compounds are readily available by consulting the synthesis scheme (process 3) described in WO 2008/023847 and WO 2010/093061 or paragraphs [0054] to[0060](synthesis process 2) in WO 2012/017876. All the disclosures in their WO pamphlets are herein incorporated by reference in the entirety.

Note that the compounds represented by general formula (EI) fall under part of the compounds represented by general formulas (AI) to (DII). Thus, these compounds are readily available by consulting WO 2008/023847, WO 2010/093061, WO 2012/008478, WO 2012/014910, and WO 2012/017876.

In addition, WO 2013/105608 discloses the compounds represented by general formulas (FI) and (FII) and WO 2015/005467 discloses the compounds represented by general formula (GI). Thus, these compounds are readily available by consulting these WO pamphlets. All the disclosures in their WO pamphlets are herein incorporated by reference in the entirety.

Further, WO 2015/005468 discloses the compounds represented by general formulas (HI) and (HII). Thus, these compounds are readily available by consulting the WO pamphlet. All the disclosures in their WO pamphlets are herein incorporated by reference in the entirety.

Meanwhile, the above WO 2010/093061, WO 2012/008478, WO 2012/014910, WO 2012/017876, WO 2013/105608, WO 2015/005467, and WO 2015/005468 describe that the compounds represented by general formulas (AI) to (HII) exert P2X4 receptor antagonistic effects.

Note that the following shows specific examples of preferable compounds and pharmaceutically acceptable salts thereof included in the compounds represented by general formulas (AI) to (HII). However, a compound or pharmaceutically acceptable salt thereof that can be utilized as an active ingredient in a medicament of the present invention is not limited to them.

(Compound A1) 5-[3-(1H-tetrazol-5-yl)phenyl]-1H-naphtho[1,2-b][1,4]diazepin-2,4(3H,5H)-dione;

(Compound A2) 5-[3-(1H-tetrazol-5-yl)phenyl]-1H-naphtho[1,2-b][1,4]diazepin-2,4(3H,5H)-dione sodium salt;

(Compound A3) 5-[3-(1H-tetrazol-5-yl)phenyl]-1H-naphtho[1,2-b][1,4]diazepin-2,4(3H,5H)-dione potassium salt;

(Compound A4) 5-[4-(1H-tetrazol-5-yl)phenyl]-1H-naphtho[1,2-b][1,4]diazepin-2,4(3H,5H)-dione;

(Compound A5) 5-[4-(1H-tetrazol-5-yl)phenyl]-1H-naphtho[1,2-b][1,4]diazepin-2,4(3H,5H)-dione sodium salt;

(Compound A6) 1-methyl-5-[3-(1H-tetrazol-5-yl)phenyl]-1H-naphtho[1,2-b][1,4]diazepin-2,4(3H,5H)-dione;

(Compound A7) 1,3-dimethyl-5-[3-(1H-tetrazol-5-yl)phenyl]-1H-naphtho[1,2-b][1,4]diazepin-2,4(3H,5H)-dione;

(Compound A8) 5-[2-chloro-5-(1H-tetrazol-5-yl)phenyl]-1H-naphtho[1,2-b][1,4]diazepin-2,4(3H,5H)-dione;

(Compound A9) 5-[2-chloro-5-(1H-tetrazol-5-yl)phenyl]-1H-naphtho[1,2-b][1,4]diazepin-2,4(3H,5H)-dione sodium salt;

(Compound A10) 5-[2-methyl-5-(1H-tetrazol-5-yl)phenyl]-1H-naphtho[1,2-b][1,4]diazepin-2,4(3H,5H)-dione;

(Compound A11) 5-[2-methyl-5-(1H-tetrazol-5-yl)phenyl]-1H-naphtho[1,2-b][1,4]diazepin-2,4(3H,5H)-dione sodium salt;

(Compound A12) 5-[2-bromo-5-(1H-tetrazol-5-yl)phenyl]-1H-naphtho[1,2-b][1,4]diazepin-2,4(3H,5H)-dione;

(Compound A13) 5-[3-(2-methyl-2H-tetrazol-5-yl)phenyl]-1H-naphtho[1,2-b][1,4]diazepin-2,4(3H,5H)-dione;

(Compound A14) 5-[3-(1-methyl-1H-tetrazol-5-yl)phenyl]-1H-naphtho[1,2-b][1,4]diazepin-2,4(3H,5H)-dione;

(Compound A15) 5-[3-(5-oxo-4H-[1,2,4]oxadiazol-3-yl)phenyl]-1H-naphtho[1,2-b][1,4]diazepin-2,4(3H,5H)-dione;

(Compound A16) 5-[3-(5-thioxo-4H-[1,2,4]oxadiazol-3-yl)phenyl]-1H-naphtho[1,2-b][1,4]diazepin-2,4(3H,5H)-dione;

(Compound A17) 5-[3-(5-thioxo-4H-[1,2,4]oxadiazol-3-yl)phenyl]-1H-naphtho[1,2-b][1,4]diazepin-2,4(3H,5H)-dione sodium salt;

(Compound A18) 5-[3-(oxazol-2-yl)phenyl]-1H-naphtho[1,2-b][1,4]diazepin-2,4(3H,5H)-dione; and (Compound A19) 5-[3-(1H-pyrazol-4-yl)phenyl]-1H-naphtho[1,2-b][1,4]diazepin-2,4(3H,5H)-dione;

(Compound A20) 5-[3-(1H-tetrazol-5-yl)phenyl]-1,3-dihydro-2H-naphtho[1,2-e][1,4]diazepin-2-one;

(Compound A21) 5-[3-(1H-tetrazol-5-yl)phenyl]-1,3-dihydro-2H-naphtho[1,2-e][1,4]diazepin-2-one sodium salt;

(Compound A22) 5-[4-fluoro-3-(1H-tetrazol-5-yl)phenyl]-1H-naphtho[1,2-b][1,4]diazepin-2,4(3H,5H)-dione; and (Compound A23) 5-[4-fluoro-3-(1H-tetrazol-5-yl)phenyl]-1H-naphtho[1,2-b][1,4]diazepin-2,4(3H,5H)-dione sodium salt.

(Compound B1) 5-(3-cyanophenyl)-8,9,10,11-tetrahydronaphtho[2,1-b][1,4]diazepin-2,4(3H,5H)-dione;

(Compound B2) 5-[3-(1H-tetrazol-5-yl)phenyl]-8,9,10,11-tetrahydronaphtho[2,1-b][1,4]diazepin-2,4(3H,5H)-dione sodium salt;

(Compound B3) 5-(3-hydroxyphenyl)-8,9,10,11-tetrahydronaphtho[2,1-b][1,4]diazepin-2,4(3H,5H)-dione;

(Compound B4) 5-(3-cyanophenyl)-5,8,9,10-tetrahydroindeno[5,4-b][1,4]diazepin-2,4(1H,3H)-dione;

(Compound B5) 5-[3-(1H-tetrazol-5-yl)phenyl]-5,8,9,10-tetrahydroindeno[5,4-b][1,4]diazepin-2,4(1H,3H)-dione sodium salt;

(Compound B6) 5-[3-(2-methyl-2H-tetrazol-5-yl)phenyl]-5,8,9,10-tetrahydroindeno[5,4-b][1,4]diazepin-2,4(1H,3H)-dione;

(Compound B7) 5-[3-(1-methyl-1H-tetrazol-5-yl)phenyl]-5,8,9,10-tetrahydroindeno[5,4-b][1,4]diazepin-2,4(1H,3H)-dione;

(Compound B8) 5-(3-tert-butoxycarbonylaminophenyl)-1,5,8,9,10,11-hexahydronaphtho[1,2-b][1,4]diazepin-2,4-dione;

(Compound B9) 5-(3-aminophenyl)-1,5,8,9,10,11-hexahydronaphtho[1,2-b][1,4]diazepin-2,4-dione hydrochloride;

(Compound B10) 5-[3-(2-methyl-2H-tetrazol-5-yl)phenyl]-1,5,8,9,10,11-hexahydronaphtho[1,2-b][1,4]diazepin-2,4-dione;

(Compound B11) 5-[3-(1-methyl-1H-tetrazol-5-yl)phenyl]-1,5,8,9,10,11-hexahydronaphtho[1,2-b][1,4]diazepin-2,4-dione;

(Compound B12) 5-(4-aminophenyl)-1,5,8,9,10,11-hexahydronaphtho[1,2-b][1,4]diazepin-2,4-dione;

(Compound B13) 5-(4-methylaminophenyl)-1,5,8,9,10,11-hexahydronaphtho[1,2-b][1,4]diazepin-2,4-dione hydrochloride;

(Compound B14) 5-(2,3-dihydrobenzo[1,4]dioxin-6-yl)-1,5,8,9,10,11-hexahydronaphtho[1,2-b][1,4]diazepin-2,4-dione;

(Compound B15) 5-(4-methoxyphenyl)-1,5,8,9,10,11-hexahydronaphtho[1,2-b][1,4]diazepin-2,4-dione;

(Compound B16) 5-(4-hydroxyphenyl)-1,5,8,9,10,11-hexahydronaphtho[1,2-b][1,4]diazepin-2,4-dione;

(Compound B17) 5-[4-(isopropylcarbonylamino)phenyl]-1,5,8,9,10,11-hexahydronaphtho[1,2-b][1,4]diazepin-2,4-dione;

(Compound B18) 5-(3-carbamoylphenyl)-1,5,8,10-tetrahydro-1H-indeno[6,7-b][1,4]diazepin-2,4-dione;

(Compound B19) 1-acetyl-5-[3-(5-methyl-[1,3,4]oxadiazol-2-yl)phenyl]-1,5,8,10-tetrahydro-1H-indeno[6,7-b][1,4]diazepin-2,4-dione;

(Compound B20) 5-[3-(5-methyl-[1,3,4]oxadiazol-2-yl)phenyl]-1,5,8,10-tetrahydro-1H-indeno[6,7-b][1,4]diazepin-2,4-dione; and (Compound B21) 5-[3-(5-phenyl-[1,3,4]oxadiazol-2-yl)phenyl]-1,5,8,10-tetrahydro-1H-indeno[6,7-b][1,4]diazepin-2,4-dione.

(Compound C1) 4-(3-cyanophenyl)-1,4-dihydrobenzo[f]quinoxalin-2,3-dione;

(Compound C2) 4-[3-(1H-tetrazol-5-yl)phenyl]-1,4-dihydrobenzo[f]quinoxalin-2,3-dione sodium salt;

(Compound C3) 4-(3-methoxyphenyl)-1,4-dihydrobenzo[f]quinoxalin-2,3-dione;

(Compound C4) 4-(3-hydroxyphenyl)-1,4-dihydrobenzo[f]quinoxalin-2,3-dione sodium salt;

(Compound C5) 5-(3-methoxyphenyl)-1,4,7,8,9,10-hexahydrobenzo[f]quinoxalin-2,3-dione;

(Compound C6) 5-(3-hydroxyphenyl)-1,4,7,8,9,10-hexahydrobenzo[f]quinoxalin-2,3-dione;

(Compound C7) 4-(3-aminophenyl)-1,4,7,8,9,10-hexahydrobenzo[f]quinoxalin-2,3-dione hydrochloride;

(Compound C8) 4-(1H-indol-4-yl)-1,4,7,8,9,10-hexahydrobenzo[f]quinoxalin-2,3-dione;

(Compound C9) N-[3-(2,3-dioxo-2,3,7,8,9,10-hexahydrobenzo[f]quinoxalin-4(1H)-yl)phenyl]-2-nitrobenzene sulfonamide;

(Compound C10) 4-(3-methylaminophenyl)-1,4,7,8,9,10-hexahydrobenzo[f]quinoxalin-2,3-dione hydrochloride;

(Compound C11) 1-methyl-4-(3-methylaminophenyl)-1,4,7,8,9,10-hexahydrobenzo[f]quinoxalin-2,3-dione hydrochloride;

(Compound C12) 4-(3-fluorophenyl)-1,4-dihydrobenzo[f]quinoxalin-2,3-dione;

(Compound C13) 4-(3-aminophenyl)-1,4-dihydrobenzo[f]quinoxalin-2,3-dione hydrochloride;

(Compound C14) 4-[3-[(2-iodophenylacetyl)amino]phenyl]-1,4-dihydrobenzo[f]quinoxalin-2,3-dione;

(Compound C15) 4-[3-(5-methyl-[1,3,4]oxadiazol-2-yl)phenyl]-1,4-dihydrobenzo[f]quinoxalin-2,3-dione;

(Compound C16) 4-[3-(3-methyl-[1,2,4]oxadiazol-5-yl)phenyl]-1,4-dihydrobenzo[f]quinoxalin-2,3-dione;

(Compound C17) 4-(4-hydroxyphenyl)-1,4-dihydrobenzo[f]quinoxalin-2,3-dione sodium salt;

(Compound C18) 4-(4-aminophenyl)-1,4-dihydrobenzo[f]quinoxalin-2,3-dione hydrochloride;

(Compound C19) N-[4-(2,3-dioxo-2,3-dihydrobenzo[f]quinoxalin-4(1H)-yl)phenyl]-2-nitrobenzene sulfonamide;

(Compound C20) 4-[4-(5-methyl-[1,3,4]oxadiazol-2-yl)phenyl]-1,4-dihydrobenzo[f]quinoxalin-2,3-dione;

(Compound C21) 4-[3-[2-(trifluoromethyl)benzoyl]aminophenyl]-2,3,7,8,9,10-hexahydro-1H-benzo[f]quinoxalin-2,3-dione;

(Compound C22) N-[3-(2,3-dioxo-2,3,7,8,9,10-hexahydro-1H-benzo[f]quinoxalin-4-yl)phenyl]benzene sulfonamide;

(Compound C23) 3-bromo-N-[3-(2,3-dioxo-2,3,7,8,9,10-hexahydro-1H-benzo[f]quinoxalin-4-yl)phenyl]benzene sulfonamide;

(Compound C24) N-[3-(2,3-dioxo-2,3,7,8,9,10-hexahydro-1H-benzo[f]quinoxalin-4-yl)phenyl]-1-naphthalenesulfonamide;

(Compound C25) N-[3-(2,3-dioxo-2,3,7,8,9,10-hexahydro-1H-benzo[f]quinoxalin-4-yl)phenyl]-2-naphthalenesulfonamide;

(Compound C26) N-[3-(2,3-dioxo-2,3,7,8,9,10-hexahydro-1H-benzo[f]quinoxalin-4-yl)phenyl]-2-thiophenesulfonamide;

(Compound C27) N-[3-(2,3-dioxo-2,3,7,8,9,10-hexahydro-1H-benzo[f]quinoxalin-4-yl)phenyl]-3-pyridine sulfonamide hydrochloride;

(Compound C28) N-[3-(2,3-dioxo-2,3,7,8,9,10-hexahydro-1H-benzo[f]quinoxalin-4-yl)phenyl]-8-quinoline sulfonamide hydrochloride; and (Compound C29) 4-[3-(1H-tetrazol-1-yl)phenyl]-2,3,7,8,9,10-tetrahydro-1H-benzo[f]quinoxalin-2,3-dione.

(Compound D1) 4-(3-cyanophenyl)-1H-benzo[h]quinazolin-2-one;

(Compound D2) 4-[3-(1H-tetrazol-5-yl)phenyl]-1H-benzo[h]quinazolin-2-one sodium salt;

(Compound D3) 4-(3-methoxyphenyl)-1H-benzo[h]quinazolin-2-one;

(Compound D4) 4-(3-hydroxyphenyl)-1H-benzo[h]quinazolin-2-one sodium salt;

(Compound D5) 4-(4-methoxyphenyl)-1H-benzo[h]quinazolin-2-one;

(Compound D6) 4-(4-hydroxyphenyl)-1H-benzo[h]quinazolin-2-one sodium salt;

(Compound D7) 4-(3-aminophenyl)-1H-benzo[h]quinazolin-2-one hydrochloride; and (Compound D8) N-[3-(2-oxo-1,2-dihydrobenzo[h]quinazolin-4-yl)phenyl]benzene sulfonamide.

(Compound E1) 5-[3-(1H-tetrazol-5-yl)phenyl]-1H-naphtho[1,2-b][1,4]diazepin-2,4(3H,5H)-dione;

(Compound E2) 5-[3-(1H-tetrazol-5-yl)phenyl]-1H-naphtho[1,2-b][1,4]diazepin-2,4(3H,5H)-dione sodium salt;

(Compound E3) 5-[3-(1H-tetrazol-5-yl)phenyl]-1H-naphtho[1,2-b][1,4]diazepin-2,4(3H,5H)-dione potassium salt;

(Compound E4) 5-[3-(5-thioxo-4H-[1,2,4]oxadiazol-3-yl)phenyl]-1H-naphtho[1,2-b][1,4]diazepin-2,4(3H,5H)-dione;

(Compound E5) 5-[3-(5-thioxo-4H-[1,2,4]oxadiazol-3-yl)phenyl]-1H-naphtho[1,2-b][1,4]diazepin-2,4(3H,5H)-dione sodium salt;

(Compound E6) 5-[3-(1H-tetrazol-5-yl)phenyl]-1,3-dihydro-2H-naphtho[1,2-e][1,4]diazepin-2-one;

(Compound E7) 5-[3-(1H-tetrazol-5-yl)phenyl]-1,3-dihydro-2H-naphtho[1,2-e][1,4]diazepin-2-one sodium salt;

(Compound E8) 5-[4-fluoro-3-(1H-tetrazol-5-yl)phenyl]-1H-naphtho[1,2-b][1,4]diazepin-2,4(3H,5H)-dione;

(Compound E9) 5-[4-fluoro-3-(1H-tetrazol-5-yl)phenyl]-1H-naphtho[1,2-b][1,4]diazepin-2,4(3H,5H)-dione sodium salt;

(Compound E10) 5-[3-(1H-tetrazol-5-yl)phenyl]-8,9,10,11-tetrahydronaphtho[2,1-b][1,4]diazepin-2,4(3H,5H)-dione;

(Compound E11) 5-[3-(1H-tetrazol-5-yl)phenyl]-8,9,10,11-tetrahydronaphtho[2,1-b][1,4]diazepin-2,4(3H,5H)-dione sodium salt;

(Compound E12) 4-[3-(1H-tetrazol-5-yl)phenyl]-1,4-dihydrobenzo[f]quinoxalin-2,3-dione;

(Compound E13) 4-[3-(1H-tetrazol-5-yl)phenyl]-1,4-dihydrobenzo[f]quinoxalin-2,3-dione sodium salt;

(Compound E14) 4-[3-(1H-tetrazol-5-yl)phenyl]-1H-benzo[h]quinazolin-2-one; and (Compound E15) 4-[3-(1H-tetrazol-5-yl)phenyl]-1H-benzo[h]quinazolin-2-one sodium salt.

(Compound F1) 5-(4-benzoylaminophenyl)-1H-naphtho[1,2-b][1,4]diazepin-2,4(3H,5H)-dione;

(Compound F2) 5-[4-[2-(trifluoromethyl)benzoyl]aminophenyl]-1H-naphtho[1,2-b][1,4]diazepin-2,4(3H,5H)-dione;

(Compound F3) 5-[4-(3-bromobenzoyl)aminophenyl]-1H-naphtho[1,2-b][1,4]diazepin-2,4(3H,5H)-dione;

(Compound F4) 5-[4-[4-(trifluoromethyl)benzoyl]aminophenyl]-1H-naphtho[1,2-b][1,4]diazepin-2,4(3H,5H)-dione;

(Compound F5) 5-[4-(2-methylbenzoyl)aminophenyl]-1H-naphtho[1,2-b][1,4]diazepin-2,4(3H,5H)-dione;

(Compound F6) 5-[4-(2,6-dimethylbenzoylamino)phenyl]-1H-naphtho[1,2-b][1,4]diazepin-2,4(3H,5H)-dione;

(Compound F7) 5-[4-(2,6-dichlorobenzoyl)aminophenyl]-1H-naphtho[1,2-b][1,4]diazepin-2,4(3H,5H)-dione;

(Compound F8) 5-[4-(3-chlorobenzoyl)aminophenyl]-1H-naphtho[1,2-b][1,4]diazepin-2,4(3H,5H)-dione;

(Compound F9) 5-[4-(2-phenylacetylamino)phenyl]-1H-naphtho[1,2-b][1,4]diazepin-2,4(3H,5H)-dione;

(Compound F10) 1-[4-(2,4-dioxo-1,2,3,4-tetrahydronaphtho[1,2-b][1,4]diazepin-5-yl)phenyl]-3-phenylthiourea;

(Compound F11) 5-[4-(2,3-dimethoxybenzoylamino)phenyl]-1H-naphtho[1,2-b][1,4]diazepin-2,4(3H,5H)-dione;

(Compound F12) 5-[4-(2-methoxybenzoylamino)phenyl]-1H-naphtho[1,2-b][1,4]diazepin-2,4(3H,5H)-dione;

(Compound F13) 5-[4-[(2-chlorophenylacetyl)amino]phenyl]-1H-naphtho[1,2-b][1,4]diazepin-2,4(3H,5H)-dione;

(Compound F14) 5-[4-(2,3-dimethylbenzoylamino)phenyl]-1H-naphtho[1,2-b][1,4]diazepin-2,4(3H,5H)-dione;

(Compound F15) 5-[4-(2,5-dimethylbenzoylamino)phenyl]-1H-naphtho[1,2-b][1,4]diazepin-2,4(3H,5H)-dione;

(Compound F16) 5-[4-(5-bromo-2-chlorobenzoylamino)phenyl]-1H-naphtho[1,2-b][1,4]diazepin-2,4(3H,5H)-dione;

(Compound F17) 5-[4-(2,4-dichlorobenzoylamino)phenyl]-1H-naphtho[1,2-b][1,4]diazepin-2,4(3H,5H)-dione;

(Compound F18) 5-[4-(2-hydroxybenzoylamino)phenyl]-1H-naphtho[1,2-b][1,4]diazepin-2,4(3H,5H)-dione;

(Compound F19) 5-[4-(2,3-dihydroxybenzoylamino)phenyl]-1H-naphtho[1,2-b][1,4]diazepin-2,4(3H,5H)-dione;

(Compound F20) 1-[4-(2,4-dioxo-1,2,3,4-tetrahydronaphtho[1,2-b][1,4]diazepin-5-yl)phenyl]-3-phenylurea;

(Compound F21) 5-[4-[(2,6-dichlorophenylacetyl)amino]phenyl]-1H-naphtho[1,2-b][1,4]diazepin-2,4(3H,5H)-dione;

(Compound F22) 5-[4-[(2-methoxyphenylacetyl)amino]phenyl]-1H-naphtho[1,2-b][1,4]diazepin-2,4(3H,5H)-dione;

(Compound F23) 5-[4-[(2-hydroxyphenylacetyl)amino]phenyl]-1H-naphtho[1,2-b][1,4]diazepin-2,4(3H,5H)-dione;

(Compound F24) 1-(2-chlorophenyl)-3-[4-(2,4-dioxo-1,2,3,4-tetrahydronaphtho[1,2-b][1,4]diazepin-5-yl)phenyl]thiourea;

(Compound F25) 5-[4-[3-(trifluoromethyl)benzoylamino]phenyl]-1H-naphtho[1,2-b][1,4]diazepin-2,4(3H,5H)-dione;

(Compound F26) 5-[4-[2-[2-(trifluoromethyl)phenyl]acetylamino]phenyl]-1H-naphtho[1,2-b][1,4]diazepin-2,4(3H,5H)-dione;

(Compound F27) 1-(2-chlorophenyl)-3-[4-(2,4-dioxo-1,2,3,4-tetrahydronaphtho[1,2-b][1,4]diazepin-5-yl)phenyl]urea;

(Compound F28) 5-[4-[(2-phenylpropionyl)amino]phenyl]-1H-naphtho[1,2-b][1,4]diazepin-2,4(3H,5H)-dione;

(Compound F29) 5-[4-(2-chloro-3-methoxybenzoylamino)phenyl]-1H-naphtho[1,2-b][1,4]diazepin-2,4(3H,5H)-dione;

(Compound F30) 5-[4-(3-phenylpropionylamino)phenyl]-1H-naphtho[1,2-b][1,4]diazepin-2,4(3H,5H)-dione;

(Compound F31) 5-[4-[(1H-indole-3-carbonyl)amino]phenyl]-1H-naphtho[1,2-b][1,4]diazepin-2,4(3H,5H)-dione;

(Compound F32) 5-[4-(2-chloro-3-hydroxybenzoylamino)phenyl]-1H-naphtho[1,2-b][1,4]diazepin-2,4(3H,5H)-dione;

(Compound F33) 5-[4-[(2-methyl-2-phenylpropionyl)amino]phenyl]-1H-naphtho[1,2-b][1,4]diazepin-2,4(3H,5H)-dione;

(Compound F34) 5-[4-(2-phenoxyacetylamino)phenyl]-1H-naphtho[1,2-b][1,4]diazepin-2,4(3H,5H)-dione;

(Compound F35) 5-[4-[2-(2-chloro-4-methoxyphenyl)acetylamino]phenyl]-1H-naphtho[1,2-b][1,4]diazepin-2,4(3H,5H)-dione;

(Compound F36) 5-[4-[(1-methyl-1H-imidazole-2-carbonyl)amino]phenyl]-1H-naphtho[1,2-b][1,4]diazepin-2,4(3H,5H)-dione;

(Compound F37) 5-[4-[2-(2,4-dichlorophenyl)acetylamino]phenyl]-1H-naphtho[1,2-b][1,4]diazepin-2,4(3H,5H)-dione;

(Compound F38) 5-[4-[2-(2-chloro-4-hydroxyphenyl)acetylamino]phenyl]-1H-naphtho[1,2-b][1,4]diazepin-2,4(3H,5H)-dione;

(Compound F39) 5-[4-(3-phenylpropenylamino)phenyl]-1H-naphtho[1,2-b][1,4]diazepin-2,4(3H,5H)-dione;

(Compound F40) 5-[4-[(3-pyridylacetyl)amino]phenyl]-1H-naphtho[1,2-b][1,4]diazepin-2,4(3H,5H)-dione hydrochloride;

(Compound F41) 5-[4-(1H-benzimidazole-2-carbonylamino)phenyl]-1H-naphtho[1,2-b][1,4]diazepin-2,4(3H,5H)-dione;

(Compound F42) 1-[4-(2,3-dimethylbenzoylamino)phenyl]-7-methoxy-1H-1,5-benzodiazepin-2,4(3H,5H)-dione;

(Compound F43) 5-[4-[(benzoylamino)methyl]phenyl]-1H-naphtho[1,2-b][1,4]diazepin-2,4(3H,5H)-dione;

(Compound F44) 5-[4-[(2-chlorobenzoylamino)methyl]phenyl]-1H-naphtho[1,2-b][1,4]diazepin-2,4(3H,5H)-dione;

(Compound F45) 1-[4-(2,3-dimethylbenzoylamino)phenyl]-7-hydroxy-1H-1,5-benzodiazepin-2,4(3H,5H)-dione;

(Compound F46) 5-[4-(2-chlorobenzoylamino)phenyl]-1H-naphtho[1,2-b][1,4]diazepin-2,4(3H,5H)-dione;

(Compound F47) 5-[4-(2-bromobenzoylamino)phenyl]-1H-naphtho[1,2-b][1,4]diazepin-2,4(3H,5H)-dione;

(Compound F48) 5-[4-(2-iodobenzoylamino)phenyl]-1H-naphtho[1,2-b][1,4]diazepin-2,4(3H,5H)-dione;

(Compound F49) 5-[4-(2,3-dimethylbenzoylamino)-3-fluorophenyl]-1H-naphtho[1,2-b][1,4]diazepin-2,4(3H,5H)-dione;

(Compound F50) 5-[4-[2-(2-methylphenyl)acetylamino]phenyl]-1H-naphtho[1,2-b][1,4]diazepin-2,4(3H,5H)-dione;

(Compound F51) 5-[4-[(quinoxalin-2yl)carbonylamino]phenyl]-1H-naphtho[1,2-b][1,4]diazepin-2,4(3H,5H)-dione;

(Compound F52) 5-[4-[(5-methylthiophen-2yl)carbonylamino]phenyl]-1H-naphtho[1,2-b][1,4]diazepin-2,4(3H,5H)-dione;

(Compound F53) 5-[3-[(2-chlorophenylacetyl)amino]phenyl]-1H-naphtho[1,2-b][1,4]diazepin-2,4(3H,5H)-dione;

(Compound F54) 5-[4-[(2,4,6-trimethylbenzoyl)amino]phenyl]-1H-naphtho[1,2-b][1,4]diazepin-2,4(3H,5H)-dione;

(Compound F55) 5-[4-(cyclohexylcarbonylamino)phenyl]-1,2,3,4,8,9,10,11-octahydronaphtho[1,2-b][1,4]diazepin-2,4(3H,5H)-dione;

(Compound F56) 1-[4-(2,3-dimethylbenzoyl)aminophenyl]-6-methyl-1H-1,5-benzodiazepin-2,4(3H,5H)-dione;

(Compound F57) 5-[4-[(2-ethylbenzoyl)amino]phenyl]-1H-naphtho[1,2-b][1,4]diazepin-2,4(3H,5H)-dione;

(Compound F58) 5-[4-[(6-methylpyridin-2-yl)carbonylamino]phenyl]-1,2,3,4,8,9,10,11-octahydronaphtho[1,2-b][1,4]diazepin-2,4(3H,5H)-dione;

(Compound F59) 5-[4-[(2-methylpyridin-3-yl)carbonylamino]phenyl]-1,2,3,4,8,9,10,11-octahydronaphtho[1,2-b][1,4]diazepin-2,4(3H,5H)-dione;

(Compound F60) 1-[4-(2,4-dioxo-1,2,3,4-tetrahydronaphtho[1,2-b][1,4]diazepin-5-yl)phenyl]-3-(2-methylphenyl)thiourea;

(Compound F61) 5-[4-(2-methoxy-3-methylbenzoyl)aminophenyl]-1,2,3,4,8,9,10,11-octahydronaphtho[1,2-b][1,4]diazepin-2,4(3H,5H)-dione;

(Compound F62) 5-[4-(2,3-dichlorobenzoyl)aminophenyl]-1,2,3,4,8,9,10,11-octahydronaphtho[1,2-b][1,4]diazepin-2,4(3H,5H)-dione;

(Compound F63) 5-[4-(2,3-dimethylbenzoylamino)-3-hydroxyphenyl]-1H-naphtho[1,2-b][1,4]diazepin-2,4(3H,5H)-dione;

(Compound F64) 5-[4-(2-chloro-3-methoxybenzoylamino)phenyl]-1,3-dihydronaphtho[1,2-e]-1,4-diazepin-2-one;

(Compound F65) 5-[4-[(4-dimethylaminobenzoyl)amino]phenyl]-1H-naphtho[1,2-b][1,4]diazepin-2,4(3H,5H)-dione;

(Compound F66) 5-[4-[2-(2,4-dichlorophenoxy)acetylamino]phenyl]-1H-naphtho[1,2-b][1,4]diazepin-2,4(3H,5H)-dione;

(Compound F67) 5-[4-[2-(2-methylphenoxy)acetylamino]phenyl]-1H-naphtho[1,2-b][1,4]diazepin-2,4(3H,5H)-dione;

(Compound F68) N-[4-(2,4-dioxo-1,2,3,4-tetrahydronaphtho[1,2-b][1,4]diazepin-5-yl)butyl]-2-chloro-3-methoxybenzamide;

(Compound F69) 5-[4-(2-chloro-3-hydroxybenzoylamino)phenyl]-1,3-dihydronaphtho[1,2-e]-1,4-diazepin-2-one;

(Compound F70) 5-[4-(2-acetylbenzoylamino)phenyl]-1H-naphtho[1,2-b][1,4]diazepin-2,4(3H,5H)-dione;

(Compound F71) 5-[4-(2-tert-butylbenzoylamino)phenyl]-1H-naphtho[1,2-b][1,4]diazepin-2,4(3H,5H)-dione;

(Compound F72) 5-[2-(2-iodobenzoyl)aminoethyl]-1H-naphtho[1,2-b][1,4]diazepin-2,4(3H,5H)-dione;

(Compound F73) 5-[3-[(2-iodobenzoyl)amino]phenyl]-1H-naphtho[1,2-b][1,4]diazepin-2,4(3H,5H)-dione;

(Compound F74) 6,7-dimethyl-1-[4-(2-iodobenzoyl)aminophenyl]-1H-1,5-benzodiazepin-2,4(3H,5H)-dione;

(Compound F75) 5-[4-[(1-methylpiperidin-4-yl)carbonylamino]phenyl]-1H-naphtho[1,2-b][1,4]diazepin-2,4(3H,5H)-dione hydrochloride;

(Compound F76) 5-[4-[(benzofuran-2-yl)carbonylamino]phenyl]-1H-naphtho[1,2-b][1,4]diazepin-2,4(3H,5H)-dione;

(Compound F77) 5-[4-[(1-methyl-1H-indol-3-yl)carbonylamino]phenyl]-1H-naphtho[1,2-b][1,4]diazepin-2,4(3H,5H)-dione;

(Compound F78) 5-[4-(2-propenylbenzoylamino)phenyl]-1H-naphtho[1,2-b][1,4]diazepin-2,4(3H,5H)-dione;

(Compound F79) 5-[4-(2-propylbenzoylamino)phenyl]-1H-naphtho[1,2-b][1,4]diazepin-2,4(3H,5H)-dione;

(Compound F80) 5-[3-fluoro-4-(2-iodobenzoylamino)phenyl]-1H-naphtho[1,2-b][1,4]diazepin-2,4(3H,5H)-dione;

(Compound F81) 5-[4-(2-hydroxy-3-methylbenzoyl)aminophenyl]-1,2,3,4,8,9,10,11-octahydronaphtho[1,2-b][1,4]diazepin-2,4(3H,5H)-dione;

(Compound F82) 5-[4-[(2-isopropoxybenzoyl)amino]phenyl]-1H-naphtho[1,2-b][1,4]diazepin-2,4(3H,5H)-dione;

(Compound F83) 5-[4-[(3-methylthiophen-2-yl)carbonylamino]phenyl]-1H-naphtho[1,2-b][1,4]diazepin-2,4(3H,5H)-dione;

(Compound F84) 5-[4-(2-phenoxypropionylamino)phenyl]-1H-naphtho[1,2-b][1,4]diazepin-2,4(3H,5H)-dione;

(Compound F85) 5-[4-[2-(4-chloro-2-methylphenoxy)acetylamino]phenyl]-1H-naphtho[1,2-b][1,4]diazepin-2,4(3H,5H)-dione;

(Compound F86) 5-[4-[(4-fluoro-2-trifluoromethyl)benzoyl]aminophenyl]-1H-naphtho[1,2-b][1,4]diazepin-2,4(3H,5H)-dione;

(Compound F87) 5-[4-(4-fluoro-2-methoxybenzoyl)aminophenyl]-1H-naphtho[1,2-b][1,4]diazepin-2,4(3H,5H)-dione;

(Compound F88) 5-[4-(4-fluoro-2-hydroxybenzoyl)aminophenyl]-1H-naphtho[1,2-b][1,4]diazepin-2,4(3H,5H)-dione;

(Compound F89) 5-[3-[(2-iodophenylacetyl)amino]phenyl]-1H-naphtho[1,2-b][1,4]diazepin-2,4(3H,5H)-dione;

(Compound F90) 5-[4-(2-methyl-2-phenoxypropionylamino)phenyl]-1H-naphtho[1,2-b][1,4]diazepin-2,4(3H,5H)-dione;

(Compound F91) 5-[4-(2-tert-butylbenzoylamino)phenyl]-1,3-dihydronaphtho[1,2-e]-1,4-diazepin-2-one;

(Compound F92) 5-[4-[(3-dimethylaminobenzoyl)amino]phenyl]-1H-naphtho[1,2-b][1,4]diazepin-2,4(3H,5H)-dione;

(Compound F93) 5-[4-(4-iodo-2-methoxybenzoylamino)phenyl]-1H-naphtho[1,2-b][1,4]diazepin-2,4(3H,5H)-dione;

(Compound F94) 5-[4-(6-fluoro-2-methoxybenzoylamino)phenyl]-1H-naphtho[1,2-b][1,4]diazepin-2,4(3H,5H)-dione;

(Compound F95) 5-[4-(2-hydroxy-4-iodobenzoylamino)phenyl]-1H-naphtho[1,2-b][1,4]diazepin-2,4(3H,5H)-dione;

(Compound F96) 5-[4-(6-fluoro-2-hydroxybenzoylamino)phenyl]-1H-naphtho[1,2-b][1,4]diazepin-2,4(3H,5H)-dione;

(Compound F97) 5-[4-(2-fluorobenzoyl)aminophenyl]-1H-naphtho[1,2-b][1,4]diazepin-2,4(3H,5H)-dione;

(Compound F98) 5-[4-[(2-dimethylaminobenzoyl)amino]phenyl]-1H-naphtho[1,2-b][1,4]diazepin-2,4(3H,5H)-dione;

(Compound F99) 5-[4-(2-methoxy-6-methylbenzoylamino)phenyl]-1H-naphtho[1,2-b][1,4]diazepin-2,4(3H,5H)-dione;

(Compound F100) 5-[4-(2-hydroxy-6-methylbenzoylamino)phenyl]-1H-naphtho[1,2-b][1,4]diazepin-2,4(3H,5H)-dione;

(Compound F101) 5-[4-[3-(2-methylphenyl)propionylamino]phenyl]-1H-naphtho[1,2-b][1,4]diazepin-2,4(3H,5H)-dione;

(Compound F102) 5-(4-phenylcarbamoylphenyl)-1H-naphtho[1,2-b][1,4]diazepin-2,4(3H,5H)-dione;

(Compound F103) 5-(4-benzylcarbamoylphenyl)-1H-naphtho[1,2-b][1,4]diazepin-2,4(3H,5H)-dione;

(Compound F104) 5-[4-[3-(2-methylphenyl)propenoylamino]phenyl]-1H-naphtho[1,2-b][1,4]diazepin-2,4(3H,5H)-dione;

(Compound F105) 5-[4-[3-(2-chlorophenyl)propionylamino]phenyl]-1H-naphtho[1,2-b][1,4]diazepin-2,4(3H,5H)-dione;

(Compound F106) 5-[4-(2-iodobenzoyl)aminophenyl]-1,2,3,4,8,9,10,11-octahydronaphtho[1,2-b][1,4]diazepin-2,4(3H,5H)-dione;

(Compound F107) 5-[4-[(1-methyl-1H-pyrrol-2-ylacetyl)amino]phenyl]-1,2,3,4,8,9,10,11-octahydronaphtho[1,2-b][1,4]diazepin-2,4(3H,5H)-dione;

(Compound F108) 5-[4-(2-chlorobenzyl)carbamoylphenyl]-1H-naphtho[1,2-b][1,4]diazepin-2,4(3H,5H)-dione;

(Compound F109) 5-[4-[3-(2-chlorophenyl)propenoylamino]phenyl]-1H-naphtho[1,2-b][1,4]diazepin-2,4(3H,5H)-dione;

(Compound F110) 5-[4-(2-chlorophenyl)carbamoylphenyl]-1H-naphtho[1,2-b][1,4]diazepin-2,4(3H,5H)-dione;

(Compound F111) 5-[4-(6-bromo-2,3-methylenedioxybenzoylamino)phenyl]-1H-naphtho[1,2-b][1,4]diazepin-2,4(3H,5H)-dione;

(Compound F112) 5-[4-(6-bromo-2-methoxybenzoylamino)phenyl]-1H-naphtho[1,2-b][1,4]diazepin-2,4(3H,5H)-dione;

(Compound F113) 5-[4-[(2-tert-butylbenzoyl)amino]phenyl]-1,2,3,4,8,9,10,11-octahydronaphtho[1,2-b][1,4]diazepin-2,4(3H,5H)-dione;

(Compound F114) 5-[2-(2-iodobenzoyl)aminopyridin-5-yl]-1H-naphtho[1,2-b][1,4]diazepin-2,4(3H,5H)-dione;

(Compound F115) 5-[4-(6-bromo-2-hydroxybenzoylamino)phenyl]-1H-naphtho[1,2-b][1,4]diazepin-2,4(3H,5H)-dione;

(Compound F116) 5-[4-(6-chloro-2-methoxybenzoylamino)phenyl]-1H-naphtho[1,2-b][1,4]diazepin-2,4(3H,5H)-dione;

(Compound F117) 5-[4-(2-iodobenzoylamino)phenyl]-1H-[1,4]diazepino[2,3-h]quinoline-2,4(3H,5H)-dione;

(Compound F118) 5-[4-(6-chloro-2-hydroxybenzoylamino)phenyl]-1H-naphtho[1,2-b][1,4]diazepin-2,4(3H,5H)-dione;

(Compound F119) 5-[4-(2-hydroxy-6-methoxybenzoylamino)phenyl]-1H-naphtho[1,2-b][1,4]diazepin-2,4(3H,5H)-dione;

(Compound F120) 5-[4-[2-methoxy-6-(trifluoromethyl)benzoylamino]phenyl]-1H-naphtho[1,2-b][1,4]diazepin-2,4(3H,5H)-dione;

(Compound F121) 5-[4-[2-hydroxy-6-(trifluoromethyl)benzoylamino]phenyl]-1H-naphtho[1,2-b][1,4]diazepin-2,4(3H,5H)-dione;

(Compound F122) 5-[4-[(2-isopropenylbenzoyl)amino]phenyl]-1,2,3,4,8,9,10,11-octahydronaphtho[1,2-b][1,4]diazepin-2,4(3H,5H)-dione;

(Compound F123) 5-[4-[(2-isopropylbenzoyl)amino]phenyl]-1,2,3,4,8,9,10,11-octahydronaphtho[1,2-b][1,4]diazepin-2,4(3H,5H)-dione;

(Compound F124) 5-[4-[2-chloro-5-(methylthio)benzoylamino]phenyl]-1H-naphtho[1,2-b][1,4]diazepin-2,4(3H,5H)-dione;

(Compound F125) 5-[4-[2-(methylthio)benzoylamino]phenyl]-1H-naphtho[1,2-b][1,4]diazepin-2,4(3H,5H)-dione;

(Compound F126) 5-[4-[3-(methylthio)benzoylamino]phenyl]-1H-naphtho[1,2-b][1,4]diazepin-2,4(3H,5H)-dione;

(Compound F127) 5-[4-[2-ethyl-6-methoxybenzoylamino]phenyl]-1H-naphtho[1,2-b][1,4]diazepin-2,4(3H,5H)-dione;

(Compound F128) 5-[4-(3-methanesulfonyl benzoylamino)phenyl]-1H-naphtho[1,2-b][1,4]diazepin-2,4(3H,5H)-dione;

(Compound F129) 6-ethyl-1-[4-(2-iodobenzoyl)aminophenyl]-1H-1,5-benzodiazepin-2,4(3H,5H)-dione;

(Compound F130) 5-[4-[2-ethyl-6-hydroxybenzoylamino]phenyl]-1H-naphtho[1,2-b][1,4]diazepin-2,4(3H,5H)-dione;

(Compound F131) 5-[4-(3-methanesulfinylbenzoylamino)phenyl]-1H-naphtho[1,2-b][1,4]diazepin-2,4(3H,5H)-dione;

(Compound F132) 5-[4-(2-chloro-5-methanesulfinylbenzoylamino)phenyl]-1H-naphtho[1,2-b][1,4]diazepin-2,4(3H,5H)-dione;

(Compound F133) 5-[4-(2-methanesulfinylbenzoylamino)phenyl]-1H-naphtho[1,2-b][1,4]diazepin-2,4(3H,5H)-dione;

(Compound F134) 5-[4-[[2-(4-morpholinyl)acetyl]amino]phenyl]-1,2,3,4,8,9,10,11-octahydronaphtho[1,2-b][1,4]diazepin-2,4(3H,5H)-dione hydrochloride;

(Compound F135) 5-[4-(2-chloro-6-methoxybenzoylamino)phenyl]-1,3-dihydronaphtho[1,2-e]-1,4-diazepin-2-one;

(Compound F136) 5-[4-[[(3-chloropyridin-2-yl)carbonyl]amino]phenyl]-1H-naphtho[1,2-b][1,4]diazepin-2,4(3H,5H)-dione;

(Compound F137) 5-[4-(2-chloro-6-hydroxybenzoylamino)phenyl]-1,3-dihydronaphtho[1,2-e]-1,4-diazepin-2-one;

(Compound F138) 5-[4-(3-chloro-2-methoxybenzoylamino)phenyl]-1H-naphtho[1,2-b][1,4]diazepin-2,4(3H,5H)-dione;

(Compound F139) 5-[4-[(3-methylpyridin-2-yl)carbonylamino]phenyl]-1H-naphtho[1,2-b][1,4]diazepin-2,4(3H,5H)-dione;

(Compound F140) 5-[4-[[(3-chloropyridin-2-yl)carbonyl]amino]phenyl]-1,2,3,4,8,9,10,11-octahydronaphtho[1,2-b][1,4]diazepin-2,4(3H,5H)-dione;

(Compound F141) 5-[4-(3-chloro-2-hydroxybenzoylamino)phenyl]-1H-naphtho[1,2-b][1,4]diazepin-2,4(3H,5H)-dione;

(Compound F142) 5-[4-[[(3-hydroxypyridin-2-yl)carbonyl]amino]phenyl]-1H-naphtho[1,2-b][1,4]diazepin-2,4(3H,5H)-dione;

(Compound F143) 5-[4-[(3-vinylpyridin-2-yl)carbonylamino]phenyl]-1H-naphtho[1,2-b][1,4]diazepin-2,4(3H,5H)-dione;

(Compound F144) 5-[4-[(3-ethylpyridin-2-yl)carbonylamino]phenyl]-1H-naphtho[1,2-b][1,4]diazepin-2,4(3H,5H)-dione;

(Compound F145) N-[4-(2,4-dioxo-1,2,3,4-tetrahydronaphtho-[1,2-b][1,4]-diazepin-5-yl)phenyl]-2-nitrobenzene sulfonamide;

(Compound F146) N-[4-(2,4-dioxo-1,2,3,4-tetrahydronaphtho[1,2-b][1,4]diazepin-5-yl)phenyl]benzene sulfonamide;

(Compound F147) 3-bromo-N-[4-(2,4-dioxo-1,2,3,4-tetrahydronaphtho[1,2-b][1,4]diazepin-5-yl)phenyl]benzene sulfonamide;

(Compound F148) N-[4-(2,4-dioxo-1,2,3,4-tetrahydronaphtho[1,2-b][1,4]diazepin-5-yl)phenyl]-3-methoxybenzene sulfonamide;

(Compound F149) N-[3-(2-oxo-2,3-dihydro-1H-naphtho[1,2-e][1,4]diazepin-5-yl)phenyl]benzene sulfonamide;

(Compound F150) N-[3-(2,4-dioxo-1,2,3,4-tetrahydronaphtho-[1,2-b][1,4]-diazepin-5-yl)phenyl]-2-nitrobenzene sulfonamide;

(Compound F151) N-[4-(2,4-dioxo-1,2,3,4,8,9,10,11-octahydro-naphtho[1,2-b][1,4]-diazepin-5-yl)phenyl]-2-nitrobenzene sulfonamide;

(Compound F152) N-[4-(2,4-dioxo-1,2,3,4,8,9,10,11-octahydro-naphtho[1,2-b][1,4]-diazepin-5-yl)phenyl]-N-methyl-2-nitrobenzene sulfonamide;

(Compound F153) N-[3-(2,4-dioxo-1,2,3,4-tetrahydronaphtho-[1,2-b][1,4]-diazepin-5-yl)phenyl]-N-methyl-2-nitrobenzene sulfonamide;

(Compound F154) 4-(2,4-dioxo-1,2,3,4,8,9,10,11-octahydronaphtho[1,2-b][1,4]diazepin-5-yl)-N-phenylbenzene sulfonamide;

(Compound F155) N-[3-(2,4-dioxo-1,2,3,4-tetrahydronaphtho[1,2-b]-[1,4]diazepin-5-yl)phenyl]-2-naphthalene sulfonamide;

(Compound F156) N-[3-(2,4-dioxo-1,2,3,4-tetrahydronaphtho[1,2-b]-[1,4]diazepin-5-yl)phenyl]-1-naphthalene sulfonamide;

(Compound F157) N-[4-(2,4-dioxo-1,2,3,4-tetrahydronaphtho[1,2-b][1,4]diazepin-5yl)phenyl]cyclohexane sulfonamide;

(Compound F158) N-[4-(2,4-dioxo-1,2,3,4-tetrahydronaphtho[1,2-b][1,4]diazepin-5yl)phenyl]-3-pyridine sulfonamide hydrochloride;

(Compound F159) N-[4-(2,4-dioxo-1,2,3,4-tetrahydronaphtho[1,2-b][1,4]diazepin-5-yl)phenyl]-4-isopropylbenzene sulfonamide;

(Compound F160) N-[4-(2,4-dioxo-1,2,3,4-tetrahydronaphtho[1,2-b][1,4]diazepin-5-yl)phenyl]phenylmethanesulfonamide;

(Compound F161) N-[4-(2,4-dioxo-1,2,3,4-tetrahydronaphtho[1,2-b][1,4]diazepin-5yl)phenyl]-3-pyridine sulfonamide;

(Compound F162) N-[4-(2,4-dioxo-1,2,3,4-tetrahydronaphtho[1,2-b][1,4]diazepin-5yl)phenyl]-2-naphthalene sulfonamide;

(Compound F163) 4-(2,4-dioxo-1,2,3,4,8,9,10,11-octahydronaphtho-[1,2-b][1,4]diazepin-5-yl)phenyl3-bromobenzene-sulfonate;

(Compound F164) N-benzyl-N-[4-(1-benzyl-2,4-dioxo-1,2,3,4-tetrahydronaphtho[1,2-b][1,4]diazepin-5yl)phenyl]-2-nitrobenzene sulfonamide;

(Compound F165) N-benzyl-N-[4-(2,4-dioxo-1,2,3,4-tetrahydronaphtho[1,2-b][1,4]diazepin-5yl)phenyl]-2-nitrobenzene sulfonamide;

(Compound F166) 3-bromo-N-[4-(2,4-dioxo-1,2,3,4-tetrahydronaphtho[1,2-b][1,4]diazepin-5-yl)phenyl]-N-methylbenzene sulfonamide;

(Compound F167) N-[4-(2,4-dioxo-1,2,3,4-tetrahydronaphtho-[1,2-b][1,4]-diazepin-5-yl)phenyl]-N-methyl-2-nitrobenzene sulfonamide;

(Compound F168) N-[4-(2,4-dioxo-1,2,3,4-tetrahydronaphtho-[1,2-b][1,4]-diazepin-5-yl)phenyl]-N-(2-hydroxyethyl)-2-nitrobenzene sulfonamide;

(Compound F169) N-[4-(7-chloro-2,4-dioxo-2,3,4,5-tetrahydro-1H-benzo[b][1,4]diazepin-1-yl)phenyl]benzene sulfonamide;

(Compound F170) N-[4-(7-bromo-2,4-dioxo-2,3,4,5-tetrahydro-1H-benzo[b][1,4]diazepin-1-yl)phenyl]benzene sulfonamide;

(Compound F171) N-[4-[(2,4-dioxo-7-(trifluoromethyl)-2,3,4,5-tetrahydro-1H-benzo[b][1,4]diazepin-1-yl)]phenyl] benzene sulfonamide;

(Compound F172) N-[4-(2,4-dioxo-2,3,4,5-tetrahydro-1H-benzo[b][1,4]diazepin-1-yl)phenyl]benzene sulfonamide;

(Compound F173) 1-(2-chlorophenyl)-N-[4-(2,4-dioxo-1,2,3,4-tetrahydronaphtho[1,2-b][1,4]diazepin-5-yl)phenyl] methanesulfonamide;

(Compound F174) 1-(3-bromophenyl)-N-[4-(2,4-dioxo-1,2,3,4-tetrahydronaphtho[1,2-b][1,4]diazepin-5-yl)phenyl] methanesulfonamide;

(Compound F175) N-[4-(2,4-dioxo-1,2,3,4-tetrahydronaphtho-[1,2-b][1,4]-diazepin-5-yl)phenyl]-2-trifluoromethyl benzene sulfonamide;

(Compound F176) N-[4-(7-bromo-6-methyl-2,4-dioxo-2,3,4,5-tetrahydro-1H-benzo[b][1,4]diazepin-1-yl)phenyl] benzene sulfonamide;

(Compound F177) 1-(2-chlorophenyl)-N-[4-(2,4-dioxo-1,2,3,4,8,9,10,11-octahydronaphtho[1,2-b][1,4]diazepin-5-yl)phenyl]methanesulfonamide;

(Compound F178) 3-bromo-N-[4-(2,4-dioxo-1,2,3,4,8,9,10,11-octahydronaphtho[1,2-b][1,4]diazepin-5-yl)phenyl] benzene sulfonamide;

(Compound F179) N-[4-(2,4-dioxo-1,2,3,4,8,9,10,11-octahydronaphtho[1,2-b][1,4]diazepin-5-yl)phenyl]-3-methoxybenzene sulfonamide;

(Compound F180) 1-(2-bromophenyl)-N-[4-(2,4-dioxo-1,2,3,4-tetrahydronaphtho[1,2-b][1,4]diazepin-5-yl)phenyl] methanesulfonamide;

(Compound F181) N-[4-(2,4-dioxo-1,2,3,4-tetrahydronaphtho[1,2-b][1,4]diazepin-5-yl)phenyl]-1-(2-methylphenyl)methanesulfonamide;

(Compound F182) N-[4-(2,4-dioxo-1,2,3,4-tetrahydronaphtho[1,2-b][1,4]diazepin-5-yl)phenyl]-1-(2-nitrophenyl)methanesulfonamide;

(Compound F183) N-[4-(2,4-dioxo-1,2,3,4-tetrahydronaphtho[1,2-b][1,4]diazepin-5-yl)phenyl]-2-phenylethane sulfonamide;

(Compound F184) 1-(2,3-dichlorophenyl)-N-[4-(2,4-dioxo-1,2,3,4,8,9,10,11-octahydronaphtho[1,2-b][1,4]diazepin-5-yl)phenyl]methanesulfonamide;

(Compound F185) 1-(2-chlorophenyl)-N-[4-(2,4-dioxo-7-methoxy-1H-benzo[1,2-b][1,4]diazepin-1-yl)phenyl] methanesulfonamide;

(Compound F186) 1-(2-chlorophenyl)-N-[4-(2,4-dioxo-7-hydroxy-1H-benzo[1,2-b][1,4]diazepin-1-yl)phenyl] methanesulfonamide;

(Compound F187) 1-(4-chlorophenyl)-N-[4-(2,4-dioxo-1,2,3,4-tetrahydronaphtho[1,2-b][1,4]diazepin-5-yl)phenyl] methanesulfonamide;

(Compound F188) 1-(2-chlorophenyl)-N-[4-(2,4-dioxo-1,2,3,4-tetrahydronaphtho[1,2-b][1,4]diazepin-5-yl)benzyl] methanesulfonamide;

(Compound F189) 1-(2-chlorophenyl)-N-[4-(2,4-dioxo-1,2,3,4-tetrahydronaphtho[1,2-b][1,4]diazepin-5-yl)-2-methoxyphenyl]methanesulfonamide;

(Compound F190) 1-(2-chlorophenyl)-N-[4-(2,4-dioxo-1,2,3,4-tetrahydronaphtho[1,2-b][1,4]diazepin-5-yl)-2-hydroxyphenyl]methanesulfonamide;

(Compound F191) 1-(2,6-dichlorophenyl)-N-[4-(2,4-dioxo-1,2,3,4,8,9,10,11-octahydronaphtho[1,2-b][1,4]diazepin-5-yl)phenyl]methanesulfonamide;

(Compound F192) 1-(2-chlorophenyl)-N-[4-(2,4-dioxo-6-methyl-1H-benzo[1,2-b][1,4]diazepin-1-yl)phenyl]methanesulfonamide;

(Compound F193) 1-(2-chlorophenyl)-N-[4-(2,4-dioxy-1,2,3,4-tetrahydronaphtho[1,2-b][1,4]diazepin-5-yl)propyl] methanesulfonamide;

(Compound F194) 1-(2-chlorophenyl)-N-[2-(2,4-dioxo-1,2,3,4-tetrahydronaphtho[1,2-b][1,4]diazepin-5-yl)ethyl] methanesulfonamide;

(Compound F195) N-[4-(2,4-dioxo-1,2,3,4,8,9,10,11-octahydronaphtho[1,2-b][1,4]diazepin-5-yl)phenyl]-1-(2-iodophenyl)methanesulfonamide;

(Compound F196) 1-(2-chlorophenyl)-N-[4-(2,4-dioxo-1,2,3,4,8,9,10,11-octahydronaphtho[1,2-b][1,4]diazepin-5-yl)phenyl]-N-methylmethanesulfonamide;

(Compound F197) 1-(2-chlorophenyl)-N-[4-(2-oxo-2,3-dihydro-1H-naphtho[1,2-e][1,4]diazepin-5-yl)phenyl]methanesulfonamide;

(Compound F198) 1-[2-(trifluoromethyl)phenyl]-N-[4-(2,4-dioxo-1,2,3,4-tetrahydronaphtho[1,2-b][1,4]diazepin-5-yl)phenyl]phenyl-N-methylmethanesulfonamide;

(Compound F199) 1-(2-ethylphenyl)-N-[4-(2,4-dioxo-1,2,3,4-tetrahydronaphtho[1,2-b][1,4]diazepin-5-yl)phenyl]phenyl-N-methylmethanesulfonamide;

(Compound F200) 1-(2,3-dimethylphenyl)-N-[4-(2,4-dioxo-1,2,3,4-tetrahydronaphtho[1,2-b][1,4]diazepin-5-yl)phenyl]phenyl-N-methylmethanesulfonamide;

(Compound F201) 2-(2-chlorophenyl)-N-[4-(2,4-dioxo-1,2,3,4-tetrahydronaphtho[1,2-b][1,4]diazepin-5-yl)phenyl]phenyl-N-methylethanesulfonamide;

(Compound F202) 1-(2-nitrophenyl)-N-[4-(2,4-dioxo-1,2,3,4-tetrahydronaphtho[1,2-b][1,4]diazepin-5-yl)phenyl]phenyl-N-methylmethanesulfonamide;

(Compound F203) 1-(2-aminophenyl)-N-[4-(2,4-dioxo-1,2,3,4-tetrahydronaphtho[1,2-b][1,4]diazepin-5-yl)phenyl]phenyl-N-methylmethanesulfonamide;

(Compound F204) 1-(2-dimethylaminophenyl)-N-[4-(2,4-dioxo-1,2,3,4-tetrahydronaphtho[1,2-b][1,4]diazepin-5-yl)phenyl]phenyl-N-methylmethanesulfonamide;

(Compound F205) 5-[4-[(pyridin-4-yl)carbonylamino]phenyl]-1H-naphtho[1,2-b][1,4]diazepin-2,4(3H,5H)-dione hydrochloride;

(Compound F206) 5-[4-[2-[(pyridin-3-yl)oxy]acetylamino]phenyl]-1H-naphtho[1,2-b][1,4]diazepin-2,4(3H,5H)-dione hydrochloride;

(Compound F207) 5-[4-[(pyridin-3-yl)carbonylamino]phenyl]-1H-naphtho[1,2-b][1,4]diazepin-2,4(3H,5H)-dione hydrochloride;

(Compound F208) 5-[4-[(2-methylpyridin-3-yl)carbonylamino]phenyl]-1H-naphtho[1,2-b][1,4]diazepin-2,4(3H,5H)-dione hydrochloride;

(Compound F209) 5-[4-[(2-chloropyridin-3-yl)carbonylamino]phenyl]-1H-naphtho[1,2-b][1,4]diazepin-2,4(3H,5H)-dione;

(Compound F210) 5-[4-[2-[(pyridin-2-yl)oxy]acetylamino]phenyl]-1H-naphtho[1,2-b][1,4]diazepin-2,4(3H,5H)-dione;

(Compound F211) 5-[4-[[4-(trifluoromethyl)pyridin-3-yl]carbonylamino]phenyl]-1H-naphtho[1,2-b][1,4]diazepin-2,4(3H,5H)-dione;

(Compound F212) 5-[4-[(2-chloropyridin-3-yl)carbonylamino]phenyl]-1H-[1,4]diazepino[2,3-f]isoquinolin-2,4(3H,5H)-dione;

(Compound F213) 5-[4-[(2-chloropyridin-3-yl)carbonylamino]phenyl]-8,9,10,11-tetrahydro-1H-[1,4]diazepino[2,3-f]isoquinolin-2,4(3H,5H)-dione; and (Compound F214) 5-[4-[(2-isopropylbenzoyl)amino]phenyl]-1H-naphtho[1,2-b][1,4]diazepin-2,4(3H,5H)-dione.

(Compound G1) N-[4-(2-oxo-2,3-dihydro-1H-naphtho[1,2-e][1,4]-diazepin-5-yl)phenyl]-3-(pyridin-2-yl)propionamide;

(Compound G2) 2-ethyl-3-hydroxy-N-[4-(2-oxo-2,3-dihydro-1H-naphtho[1,2-e][1,4]-diazepin-5-yl)phenyl]benzamide;

(Compound G3) 2-ethyl-N-[4-(2-oxo-2,3-dihydro-1H-naphtho[1,2-e][1,4]-diazepin-5-yl)phenyl]nicotinamide dihydrochloride;

(Compound G4) 2-ethyl-6-hydroxy-N-[4-(2-oxo-2,3-dihydro-1H-naphtho[1,2-e][1,4]-diazepin-5-yl)phenyl]benzamide;

(Compound G5) 3-ethyl-N-[4-(2-oxo-2,3-dihydro-1H-naphtho[1,2-e][1,4]-diazepin-5-yl)phenyl]picolinamide hydrochloride;

(Compound G6) N-[4-(2-oxo-2,3-dihydro-1H-naphtho[1,2-e][1,4]-diazepin-5-yl)phenyl]-2-(pyridin-2-yloxy)acetamide hydrochloride;

(Compound G7) 2-(2-methoxyphenyl)-N-[4-(2-oxo-2,3-dihydro-1H-naphtho[1,2-e][1,4]-diazepin-5-yl)phenyl]acetamide;

(Compound G8) N-[4-(2-oxo-2,3-dihydro-1H-naphtho[1,2-e][1,4]diazepin-5-yl)-phenyl]-3-(pyridin-3-yl)propionamide dihydrochloride;

(Compound G9) N-[4-(2-oxo-2,3-dihydro-1H-naphtho[1,2-e][1,4]diazepin-5-yl)phenyl]-3-phenylpropanamide;

(Compound G10) N-[4-(2,4-dioxo-3,4-dihydro-1H-naphtho[1,2-b][1,4]diazepin-5(2H)-yl)-phenyl]-3-(pyridin-3-yl)propionamide hydrochloride;

(Compound G11) N-[4-(2,4-dioxo-3,4-dihydro-1H-naphtho[1,2-b][1,4]diazepin-5(2H)-yl)-phenyl]-3-(pyridin-4-yl)propionamide hydrochloride;

(Compound G12) 2-tert-butyl-N-[4-(2,4-dioxo-3,4-dihydro-1H-naphtho[1,2-b][1,4]diazepin-5 (2H)-yl)2-fluorophenyl]benzamide;

(Compound G13) N-[4-(2,4-dioxo-3,4-dihydro-1H-naphtho[1,2-b][1,4]diazepin-5(2H)-yl)-phenyl]-3-(pyridin-2-yl)propionamide hydrochloride;

(Compound G14) 2-(dimethylamino)-N-[4-(2,4-dioxo-2,3-dihydro-1H-naphtho[1,2-b][1,4]diazepin-5 (2H)-yl)phenyl]nicotinamide hydrochloride;

(Compound G15) 2-(dimethylamino)-N-[4-(2-oxo-2,3-dihydro-1H-naphtho[1,2-e][1,4]diazepin-5-yl)phenyl]nicotineamide;

(Compound G16) 2-(dimethylamino)-N-[4-(2-oxo-2,3-dihydro-1H-naphtho[1,2-e][1,4]diazepin-5-yl)phenyl]nicotineamide dihydrochloride;

(Compound G17) 2-(dimethylamino)-N-[4-(2-oxo-2,3-dihydro-1H-naphtho[1,2-e][1,4]diazepin-5-yl)phenyl]nicotinamide dimethanesulfonate;

(Compound G18) N-[4-(2,4-dioxo-3,4-dihydro-1H-naphtho[1,2-b][1,4]-diazepin-5 (2H)-yl)phenyl]-2-(morpholin-4-yl)-nicotinamide hydrochloride;

(Compound G19) N-[4-(2-oxo-2,3-dihydro-1H-naphtho[1,2-e][1,4]-diazepin-5-yl)phenyl]-2-(1H-pyrrol-1-yl)nicotinamide dihydrochloride;

(Compound G20) 2-(morpholin-4-yl)-N-[4-(2-oxo-2,3-dihydro-1H-naphtho[1,2-e][1,4]-diazepin-5-yl)phenyl]nicotinamide dihydrochloride;

(Compound G21) N-[4-(2-oxo-2,3-dihydro-1H-naphtho[1,2-e][1,4]-diazepin-5-yl)phenyl]-2-(pyrrolidin-1-yl)nicotinamide dihydrochloride;

(Compound G22) 4-(dimethylamino)-N-[4-(2-oxo-2,3-dihydro-1H-naphtho[1,2-e][1,4]-diazepin-5-yl)phenyl]nicotineamide dihydrochloride;

(Compound G23) 2-isopropyl-N-[4-(2-oxo-2,3-dihydro-1H-naphtho[1,2-e][1,4]-diazepin-5-yl)phenyl]nicotinamide dihydrochloride; and (Compound G24) 2-(isopropylamino)-N-[4-(2-oxo-2,3-dihydro-1H-naphtho[1,2-e][1,4]diazepin-5-yl)phenyl]nicotineamide dihydrochloride.

(Compound H1) 5-[4-[5-(2-methoxybenzyl)-1H-tetrazol-1-yl]phenyl]-1H-naphtho[1,2-b][1,4]diazepin-2,4(3H,5H)-dione;

(Compound H2) 5-[4-[5-(2-hydroxybenzyl)-1H-tetrazol-1-yl]phenyl]-1H-naphtho[1,2-b][1,4]diazepin-2,4(3H,5H)-dione;

(Compound H3) 5-[4-[5-[2-(pyridin-3-yl)ethyl]-1H-tetrazol-1-yl]phenyl]-1H-naphtho[1,2-b][1,4]diazepin-2,4(3H,5H)-dione hydrochloride;

(Compound H4) 5-[4-(5-phenethyl-1H-tetrazol-1-yl)phenyl]-1H-naphtho[1,2-b][1,4]diazepin-2,4(3H,5H)-dione;

(Compound H5) 5-[4-[5-(pyridin-4-ylmethyl)-1H-tetrazol-1-yl]phenyl]-1H-naphtho[1,2-b][1,4]diazepin-2,4(3H,5H)-dione;

(Compound H6) 5-[4-(5-benzyl-1H-tetrazol-1-yl)phenyl]-1H-naphtho[1,2-b][1,4]diazepin-2,4(3H,5H)-dione;

(Compound H7) 5-[4-[5-(pyridin-3-ylmethyl)-1H-tetrazol-1-yl]phenyl]-1H-naphtho[1,2-b][1,4]diazepin-2,4(3H,5H)-dione;

(Compound H8) 7-methoxy-1-[4-[5-(2-methoxybenzyl)-1H-tetrazol-1-yl]phenyl]-1H-benzo[b][1,4]diazepin-2,4(3H,5H)-dione;

(Compound H9) 5-[6-[5-(2-methoxybenzyl)-1H-tetrazol-1-yl]pyridin-3-yl]-1H-naphtho[1,2-b][1,4]diazepin-2,4(3H,5H)-dione;

(Compound H10) 5-[4-[5-(2-cyclohexylethyl)-1H-tetrazol-1-yl]phenyl]-1H-naphtho[1,2-b][1,4]diazepin-2,4(3H,5H)-dione;

(Compound H11) 5-[6-[5-(2-hydroxybenzyl)-1H-tetrazol-1-yl]pyridin-3-yl]-1H-naphtho[1,2-b][1,4]diazepin-2,4(3H,5H)-dione;

(Compound H12) 5-[4-[5-[2-(pyridin-4-yl)ethyl]-1H-tetrazol-1-yl]phenyl]-1H-naphtho[1,2-b][1,4]diazepin-2,4(3H,5H)-dione hydrochloride;

(Compound H13) 5-[4-[5-(pyridin-2-ylmethyl)-1H-tetrazol-1-yl]phenyl]-1H-naphtho[1,2-b][1,4]diazepin-2,4(3H,5H)-dione;

(Compound H14) 5-[4-[5-[2-(pyridin-2-yl)ethyl]-1H-tetrazol-1-yl]phenyl]-1H-naphtho[1,2-b][1,4]diazepin-2,4(3H,5H)-dione hydrochloride;

(Compound H15) 5-[4-[5-[(1H-imidazol-1-yl)methyl]-1H-tetrazol-1-yl]phenyl]-1H-naphtho[1,2-b][1,4]diazepin-2,4(3H,5H)-dione;

(Compound H16) 5-[4-[5-[2-(1H-imidazol-1-yl)ethyl]-1H-tetrazol-1-yl]phenyl]-1H-naphtho[1,2-b][1,4]diazepin-2,4(3H,5H)-dione;

(Compound H17) 5-[4-[5-[2-(pyridin-2-yl)ethyl]-1H-tetrazol-1-yl]phenyl]-1H-naphtho[1,2-e][1,4]diazepin-2 (3H)-one dihydrochloride;

(Compound H18) 5-[4-[5-(2-methoxyphenethyl)-1H-tetrazol-1-yl]phenyl]-1H-naphtho[1,2-b][1,4]diazepin-2,4(3H,5H)-dione;

(Compound H19) 5-[4-[5-(2-methoxybenzyl)-1H-tetrazol-1-yl]phenyl]-1H-naphtho[1,2-e][1,4]diazepin-2(3H)-one;

(Compound H20) 5-[4-[5-(3-phenylpropyl)-1H-tetrazol-1-yl]phenyl]-1H-naphtho[1,2-b][1,4]diazepin-2,4(3H,5H)-dione;

(Compound H21) 5-[4-(2-phenethyl-1H-imidazol-1-yl)phenyl]-1H-naphtho[1,2-b][1,4]diazepin-2,4(3H,5H)-dione hydrochloride;

(Compound H22) 5-[4-(1-phenethyl-1H-imidazol-2-yl)phenyl]-1H-naphtho[1,2-b][1,4]diazepin-2,4(3H,5H)-dione hydrochloride;

(Compound H23) 5-[4-[1-(4-chlorobenzyl)-1H-imidazol-2-yl]phenyl]-1H-naphtho[1,2-b][1,4]diazepin-2,4(3H,5H)-dione hydrochloride;

(Compound H24) 5-[4-[1-(2-methoxybenzyl)-1H-imidazol-2-yl]phenyl]-1H-naphtho[1,2-b][1,4]diazepin-2,4(3H,5H)-dione;

(Compound H25) 5-[4-[1-(3-methoxyphenethyl)-1H-imidazol-2-yl]phenyl]-1H-naphtho[1,2-b][1,4]diazepin-2,4(3H,5H)-dione;

(Compound H26) 5-[4-[1-(3-methoxyphenethyl)-1H-imidazol-2-yl]phenyl]-1H-naphtho[1,2-b][1,4]diazepin-2,4(3H,5H)-dione hydrochloride;

(Compound H27) 5-[4-[1-(3-hydroxyphenethyl)-1H-imidazol-2-yl]phenyl]-1H-naphtho[1,2-b][1,4]diazepin-2,4(3H,5H)-dione;

(Compound H28) 5-[4-[1-(2,4,6-trimethylbenzyl)-1H-imidazol-2-yl]phenyl]-1H-naphtho[1,2-b][1,4]diazepin-2,4(3H,5H)-dione hydrochloride;

(Compound H29) 4-[3-[5-[2-(pyridin-2-yl)ethyl]-1H-tetrazol-1-yl]phenyl]-benzo[f]quinoxalin-2,3(1H,4H)-dione hydrochloride;

(Compound H30) 5-[4-[5-[2-(6-methylpyridin-2-ylethyl)-1H-tetrazol-1-yl]-phenyl]-1H-naphtho[1,2-b][1,4]diazepin-2,4(3H,5H)-dione hydrochloride;

(Compound H31) 5-[4-[(2-(3-fluorophenyl)ethyl)-1H-imidazol-1-yl]phenyl]-1H-naphtho[1,2-b][1,4]diazepin-2,4(3H,5H)-dione hydrochloride;

(Compound H32) 5-[4-[(2-(2-methoxyphenyl)ethyl)-1H-imidazol-1-yl]phenyl]-1H-naphtho[1,2-b][1,4]diazepin-2,4(3H,5H)-dione hydrochloride;

(Compound H33) 5-[4-[(2-(4-fluorophenyl)ethyl)-1H-imidazol-1-yl]phenyl]-1H-naphtho[1,2-b][1,4]diazepin-2,4(3H,5H)-dione hydrochloride;

(Compound H34) 5-[4-[(2-(2-fluorophenyl)ethyl)-1H-imidazol-1-yl]phenyl]-1H-naphtho[1,2-b][1,4]diazepin-2,4(3H,5H)-dione hydrochloride;

(Compound H35) 5-[4-[1-[2-(trifluoromethyl)benzyl]-1H-imidazol-2-yl]phenyl]-1H-naphtho[1,2-b][1,4]diazepin-2,4(3H,5H)-dione hydrochloride;

(Compound H36) 5-[4-[2-[4-(trifluoromethyl)phenylethyl]-1H-imidazol-1-yl]phenyl]-1H-naphtho[1,2-b][1,4]diazepin-2,4(3H,5H)-dione hydrochloride;

(Compound H37) 5-[4-[2-(2,6-dimethylphenylethyl)-1H-imidazol-1-yl]phenyl]-1H-naphtho[1,2-b][1,4]diazepin-2,4(3H,5H)-dione hydrochloride;

(Compound H38) 5-[4-[2-[3-(trifluoromethyl)phenylethyl]-1H-imidazol-1-yl]phenyl]-1H-naphtho[1,2-b][1,4]diazepin-2,4(3H,5H)-dione hydrochloride;

(Compound H39) 5-[4-[5-[2-(pyridin-2-yl)ethyl]-1H-tetrazol-1-yl]phenyl]-1H-naphtho[1,2-e][1,4]diazepin-2 (3H)-one dihydrochloride;

(Compound H40) 5-[4-(5-phenethyl-1H-tetrazol-1-yl)phenyl]-1H-naphtho[1,2-e][1,4]diazepin-2(3H)-one;

(Compound H41) 5-[4-(2-phenethyl-1H-imidazol-1-yl)phenyl]-1H-naphtho[1,2-e][1,4]diazepin-2(3H)-one dihydrochloride;

(Compound H42) 5-[4-[2-(3-methoxyphenethyl)-1H-imidazol-1-yl]phenyl]-1H-naphtho[1,2-b][1,4]diazepin-2,4(3H,5H)-dione hydrochloride;

(Compound H43) 5-[4-[2-(3-hydroxyphenethyl)-1H-imidazol-1-yl]phenyl]-1H-naphtho[1,2-b][1,4]diazepin-2,4(3H,5H)-dione hydrochloride;

(Compound H44) 3-[2-[1-[4-(2,4-dioxo-3,4-dihydro-1H-naphtho[1,2-b][1,4]diazepin-5(2H)-yl]phenyl]-1H-tetrazol-5-yl]ethyl]benzonitrile;

(Compound H45) 3-[2-[1-[4-(2,4-dioxo-3,4-dihydro-1H-naphtho[1,2-b][1,4]diazepin-5(2H)-yl]phenyl]-1H-tetrazol-5-yl]ethyl]benzamide;

(Compound H46) 5-[4-[5-[2-(2-methoxypyridin-3-yl)ethyl]-1H-tetrazol-1-yl]phenyl]-1H-naphtho[1,2-b][1,4]diazepin-2,4(3H,5H)-dione;

(Compound H47) 5-[4-[5-[2-(dimethylamino)benzyl]-1H-tetrazol-1-yl]phenyl]-1H-naphtho[1,2-b][1,4]diazepin-2,4(3H,5H)-dione mesylate;

(Compound H48) 4-[2-[1-[4-(2,4-dioxo-3,4-dihydro-1H-naphtho[1,2-b][1,4]diazepin-5(2H)-yl]phenyl]-1H-imidazol-2-yl]ethyl]benzonitrile;

(Compound H49) 4-[2-[1-[4-(2,4-dioxo-3,4-dihydro-1H-naphtho[1,2-b][1,4]diazepin-5(2H)-yl]phenyl]-1H-imidazol-2-yl]ethyl]benzamide;

(Compound H50) 5-[4-(2-phenyl-1H-imidazol-1-yl)phenyl]-1H-naphtho[1,2-b][1,4]diazepin-2,4(3H,5H)-dione;

(Compound H51) 5-[4-[2-(2-methoxyphenyl)-1H-imidazol-1-yl]phenyl]-1H-naphtho[1,2-b][1,4]diazepin-2,4(3H,5H)-dione;

(Compound H52) 2-[[2-[4-(2,4-dioxo-3,4-dihydro-1H-naphtho[1,2-b][1,4]diazepin-5(2H)-yl]phenyl]-1H-imidazol-1-yl]methyl]benzonitrile;

(Compound H53) 2-[[2-[4-(2,4-dioxo-3,4-dihydro-1H-naphtho[1,2-b][1,4]diazepin-5(2H)-yl]phenyl]-1H-imidazol-1-yl]methyl]benzamide;

(Compound H54) 2-[2-[1-[4-(2,4-dioxo-3,4-dihydro-1H-naphtho[1,2-b][1,4]diazepin-5(2H)-yl]phenyl]-1H-imidazol-2-yl]ethyl]benzonitrile;

(Compound H55) 2-[2-[1-[4-(2,4-dioxo-3,4-dihydro-1H-naphtho[1,2-b][1,4]diazepin-5(2H)-yl]phenyl]-1H-imidazol-2-yl]ethyl]benzamide;

(Compound H56) 3-[2-[1-[4-(2,4-dioxo-3,4-dihydro-1H-naphtho[1,2-b][1,4]diazepin-5(2H)-yl]phenyl]-1H-imidazol-2-yl]ethyl]benzonitrile;

(Compound H57) 3-[2-[1-[4-(2,4-dioxo-3,4-dihydro-1H-naphtho[1,2-b][1,4]diazepin-5(2H)-yl]phenyl]-1H-imidazol-2-yl]ethyl]benzamide;

(Compound H58) 3-[2-[1-[4-(2,4-dioxo-3,4-dihydro-1H-naphtho[1,2-b][1,4]diazepin-5(2H)-yl]phenyl]-1H-imidazol-2-yl]ethyl]benzamide hydrochloride;

(Compound H59) 5-[4-[2-[4-(methylsulfonyl)phenethyl]-1H-imidazol-1-yl]phenyl]-1H-naphtho[1,2-b][1,4]diazepin-2,4(3H,5H)-dione hydrochloride;

(Compound H60) 5-[4-[2-(2-fluoro-3-methoxyphenethyl)-1H-imidazol-1-yl]phenyl]-1H-naphtho[1,2-b][1,4]diazepin-2,4(3H,5H)-dione hydrochloride;

(Compound H61) 5-[4-[2-(3-methoxyphenethyl)-1H-imidazol-1-yl]phenyl]-5,8,9,10-tetrahydroindeno[4,5-b][1,4]diazepin-2,4(1H,3H)-dione hydrochloride;

(Compound H62) 5-[4-[2-[2-(thiophen-3-yl)ethyl]-1H-imidazol-1-yl]phenyl]-1H-naphtho[1,2-b][1,4]diazepin-2,4(3H,5H)-dione hydrochloride;

(Compound H63) 5-[4-[1-(2-aminobenzyl)-1H-imidazol-2-yl]phenyl]-1H-naphtho[1,2-b][1,4]diazepin-2,4(3H,5H)-dione;

(Compound H64) 5-[3-methoxy-4-(1-phenethyl-1H-imidazol-2-yl)-phenyl]-1H-naphtho[1,2-b][1,4]diazepin-2,4(3H,5H)-dione;

(Compound H65) 5-[3-hydroxy-4-(1-phenethyl-1H-imidazol-2-yl)-phenyl]-1H-naphtho[1,2-b][1,4]diazepin-2,4(3H,5H)-dione;

(Compound H66) 5-[4-[2-[2-(furan-2-yl)ethyl]-1H-imidazol-1-yl]-phenyl]-1H-naphtho[1,2-b][1,4]diazepin-2,4(3H,5H)-dione hydrochloride;

(Compound H67) 5-[4-[2-(2-fluorophenethyl)-1H-imidazol-1-yl]phenyl]-5,8,9,10-tetrahydroindeno[4,5-b][1,4]diazepin-2,4(1H,3H)-dione;

(Compound H68) 5-[4-[2-(phenoxymethyl)-1H-imidazol-1-yl]phenyl]-1H-naphtho[1,2-b][1,4]diazepin-2,4(3H,5H)-dione;

(Compound H69) 5-[4-[5-[2-methyl-2-(pyridin-2-yl)propyl]-1H-tetrazol-1-yl]phenyl]-1H-naphtho[1,2-b][1,4]diazepin-2,4(3H,5H)-dione hydrochloride;

(Compound H70) 5-[4-[5-[2-(3-methoxypyridin-2-yl)ethyl]-1H-tetrazol-1-yl]phenyl]-1H-naphtho[1,2-b][1,4]diazepin-2,4(3H,5H)-dione hydrochloride;

(Compound H71) 5-[4-[[2-(pyridin-2-yl)ethyl]-1H-imidazol-1-yl]phenyl]-1H-naphtho[1,2-b][1,4]diazepin-2,4(3H,5H)-dione dihydrochloride;

(Compound H72) 5-[4-(5-phenyl-1H-imidazol-4-yl)phenyl]-1H-naphtho[1,2-b][1,4]diazepin-2,4(3H,5H)-dione hydrochloride;

(Compound H73) 5-[4-[(5-phenylethyl)-1H-imidazol-4-yl]phenyl]-1H-naphtho[1,2-b][1,4]diazepin-2,4(3H,5H)-dione hydrochloride;

(Compound H74) 5-[4-(4,4-dimethyl-2-phenethyl-4,5-dihydro-1H-imidazol-1-yl)phenyl]-1H-naphtho[1,2-b][1,4]diazepin-2,4(3H,5H)-dione hydrochloride;

(Compound H75) 5-[4-[2-[(2-methoxyphenyl)amino]-1H-imidazol-1-yl]phenyl]-1H-naphtho[1,2-b][1,4]diazepin-2,4(3H,5H)-dione;

(Compound H76) 5-[4-[2-(phenylamino)-1H-imidazol-1-yl]phenyl]-1H-naphtho[1,2-b][1,4]diazepin-2,4(3H,5H)-dione;

(Compound H77) 5-[4-[1-[(6-methoxypyridin-2-yl)methyl]-1H-imidazol-2-yl]phenyl]-1H-naphtho[1,2-b][1,4]diazepin-2,4(3H,5H)-dione hydrochloride;

(Compound H78) 5-[4-[1-[(6-hydroxypyridin-2-yl)methyl]-1H-imidazol-2-yl]phenyl]-1H-naphtho[1,2-b][1,4]diazepin-2,4(3H,5H)-dione hydrochloride;

(Compound H79) 5-[4-[2-(3-fluorophenethyl)-1H-imidazol-1-yl]phenyl]-5,8,9,10-tetrahydroindeno[4,5-b][1,4]diazepin-2,4(1H,3H)-dione hydrochloride;

(Compound H80) 5-[4-[2-[(phenylamino)methyl]-1H-imidazol-1-yl]phenyl]-1H-naphtho[1,2-b][1,4]diazepin-2,4(3H,5H)-dione;

(Compound H81) 3-[[2-[4-[2,4-dioxo-3,4-dihydro-1H-naphtho[2,1-b][1,4]diazepin-5-(2H)-yl]phenyl]-1H-imidazol-1-yl]methyl]benzonitrile;

(Compound H82) 3-[[2-[4-[2,4-dioxo-3,4-dihydro-1H-naphtho[2,1-b][1,4]diazepin-5-(2H)-yl]phenyl]-1H-imidazol-1-yl]methyl]benzamide; and (Compound H83) 5-[4-[(2-(3-fluoro-2-methoxyphenyl)ethyl)-1H-imidazol-1-yl]phenyl]-1H-naphtho[1,2-b][1,4]diazepin-2,4(3H,5H)-dione hydrochloride.

Note that the following shows specific examples of preferable compounds and pharmaceutically acceptable salts thereof included in the compounds represented by general formulas (AI) to (HII). However, a compound or pharmaceutically acceptable salt thereof that can be utilized as an active ingredient in a medicament of the present invention is not limited to them. More specifically, examples include: 5-[3-(1H-tetrazol-5-yl)phenyl]-1H-naphtho[1,2-b][1,4]diazepin-2,4(3H,5H)-dione; 5-[3-(1H-tetrazol-5-yl)phenyl]-1H-naphtho[1,2-b][1,4]diazepin-2,4(3H,5H)-dione sodium salt; 5-[3-(1H-tetrazol-5-yl)phenyl]-1H-naphtho[1,2-b][1,4]diazepin-2,4(3H,5H)-dione potassium salt; 5-[3-(5-thioxo-4H-[1,2,4]oxadiazol-3-yl)phenyl]-1H-naphtho[1,2-b][1,4]diazepin-2,4(3H,5H)-dione; 5-[3-(5-thioxo-4H-[1,2,4]oxadiazol-3-yl)phenyl]-1H-naphtho[1,2-b][1,4]diazepin-2,4(3H,5H)-dione sodium salt; 5-[3-(1H-tetrazol-5-yl)phenyl]-1,3-dihydro-2H-naphtho[1,2-e][1,4]diazepin-2-one; 5-[3-(1H-tetrazol-5-yl)phenyl]-1,3-dihydro-2H-naphtho[1,2-e][1,4]diazepin-2-one sodium salt; 5-[4-fluoro-3-(1H-tetrazol- 5-yl)phenyl]-1H-naphtho[1,2-b][1,4]diazepin-2,4(3H,5H)-dione; 5-[4-fluoro-3-(1H-tetrazol-5-yl)phenyl]-1H-naphtho[1,2-b][1,4]diazepin-2,4(3H,5H)-dione sodium salt; 5-[3-(1H-tetrazol-5-yl)phenyl]-8,9,10,11-tetrahydronaphtho[2,1-b][1,4]diazepin-2,4(3H,5H)-dione; 5-[3-(1H-tetrazol-5-yl)phenyl]-8,9,10,11-tetrahydronaphtho[2,1-b][1,4]diazepin-2,4(3H,5H)-dione sodium salt; 4-[3-(1H-tetrazol-5-yl)phenyl]-1,4-dihydrobenzo[f]quinoxaline-2,3-dione; 4-[3-(1H-tetrazol-5-yl)phenyl]-1,4-dihydrobenzo[f]quinoxaline-2,3-dione sodium salt; 4-[3-(1H-tetrazol-5-yl)phenyl]-1H-benzo[h]quinazolin-2-one; 4-[3-(1H-tetrazol-5-yl)phenyl]-1H-benzo[h]quinazolin-2-one sodium salt; 5-[4-[2-(trifluoromethyl)benzoyl]aminophenyl]-1H-naphtho[1,2-b][1,4]diazepin-2,4(3H,5H)-dione; 5-[4-(2-iodobenzoylamino)phenyl]-1H-naphtho[1,2-b][1,4]diazepin-2,4(3H,5H)-dione; 5-[4-[(2-ethylbenzoyl)amino]phenyl]-1H-naphtho[1,2-b][1,4]diazepin-2,4(3H,5H)-dione; 5-[4-(2-tert-butylbenzoylamino)phenyl]-1H-naphtho[1,2-b][1,4]diazepin-2,4(3H,5H)-dione; 5-[4-(6-chloro-2-hydroxybenzoylamino)phenyl]-1H-naphtho[1,2-b][1,4]diazepin-2,4(3H,5H)-dione; 1-(2-chlorophenyl)-N-[4-(2,4-dioxo-1,2,3,4-tetrahydronaphtho[1,2-b][1,4]diazepin-5-yl)phenyl]methanesulfonamide; 5-[4-[(2-isopropylbenzoyl)amino]phenyl]-1H-naphtho[1,2-b][1,4]diazepin-2,4(3H,5H)-dione; 5-[4-[5-(2-methoxybenzyl)-1H-tetrazol-1-yl]phenyl]-1H-naphtho[1,2-b][1,4]diazepin-2,4(3H,5H)-dione; 5-[4-[5-(2-hydroxybenzyl)-1H-tetrazol-1-yl]phenyl]-1H-naphtho[1,2-b][1,4]diazepin-2,4(3H,5H)-dione; 5-[4-(5-phenethyl-1H-tetrazol-1-yl)phenyl]-1H-naphtho[1,2-b][1,4]diazepin-2,4(3H,5H)-dione; 5-[6-[5-(2-hydroxybenzyl)-1H-tetrazol-1-yl]pyridin-3-yl]-1H-naphtho[1,2-b][1,4]diazepin-2,4(3H,5H)-dione; 5-[4-(2-phenethyl-1H-imidazol-1-yl)phenyl]-1H-naphtho[1,2-b][1,4]diazepin-2,4(3H,5H)-dione hydrochloride; 5-[4-(1-phenethyl-1H-imidazol-2-yl)phenyl]-1H-naphtho[1,2-b][1,4]diazepin-2,4(3H,5H)-dione hydrochloride; 5-[4-[1-(3-methoxyphenethyl)-1H-imidazol-2-yl]phenyl]-1H-naphtho[1,2-b][1,4]diazepin-2,4(3H,5H)-dione; 5-[4-[1-(3-hydroxyphenethyl)-1H-imidazole-2-yl]phenyl]-1H-naphtho[1,2-b][1,4]diazepine-2,4(3H,5H)-dione; 5-[4-[(2-(3-fluorophenyl)ethyl)-1H-imidazol-1-yl]phenyl]-1H-naphtho[1,2-b][1,4]diazepin-2,4(3H,5H)-dione hydrochloride; 5-[4-[2-(2,6-dimethylphenylethyl)-1H-imidazol-1-yl]phenyl]-1H-naphtho[1,2-b][1,4]diazepin-2,4(3H,5H)-dione hydrochloride; 5-[4-[2-(3-methoxyphenethyl)-1H-imidazole-1-yl]phenyl]-1H-naphtho[1,2-b][1,4]diazepin-2,4(3H,5H)-dione hydrochloride; 5-[4-[2-(3-hydroxyphenethyl)-1H-imidazol-1-yl]phenyl]-1H-naphtho[1,2-b][1,4]diazepin-2,4(3H,5H)-dione hydrochloride; 5-[4-[5-[2-(dimethylamino)benzyl]-1H-tetrazol-1-yl]phenyl]-1H-naphtho[1,2-b][1,4]diazepin-2,4(3H,5H)-dione mesylate; 5-[4-[2-(3-methoxyphenethyl)-1H-imidazol-1-yl]phenyl]-5,8,9,10-tetrahydroindeno[4,5-b][1,4]diazepin-2,4(1H,3H)-dione hydrochloride; 5-[4-[2-[2-(thiophen-3-yl)ethyl]-1H-imidazol-1-yl]phenyl]-1H-naphtho[1,2-b][1,4]diazepin-2,4(3H,5H)-dione hydrochloride; 5-[4-[2-(2-fluorophenethyl)-1H-imidazol-1-yl]phenyl]-5,8,9,10-tetrahydroindeno[4,5-b][1,4]diazepin-2,4(1H,3H)-dione; 5-[4-[2-(3-fluorophenethyl)-1H-imidazol-1-yl]phenyl]-5,8,9,10-tetrahydroindeno[4,5-b][1,4]diazepin-2,4(1H,3H)-dione hydrochloride; 5-[4-[(2-(3-fluoro-2-methoxyphenyl)ethyl)-1H-imidazol-1-yl]phenyl]-1H-naphtho[1,2-b][1,4]diazepin-2,4(3H,5H)-dione hydrochloride; 2-(dimethylamino)-N-[4-(2-oxo-2,3-dihydro-1H-naphtho[1,2-e][1,4]diazepin-5-yl)phenyl]nicotinamide; 2-(dimethylamino)-N-[4-(2-oxo-2,3-dihydro-1H-naphtho[1,2-e][1,4]diazepin-5-yl)phenyl]nicotinamide dihydrochloride; and 2-(dimethylamino)-N-[4-(2-oxo-2,3-dihydro-1H-naphtho[1,2-e][1,4]diazepin-5-yl)phenyl]nicotinamide dimethanesulfonate. Here, an active ingredient in a medicament of the present invention is not limited to the above specific compounds or pharmaceutically acceptable salts thereof.

Each compound or a pharmaceutically acceptable salt thereof more suitable as an active ingredient in a medicament of the present invention is included in compounds or pharmaceutically acceptable salts thereof represented by general formulas (AI) to (HII). Still more specifically, examples include: 5-[3-(1H-tetrazol-5-yl)phenyl]-1H-naphtho[1,2-b][1,4]diazepin-2,4(3H,5H)-dione; 5-[3-(1H-tetrazol-5-yl)phenyl]-1H-naphtho[1,2-b][1,4]diazepin-2,4(3H,5H)-dione sodium salt; 5-[4-(2-iodobenzoylamino)phenyl]-1H-naphtho[1,2-b][1,4]diazepin-2,4(3H,5H)-dione; 5-[4-[2-(trifluoromethyl)benzoyl]aminophenyl]-1H-naphtho[1,2-b][1,4]diazepin-2,4(3H,5H)-dione; 2-(dimethylamino)-N-[4-(2-oxo-2,3-dihydro-1H-naphtho[1,2-e][1,4]diazepin-5-yl)phenyl]nicotinamide; and 2-(dimethylamino)-N-[4-(2-oxo-2,3-dihydro-1H-naphtho[1,2-e][1,4]diazepin-5-yl)phenyl]nicotinamide dihydrochloride. Here, an active ingredient in a medicament of the present invention is not limited to the above specific compounds or pharmaceutically acceptable salts thereof.

The compounds represented by general formulas (AI) to (HII) may have stereoisomers such as cis/trans isomers, enantiomers, and/or racemates, all of which are included in the present invention.

In addition, the compounds represented by general formulas (AI) to (HII) may have one or two or more asymmetric carbon atoms depending on the kinds of substituent(s). Here, any enantiomers based on the asymmetric carbon(s), any mixture of the enantiomers, racemates, diastereomers based on the two or more asymmetric carbon atoms, or any mixture of the diastereomers, for instance, may be used as an active ingredient in a medicament of the present invention. When the compounds represented by general formulas (AI) to (HII) contain a double bond and/or a ring structure, a geometrical isomer(s) may be present. In addition to geometrical isomers in a pure form, a mixture of the geometrical isomers at any ratio may be used as an active ingredient in a medicament of the present invention.

As an active ingredient in a medicament of the present invention, it is possible to use, in addition to the compounds represented by general formulas (AI) to (HII), any acid adduct or any base adduct of these compounds. Examples of the acid adduct that can be used include, but are not limited to, a mineral acid salt (e.g., hydrochloride, sulfate, nitrate) or an organic acid salt (e.g., methanesulfonate, p-toluenesulfonate, oxalate, malate). Examples of the base adduct include, but are not limited to, a metal salt (e.g., a lithium salt, a sodium salt, a potassium salt, a magnesium salt, or a calcium salt), an ammonium salt, or an organic amine salt (e.g. a triethylamine salt or an ethanolamine salt). Among these salts, it is preferable to use any pharmaceutically acceptable salt as an active ingredient in a medicament of the present invention. Besides, it is possible to use, as an active ingredient in a medicament of the present invention, any hydrate or solvate of each compound in a free form or in a salt form.

A medicament of the present invention may be used for preventing or treating cough. Preferably, the medicament may be used for preventing or treating acute cough, persistent cough, or chronic cough. More preferably, the medicament may be used for preventing or treating chronic cough. A medicament of the present invention can elicit high efficacy on cough such as a disease responsible for chronic cough including dry cough (e.g., cough caused by cough variant asthma, atopic cough, cough caused by gastroesophageal reflux, chemical-induced cough, or allergic cough) or wet cough (e.g., cough caused by sinobronchial syndrome, cough caused by chronic bronchitis, cough caused by chronic obstructive pulmonary disease, or cough caused by asthma). Each cough is indicated for a medicament of the present invention. However, the indication for a medicament of the present invention is not limited to them.

Conventionally, treatment of dry cough, for instance, treatment of cough variant asthma aims at enlarging the narrowed trachea and suppressing tracheal hypersensitivity. Examples of a therapeutic used include an inhaled steroid agent or a bronchodilator (e.g., a β2 stimulator).

However, the β2 stimulator, which is a bronchodilator, may have an adverse effect(s) such as tachycardia, tremor, and/or hypokalemia. Thus, it should be carefully administered to, for instance, patients with hypertension and/or patients with heart disease.

Meanwhile, a medicament of the present invention is presumed to exert no effects on α1, β2, or M3 receptors, and should not exert any of the adverse effects caused by the existing bronchodilator (e.g., a β2 stimulator). Thus, the medicament of the present invention can be expected to be positively used for dry cough in the patients.

Conventionally, in treatment of wet cough, for instance, treatment of bronchial asthma, airway inflammation and airway stenosis may be major targets. Examples of a therapeutic used include an inhaled steroid agent having anti-inflammatory action. In addition, a bronchodilator (e.g., a β2 stimulator or a theophylline sustained-release agent) or an allergic response-suppressing anti-inflammatory may be used in combination with the inhaled steroid agent depending on the patient conditions.

In the above treatment, the bronchodilator (β2 stimulator) fails to have anti-inflammatory action, and can thus be used in combination with an inhaled steroid agent. Meanwhile, a bronchodilator (β2 stimulator) and a medicament of the present invention should be used in combination to be able to treat wet cough.

The inhaled steroid agent may have an adverse effect(s) such as dysphonia involving, for instance, hoarse voice. A medicament of the present invention can avoid the adverse effect(s) and should be able to treat dry cough such as cough variant asthma.

Specifically, a medicament of the present invention is presumed to exert no effects on α1, β2, or M3 receptors, and should not augment adverse effects (e.g., tachycardia, tremor, and/or hypokalemia) caused by the existing bronchodilator (e.g., a β2 stimulator). Thus, the medicament of the present invention can be expected to be positively used for wet cough in, for instance, patients with hypertension and/or patients with heart disease.

Any compound suitable as an active ingredient in a medicament of the present invention elicits a dose-dependent, potent antitussive effect.

For instance, any compound suitable as an active ingredient in a medicament of the present invention can elicit substantially the same antitussive effect as of dihydrocodeine, a central nervous system acting antitussive agent. In addition, the compound can inhibit only cough reflux increased by LPS stimulation in cough reflux caused by citric acid stimulation when administered at a low dose (0.3 mg/kg) to airway inflammation model animals (e.g., airway inflammation model mice), which are chronic cough model animals, and does not affect any cough reflux (the level corresponding to cough reflux caused by citric acid stimulation in normal mice) caused by citric acid stimulation alone. In addition, the compound has elicited medicament efficacy upon not only oral administration, but also local application using a nebulizer.

Further, the compound can inhibit only cough reflux increased due to airway inflammation accompanied by eosinophil infiltration induced by OVA sensitization in cough reflux caused by citric acid stimulation when administered at a low dose (1.0 mg/kg) to airway inflammation model animals (e.g., an antigen OVA-sensitized guinea pigs (allergic cough and atopic cough models)), which are chronic cough model animals, and does not affect any cough reflux (the level corresponding to cough reflux caused by citric acid stimulation in normal guinea pigs) caused by citric acid stimulation alone.

Collectively, as one embodiment, any compound suitable as an active ingredient in a medicament of the present invention has no problem of water solubility, the osmotic pressure and pH of solution administered, other stimulant properties, etc., and does not have a risk of stopping cough that is necessary as biological defense and should not be stopped essentially as caused by a central nervous system acting medicament. Hence, the medicament of the present invention can exert a better peripheral antitussive effect in humans suffering from chronic cough than healthy individuals.

A medicament of the present invention may be administered orally or parenterally. A medicament of the present invention may be produced, by a regular procedure in the art of formulation, as a medicament in suitable dosage forms including tablets, granules, powders, capsules, suspensions, inhalants, inhalation powders, inhalation solutions, inhalation aerosols, ointments, creams, gels, compresses, patches, liniments, tapes, poultices, injections, or suppositories.

These formulations can be produced by common techniques. In the case of tablets, for instance, common excipients, disintegrants, binders, lubricants, and/or pigments may be used. Examples of the excipients include lactose, D-mannitol, crystalline cellulose, and glucose. Examples of the disintegrants include starch and carboxymethylcellulose calcium (CMC-Ca). Examples of the lubricants include magnesium stearate and talc. Examples of the binders include hydroxypropyl cellulose (HPC), gelatin, and polyvinylpyrrolidone (PVP).

A solvent, a stabilizer, a solubilizer aid, a suspending agent, an emulsifier, a soothing agent, a buffer, and/or a preservative, for instance, are used to adjust an injection. Those skilled in the art can select, if appropriate, these additives for formulation and a process for preparing the formulation.

Examples of the inhalants for parenteral administration include aerosols, powders for inhalation, liquids for inhalation (e.g., solutions for inhalation, suspensions for inhalation), or capsule inhalants. The liquids for inhalation may be in a form used while dissolved or suspended in water or other suitable solvents when used. Each inhalant may be applied using a suitable inhalant container. For instance, when liquid for inhalation is administered, a spray (e.g., an atomizer, a nebulizer) may be used and when powder for inhalation is administered, an inhalant applicator for powder agent may be used.

These inhalants can be produced in accordance with publicly known procedures. For instance, any of the compounds represented by general formulas (AI) to (HII) may be made powder or liquid, which is then formulated in an inhalation spray preparation or a carrier and filled in a suitable inhalant container for production. When any of the compounds represented by general formulas (AI) to (HII) is made powder, a common procedure is used to make the compound powder. For instance, the compound is made fine powder with lactose, starch, and/or magnesium stearate to prepare a homogenous mixture or is granulated therewith to prepare a powder agent. In addition, when any of the compounds represented by general formulas (AI) to (HII) is made liquid, the compound, for instance, may be dissolved in a liquid carrier such as water, saline, or an organic solvent. As the spray preparation, it is possible to use a conventionally known spray preparation such as alternative freon, a liquefied gas spray preparation (e.g., fluorohydrocarbon, liquefied petroleum, diethyl ether, dimethyl ether), compressed gas (e.g., soluble gas (e.g., carbon dioxide, nitrous oxide gas)), or insoluble gas (e.g., nitrogen gas).

Each inhalant may be optionally combined, if appropriate, with an additive(s). Any commonly used additive(s) may be allowed as the additive(s). Examples of the additives that can be used include solid excipients (e.g., sucrose, lactose, glucose, mannitol, sorbitol, maltose, cellulose), liquid excipients (e.g., propylene glycol), binders (starch, dextrin, methylcellulose, hydroxypropylcellulose, polyvinyl pyrrolidone, polyethylene glycol, white sugar), lubricants (e.g., magnesium stearate, light silicic anhydride, talc, sodium lauryl sulfate), flavoring agents (e.g., citric acid, menthol, a glycyrrhizin ammonium salt, glycine, orange powder), preservatives (e.g., sodium benzoate, sodium bisulfite, methyl paraben, propyl paraben), stabilizers (e.g., citric acid, sodium citrate), suspending agents or emulsifiers (e.g., methyl cellulose, polyvinyl pyrrolidone, polyvinyl alcohol, lecithin, sorbitan trioleate), dispersants (e.g., a surfactant), solvents (e.g., water), tonicity agents (e.g., sodium chloride, concentrated glycerin), pH modifiers (e.g., hydrochloric acid, sulfuric acid), solubilizers (e.g., ethanol), antiseptics (e.g., benzalkonium chloride, paraben), coloring agents, buffering agents (e.g., sodium phosphate, sodium acetate), thickeners (e.g., kariboxy vinyl polymer, etc.), and/or absorption promoters. In the case of liquid for inhalation, for instance, the liquid may be prepared by optionally selecting, if appropriate, an antiseptic, a coloring agent, a buffering agent, a tonicity agent, a thickener, and/or an absorption promoter. In addition, in the case of powder for inhalation, for instance, the powder may be prepared by optionally selecting, if appropriate, a lubricant, a binder, an excipient, a coloring agent, an antiseptic, and/or an absorption promoter (e.g., a bile acid salt, chitosan).

Further, to give sustained release property to the compounds represented by general formulas (AI) to (HII), each inhalant may contain a biodegradable polymer. Examples of the biodegradable polymer include fatty acid ester polymers or copolymers thereof, polyacrylic esters, polyhydroxybutyric acids, polyalkylene oxalates, polyorthoesters, polycarbonates, and polyamino acids. The polymers may be used singly, or more kinds of them may be mixed and used. In addition, a phospholipid such as egg yolk lecithin, chitosan, or the like may be used. Examples of the fatty acid ester polymers or copolymers thereof include polylactic acid, polyglycolic acid, polycitric acid, polymalic acid, and a lactic acid-glycolic acid copolymer. They may be used singly, or more kinds of them may be mixed and used. Other examples include poly α-cyanoacrylate, poly β-hydroxybutyric acid, polytrimethyleneoxate, polyorthoester, polyorthocarbonate, polyethylene carbonate, poly γ-benzyl-L-glutamic acid, and poly L-alanine. They may be used singly, or more kinds of them may be mixed and used. Preferred is polylactic acid, polyglycolic acid, or a lactic acid-glycolic acid copolymer. More preferred is a lactic acid-glycolic acid copolymer. In addition, a biodegradable polymer such as a lactic acid-glycolic acid copolymer may be used to prepare a medicament-encapsulating microsphere or nanosphere.

Ointments may be produced by publicly known or commonly used formulation. For instance, one or more active substances are ground or melted into a base for production and preparation. The ointment base may be selected from those publicly known or commonly used. Examples include higher fatty acids or higher fatty acid esters (e.g., adipic acid, myristic acid, palmitic acid, stearic acid, oleic acid, adipic acid ester, myristic acid ester, palmitic acid ester, stearic acid ester, oleic acid ester), waxes (e.g., beeswax, whale wax, ceresin), surfactants (e.g., polyoxyethylene alkyl ether phosphate), higher alcohols (e.g., cetanol, stearyl alcohol, cetostearyl alcohol, etc.), silicone oil (e.g., dimethylpolysiloxane), hydrocarbons (e.g., hydrophilic petrolatum, white petrolatum, purified lanolin, liquid paraffin), glycols (e.g., ethylene glycol, diethylene glycol, propylene glycol, polyethylene glycol, macrogol), vegetable oils (e.g., castor oil, olive oil, sesame oil, turpentine oil), animal oils (e.g., mink oil, egg yolk oil, squalane, squalene), water, absorption enhancers, or anti-rash agents. Those selected from them may be used singly, or two or more kinds of them may be mixed and used. It is possible to further contain, for instance, a moisturizer, a preservative, a stabilizer, an antioxidant, and/or a flavoring agent.

Gels may be produced by publicly known or commonly used formulation. For instance, one or more active substances are melted into a base for production and preparation. The gel base may be selected from those publicly known or commonly used. Examples include lower alcohols (e.g., ethanol, isopropyl alcohol), gelling agents (e.g., carboxymethylcellulose, hydroxyethylcellulose, hydroxypropylcellulose, ethylcellulose), neutralizing agents (e.g., triethanolamine, diisopropanolamine), surfactants (e.g., polyethylene glycol monostearate), gums, water, absorption enhancers, or anti-rash agents. Those selected from them may be used singly, or two or more kinds of them may be mixed and used. It is possible to further contain, for instance, a preservative, an antioxidant, and/or a flavoring agent.

Creams may be produced by publicly known or commonly used formulation. For instance, one or more active substances are melted or emulsified into a base for production and preparation. The cream base may be selected from those publicly known or commonly used. Examples include higher fatty acid esters, lower alcohols, hydrocarbons, polyhydric alcohols (e.g., propylene glycol, 1,3-butylene glycol), higher alcohols (e.g., 2-hexyldecanol, cetanol), emulsifiers (e.g., polyoxyethylene alkyl ethers, fatty acid esters), water, absorption enhancers, or anti-rash agents. Those selected from them may be used singly, or two or more kinds of them may be mixed and used. It is possible to further contain, for instance, a preservative, an antioxidant, and/or a flavoring agent.

Poultices may be produced by publicly known or commonly used formulation. For instance, one or more active substances are melted into a base to prepare a kneaded material, which is then applied and extended on a support for production. The poultice base may be selected from those publicly known or commonly used. Examples include thickeners (e.g., polyacrylic acid, polyvinylpyrrolidone, gum arabic, starch, gelatin, methylcellulose), wetting agents (e.g., urea, glycerin, propylene glycol), fillers (e.g., kaolin, zinc oxide, talc, calcium, magnesium), water, dissolution aids, tackifiers, or anti-rash agents. Those selected from them may be used singly, or two or more kinds of them may be mixed and used. It is possible to further contain, for instance, a preservative, an antioxidant, and/or a flavoring agent.

Patches may be produced by publicly known or commonly used formulation. For instance, one or more active substances are melted into a base, which is then applied and extended on a support for production. The base for patches may be selected from those publicly known or commonly used. Examples include polymer bases, oils and fats, higher fatty acids, tackifiers, or anti-rash agents. Those selected from them may be used singly, or two or more kinds of them may be mixed and used. It is possible to further contain, for instance, a preservative, an antioxidant, and/or a flavoring agent.

Liniments may be produced by publicly known or commonly used formulation. For instance, one or more active substances may be dissolved, suspended, or emulsified into one or two or more kinds selected from, for instance, water, alcohol (e.g., ethanol, polyethylene glycol), higher fatty acid, glycerin, a soap, an emulsifier, or a suspending agent. Then, each liniment is so produced and prepared. It is possible to further contain, for instance, a preservative, an antioxidant, and/or a flavoring agent.

The dose of a medicament of the present invention is not particularly limited, and the medicament may be typically administered to an adult such that a daily dose as an active ingredient amount in an inhalant, inhalation powder, inhalation liquid, or inhalation aerosol is from about 0.01 μg to 100 mg and preferably from 0.3 μg to 10 mg; a daily dose as an active ingredient amount in an ointment, cream, gel, compress, patch, liniment, tape, or cataplasm is from about 0.01 mg to 1000 mg; a daily dose as an active ingredient amount in an injection is from about 0.01 mg to 100 mg; and a daily dose by orally administration is somewhat from 0.01 mg to 2000 mg. Here, the dose is not limited to the above-described doses, and can be changed depending on the age and/or symptoms, etc.

A medicament of the present invention may be used in combination with another agent useful for treating or preventing a variety of cough. Individual ingredients in such a combination may be administered at different time points or the same time during a treatment or prevention period and may be administered as separate formulations or a single formulation. Thus, the present invention should be interpreted to include any of simultaneous administration or administration at different time points. Thus, administration in the present invention should be construed in this way. The scope of the above combination between a medicament of the present invention and another agent useful for treating or preventing a variety of cough encompasses, in principle, combinations with any pharmaceutical formulation useful for treating or preventing a variety of cough described above.

Various forms of each formulation among the combination formulations in the present invention can be selected and each formulation can be produced in the same fashion as for the above formulations. In addition, in the case of a combination comprising a medicament of the present invention and a therapeutic or prophylactic for a variety of cough, a skilled artisan can easily produce the combination in accordance with a common procedure or a conventional technique.

The above combinations include not only a combination between a medicament of the present invention and another active substance, but also a combination with two or more additional active substances. Many examples exist for combinations between a medicament of the present invention and one or two or more active substances selected from various cough therapeutics or prophylactics described above.

Examples of the medicament used in combination with a medicament of the present invention include steroids, β2 agonists, muscarinic receptor antagonists, antihistamines, antiallergic agents, bronchodilators, leukotriene synthesis inhibitors, prostaglandins, leukotriene receptor antagonists, additional antitussives, and expectorants. Among them, it is preferable to use a combination with an antihistamine or an antiallergic agent and to use a combination with, for instance, a steroid, a β2 agonist, or a muscarinic receptor antagonist effective in wet cough. Further, a medicament of the present invention may be used in combination with a herbal medicine.

Examples of the steroid include: an external medicine (e.g., clobetasol propionate, diflorazone acetate, fluocinonide, mometasone furoate, betamethasone dipropionate, betamethasone butyrate propionate, betamethasone valerate, difluprednate, pudesonide, diflucortron valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone propionate, triamcinolone acetonide, flumethasone pivalate, alclometasone propionate, clobetasone butyrate, prednisolone, peclomethasone propionate, fludroxycortide); an internal medicine or injection (e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methyl prednisolone, methyl prednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone); or an inhalant (e.g., beclomethasone propionate, fluticasone propionate, budesonide, flunisolide, triamcinolone, ST-126P, ciclesonide, dexamethasone paromithionate, mometasone furan carbonate, plasterone sulfonate, deflazacort, methylprednisolone suleptanate, methylprednisolone sodium succinate).

Examples of the (2 agonist include formoterol, salmeterol, carmoterol, indacaterol, bilanterol, alformoterol, bambuterol, isoproterenol, milbeterol, clenbuterol, olodaterol, fenoterol, salbutamol, levalbuterol, procaterol, terbutaline, pyrbuterol, procaterol, metaproterol, bitolterol, ritodrine, or albuterol.

Examples of the muscarinic receptor antagonist include tiotropium, ipratropium, flutropium, oxitropium, acridinium, darotropium, glycopyrrolate, or umecridinium.

Examples of the antihistamine include diphenhydramine, diphenylpyraline hydrochloride, diphenylpyraline teocoleate, clemastine fumarate, dimenhydrinate, dl-chlorpheniramine maleate, d-chlorpheniramine maleate, triprolidine hydrochloride, promethazine hydrochloride, alimemazine tartrate, isotipendil hydrochloride, homochlorcyclidine hydrochloride, hydroxyzine, cyproheptadine hydrochloride, levocabastine hydrochloride, astemizole, bepotastine, desloratadine, TAK-427, ZCR-2060, NIP-530, mometasone furoate, mizolastine, BP-294, andlast, auranofin, or akrivastin.

Examples of the antiallergic agent include: a chemical mediator release inhibitor (e.g., sodium cromoglycate, tranilast, amlexanox, repirinast, ibudilast, pemirolast potassium, dazanolast, nedocromil, cromoglycate, israpafant); a histamine antagonist (e.g., ketotifen fumarate, azelastine hydrochloride, oxatomide, mequitazine, terfenadine, emedastine fumarate, epinastine hydrochloride, ebastine, cetirizine hydrochloride, olopatadine hydrochloride, loratadine, fexofenadine); a thromboxane synthase inhibitor (e.g., osagrel hydrochloride, imitrodast sodium); a thromboxane antagonist (e.g., seratrodast, ramatroban, domitroban calcium hydrate, KT-2-962); or a Th2 cytokine inhibitor (e.g., suplatast tosilate).

Examples of the bronchodilator include: a xanthine derivative (e.g., aminophylline, theophylline, doxophylline, sipamphylline, diprofylline, proxyphylline, cholinetheophylline); a sympathetic stimulant (e.g., epinephrine, ephedrine hydrochloride, dl-methylephedrine hydrochloride, methoxyphenamine hydrochloride, isoproterenol sulfate, isoproterenol hydrochloride, orciprenaline sulfate, chlorprenaline hydrochloride, trimethokinol hydrochloride, salbutamol sulfate, terbutaline sulfate, hexoprenaline sulfate, tulobuterol hydrochloride, procaterol hydrochloride, fenoterol hydrobromide, formoterol fumarate, clenbuterol hydrochloride, mabuterol hydrochloride, salmeterol xinafoate, R,R-formoterol, tulobuterol, pyrbuterol hydrochloride, ritodrine hydrochloride, bambuterol, dopexamine hydrochloride, meradrine tartrate, AR-C68397, levosalbutamol, KUR-1246, KUL-7211, AR-C89855, S-1319); or a parasympathetic blocker (e.g., ipratropium bromide, flutropium bromide, oxitropium bromide, cimetropium bromide, temiverine, tiotropium bromide, revatropate)

Examples of the leukotriene synthesis inhibitor include auranofin, progamatasin maleate, L-674636, A-81834, UPA-780, A-93178, MK-886, REV-5901A, SCH-40120, MK-591, Bay-x-1005, Bay-y-1015, DTI-0026, amlexanox, or E-6700.

Examples of the prostaglandin compound include an agonist or antagonist for PGE2EP1 receptor, PGE2EP2 receptor, PGE2EP3 receptor, or PGE2EP4 receptor; an agonist or antagonist for PGD2 receptor or CRTH2 receptor; an agonist or antagonist for PGFFP receptor; an agonist or antagonist for PGIIP receptor; or an agonist or antagonist for TX receptor.

Examples of the leukotriene receptor antagonist include pranlukast hydrate, montelukast, zafirlukast, seratrodast, MCC-8-[7, KCA-757, CS-615, YM-158, L-740515, CP-195494, LM-1484, RS-635, A-93178, S-36496, BIIL-284, or ONO-4057.

Examples of the additional antitussive include codeine phosphate, dihydrocodeine phosphate, oxymethebanol, dextromethorphan hydrobromide, pentoxiverine citrate, dimemorphane phosphate, oxeradine citrate, cloperastine, benproperin phosphate, clofedanol hydrochloride, hominoben hydrochloride, noscapine, tipemidine hibenzanate, epradinone hydrochloride, or plantago herb extract.

Examples of the expectorant include foeniculated ammonia spirit, sodium bicarbonate, potassium iodide, bromhexine hydrochloride, cherry bark extract, carbocisteine, fudostein, ambroxol hydrochloride, ambroxol hydrochloride sustained-release agent, methyl cysteine hydrochloride, acetylcysteine, L-ethylcysteine hydrochloride, or tyloxapol.

The present invention has the following aspects.

<1a> A method for preventing or treating cough, the method comprising administering, to a subject (e.g., a mammal comprising a human) in need thereof, a therapeutically effective amount of a compound having P2X4 receptor antagonistic action, a tautomer, stereoisomer, or pharmaceutically acceptable salt of the compound, or a hydrate or solvate thereof.

<2a> The method according to <1a>, wherein the cough is acute cough, persistent cough, or chronic cough.

<3a> The method according to <2a>, wherein the cough is chronic cough.

<4a> The method according to <1a>, wherein the cough is dry cough that is cough caused by cough variant asthma, atopic cough, cough caused by gastroesophageal reflux, chemical-induced cough, or allergic cough.

<5a> The method according to <4a>, wherein the cough is dry cough that is cough caused by cough variant asthma, atopic cough, or allergic cough.

<6a> The method according to <1a>, wherein the cough is wet cough that is cough caused by sinobronchial syndrome, cough caused by chronic bronchitis, cough caused by chronic obstructive pulmonary disease, or cough caused by asthma.

<7a> A method for peripheral cough suppression of dry cough, the method comprising administering, to a subject (e.g., a mammal comprising a human) in need thereof, a therapeutically effective amount of a compound having P2X4 receptor antagonistic action, a tautomer, stereoisomer, or pharmaceutically acceptable salt of the compound, or a hydrate or solvate thereof.

<8a> The method according to <7a>, which is selective to the peripheral cough suppression of dry cough.

<9a> The method according to <7a> or <8a>, wherein the dry cough is cough caused by cough variant asthma, atopic cough, or allergic cough.

<10a> The method according to any one of <1a> to <9a>, wherein the compound having P2X4 receptor antagonistic action is a compound represented by any one of general formulas (AI) to (HII) (where specific examples and preferable examples of the compound represented by any one of general formulas (AI) to (HII) are as described herein).

<1b> A compound having P2X4 receptor antagonistic action, a tautomer, stereoisomer, or pharmaceutically acceptable salt of the compound, or a hydrate or solvate thereof for use in prophylaxis or treatment of cough.

<2b> The compound having P2X4 receptor antagonistic action, a tautomer, stereoisomer, or pharmaceutically acceptable salt of the compound, or a hydrate or solvate thereof for use according to <1b>, wherein the cough is acute cough, persistent cough, or chronic cough.

<3b> The compound having P2X4 receptor antagonistic action, a tautomer, stereoisomer, or pharmaceutically acceptable salt of the compound, or a hydrate or solvate thereof for use according to <2b>, wherein the cough is chronic cough.

<4b> The compound having P2X4 receptor antagonistic action, a tautomer, stereoisomer, or pharmaceutically acceptable salt of the compound, or a hydrate or solvate thereof for use according to <1b>, wherein the cough is dry cough that is cough caused by cough variant asthma, atopic cough, cough caused by gastroesophageal reflux, chemical-induced cough, or allergic cough.

<5b> The compound having P2X4 receptor antagonistic action, a tautomer, stereoisomer, or pharmaceutically acceptable salt of the compound, or a hydrate or solvate thereof for use according to <4b>, wherein the cough is dry cough that is cough caused by cough variant asthma, atopic cough, or allergic cough.

<6b> The compound having P2X4 receptor antagonistic action, a tautomer, stereoisomer, or pharmaceutically acceptable salt of the compound, or a hydrate or solvate thereof for use according to <1b>, wherein the cough is wet cough that is cough caused by sinobronchial syndrome, cough caused by chronic bronchitis, cough caused by chronic obstructive pulmonary disease, or cough caused by asthma.

<7b> The compound having P2X4 receptor antagonistic action, a tautomer, stereoisomer, or pharmaceutically acceptable salt of the compound, or a hydrate or solvate thereof for use according to <1b>, wherein the prophylaxis or treatment of cough is peripheral cough suppression of dry cough.

<8b> The compound having P2X4 receptor antagonistic action, a tautomer, stereoisomer, or pharmaceutically acceptable salt of the compound, or a hydrate or solvate thereof for use according to <7b>, which is selective to peripheral cough suppression of dry cough.

<9b> The compound having P2X4 receptor antagonistic action, a tautomer, stereoisomer, or pharmaceutically acceptable salt of the compound, or a hydrate or solvate thereof for use according to <7b> or <8b>, wherein the dry cough is cough caused by cough variant asthma, atopic cough, or allergic cough.

<10b> The compound having P2X4 receptor antagonistic action, a tautomer, stereoisomer, or pharmaceutically acceptable salt of the compound, or a hydrate or solvate thereof for use according to any one of <1b> to <9b>, wherein the compound having P2X4 receptor antagonistic action is a compound represented by any one of general formulas (AI) to (HII) (where specific examples and preferable examples of the compound represented by any one of general formulas (AI) to (HII) are as described herein).

<1c> Use of a compound having P2X4 receptor antagonistic action, a tautomer, stereoisomer, or pharmaceutically acceptable salt of the compound, or a hydrate or solvate thereof in the manufacture of a medicament for preventing or treating cough.

<2c> The use according to <1c>, wherein the cough is acute cough, persistent cough, or chronic cough.

<3c> The use according to <2c>, wherein the cough is chronic cough.

<4c> The use according to <1c>, wherein the cough is dry cough that is cough caused by cough variant asthma, atopic cough, cough caused by gastroesophageal reflux, chemical-induced cough, or allergic cough.

<5c> The use according to <4c>, wherein the cough is dry cough that is cough caused by cough variant asthma, atopic cough, or allergic cough.

<6c> The use according to <1c>, wherein the cough is wet cough that is cough caused by sinobronchial syndrome, cough caused by chronic bronchitis, cough caused by chronic obstructive pulmonary disease, or cough caused by asthma.

<7c> Use of a compound having P2X4 receptor antagonistic action, a tautomer, stereoisomer, or pharmaceutically acceptable salt of the compound, or a hydrate or solvate thereof for the manufacture of a peripheral antitussive agent for dry cough.

<8c> Use according to <7c>, wherein the peripheral antitussive agent for dry cough is a medicament selective to peripheral cough suppression of dry cough.

<9c> The use according to <7c> or <8c>, wherein the dry cough is cough caused by cough variant asthma, atopic cough, or allergic cough.

<10c> The use according to any one of <1c> to <9c>, wherein the compound having P2X4 receptor antagonistic action is a compound represented by any one of general formulas (AI) to (HII) (where specific examples and preferable examples of the compound represented by any one of general formulas (AI) to (HII) are as described herein).

As one aspect, the "dry cough" is a counter concept of "wet cough". As another aspect, the "peripheral cough suppression" is a counter concept of "central cough suppression". As used herein, the expression "selective" to A includes that efficacy and effects on A is relatively superior over efficacy and effects on the others, and indicates a concept that may include the idea where there are efficacy and effects on just A and there are neither efficacy nor effects on the others. Accordingly, as used herein, the expression "selective to peripheral cough suppression of dry cough" encompasses that the effectiveness on "dry cough" is relatively superior over the effectiveness on "wet cough", and also encompasses that there is effectiveness on only "dry cough" and there is no effectiveness on "wet cough" and includes that the effects on "peripheral cough suppression" is relatively superior over the effects on "central cough suppression" and also represents a concept that may include the idea where there are effects on just "peripheral cough suppression" and there are no effects on "central cough suppression".

EXAMPLES

Hereinafter, the present invention will be further specifically described by using Examples. However, the scope of the present invention is not limited to the following Examples.

In the following Examples, P2X4 antagonists were used, including: 5-[3-(1H-tetrazol-5-yl)phenyl]-1H-naphtho[1,2-b][1,4]diazepin-2,4(3H,5H)-dione sodium salt (WO2010/093061, a sodium salt of the compound of Example 1: hereinafter referred to as "compound A"); 5-[4-(2-iodobenzoylamino)phenyl]-1H-naphtho[1,2-b][1,4]diazepin-2,4 (3H,5H)-dione (WO2013/105608, the compound of Example 48: hereinafter referred to as "compound B"); 5-[4-[2-(trifluoromethyl)benzoyl]aminophenyl]-1H-naphtho[1,2-b][1,4]diazepin-2,4(3H,5H)-dione (WO2013/105608, the compound of Example 2: hereinafter referred to as "compound C"); 2-(dimethylamino)-N-[4-(2-oxo-2,3-dihydro-1H-naphtho[1,2-e][1,4]diazepin-5-yl)phenyl]nicotinamide dihydrochloride (WO2015/005467, the compound of Example 15: hereinafter referred to as "compound D"); and other compounds shown below.

Example 1

To Measure P2X4 Receptor Antagonistic Action of Compound as Active Ingredient of the present invention.
(Test Protocol)

The P2X4 receptor antagonistic action of a compound as an active ingredient of the present invention was measured. An ATP receptor (human P2X4) was introduced in 1321N1 cells, which were then used as a system in which P2X4 receptor was expressed stably. The P2X4 receptor-expressing cells were seeded on a 96-well plate, were cultured for 24 h under conditions at 37° C. and 5% C02, and were then used for calcium measurement. Fura-2AM, which is a calcium fluorescence indicator, was dissolved in an extracellular solution for calcium imaging and applied to the seeded cells. Then, the cells were allowed to stand at room temperature for 45 min. In this way, the Fura-2AM was taken up in the cells. A micro plate reader EnVision (PerkinElmer) was used for the measurement. Light emitted from a xenon lamp was made to pass through a 340-nm or 380-nm filter, and F340 or F380, which is 510-nm fluorescence emitted when the cells were irradiated, were observed. Then, a change in the ratio value F340/F380 was an index for the intracellular calcium change. The measurement was carried out by adding ATP at the final concentration of 1 µM to each well and by recording, over time, the ATP-induced intracellular calcium response. The inhibitory activity of each test substance was measured by conducting 15-min pretreatment with each test substance before ATP application, and was calculated while compared to the case of the absence of the test substance. Table 131 below shows the results.
(Test Results)

TABLE 131

| Test substance | IC50 (µM) |
|---|---|
| Compound A2 (Compound A) | 0.53 |
| Compound A17 | 0.27 |
| Compound A21 | 0.91 |
| Compound A23 | 0.49 |
| Compound B2 | 0.36 |
| Compound C2 | 0.57 |
| Compound D2 | 0.33 |

Example 2

To Produce Model Mice with Chronic Cough Caused by Airway Inflammation.

Model mice with chronic cough caused by airway inflammation (referred to as "airway inflammation model mice") were produced.

The airway inflammation model mice were produced while the mice were nasally instilled with lipopolysaccharide (LPS:1 µg/100 µL) daily for 3 days under diethyl ether inhalation anesthesia.

In addition, experiments for evaluating medicament efficacy on the airway inflammation model mice were conducted at 24 h after the final LPS administration.

Example 3

To Test Antitussive Action of Compound A

To test the presence or absence of antitussive action of compound A, mice that had orally received purified water or compound A in an amount of 0.3, 1, 3, or 10 mg/kg were stimulated with citric acid using a nebulizer at 1 h after the administration to induce cough reflux. In this way, the effects were investigated.

Note that, as used herein, mice that have been given neither administration nor treatment are referred to as "pretreatment mice"; mice, namely pretreatment mice that have received purified water are referred to as "control group mice"; and mice, namely pretreatment mice that have received a test subject compound are referred to as "test group mice".

Citric acid stimulation-induced cough reflux was measured by the following procedure.

At this time, ICR strain mice were used as the mice and 0.25 M citric acid was used as the citric acid.
(Cough Reflux-Measuring Procedure)

Cough reflux is induced by inhalation of (in the case of mice, 0.1 M or 0.25 M and in the case of guinea pigs, 0.25 M or 0.5 M) citric acid by mice or guinea pigs under non-anesthesia conditions. The citric acid is made aerosol by using an ultrasonic nebulizer (NE-U17: OMRON Corporation), and is inhaled while the air is supplied with an artificial respirator (SN-480-7: Shinano Seisakusho). The citric acid aerosol has an average particle size of from 1 to 8 µm, and the artificial respirator is used to supply the air at a one-time ventilation volume of 6 mL, a frequency of 30 times per min, and an inhalation period of 3 min.

The respiration and the cough reflux are measured in accordance with the body-plethysmograph method. The plethysmograph used includes: a plastic-made, cylindrical cylinder part in which the trunk of each mouse or guinea pig is housed; and a cap part that covers the head portion (any plastic-made cylinder is allowed as long as each experimental animal can be put in; in the case of the mouse, for instance, the part with a diameter of 4 cm and a length of 7 cm was used). An exhaust hole is created at an upper cylinder portion so as to be able to connect, via a silicon tube, to a respiratory flow meter (TP-602T: NIHON KOHDEN CORPORATION). To tightly seal the inside of the cylinder, a rubber or celluloid collar is attached to the neck of each animal, and the cap covering the whole head is used to fix them. The head-attached cap part has an exhaust port and an inhalation port created for inhalation of a cough-inducing substance. In addition, a screw-type lid is attached to a tail portion of the cylinder so as to move in or out each experimental animal. Each mouse is put in the cylinder, allowed to play for at least 30 min, adapted to an experimental environment, and then subjected to the experiment. The respiration is recorded in a PC (IdeaPad 300: Lenovo) for measurement by measuring, as a change in volume of the cylinder, the chest movement of each experimental animal in the cylinder by using a PowerLab (ML826 PowerLab 2/26: AD Instruments) via a respiratory flow meter. When a cough is induced, the chest of the experimental animal is moved vigorously, which causes an instantaneous large volume change in the cylinder. This change is recorded using the respiratory flow meter. This frequency is recorded to measure the number of coughs. The data is analyzed by LabChart version 8 (ADInstruments). In addition, immediately before inhalation of citric acid, the respiratory frequency per 15 sec is measured.
(Test Results)

Figure 2:
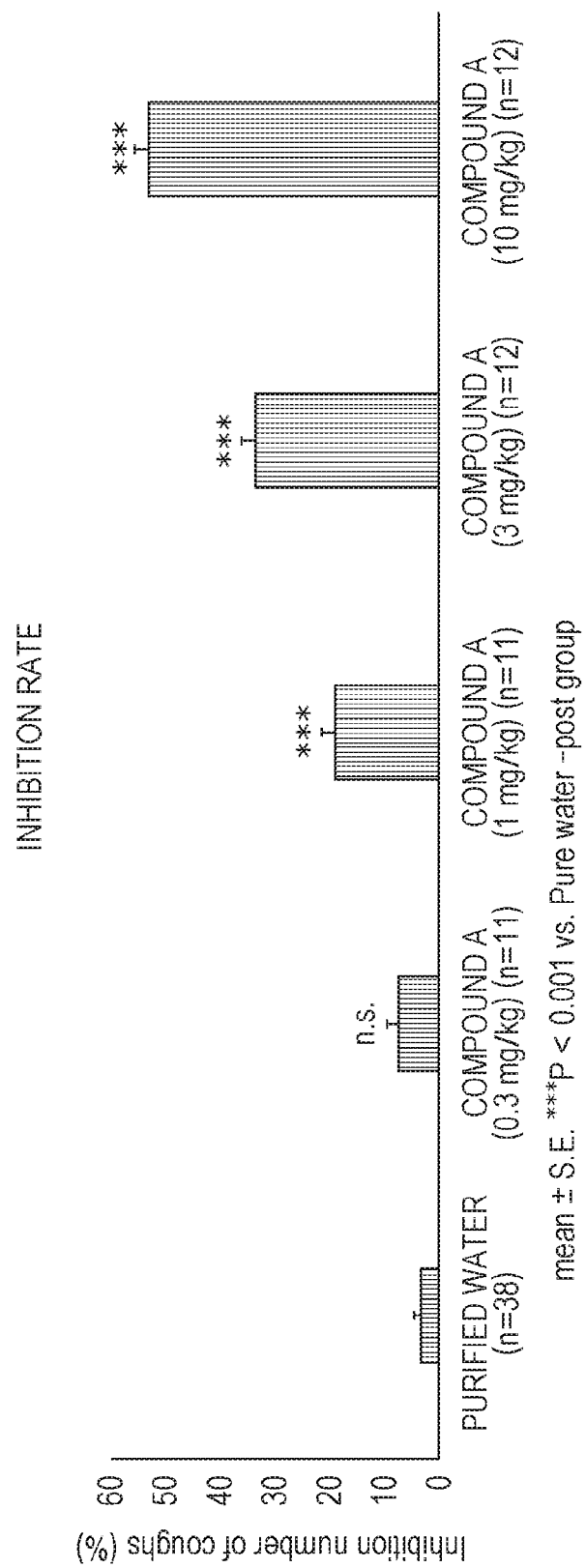
FIG. 2 is a graph showing an inhibition rate while the rate obtained from the test results in FIG. 1 was 100% when the number of coughs was 0.

FIGS. 1 and 2 show the results obtained.

The pre group in FIG. 1 shows the number of coughs after pretreatment mice were stimulated with 0.25 M citric acid. The post group in FIG. 1 shows the number of coughs after the control group mice in which purified water had been orally administered beforehand (at 1 h before citric acid administration) to the pretreatment mice or the test group mice in which 0.3, 1, 3, or 10 mg/kg of compound A had been orally administered beforehand (at 1 h before citric acid administration) to the pretreatment mice were stimulated with 0.5 M citric acid.

Here, FIG. 2 shows an inhibition rate while the rate obtained from the results (FIG. 1) of this Example was 0% when the number of coughs was neither increased nor decreased and the rate was 100% when the number of coughs was 0.

Compound A inhibited citric acid-induced cough in a dose-dependent manner, and a significant inhibitory action was exhibited at 1 mg/kg or higher.

Example 4

To Measure Antitussive Efficacy of Dihydrocodeine

Figure 3:
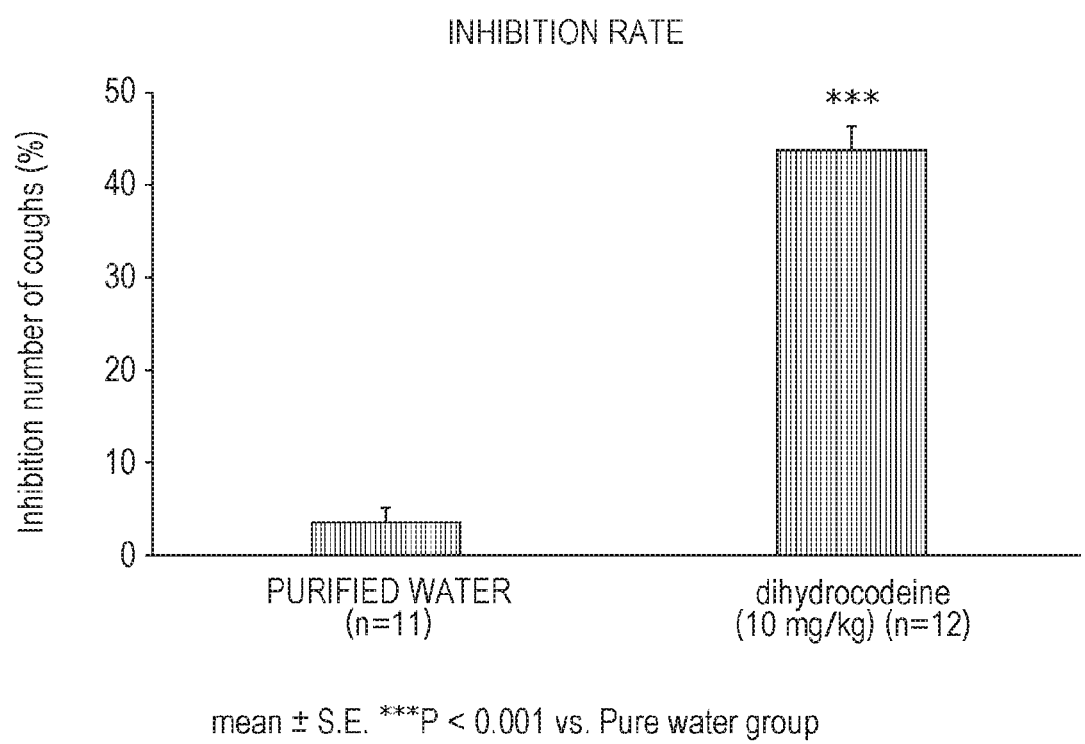
FIG. 3 is a graph indicating cough inhibitory action of dihydrocodeine on citric acid (0.25 M)-induced cough after 10 mg/kg of dihydrocodeine was orally administered to pretreatment mice and showing an inhibition rate while the rate obtained from the test results was 100% when the number of coughs was 0.

Meanwhile, to compare compound A and dihydrocodeine, the control group mice and the test group mice in which 10 mg/kg of dihydrocodeine had been orally administered to pretreatment mice were tested by substantially the same procedure as of Example 3. At that time, ICR strain mice were used as the mice. FIG. 3 shows the results.
(Test Results)

In a case in which 1 h after administration of purified water or dihydrocodeine, cough was triggered with 0.25 M citric acid by using a nebulizer, the cough inhibition rate was comparable between compound A and the same dose of dihydrocodeine.

Example 5

Effects of Compound A on Chronic Cough in Airway Inflammation Model Mice Used.

Figure 4:
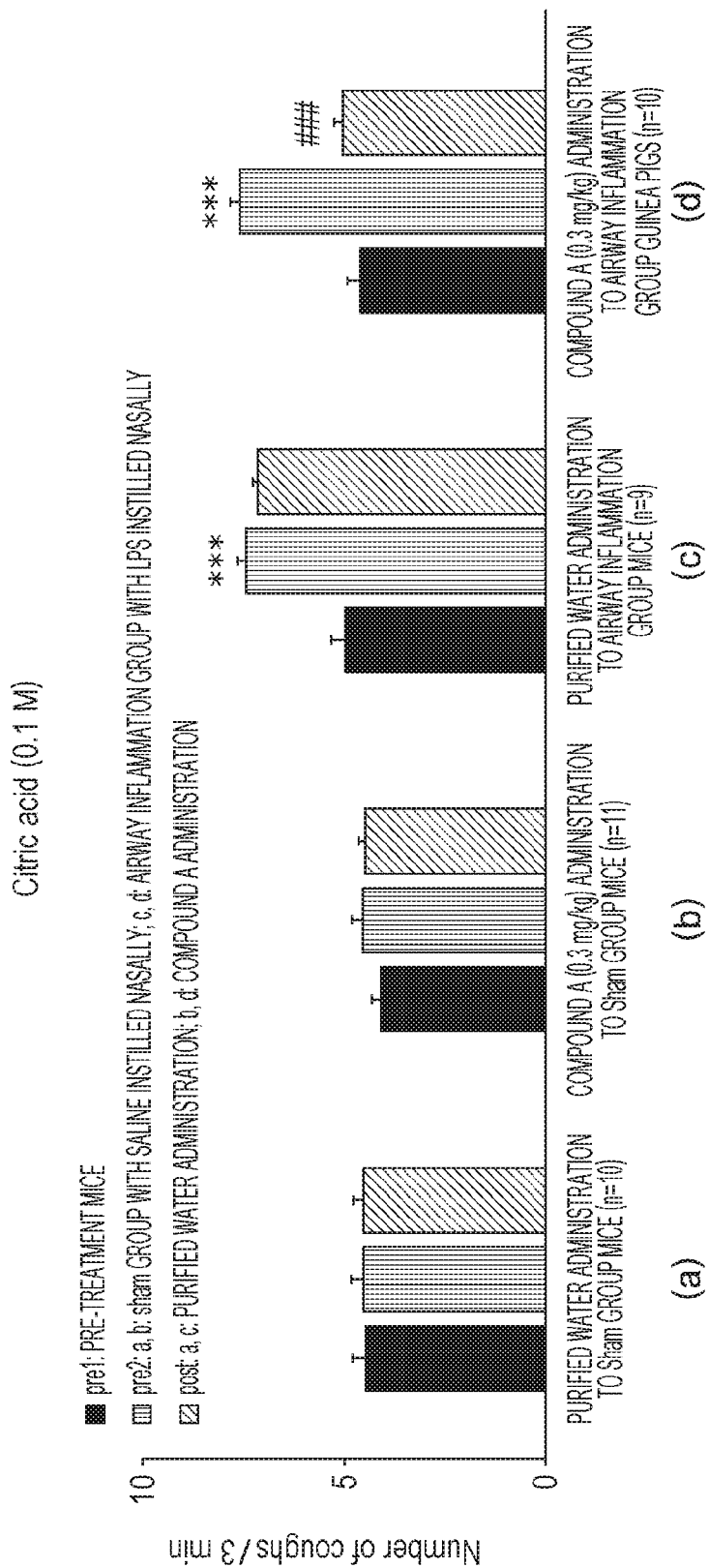
FIG. 4 is a graph indicating cough inhibitory action of compound A on citric acid (0.1 M)-induced cough after compound A (0.3 mg/kg) was orally administered to airway inflammation model mice with airway inflammation. The stimulation with citric acid (0.1 M) was conducted at 1 h after the compound A administration.

FIG. 4 shows the results of using airway inflammation model mice to investigate medicament efficacy of compound A on chronic cough.
(Test Results)

Airway inflammation model mice were used to induce cough reflux by substantially the same procedure as of Example 3.

At this time, ICR strain mice were used for producing the airway inflammation model mice and 0.1 M citric acid was used as the citric acid.

Compared to a case where pretreatment mice (pre1 of (a), (b), (c), and (d) in FIG. 4) were stimulated with 0.1 M citric acid to induce cough reflux, a case of mice (hereinafter, herein referred to as "sham group mice"; (a) and (b) in FIG. 4) where the pretreatment mice were nasally instilled with saline instead of LPS in Example 2 and then stimulated with 0.1 M citric acid had no observed change in the number of coughs (pre2 of (a) and (b) in FIG. 4).

By contrast, when airway inflammation model mice (hereinafter, herein referred to as "airway inflammation group mice"; (c) and (d) in FIG. 4) produced from the pretreatment mice by the procedure in Example 2 were stimulated with 0.1 M citric acid, an increase in cough response was observed (pre2 of (c) and (d) in FIG. 4).

When 0.3 mg/kg of compound A was orally administered beforehand (at 1 h before citric acid stimulation) to the airway inflammation group mice being sensitive to this cough stimulation, the cough response increased due to airway inflammation was inhibited completely (post of (d) in FIG. 4). On the contrary, when 0.3 mg/kg of compound A was orally administered beforehand (at 1 h before citric acid stimulation) to the sham group mice, a change in the number of coughs was unobserved (post of (b) in FIG. 4).

Thus, 0.3 mg/kg of compound A did not elicit any significant medicament efficacy when the sham group mice were examined (when pre2 and post in FIG. 4(b) were compared) (0.3 mg/kg of compound A did not elicit any significant medicament efficacy in the examination of Example 3). This has revealed that cough necessary for biological defense (0.1 M citric acid-induced cough) was not inhibited and only cough sensitive to cough reflux due to airway inflammation was inhibited. This feature seems to be distinct from that of a central nervous system acting antitussive agent such as dihydrocodeine that inhibits all the necessary cough.

Note that post of (a) or (c) in FIG. 4 shows, compared with the case of compound A, the results of the control group in which purified water was administered beforehand (at 1 h before citric acid stimulation) to the sham group mice or the airway inflammation group mice, respectively.

Example 6

To Evaluate Medicament Efficacy of Compound A by Local Application Using Nebulizer.

Figure 5:
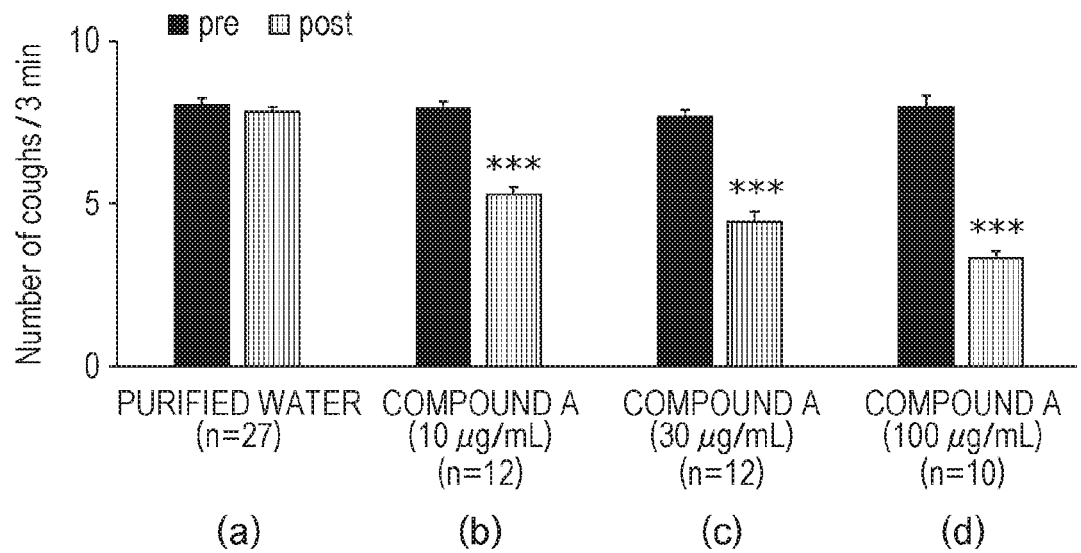
FIG. 5 is a graph indicating cough inhibitory action of compound A upon citric acid (0.25 M) stimulation after airway inflammation model mice with airway inflammation received compound A (10 to 100 μg/mL) by inhalation using a nebulizer. The stimulation with citric acid (0.25 M) was conducted at 4 min after the compound A administration.
Figure 6:
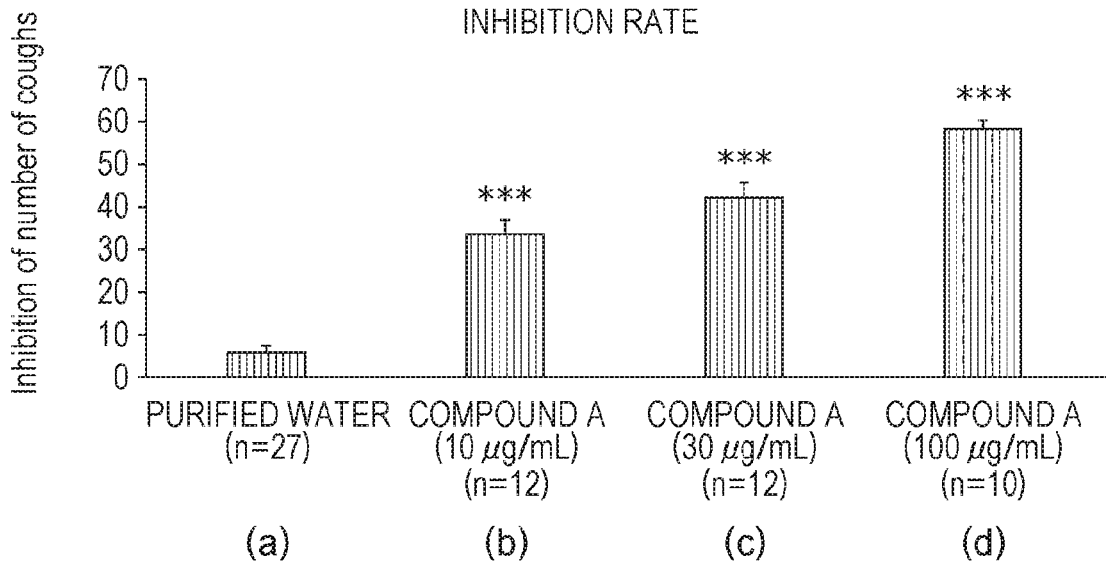
FIG. 6 is a graph showing an inhibition rate while the rate obtained from the test results in FIG. 5 was 100% when the number of coughs was 0.

FIGS. 5 and 6 show the results of evaluating medicament efficacy of compound A by local application using a nebulizer instead of orally administration. At that time, ICR strain mice were used as the mice. Here, FIG. 6 shows an inhibition rate while the rate obtained from the results (FIG. 5) of this Example was 0% when the number of coughs was neither increased nor decreased and the rate was 100% when the number of coughs was 0.
(Test Results)

Control group mice (post of (a) in FIG. 5) in which nebulizer-processed purified water was given, by inhalation, to pretreatment mice (the pre group in FIG. 5) or test group mice in which compound A in a concentration of 10 μg/mL (post of (b) in FIG. 5), 30 μg/mL (post of (c) in FIG. 5), or 100 μg/mL (post of (d) in FIG. 5) was given, by inhalation, to pretreatment mice were stimulated using a nebulizer with 0.25 M citric acid after 4 min to trigger cough.

As a result, the local application of compound A elicited an antitussive effect, in a dose-dependent manner, more strongly and more rapidly using a lower dose than the case of oral administration.

Example 7

(P2X4 Receptor Antagonistic Action)
The P2X4 receptor antagonistic action of compounds of the present invention was measured.
(Test Protocol)

The same protocol as of Example 1 was used to measure P2X4 receptor antagonistic action. Table 132 shows the results.
(Test Results)

TABLE 132

| Test substance | IC50 (μM) |
| --- | --- |
| Compound F2 | 0.75 |
| Compound F20 | 1.20 |
| Compound F48 (Compound B) | 0.30 |
| Compound F57 | 0.72 |
| Compound F71 | 0.40 |
| Compound F106 | 1.80 |
| Compound F118 | 1.10 |
| Compound F173 | 0.06 |
| Compound F196 | 0.97 |
| Compound F197 | 0.44 |
| Compound F208 | 1.30 |
| Compound F209 | 0.94 |
| Compound F210 | 1.40 |
| Compound F214 | 0.62 |

Example 8

(P2X4 Receptor Antagonistic Action)
The P2X4 receptor antagonistic action of compounds of the present invention was measured.
(Test Protocol)

The same protocol as of Example 1 was used to measure P2X4 receptor antagonistic action. Table 133 shows the results.
(Test Results)

TABLE 133

| Test compound | Inhibitory action IC50 (μM) |
| --- | --- |
| Compound G15 | 0.88 |

Example 9

(To Test Antitussive Action of Compound A in Guinea Pigs)

To test the presence or absence of antitussive action of compound A in accordance with the (Cough Reflux-measuring Procedure) described in Example 3, guinea pigs that had orally received purified water or compound A in an amount of 1, 3, or 10 mg/kg were stimulated with citric acid using a nebulizer at 1 h after the administration to induce cough reflux. In this way, the effects were investigated.

At that time, Hartly strain guinea pigs were used as the guinea pigs, and 0.5 M citric acid was used as the citric acid.
(Test Results)

Figure 7:
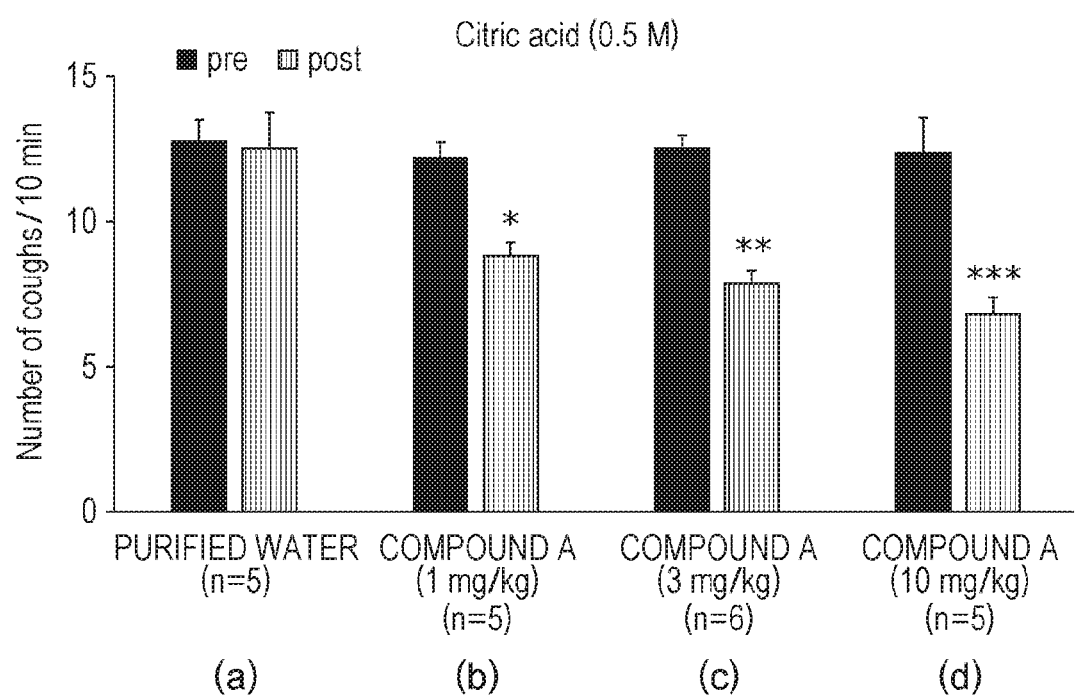
FIG. 7 is a graph showing cough inhibitory action of compound A on citric acid (0.5 M)-induced cough after compound A was orally administered to pretreatment guinea pigs.
Figure 8:
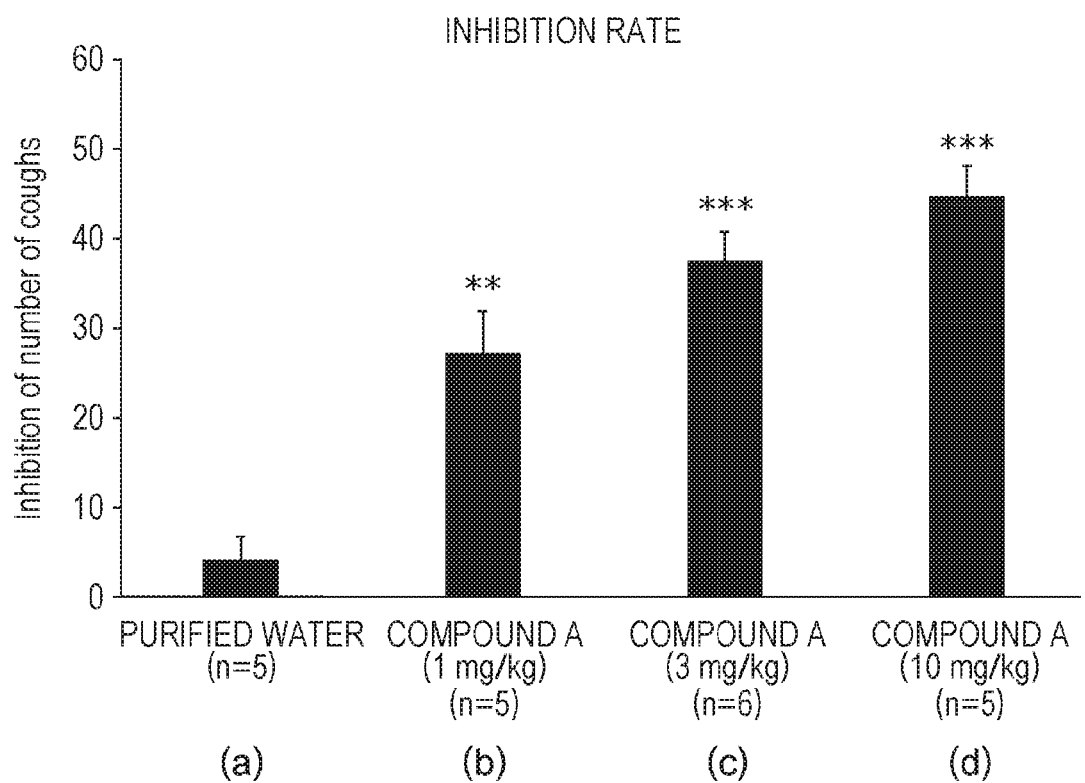
FIG. 8 is a graph showing an inhibition rate while the rate obtained from the test results in FIG. 7 was 100% when the number of coughs was 0.

FIGS. 7 and 8 show the results obtained.

The pre group in FIG. 7 shows the number of coughs after Hartly strain guinea pigs that had been given neither treatment nor administration were stimulated with 0.5 M citric acid. The post group in FIG. 7 shows the number of coughs after the guinea pigs in which purified water or 1, 3, or 10 mg/kg of compound A had been orally administered beforehand (at 1 h before citric acid administration) to the pretreatment guinea pigs were stimulated with 0.5 M citric acid.

Note that as used herein, the "pretreatment guinea pigs" are referred to as guinea pigs that have been given neither treatment nor administration; the "control group guinea pigs" are referred to as guinea pigs in which purified water has been administered to pretreatment guinea pigs; and the "test group guinea pigs" are referred to as guinea pigs in which a test subject compound has been administered to pretreatment guinea pigs.

In addition, FIG. 8 shows an inhibition rate while the rate obtained from the results (FIG. 7) of this Example was 0% when the number of coughs was neither increased nor decreased and the rate was 100% when the number of coughs was 0.

These results have demonstrated that compound A inhibited citric acid-induced cough in a dose-dependent manner and elicited a significant inhibitory action at 1 mg/kg or higher.

Example 10

(To Test Antitussive Action of Compound B in Guinea Pigs)

To test the presence or absence of antitussive action of compound B in accordance with the (Cough Reflux-measuring Procedure) described in Example 3, guinea pigs that had orally received purified water or compound B in an amount of 1, 3, 10, or 30 mg/kg were stimulated with citric acid using a nebulizer at 1 h after the administration to induce cough reflux. In this way, the effects were investigated.

At that time, Hartly strain guinea pigs were used as the guinea pigs, and 0.5 M citric acid was used as the citric acid.
(Test Results)

Figure 9:
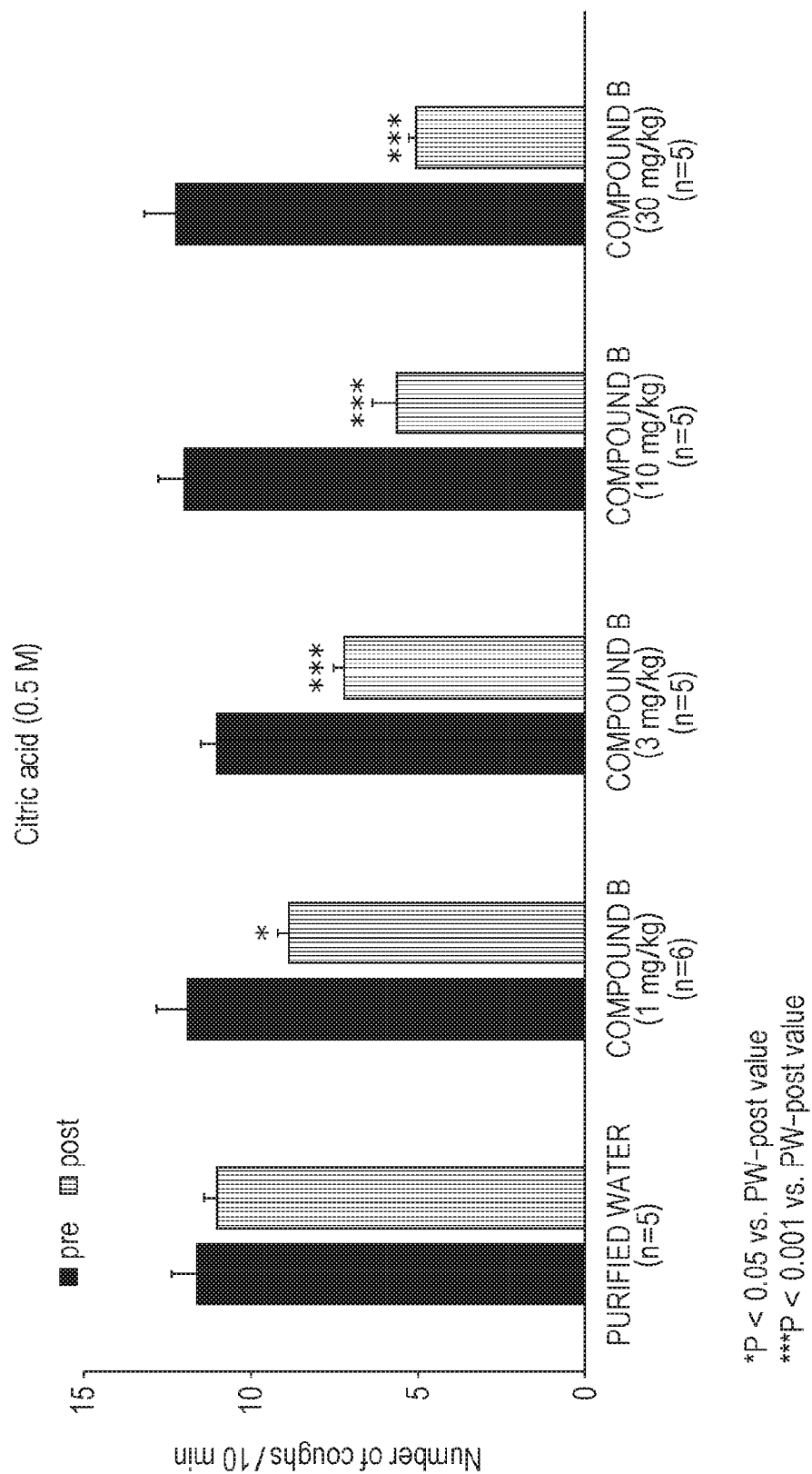
FIG. 9 is a graph showing cough inhibitory action of compound B on citric acid (0.5 M)-induced cough after compound B was orally administered to pretreatment guinea pigs.
Figure 10:
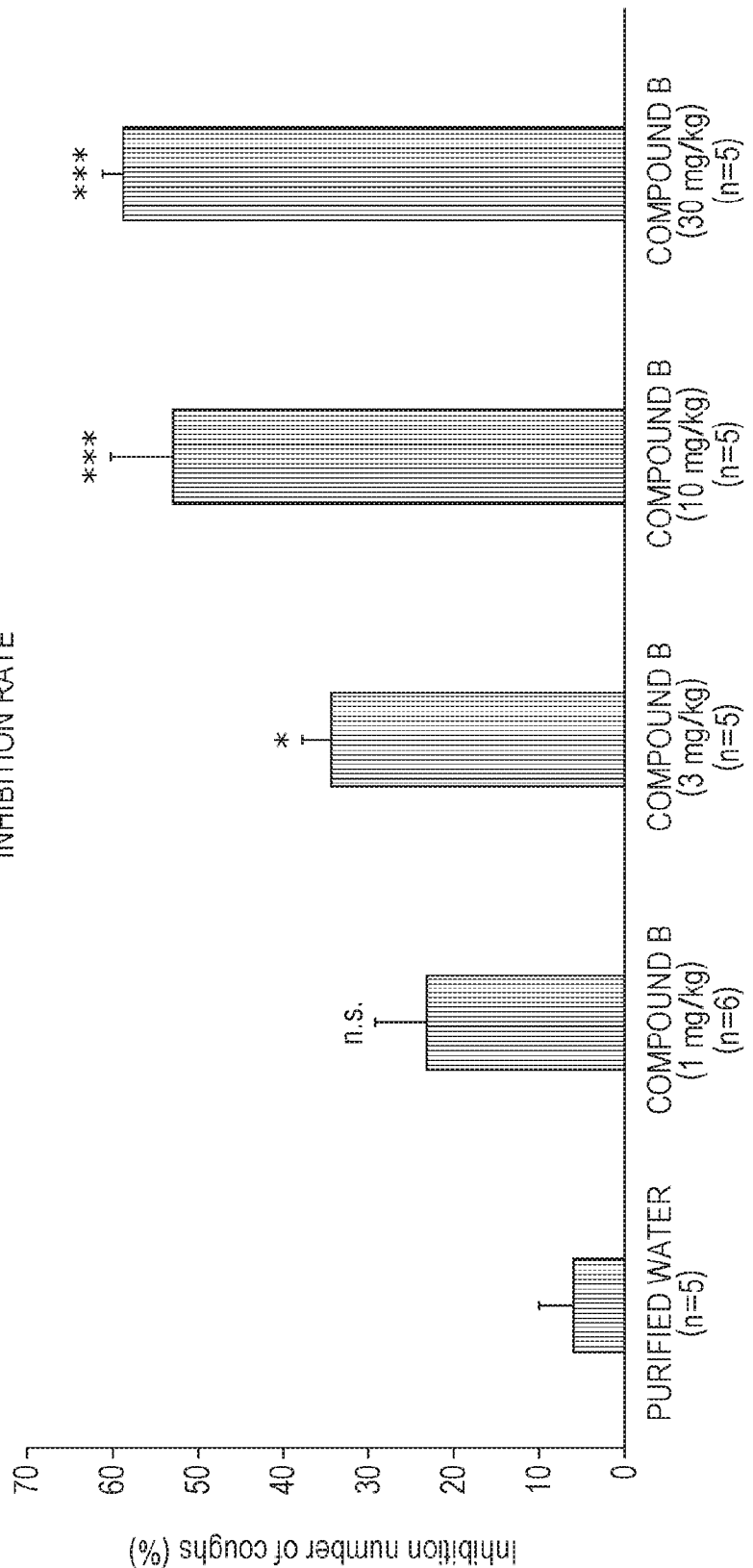
FIG. 10 is a graph showing an inhibition rate while the rate obtained from the test results in FIG. 9 was 100% when the number of coughs was 0.

FIGS. 9 and 10 show the results obtained.

The pre group of FIG. 9 shows the results of inducing cough reflux by stimulating pretreatment guinea pigs with 0.5 M citric acid. In addition, the post group of FIG. 9 shows the results of inducing cough reflux by stimulating, with 0.5 M citric acid, control group guinea pigs or test group guinea pigs in which purified water or 1, 3, 10, or 30 mg/kg of compound B had been orally administered beforehand (at 1 before citric acid administration) to the pretreatment guinea pigs.

FIG. 10 shows an inhibition rate while the rate obtained from the results (FIG. 9) of this Example was 0% when the number of coughs was neither increased nor decreased and the rate was 100% when the number of coughs was 0.

As a result, compound B inhibited citric acid-induced cough in a dose-dependent manner, and a significant inhibitory action was exhibited at 1 mg/kg or higher.

Example 11

(To Produce OVA-Sensitized Cough Model Guinea Pigs)

When OVA, a foreign antigen, is inhaled, airway inflammation accompanied by eosinophil infiltration is induced. Consequently, OVA-sensitized guinea pigs present symptoms of allergic cough and atopic cough. Thus, the guinea pigs have been widely used as a pathological model (antigen-induced airway inflammation model animals) reflecting human clinical conditions. Here, in the Examples of the present application, whether a compound(s) of the present application elicited cough inhibitory action against the pathological model was evaluated.

The OVA-sensitized cough model guinea pigs were produced specifically by the following procedure.

Note that in the following procedure, Ovalbumin or mepyramine maleate is dissolved in saline and then used.

The number of citric acid-induced coughs is measured. Then, a mixture of 200 µL of 0.05% OVA (Ovalbumin) and 100 µL of Imject Alum (prepared by suspending aluminum hydroxide and magnesium hydroxide, each at a concentration of 40 mg/mL, in water and by adding an inactivating stabilizer thereto) per guinea pig is administered intraperitoneally (i.p.).

After the intraperitoneal administration, 0.5% OVA is given for 5 min by inhalation at days 7, 14, 21, and 28.

Note that at 30 min before the inhalation, mepyramine maleate (10 mg/kg) is given i.p. to prevent a shock symptom.

At Day 35, 0.5% ovalbumin is given for 60 min by inhalation. Note that at 30 min before the inhalation, mepyramine maleate (10 mg/kg) is given i.p. to prevent a shock symptom.

The next day of the final 0.5% ovalbumin challenge (day 35), the test is conducted.

Example 12

(Effects of Compound a on OVA Sensitization-Induced Cough in Guinea Pigs)

Figure 11:
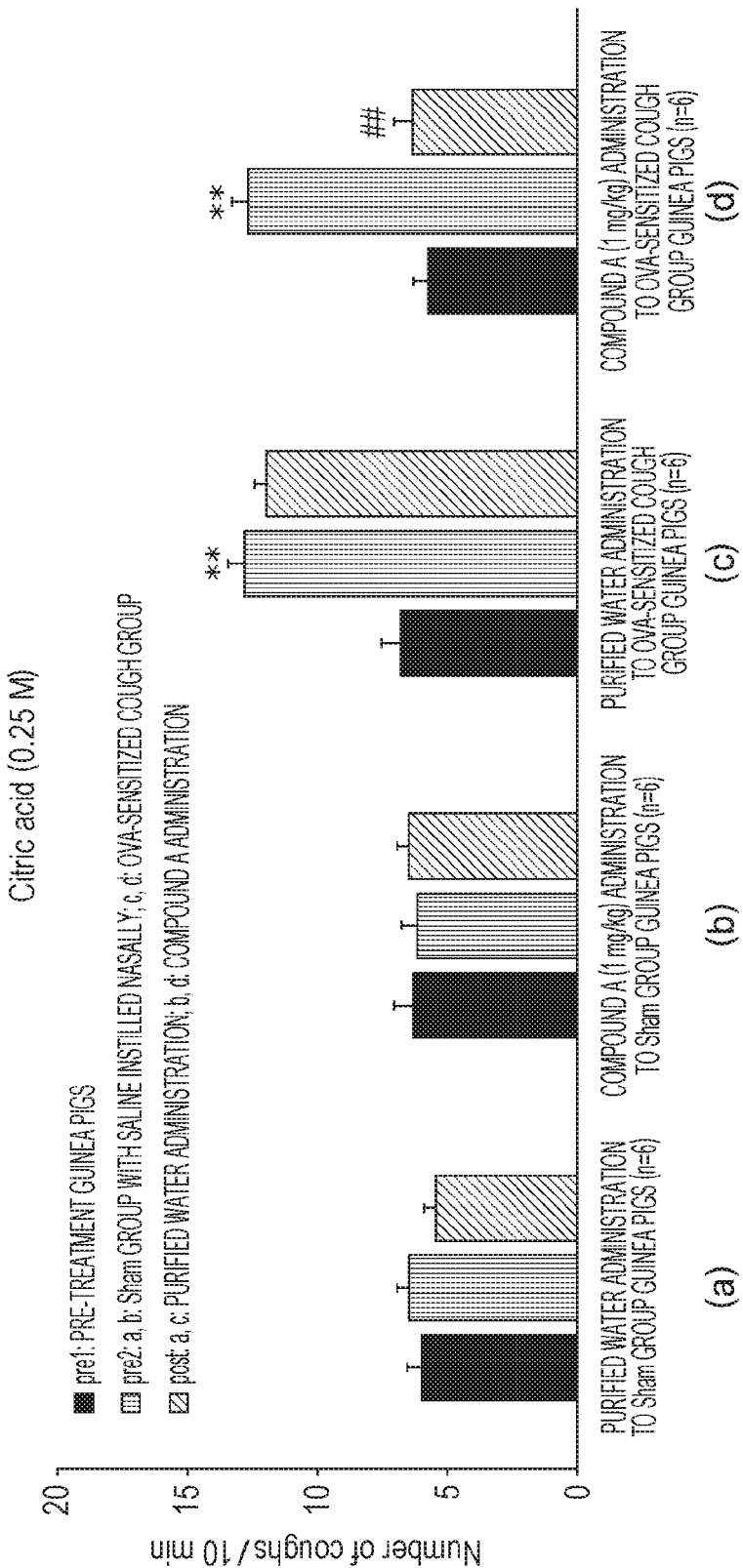
FIG. 11 is a graph indicating cough inhibitory action of compound A on citric acid (0.25 M)-induced cough after compound A (1.0 mg/kg) was orally administered to ovalbumin (hereinafter, referred to as "OVA")-sensitized guinea pigs (OVA-sensitized cough model guinea pigs). The stimulation with citric acid (0.25 M) was conducted at 1 h after the compound A administration.

FIG. 11 shows the results of investigating medicament efficacy of compound A on OVA sensitization-induced cough in a guinea pig OVA-sensitized cough model, which is a pathological model reflecting clinical conditions.
(Test Results)

OVA-sensitized cough model guinea pigs were used and stimulated with 0.25 M citric acid by the same procedure as of Example 9 to induce cough reflux. For guinea pigs used in this Example, Hartly strain guinea pigs were used for any of the below-described pretreatment guinea pigs, sham group guinea pigs, and OVA-sensitized cough group guinea pigs.

Compared to a case where pretreatment guinea pigs (pre1 of (a), (b), (c), and (d) in FIG. 11) were stimulated with 0.25 M citric acid to induce cough reflux, a case of guinea pigs (hereinafter, herein referred to as "sham group guinea pigs"; (a) and (b) in FIG. 11) where the pretreatment guinea pigs were nasally instilled with saline instead of OVA and then stimulated with 0.1 M citric acid in accordance with the procedure of Example 11 had no observed change in the number of coughs (pre2 of (a) and (b) in FIG. 11).

By contrast, when OVA-sensitized cough model guinea pigs (hereinafter, herein referred to as "OVA-sensitized cough group guinea pigs"; (c) and (d) in FIG. 11) produced from the pretreatment guinea pigs by the procedure in Example 11 were stimulated with 0.1 M citric acid, an increase in cough response was observed (pre2 of (c) and (d) in FIG. 11).

When 1 mg/kg of compound A was orally administered beforehand (at 1 h before citric acid stimulation) to the OVA-sensitized cough group guinea pigs being sensitive to this cough stimulation, the cough response increased due to airway inflammation was inhibited completely (post of (d) in FIG. 11). On the contrary, when 1 mg/kg of compound A was orally administered beforehand (at 1 h before citric acid stimulation) to the sham group guinea pigs, a change in the number of coughs was unobserved (post of (b) in FIG. 11).

Note that post of (a) or (c) in FIG. 11 shows, compared with the case of compound A, the results of the control group in which purified water was administered beforehand (at 1 h before citric acid stimulation) to the sham group guinea pigs or the OVA-sensitized cough group guinea pigs, respectively.

The above results have revealed, even in the pathological model reflecting clinical conditions, that cough necessary for biological defense (0.25 M citric acid-induced cough) was not inhibited and only cough sensitive to cough reflux due to airway inflammation was inhibited. This feature seems to be distinct from that of a central nervous system acting antitussive agent such as dihydrocodeine that inhibits all the necessary cough.

Example 13

(Effects of Compound B on OVA Sensitization-Induced Cough in Guinea Pigs)

Figure 12:
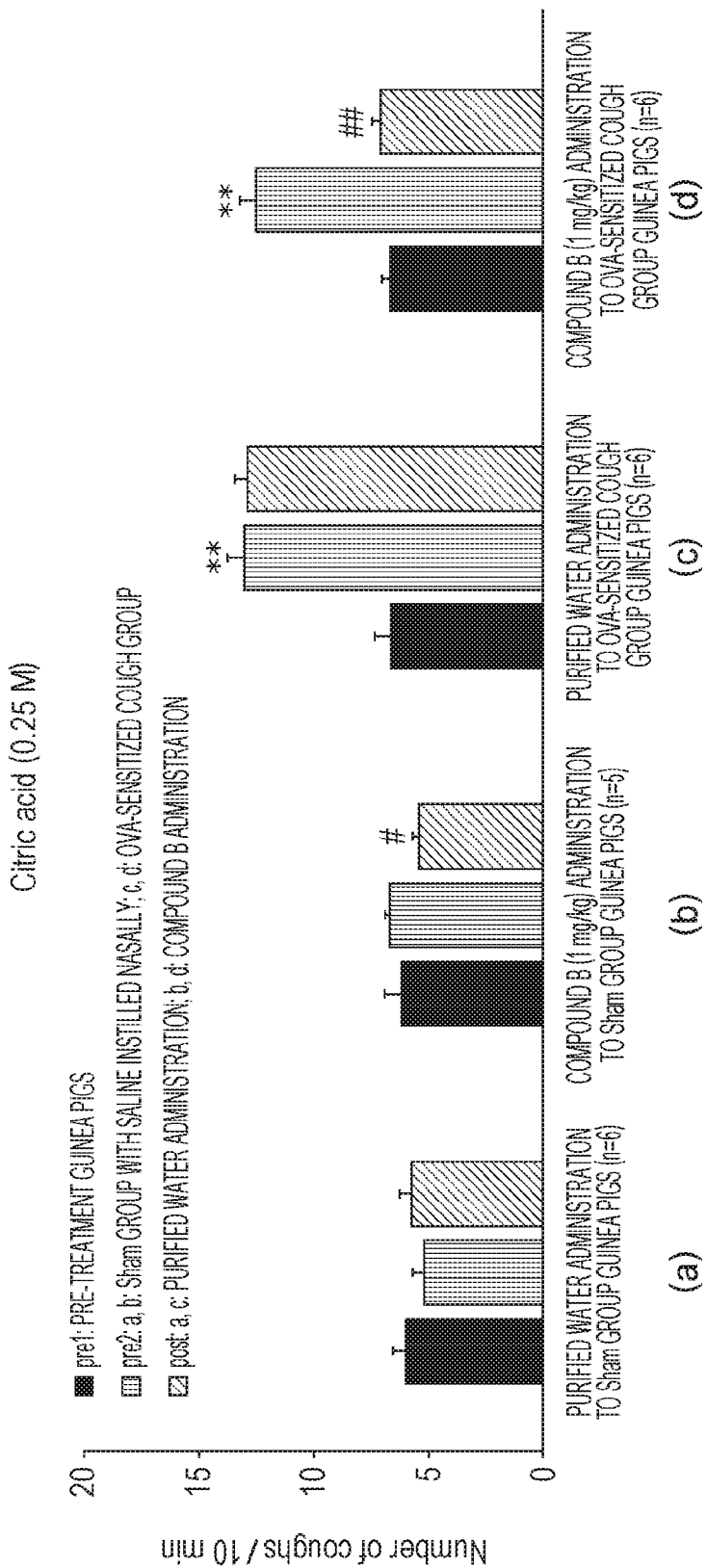
FIG. 12 is a graph indicating cough inhibitory action of compound B on citric acid (0.25 M)-induced cough after compound B (1.0 mg/kg) was orally administered to OVA-sensitized cough model guinea pigs. The stimulation with citric acid (0.25 M) was conducted at 1 h after the compound B administration.

FIG. 12 shows the results of investigating medicament efficacy of compound B on OVA sensitization-induced cough in a guinea pig OVA-sensitized cough model, which is a pathological model reflecting clinical conditions.
(Test Results)

OVA-sensitized cough model guinea pigs were used and stimulated with 0.25 M citric acid by the same procedure as of Example 10 to induce cough reflux. For guinea pigs used in this Example, Hartly strain guinea pigs were used for any of the below-described pretreatment guinea pigs, sham group guinea pigs, and OVA-sensitized cough group guinea pigs.

Compared to a case where pretreatment guinea pigs (pre1 of (a), (b), (c), and (d) in FIG. 12) were stimulated with 0.25 M citric acid to induce cough reflux, a case of sham group guinea pigs ((a) and (b) in FIG. 12) that had received 0.1 M citric acid stimulation had no observed change in the number of coughs (pre2 of (a) and (b) in FIG. 11).

By contrast, when OVA-sensitized cough group guinea pigs ((c) and (d) in FIG. 12) are stimulated with 0.1 M citric acid, an increase in cough response is observed (pre2 of (c) and (d) in FIG. 12).

When 1 mg/kg of compound B was orally administered beforehand (at 1 h before citric acid stimulation) to the OVA-sensitized cough group guinea pigs being sensitive to this cough stimulation, the cough response increased due to airway inflammation was inhibited completely (post of (d) in FIG. 12). On the contrary, when 1 mg/kg of compound B was orally administered beforehand (at 1 h before citric acid stimulation) to the sham group guinea pigs, a change in the number of coughs was unobserved (post of (b) in FIG. 12).

Further, 1 mg/kg of compound B does not elicit any significant medicament efficacy in the investigation of Example 10 (FIG. 10).

Note that post of each of (a) or (c) in FIG. 12 shows, compared with the case of compound B, the results of the control group in which purified water was administered beforehand (at 1 h before citric acid stimulation) to the sham group guinea pigs or the OVA-sensitized cough group guinea pigs, respectively.

The above results have revealed, even in the pathological model reflecting clinical conditions, that cough necessary for biological defense (0.25 M citric acid-induced cough) was not inhibited and only cough sensitive to cough reflux due to airway inflammation was inhibited. This feature seems to be distinct from that of a central nervous system acting antitussive agent such as dihydrocodeine that inhibits all the necessary cough.

Example 14

(P2X4 Receptor Antagonistic Action)

The P2X4 receptor antagonistic action of compounds of the present invention was measured.
(Test Protocol)

The same protocol as of Example 1 was used to measure P2X4 receptor antagonistic action. Tables 134 to 136 show the results.
(Test Results)

TABLE 134

| Test compound | Inhibitory action IC50 (µM) |
|---|---|
| Compound H1 | 0.025 |
| Compound H2 | 0.037 |
| Compound H4 | 0.044 |
| Compound H11 | 0.077 |
| Compound H21 | 0.078 |

TABLE 135

| Test compound | Inhibitory action IC50 (µM) |
|---|---|
| Compound H22 | 0.091 |
| Compound H25 | 0.082 |
| Compound H27 | 0.078 |
| Compound H31 | 0.051 |
| Compound H37 | 0.079 |
| Compound H42 | 0.092 |
| Compound H43 | 0.053 |
| Compound H47 | 0.094 |

TABLE 136

| Test compound | Inhibitory action IC50 (µM) |
|---|---|
| Compound H61 | 0.074 |
| Compound H62 | 0.088 |
| Compound H67 | 0.053 |
| Compound H79 | 0.039 |
| Compound H83 | 0.087 |

Example 15

(Effects of Compound C or Compound D on Citric Acid-Induced Cough in Guinea Pigs)

Figure 13:
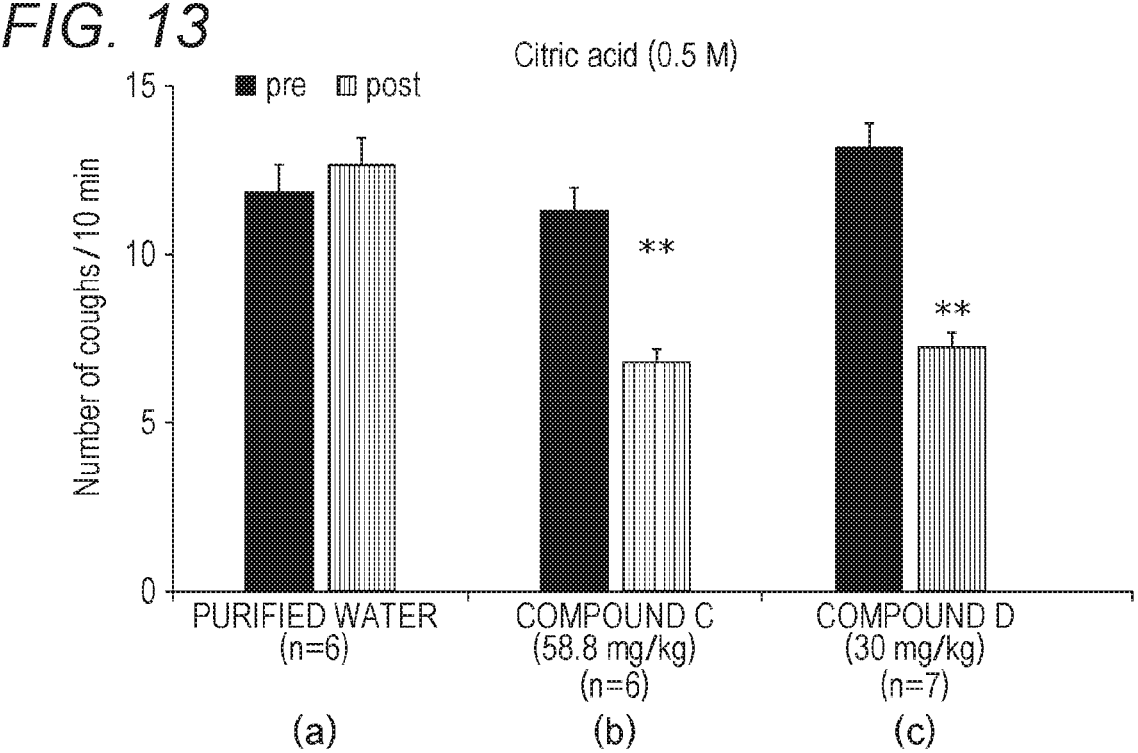
FIG. 13 is a graph showing cough inhibitory action of compounds C and D on citric acid (0.5 M)-induced cough after compounds C and D was orally administered to pretreatment guinea pigs.

Hartly strain guinea pigs that had been given neither treatment nor administration (pretreatment guinea pigs)

were stimulated with citric acid to induce cough reflux. Then, the effects were investigated. FIG. 13 shows the results of investigating medicament efficacy of compound C or compound D on cough reflux induced by citric acid stimulation.
(Method)
To test, by using pretreatment guinea pigs, the presence or absence of antitussive action of compound C or D in accordance with the (Cough Reflux-measuring Procedure) described in Example 3, guinea pigs that had orally received purified water or compound C in an amount of 58.8 mg/kg or compound D in an amount of 30 mg/kg were stimulated with citric acid using a nebulizer at 1 h after the administration to induce cough reflux. In this way, the effects were investigated. Here, 0.5 M citric acid was used as the pretreated citric acid.
(Test Results)
FIG. 13 shows the results obtained.
A change in the number of coughs was unobserved between the cough response (pre of (a) in FIG. 13) of pretreatment guinea pigs ((a) to (c) in FIG. 13) when stimulated with 0.5 M citric acid and the cough response (post of (a) in FIG. 13) of the pretreatment guinea pigs to which purified water was orally administered beforehand (at 1 h before citric acid stimulation) and 0.5 M citric acid stimulation was then given.

By contrast, the number of coughs was significantly decreased between the cough response (pre of (b) in FIG. 13) of the pretreatment guinea pigs when stimulated with 0.5 M citric acid and the cough response (post of (b) in FIG. 13) of the pretreatment guinea pigs to which 58.8 mg/kg of compound C was orally administered beforehand (at 1 h before citric acid stimulation) and 0.5 M citric acid stimulation was then given. Like Examples 12 and 13, the cough response increased due to airway inflammation was demonstrated to be inhibited completely.

Likewise, the number of coughs was significantly decreased between the cough response (pre of (c) in FIG. 13) of the pretreatment group guinea pigs when stimulated with 0.5 M citric acid and the cough response (post of (c) in FIG. 13) of the pretreatment guinea pigs to which 30 mg/kg of compound D was orally administered beforehand (at 1 h before citric acid stimulation) and 0.5 M citric acid stimulation was then given. Like Examples 12 and 13, compound D has been demonstrated to completely inhibit the cough response increased due to airway inflammation.

Figure 14:
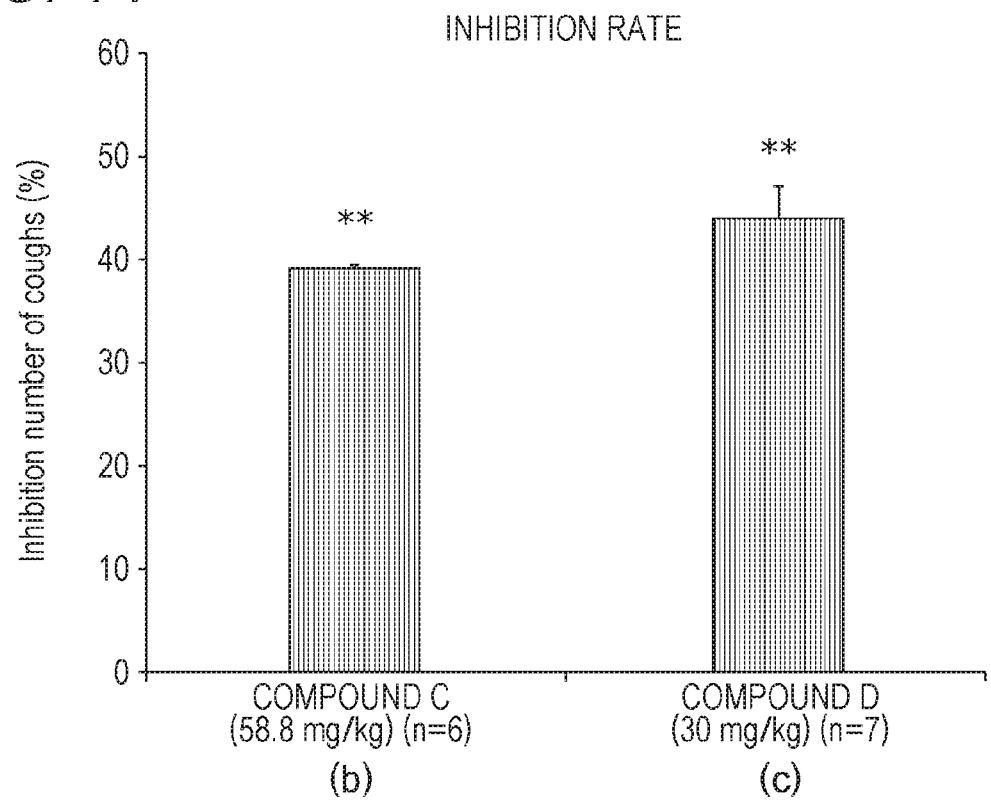
FIG. 14 is a graph showing an inhibition rate while the rate obtained from the test results in FIG. 13 was 0% when the number of coughs was neither increased nor decreased and the rate was 100% when the number of coughs was 0.

In addition, FIG. 14 shows an inhibition rate while the rate obtained from the results ((b) and (c) of FIG. 13) of this Example was 0% when the number of coughs was neither increased nor decreased and the rate was 100% when the number of coughs was 0.

The above results have revealed, even in the pathological model reflecting clinical conditions, that compound C or D does not inhibit cough necessary for biological defense (0.5 M citric acid-induced cough) and does inhibit only cough sensitive to cough reflux due to airway inflammation. This feature seems to be distinct from that of a central nervous system acting antitussive agent such as dihydrocodeine that inhibits all the necessary cough.

Example 16

Synthesis of 5-[3 (1H-Tetrazol-5-yl)phenyl]-1H-naphtho [1,2-b][1,4]diazepin-2,4(3H,5H)-dione Sodium Salt Here, 5-[3 (1H-tetrazol-5-yl)phenyl]-1H-naphtho [1,2-b][1,4]diazepin-2,4(3H,5H)-dione, which is described in Example 1 of WO 2010/093061, was obtained with reference to the process of Example 2(2) disclosed in WO 2012/008478 to produce the titled compound.

$^1$H NMR (DMSO-$d_6$, 400 MHz) δ:3.17 (1H, d, J=12 Hz), 3.73 (1H, d, J=12 Hz), 7.05 (1H, d, J=9 Hz), 7.19 (1H, d, J=9 Hz), 7.47 (1H, t, J=8 Hz), 7.5-7.7 (4H, m), 7.88 (1H, d, J=8 Hz), 7.93 (1H, d, J=8 Hz), 8.26 (1H, d, J=8 Hz), 10.92 (1H, br s)

Example 17

Synthesis of 5-[3-(1H-Tetrazol-5-yl)phenyl]-1,3-dihydro-2H-naphtho[1,2-e][1,4]diazepin-2-one Sodium Salt Here, 5-(3-Hydroxyphenyl)-1,3-dihydro-2H-naphtho[1,2-e]-1,4-diazepin-2-one obtained by the process described in Example 2 of WO 2008/023847 was obtained in reference to the synthesis scheme (method 3) described in WO 2010/093061 or the process (synthesis method 2) described in paragraphs[0054] to [0060] of WO 2012/017876 to produce 5-[3-(1H-tetrazol-5-yl)phenyl]-1,3-dihydro-2H-naphtho[1,2-e][1,4]diazepin-2-one. Here, 5-[3-(1H-tetrazol-5-yl)phenyl]-1,3-dihydro-2H-naphtho[1,2-e][1,4]diazepin-2-one was obtained with reference to the process of Example 2(2) disclosed in WO 2012/008478 to produce the titled compound.

$^1$H NMR (DMSO-$d_6$, 400 MHz) δ:3.81 (1H, d, J=9 Hz), 4.60 (1H, d, J=9 Hz), 7.21 (1H, d, J=8 Hz), 7.4-7.5 (2H, m), 7.6-7.8 (3H, m), 7.9-8.2 (3H, m), 8.3-8.5 (1H, m), 10.85 (1H, br s)

Example 18

Synthesis of 5-[4-Fluoro-3-(1H-tetrazol-5-yl)phenyl]-1H-naphtho[1,2-b][1,4]diazepin-2,4(3H,5H)-dione Sodium Salt Synthesis method 3 (paragraph[0043]) of synthesis scheme described in WO 2013/105608 or the synthesis scheme (method 3) described in WO 2010/093061 was referenced to produce 5-[4-fluoro-3-(1H-tetrazol-5-yl)phenyl]-1H-naphtho[1,2-b][1,4]diazepin-2,4(3H,5H)-dione. Here, 5-[4-fluoro-3-(1H-tetrazol-5-yl)phenyl]-1H-naphtho[1,2-b][1,4]diazepin-2,4(3H,5H)-dione was obtained with reference to the process of Example 2(2) disclosed in WO 2012/008478 to produce the titled compound.

$^1$H NMR (DMSO-$d_6$, 400 MHz) δ:3.12 (1H, d, J=12 Hz), 3.97 (1H, d, J=12 Hz), 7.01 (1H, d, J=9 Hz), 7.2-7.4 (2H, m), 7.6-7.7 (4H, m), 7.87 (1H, d, J=8 Hz), 8.22 (1H, d, J=9 Hz), 10.89 (1H, br s)

Example 19

A medicament of the present invention can be prepared as a capsule as follows.

Compound A, lactose, corn starch, and low-substituted hydroxypropylcellulose can be charged into a V-type mixer and mixed to obtain a capsule formulation.

Components in 270 mg of granules

Compound A: 100 mg, lactose: 94 mg, corn starch: 40 mg, low-substituted hydroxypropylcellulose: 21 mg, and hydroxypropylcellulose: 15 mg.

Here, 270 mg of the resulting capsule formulation can be manually filled into No. 3 capsule to give a capsule.

In addition, any of compounds B to D can be likewise processed to give a capsule.

Example 20

A medicament of the present invention can be prepared as a nebulizer formulation as follows.

Compound A can be dissolved in sterile purified water to make a 10 to 100 μg/mL solution. Next, 9 mg/mL NaCl solution can be added thereto to prepare a nebulizer formulation.

Example 21

(Action of Compound A on Contraction of Tracheobronchial Smooth Muscles Excised from Guinea Pig)
(Test Protocol)

An animal was sacrificed by phlebotomy while the ventral aorta was dissected under urethane (2 g/kg, i.p.) anesthesia. Then, a left major bronchial tissue was excised. After a connective tissue and blood vessels were removed, each ring specimen with a width of about 3 mm was prepared and suspended in an organ bath. Then, the isometric tension was measured while the resting tension was set to 1.0 g. After the baseline tension was stabilized, whether each ring specimen was subject to an acetylcholine (ACh: $10^{-3}$ M)-mediated contraction reaction was verified. Then, the following mater was investigated.

The ACh-inducible contractile muscles were used to mimic airway contraction during parasympathetic excitation in vitro, and action of compound A on the contraction reaction was observed. Water was used as a solvent for compound A, which was then used at the final concentration of $10^{-5}$ M.
(Test Results)

Figure 15:
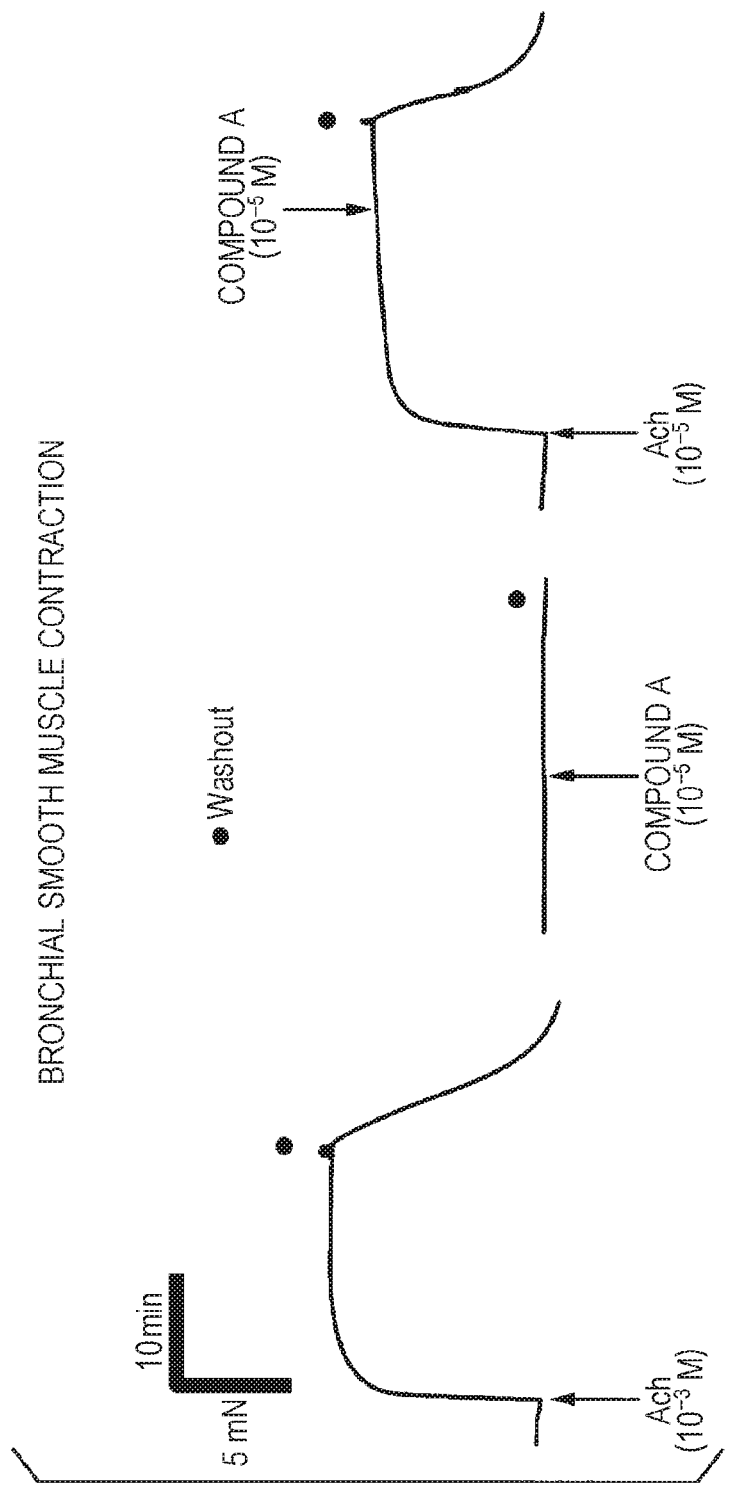
FIG. 15 is a chart indicating action of compound A on contraction of tracheobronchial smooth muscles excised from a guinea pig.

Compound A (at $10^{-5}$ M) did not affect the baseline tension or $10^{-5}$ M Ach-induced contraction reaction (about 50% contraction of the maximum contraction) of bronchial smooth muscle. FIG. 15 shows the results obtained.

Example 22

(Action of Compound B on Contraction of Tracheobronchial Smooth Muscles Excised from Guinea Pig)
(Test Protocol)

An animal was sacrificed by phlebotomy while the ventral aorta was dissected under urethane (2 g/kg, i.p.) anesthesia. Next, a tracheal or left major bronchial tissue was excised. After a connective tissue and blood vessels were removed, each ring specimen with a width of about 3 mm was prepared and suspended in an organ bath. Then, the isometric tension was measured while the resting tension was set to 1.0 g. After the baseline tension was stabilized, whether each ring specimen was subject to an acetylcholine (ACh: $10^{-3}$ M)-mediated contraction reaction was verified. Then, the following mater was investigated.

The Ach-inducible contractile muscles were used to mimic airway contraction during parasympathetic excitation in vitro, and action of compound B on the contraction reaction was observed. DMSO at the final concentration of 0.1% was used as a solvent for compound B. After $10^{-5}$ M ACh-induced contraction reaction (about 50% contraction of the maximum contraction) was stabilized, the specimen was treated with $10^{-6}$ M compound B (in DMSO at final 0.1%). The specimen was likewise treated with just 0.1% DMSO.

Figure 16:
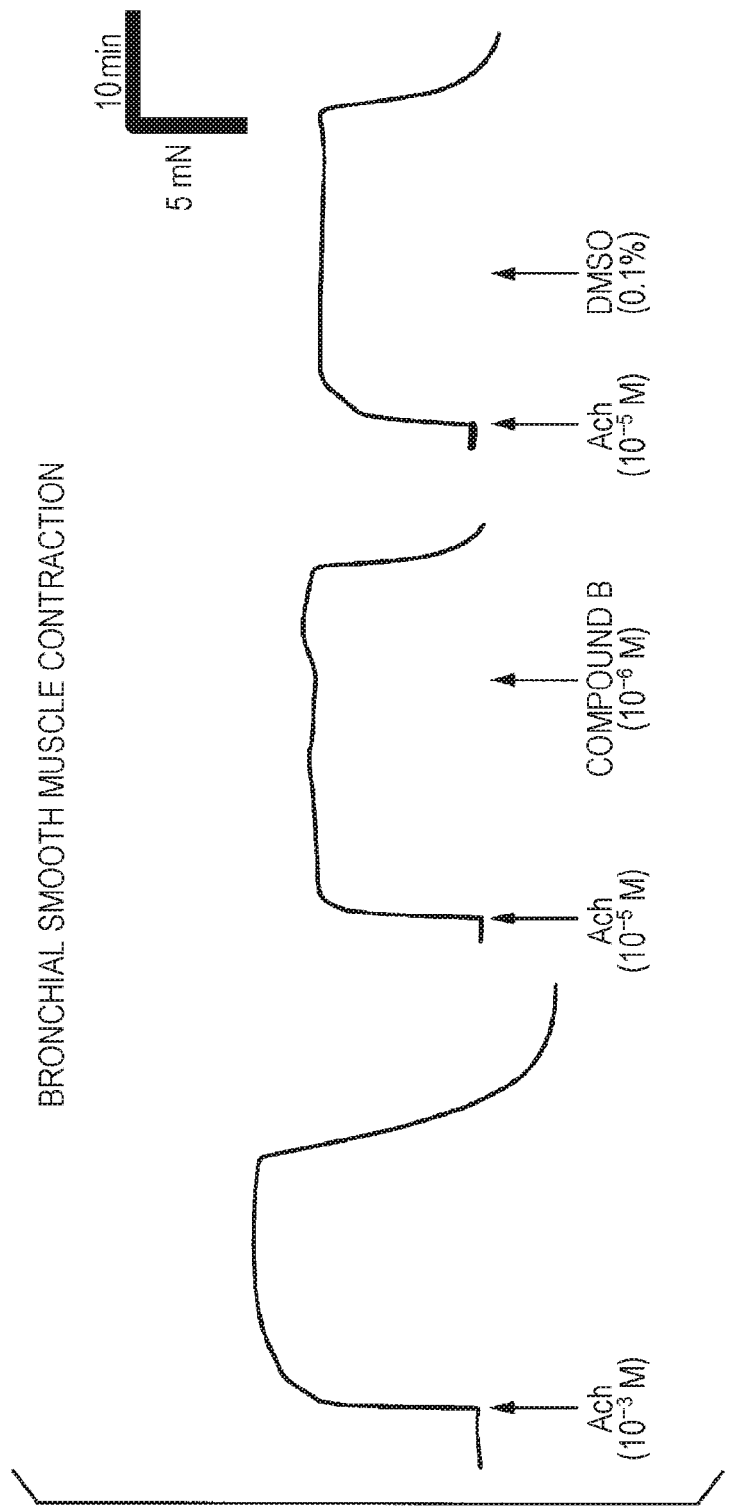
FIG. 16 is a chart indicating action of compound B on contraction of tracheobronchial smooth muscles excised from a guinea pig.

(Test Results)
Neither 0.1% DMSO itself, which was a solvent, nor compound B (at $10^{-6}$ M) affected the ACh-induced contraction of bronchial smooth muscle. FIG. 16 shows the results obtained.

INDUSTRIAL APPLICABILITY

A medicament of the present invention is useful as a medicament for preventing or treating cough, preferably acute cough, persistent cough, or chronic cough and more preferably chronic cough, and should be further highly effective in prophylaxis or treatment of cough such as a disease responsible for chronic cough including dry cough (e.g., cough caused by cough variant asthma, atopic cough, cough caused by gastroesophageal reflux, chemical-induced cough, or allergic cough) or wet cough (e.g., cough caused by sinobronchial syndrome, cough caused by chronic bronchitis, cough caused by chronic obstructive pulmonary disease, or cough caused by asthma). The medicament is useful, in particular, for dry cough, and is especially useful for cough caused by cough variant asthma, atopic cough, or allergic cough.

The invention claimed is:

1. A method for treating cough, the method comprising administering, to a subject in need thereof, a therapeutically effective amount of a compound having P2X4 receptor antagonistic action, or pharmaceutically acceptable salt thereof, wherein the compound having P2X4 receptor antagonistic action is a compound being selected from the group consisting of:
    (1) a compound having the following formula FI or pharmaceutically acceptable salt thereof;
    (2) a compound having the following formula AI or pharmaceutically acceptable salt thereof;
    (3) a compound having the following formula GI or pharmaceutically acceptable salt thereof;
    (4) a compound having the following formula HI or pharmaceutically acceptable salt thereof;
    (5) a compound having the following formula HII or pharmaceutically acceptable salt thereof;
    (6) a compound having the following formula EI or pharmaceutically acceptable salt thereof; and
    (7) a compound having the following formula BI or pharmaceutically acceptable salt thereof:

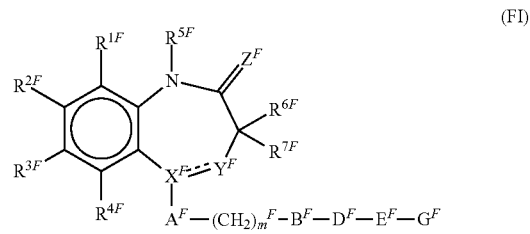

(FI)

wherein $R^{1F}$ and $R^{2F}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), an optionally substituted phenyl group, an optionally substituted pyridyl group, or an aralkyl group (the number of carbon atoms in an aryl moiety is from 6 to 10 and the number of carbon atoms in an alkylene moiety is from 1 to 8), or $R^{1F}$ and $R^{2F}$ are optionally fused with a benzene ring bonded thereto to form a condensed ring selected from a naphthalene ring, a quinoline ring, an isoquinoline ring, a tetrahydronaphthalene ring, an indane ring, a tetrahydroquinoline ring, or a tetrahydroisoquinoline ring and a ring fused with $R^{1F}$ and $R^{2F}$ and comprising carbon atoms bonded to respective $R^{1F}$ and $R^{2F}$ is optionally substituted with 1 to 4 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{3F}$ and $R^{4F}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{5F}$ represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $R^{6F}$ and $R^{7F}$ represent a hydrogen atom, $X^F$ represents C, $Y^F$ represents N, a double line composed of a solid line and a dashed line denotes a double bond, $Z^F$ represents an oxygen atom, $A^F$ represents a bond or represents a benzene ring, a pyridine ring, a thiophene ring, a pyrimidine ring, a naphthalene ring, a quinoline ring, or an indole ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, an aralkyl group (the number of carbon atoms in an aryl moiety is from 6 to 10 and the number of carbon atoms in an alkylene moiety is from 1 to 8), a phenyl group, or a pyridyl group, $B^F$ represents $N(R^{8F})C(=O)$, NHCONH, $CON(R^{9F})$, $NHC(=S)NH$, $N(R^{10F})SO_2$, $SO_2N(R^{11F})$, or $OSO_2$, $R^{8F}$, $R^{9F}$, $R^{10F}$, and $R^{11F}$ here represent a hydrogen atom, a $C_{1-8}$ alkyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $D^F$ represents a bond or a $C_{1-6}$ alkylene chain optionally having, as substituents, 1 to 4 substituents, which are the same or different, selected from a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8) and further optionally having a double bond, $E^F$ represents O, S, $NR^{12F}$, or a bond, $R^{12F}$ here represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $G^F$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine or pyrimidine optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acyl group, a methylenedioxy group, a carboxyl group, a $C_{1-6}$ alkylsulfinyl group, a $C_{1-6}$ alkylthio group, a $C_{1-6}$ alkylsulfonyl group, an aralkyl group (the number of carbon atoms in an aryl moiety is from 6 to 10 and the number of carbon atoms in an alkylene moiety is from 1 to 8), an optionally substituted phenyl, an optionally substituted pyridyl group, an optionally substituted imidazolyl group, an optionally substituted oxazolyl group, or an optionally substituted thiazolyl group, and $m^F$ represents an integer of 0 to 5, provided that a case is excluded where $R^{1F}$ and $R^{2F}$ are not fused to form a ring and where $X^F$ is C, YF is N, the double line composed of a solid line and a dashed line denotes a double bond, $Z^F$ is an oxygen atom, $A^F$ is a benzene ring, mf is 0, $B^F$ is C(=O) NH, $E^F$ is a bond, and $G^F$ is a phenyl group;

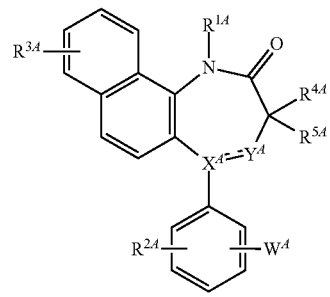

(AI)

wherein $R^{1A}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{2A}$ and $R^{3A}$ are the same or different and represent a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{4A}$ and $R^{5A}$ represent a hydrogen atom, $W^{A}$ represents an optionally substituted, 5- or 6-membered heterocyclic ring comprising 1 to 4 atoms of nitrogen as a ring constituent element, and $X^{A}$ is C, $Y^{A}$ is N and a double line composed of a solid line and a dashed line denotes a double bond;

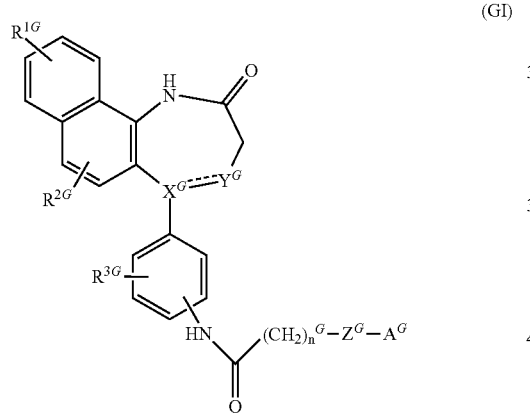

(GI)

wherein $R^{1G}$, $R^{2G}$, and $R^{3G}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $X^{G}$ represents C, $Y^{G}$ represents N, a double line composed of a solid line and a dashed line denotes double bond, $n^{G}$ represents an integer of 0 to 6, $Z^{G}$ represents O, S, or a bond, and $A^{G}$ represents a benzene ring, a pyridine ring, a piperazine ring, a piperidine ring, or a morpholine ring optionally having, as substituents, 1 to 5 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or N ($R^{4G}$) ($R^{5G}$) where $R^{4G}$ and $R^{5G}$ are the same or different and represent a $C_{1-8}$ alkyl group or $R^{4G}$ and $R^{5G}$ and a nitrogen atom bonded to $R^{4G}$ and $R^{5G}$ are fused to represent a 5- to 7-membered ring further optionally comprising, as a ring forming atom, an oxygen atom or a sulfur atom as a heteroatom;

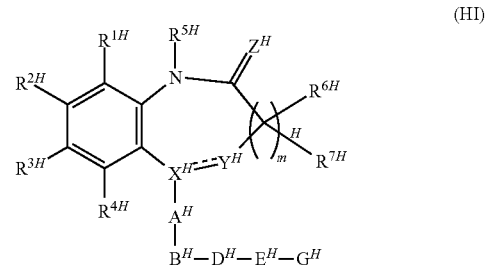

(HI)

wherein $R^{1H}$ and $R^{2H}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), an optionally substituted phenyl group, an optionally substituted pyridyl group, or an aralkyl group (the number of carbon atoms in an aryl moiety is from 6 to 10 and the number of carbon atoms in an alkylene moiety is from 1 to 8), or $R^{1H}$ and $R^{2H}$ are optionally fused with a benzene ring bonded thereto to form a condensed ring selected from a naphthalene ring, a quinoline ring, an isoquinoline ring, a tetrahydronaphthalene ring, an indane ring, a tetrahydroquinoline ring, or a tetrahydroisoquinoline ring and a ring fused with $R^{1H}$ and $R^{2H}$ and comprising carbon atoms bonded to respective $R^{1H}$ and $R^{2H}$ is optionally substituted with 1 to 4 substituents, which are the same or different, selected from a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{3H}$ and $R^{4H}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), or an aralkyl group (the number of carbon atoms in an aryl moiety is from 6 to 10 and the number of carbon atoms in an alkylene moiety is from 1 to 8), $R^{5H}$ represents a hydrogen atom, a $C_{1-8}$ alkyl group, a $C_{2-8}$ alkenyl group, a $C_{1-8}$ alkyl group substituted with 1 to 3 halogen atoms, a hydroxyl-substituted $C_{1-8}$ alkyl group, or an aralkyl group (the number of carbon atoms in an aryl moiety is from 6 to 10 and the number of carbon atoms in an alkylene moiety is from 1 to 8), $R^{6H}$ and $R^{7H}$ represent a hydrogen atom, $X^H$ represents C, $Y^H$ represents N, a double line composed of a solid line and a dashed line denotes a double bond, $Z^H$ represents O, $A^H$ represents a benzene ring, a pyridine ring, a pyrimidine ring, a pyridazine ring, a thiophene ring, a furan ring, a pyrazole ring, an imidazole ring, a quinoline ring, a benzimidazole ring, or an indane ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $B^H$ represents O, S, $NR^{8H}$, or a bond, $R^{8H}$ here represents a hydrogen atom or a $C_{1-8}$ alkyl group, $D^H$ represents a benzene ring, a pyridine ring, a pyrimidine ring, a pyridazine ring, a thiophene ring, a furan ring, a tetrazole ring, an imidazole ring, an imidazoline ring, a triazole ring, a thiazole ring, an oxazole ring, an isoxazole ring, a pyrazole ring, a pyrrole ring, a pyrrolidine ring, a piperazine ring, a piperidine ring, or a 5- to 8-membered cycloalkyl ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $E^H$ represents $-(CR^{9H}R^{10H})_{m}H-T^H-$, $R^{9H}$ and $R^{10H}$ here are the same or different and represent a hydrogen atom, a hydroxyl group, or a $C_{1-8}$ alkyl group, or $R^{9H}$ and $R^{10H}$ are optionally fused to form an ethylene chain, $n^H$ represents an integer of 0 to 8, $T^H$ represents O, S, $NR^{11H}$, or a bond, $R^{11H}$ here represents a hydrogen atom or a $C_{1-8}$ alkyl group, $G^H$ represents a benzene ring, a pyridine ring, an imidazole ring, a pyrrole ring, a pyrazole ring, a thiophene ring, a furan ring, a thiazole ring, an oxazole ring, a pyrimidine ring, a pyridazine ring, a pyrazine ring, a naphthalene ring, a quinoline ring, a quinazoline ring, an indole ring, an indoline ring, a piperazine ring, a piperidine ring, a morpholine ring, or a 5- to 8-membered cycloalkyl ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group, and $m^H$ represents an integer of 1;

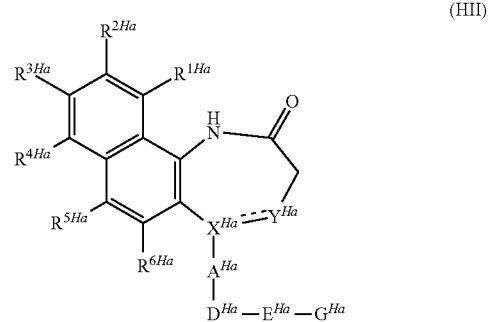

(HII)

wherein $R^{1Ha}$, $R^{2Ha}$, $R^{3Ha}$, $R^{4Ha}$, $R^{5Ha}$, and $R^{6Ha}$ are the same or different and represent a hydrogen atom, a $C_{1-8}$ alkyl group, a $C_{3-8}$ cycloalkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a carboxyl group, a $C_{2-8}$ acyl group, an alkoxycarbonyl group (the number of carbon atoms in an alkoxy moiety is from 1 to 8), an optionally substituted phenyl group, an optionally substituted pyridyl group, or an aralkyl group (the number of carbon atoms in an aryl moiety is from 6 to 10 and the number of carbon atoms in an alkylene moiety is from 1 to 8), $X^{Ha}$ represents C, $Y^{Ha}$ represents N, a double line composed of a solid line and a dashed line denotes a double bond, $A^{Ha}$ represents a benzene ring, a pyridine ring, a pyrimidine ring, a pyridazine ring, a thiophene ring, a furan ring, a pyrazole ring, an imidazole ring, a quinoline ring, a benzimidazole ring, or an indane ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $D^{Ha}$ represents a benzene ring, a pyridine ring, a pyrimidine ring, a pyridazine ring, a thiophene ring, a furan ring, a tetrazole ring, an imidazole ring, an imidazoline ring, a triazole ring, a thiazole ring, an oxazole ring, an isoxazole ring, a pyrazole ring, a pyrrole ring, a pyrrolidine ring, a piperazine ring, a piperidine ring, or a 5- to 8-membered cycloalkyl ring optionally having, as substituents, 1 to 4 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, or a $C_{2-8}$ dialkylamino group, $E^{Ha}$ represents $-(CR^{9Ha}R^{10Ha})_p-T^{Ha}-$, $R^{9Ha}$ and $R^{10Ha}$ here are the same or different and represent a hydrogen atom, a hydroxyl group, or a $C_{1-8}$ alkyl group, or $R^{9Ha}$ and $R^{10Ha}$ are optionally fused to form an ethylene chain, p represents an integer of 0 to 8, $T^{Ha}$ represents O, S, $NR^{11Ha}$, or a bond, $R^{11Ha}$ here represents a hydrogen atom or a $C_{1-8}$ alkyl group, and $G^{Ha}$ represents a benzene ring, a pyridine ring, an imidazole ring, a pyrrole ring, a pyrazole ring, a thiophene ring, a furan ring, a thiazole ring, an oxazole ring, a pyrimidine ring, a pyridazine ring, a pyrazine ring, a naphthalene ring, a quinoline ring, a quinazoline ring, an indole ring, an indoline ring, a piperazine ring, a piperidine ring, a morpholine ring, or a 5- to 8-membered cycloalkyl ring optionally having, as substituents, 1 to 5 substituents, which are the same or different, selected from a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a carbamoyl group, or a methanesulfonyl group;

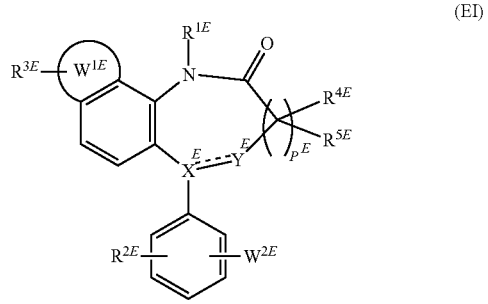

(EI)

wherein $R^{1E}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{2E}$ and $R^{3E}$ are the same or different and represent a hydrogen atom, a $C_{1-8}$ alkyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{4E}$ and $R^{5E}$ represent a hydrogen atom,

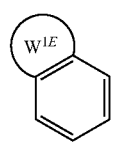

represents naphthalene or tetrahydronaphthalene, $W^{2E}$ represents an optionally substituted heterocyclic ring, $X^E$ is C, $Y^E$ is N and a double line composed of a solid line and a dashed line denotes a double bond, and $P^E$ is 1;

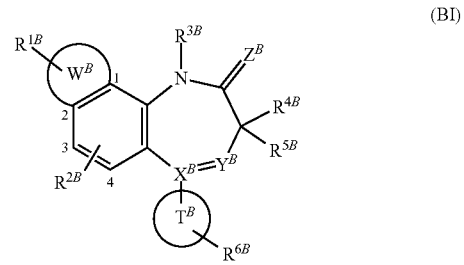

(BI)

wherein $R^{1B}$ and $R^{2B}$ are the same or different and represent a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, or a sulfamoyl group, $R^{3B}$ represents a hydrogen atom, a $C_{1-8}$ alkyl group, a $C_{2-8}$ alkenyl group, a $C_{1-8}$ alkyl group substituted with 1 to 3 halogen atoms, or a phenyl-substituted $C_{1-3}$ alkyl group, $R^{4B}$ and $R^{5B}$ represent a hydrogen atom, $R^{6B}$ represents a hydrogen atom, a $C_{1-8}$ alkyl group, a $C_{2-8}$ alkenyl group, a $C_{1-8}$ alkoxy group, a $C_{1-8}$ alkyl group substituted with 1 to 3 halogen atoms, a $C_{1-8}$ alkoxy group substituted with 1 to 3 halogen atoms, a halogen atom, a hydroxyl group, a nitro group, a cyano group, an amino group, a $C_{1-8}$ alkylamino group, a $C_{2-8}$ dialkylamino group, a $C_{2-8}$ acylamino group, a $C_{2-8}$ acylamino group substituted with 1 to 3 halogen atoms, a $C_{1-8}$ alkylsulfonylamino group, a carboxyl group, a $C_{2-8}$ acyl group, an alkoxycarbonyl group (the number of carbon atoms in an alkoxy moiety is from 1 to 8), a carbamoyl group, a $C_{1-8}$ alkylthio group, a $C_{1-8}$ alkylsulfinyl group, a $C_{1-8}$ alkylsulfonyl group, a sulfamoyl group, an optionally substituted phenyl group, or an optionally substituted heterocyclic ring group,

optionally contains, as ring constituent elements, 1 to 2 heteroatoms selected from N, S, or O and represents a 5- to 8-membered non-aromatic ring condensed with a benzene ring at positions 1 and 2,

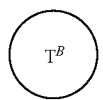

represents an aromatic ring selected from a benzene ring, a naphthalene ring, a thiophene ring, a pyridine ring, a pyrimidine ring, an indole ring, an indazole ring, a benzotriazole ring, a benzisoxazole ring, a benzimidazole ring, or a quinoline ring, $Z^B$ represents O, and $X^B$ is C, $Y^B$ is N and a double line composed of a solid line and a dashed line denotes a double bond.

2. The method according to claim 1, wherein the compound having P2X4 receptor antagonistic action or pharmaceutically acceptable salt thereof is a compound or a pharmaceutically acceptable salt being selected from the group consisting of:

(A20) 5-[3-(1H-tetrazol-5-yl)phenyl]-1,3-dihydro-2H-naphtho [1,2-e][1,4]diazepin-2-one;

(F64) 5-[4-(2-chloro-3-methoxybenzoylamino)phenyl]-1, 3-dihydronaphtho [1,2-e]-1,4-diazepin-2-one;

(F69) 5-[4-(2-chloro-3-hydroxybenzoylamino)phenyl]-1, 3-dihydronaphtho [1,2-e]-1,4-diazepin-2-one;

(F91) 5-[4-(2-tert-butylbenzoylamino)phenyl]-1,3-dihydronaphtho [1,2-e]-1,4-diazepin-2-one;

(F135) 5-[4-(2-chloro-6-methoxybenzoylamino)phenyl]-1,3-dihydronaphtho [1,2-e]-1,4-diazepin-2-one;

(F137) 5-[4-(2-chloro-6-hydroxybenzoylamino)phenyl]-1,3-dihydronaphtho [1,2-e]-1,4-diazepin-2-one;

(F149) N-[3-(2-oxo-2,3-dihydro-1H-naphtho [1,2-e][1,4] diazepin-5-yl)phenyl]benzene sulfonamide;

(F197) 1-(2-chlorophenyl)-N-[4-(2-oxo-2,3-dihydro-1H-naphtho [1,2-e][1,4]diazepin-5-yl)phenyl]methanesulfonamide;

(G1) N-[4-(2-oxo-2,3-dihydro-1H-naphtho [1,2-e][1,4]-diazepin-5-yl)phenyl]-3-(pyridin-2-yl)propionamide;

(G2) 2-ethyl-3-hydroxy-N-[4-(2-oxo-2,3-dihydro-1H-naphtho [1,2-e][1,4]-diazepin-5-yl)phenyl]benzamide;

(G3) 2-ethyl-N-[4-(2-oxo-2,3-dihydro-1H-naphtho [1,2-e][1,4]-diazepin-5-yl)phenyl]nicotinamide;

(G4) 2-ethyl-6-hydroxy-N-[4-(2-oxo-2,3-dihydro-1H-naphtho [1,2-e][1,4]-diazepin-5-yl)phenyl]benzamide;

(G5) 3-ethyl-N-[4-(2-oxo-2,3-dihydro-1H-naphtho [1,2-e][1,4]-diazepin-5-yl)phenyl]picolinamide;

(G6) N-[4-(2-oxo-2,3-dihydro-1H-naphtho [1,2-e][1,4]-diazepin-5-yl)phenyl]-2-(pyridin-2-yloxy) acetamide;

(G7) 2-(2-methoxyphenyl)-N-[4-(2-oxo-2,3-dihydro-1H-naphtho [1,2-e][1,4]diazepin-5-yl)phenyl]Acetamide;

(G8) N-[4-(2-oxo-2,3-dihydro-1H-naphtho [1,2-e][1,4]diazepin-5-yl)-phenyl]-3-(pyridin-3-yl)propionamide;

(G9) N-[4-(2-oxo-2,3-dihydro-1H-naphtho [1,2-e][1,4]diazepin-5-yl)phenyl]-3-phenylpropanamide;

(G15) 2-(dimethylamino)-N-[4-(2-oxo-2,3-dihydro-1H-naphtho [1,2-e][1,4]diazepin-5-yl)phenyl]nicotineamide;

(G19) N-[4-(2-oxo-2,3-dihydro-1H-naphtho [1,2-e][1,4]-diazepin-5-yl)phenyl]-2-(1H-pyrrole-1-yl)nicotinamide;

(G20) 2-(morpholin-4-yl)-N-[4-(2-oxo-2,3-dihydro-1H-naphtho [1,2-e][1,4]-diazepin-5-yl)phenyl]nicotinamide;

(G21) N-[4-(2-oxo-2,3-dihydro-1H-naphtho [1,2-e][1,4]-diazepin-5-yl)phenyl]-2-(pyrrolidine-1-yl)nicotinamide;

(G22) 4-(dimethylamino)-N-[4-(2-oxo-2,3-dihydro-1H-naphtho [1,2-e][1,4]diazepin-5-y1)phenyl]nicotineamide;

(G23) 2-isopropyl-N-[4-(2-oxo-2,3-dihydro-1H-naphtho [1,2-e][1,4]diazepin-5-yl)phenyl]nicotinamide;

(G24) 2-(isopropylamino)-N-[4-(2-oxo-2,3-dihydro-1H-naphtho [1,2-e][1,4]diazepin-5-yl)phenyl]nicotineamide;

(H17) 5-[4-[5-[2-(pyridin-2-yl)ethyl]-1H-tetrazol-1-yl] phenyl]-1H-naphtho [1,2-e][1,4]diazepin-2 (3H)-one;

(H19) 5-[4-[5-(2-methoxybenzyl)-1H-tetrazol-1-yl]phenyl]-1H-naphtho [1,2-e][1,4]diazepin-2 (3H)-one;

(H40) 5-[4-(5-phenethyl-1H-tetrazol-1-yl)phenyl]-1H-naphtho [1,2-e][1,4]diazepin-2 (3H)-one; and (H41) 5-[4-(2-phenethyl-1H-imidazol-1-yl)phenyl]-1H-naphtho [1,2-e][1,4]diazepin-2 (3H)-one.

3. The method according to claim 1, wherein the compound having P2X4 receptor antagonistic action or pharmaceutically acceptable salt thereof is 1-(2-chlorophenyl)-N-[4-(2-oxo-2,3-dihydro-1H-naphtho [1,2-e][1,4]diazepin-5-yl)phenyl]methanesulfonamide.

4. The method according to claim 1, wherein the compound having P2X4 receptor antagonistic action is 2-(dimethylamino)-N-[4-(2-oxo-2,3-dihydro-1H-naphtho [1,2-e][1,4]diazepin-5-yl)phenyl]nicotinamide dihydrochloride.

5. The method according to claim 1, wherein the cough is acute cough, persistent cough, or chronic cough.

6. The method according to claim 1, wherein the cough is chronic cough.

7. The method according to claim 1, wherein the cough is dry cough that is cough caused by cough variant asthma, atopic cough, cough caused by gastroesophageal reflux, chemical-induced cough, or allergic cough.

8. The method according to claim 1, wherein the cough is dry cough that is cough caused by cough variant asthma, atopic cough, or allergic cough.

9. The method according to claim 1, wherein the cough is wet cough that is cough caused by sinobronchial syndrome, cough caused by chronic bronchitis, cough caused by chronic obstructive pulmonary disease, or cough caused by asthma.

10. The method according to claim 1, which is peripheral cough suppression of dry cough.

11. The method according to claim 10, which is selective to the peripheral cough suppression of dry cough.

12. The method according to claim 11, wherein the dry cough is cough caused by cough variant asthma, atopic cough, or allergic cough.

* * * * *

UNITED STATES PATENT AND TRADEMARK OFFICE
CERTIFICATE OF CORRECTION

PATENT NO. : 12,233,071 B2
APPLICATION NO. : 18/135499
DATED : February 25, 2025
INVENTOR(S) : T. Imai et al.

Page 1 of 1

It is certified that error appears in the above-identified patent and that said Letters Patent is hereby corrected as shown below:

In the Claims

Column 166, Line 50 (Claim 1, Line 148) please change "mf" to -- $m^F$ --
Column 167, Line 55 (Claim 1, Line 184) please change "denotes double" to -- denotes a double --
Column 169, Line 45 (Claim 1, Line 295) please change ")$_m$H" to -- )$_n^H$ --

Signed and Sealed this
Twenty-second Day of July, 2025

Coke Morgan Stewart
*Acting Director of the United States Patent and Trademark Office*